(12) United States Patent
Seo et al.

(10) Patent No.: US 9,065,058 B2
(45) Date of Patent: *Jun. 23, 2015

(54) LIGHT-EMITTING ELEMENT AND ELECTRONIC DEVICE

(71) Applicant: Semiconductor Energy Laboratory Co., Ltd., Kanagawa-ken (JP)

(72) Inventors: Satoshi Seo, Kanagawa (JP); Harue Osaka, Kanagawa (JP); Sachiko Kawakami, Kanagawa (JP); Nobuharu Ohsawa, Kanagawa (JP); Tsunenori Suzuki, Kanagawa (JP); Hiromi Nowatari, Kanagawa (JP); Hiroki Suzuki, Kanagawa (JP); Kyoko Takeda, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/208,356

(22) Filed: Mar. 13, 2014

(65) Prior Publication Data

US 2014/0206887 A1   Jul. 24, 2014

Related U.S. Application Data

(63) Continuation of application No. 13/228,644, filed on Sep. 9, 2011, now Pat. No. 8,673,459.

(30) Foreign Application Priority Data

Sep. 10, 2010 (JP) .................................. 2010-203396

(51) Int. Cl.
   *H01L 51/50* (2006.01)
   *H01L 51/00* (2006.01)
   (Continued)

(52) U.S. Cl.
   CPC .......... *H01L 51/0054* (2013.01); *C07D 405/04* (2013.01); *C07D 405/14* (2013.01);
   (Continued)

(58) Field of Classification Search
   None
   See application file for complete search history.

(56) References Cited

U.S. PATENT DOCUMENTS 7,989,644 B2   8/2011   Tanabe et al.
8,007,927 B2   8/2011   Lin et al.
(Continued)

FOREIGN PATENT DOCUMENTS

CN   101184822 A   5/2008
EP   2 399 906 A1   12/2011
(Continued)

OTHER PUBLICATIONS

Goldsmith, C.R. et al., "C-H Bond Activation by a Ferric Methoxide Complex: Modeling the Rate-Determining Step in the Mechanism of Lipoxygenase," Journal of the American Chemical Society, vol. 124, No. 1, 2002, pp. 83-96.
(Continued)

*Primary Examiner* — Gregory Clark
(74) *Attorney, Agent, or Firm* — Husch Blackwell LLP

(57) ABSTRACT

An object is to provide a light-emitting element with high emission efficiency which includes a novel carbazole derivative that has a wide energy gap and can be used for a transport layer or a host material in a light-emitting element. A carbazole derivative in which the 4-position of dibenzothiophene or dibenzofuran is bonded to the 2- or 3-position of carbazole has been able to be provided by use of the carbazole derivative. Further, a light-emitting element having high emission efficiency has been able to be provided by use of the carbazole derivative.

19 Claims, 97 Drawing Sheets

(51) Int. Cl.
*C07D 405/04* (2006.01)
*C07D 405/14* (2006.01)
*C07D 409/04* (2006.01)
*C07D 409/14* (2006.01)

(52) U.S. Cl.
CPC ............ *C07D409/04* (2013.01); *C07D 409/14* (2013.01); *H01L 51/006* (2013.01); *H01L 51/0072* (2013.01); *H01L 51/0074* (2013.01); *H01L 51/0085* (2013.01); *H01L 51/0073* (2013.01)

(56) References Cited

U.S. PATENT DOCUMENTS

| | | | |
|---|---|---|---|
| 8,221,905 | B2 | 7/2012 | Lin et al. |
| 8,367,850 | B2 | 2/2013 | Ma et al. |
| 8,580,402 | B2 | 11/2013 | Lin et al. |
| 8,586,204 | B2 | 11/2013 | Xia et al. |
| 8,652,652 | B2 | 2/2014 | Brooks et al. |
| 8,822,708 | B2 | 9/2014 | Ma et al. |
| 8,866,377 | B2 | 10/2014 | Adamovich et al. |
| 2009/0015140 | A1 | 1/2009 | Kawakami et al. |
| 2009/0131673 | A1 | 5/2009 | Tanabe et al. |
| 2009/0153034 | A1 | 6/2009 | Lin et al. |
| 2009/0160323 | A1 | 6/2009 | Nomura et al. |
| 2010/0069647 | A1 | 3/2010 | Suzuki et al. |
| 2011/0006670 | A1 | 1/2011 | Katakura et al. |
| 2011/0248217 | A1 | 10/2011 | Tanabe et al. |
| 2011/0297924 | A1 | 12/2011 | Yabunouchi et al. |
| 2012/0071668 | A1 | 3/2012 | Suzuki et al. |
| 2012/0080667 | A1 | 4/2012 | Nowatari et al. |
| 2012/0091887 | A1 | 4/2012 | Osaka et al. |
| 2012/0132896 | A1 | 5/2012 | Kawata et al. |
| 2012/0133274 | A1 | 5/2012 | Kawakami et al. |
| 2012/0289708 | A1 | 11/2012 | Kawakami et al. |
| 2014/0008643 | A1 | 1/2014 | Lin et al. |
| 2014/0042413 | A1 | 2/2014 | Xia et al. |
| 2014/0054564 | A1 | 2/2014 | Kim et al. |
| 2014/0103327 | A1 | 4/2014 | Brooks et al. |
| 2014/0326977 | A1 | 11/2014 | Ma et al. |

FOREIGN PATENT DOCUMENTS

| | | | |
|---|---|---|---|
| EP | 2 511 254 | A2 | 10/2012 |
| EP | 2 599 851 | A2 | 6/2013 |
| EP | 2 757 094 | A1 | 7/2014 |
| EP | 2 806 008 | A1 | 11/2014 |
| EP | 2 857 395 | A1 | 4/2015 |
| JP | 2007-15933 | | 1/2007 |
| JP | 2008-21687 | | 1/2008 |
| JP | 2008-545729 | | 12/2008 |
| JP | 2009-267255 | | 11/2009 |
| JP | 2013-539206 | | 10/2013 |
| KR | 10-2008-0018218 | | 2/2008 |
| WO | WO 2006/128800 | A1 | 12/2006 |
| WO | WO 2009/021107 | A1 | 2/2009 |
| WO | WO 2009/021126 | A2 | 2/2009 |
| WO | WO 2009/030981 | A2 | 3/2009 |
| WO | WO 2009/072587 | A1 | 6/2009 |
| WO | WO 2009/085344 | A2 | 7/2009 |
| WO | WO 2009/086028 | A2 | 7/2009 |
| WO | WO 2010/095621 | A1 | 8/2010 |
| WO | WO 2011/004639 | A1 | 1/2011 |
| WO | WO 2011/052250 | A1 | 5/2011 |
| WO | WO 2012/015274 | A2 | 2/2012 |

OTHER PUBLICATIONS

Onishi, T. et al, "A Method of Measuring an Energy Level," *High Molecular EL Materials—Development of Light-Emitting High Molecular Compounds*, Kyoritsu Shuppan, Dec. 25, 2004, pp. 64-67 (with English translation, pp. 1-3).

International Search Report re application No. PCT/JP2011/070310, dated Nov. 1, 2011.

Written Opinion re application No. PCT/JP2011/070310, dated Nov. 1, 2011.

LIGHT-EMITTING ELEMENT AND ELECTRONIC DEVICE

This application is a continuation of copending U.S. application Ser. No. 13/228,644 filed on Sep. 9, 2011, which is incorporated herein by reference.

TECHNICAL FIELD

The present invention relates to a light-emitting element and an electronic device each using a carbazole derivative. The present invention further relates to the carbazole derivative and a light-emitting material and a light-emitting element material each using the carbazole derivative.

BACKGROUND ART

A display device using a light-emitting element (organic EL element) in which an organic compound is used as a light-emitting substance has been developed rapidly as a next generation lighting device or display device because it has advantages that such a light-emitting element can be manufactured to be thin and lightweight, has very high response speed, and has low power consumption.

In an organic EL element, when a voltage is applied between a pair of electrodes between which a light-emitting layer is interposed, electrons and holes are injected from the electrodes. The injected electrons and holes are recombined to form an excited state of a light-emitting substance contained in the light-emitting layer, and when the excited state relaxes to a ground state, light is emitted. A wavelength of light emitted from a light-emitting substance is peculiar to the light-emitting substance; thus, by using different types of organic compounds as light-emitting substances, light-emitting elements which exhibit various wavelengths, i.e., various colors can be obtained.

In a case of a display device which is expected to display images, such as a display, at least three colors of light, i.e., red, green, and blue are required to be obtained in order to reproduce full-color images. In the case of a lighting device, in order to obtain high color rendering property, light having wavelength components thoroughly in the visible light region is ideally obtained. Actually, two or more kinds of light having different wavelengths are mixed to be used for lighting application in many cases. Note that it is known that by mixing light of three colors, red, green, and blue, white light emission having high color rendering property can be obtained.

Light emitted from a light-emitting substance is peculiar to the substance as described above. However, important performances as a light-emitting element, such as lifetime or power consumption, are not only dependent on a light-emitting substance but also greatly dependent on layers other than a light-emitting layer, an element structure, properties of the light-emitting substance and a host, compatibility between them, or the like. Therefore, it is true that many kinds of materials are necessary for light-emitting elements in order to show the growth of this field. For the above-described reasons, materials for light-emitting elements which have a variety of molecular structures have been proposed (for example, see Patent Document 1).

REFERENCE

Patent Document

[Patent Document 1] Japanese Published Patent Application No. 2007-15933

DISCLOSURE OF INVENTION

Now there is a problem with light-emitting elements under current development: light-emitting elements that emit blue light have poorer characteristics than light-emitting elements that emit red to green light. This is due to the fact that a light-emitting substance having a wide energy gap is needed to emit blue light, and a further wider energy gap is needed for a substance used for a host for dispersion of the light-emitting substance in a light-emitting layer or a substance used for a transport layer adjacent to a light-emitting region containing the light-emitting substance If a material whose energy gap is not wide enough is used as a host material or a material for a layer adjacent to a light-emitting region, exciton energy is transferred to the material; thus, there occurs a problem such as reduction in the emission efficiency and color purity of the light-emitting element.

Therefore, an object of one embodiment of the present invention is to provide a novel carbazole derivative that has a wide energy gap and can be used for a transport layer or a host material in a light-emitting element or to provide a light-emitting element with high emission efficiency which includes the carbazole derivative.

Another object of one embodiment of the present invention is to provide a light-emitting element driven with a low driving voltage in which the above novel carbazole derivative is used.

Another object of one embodiment of the present invention is to provide a light-emitting element having a long lifetime in which the above novel carbazole derivative is used.

Note that in one embodiment of the present invention, it is only necessary that at least one of the above-described objects is achieved.

The present inventors have been able to synthesize a carbazole derivative in which the 4-position of dibenzothiophene or dibenzofuran is bonded to the 2- or 3-position of carbazole, as a substance having a wide band gap and a moderate carrier-transport property which can be suitably used as a material of a light-emitting element. Further, a light-emitting element having high emission efficiency has been able to be provided by use of the carbazole derivative. Furthermore, a light-emitting element driven with a low driving voltage has been able to be provided by use of the carbazole derivative. Further, a light-emitting element having a long lifetime has also been able to be provided by use of the carbazole derivative.

Specifically, one embodiment of the present invention is a light-emitting element including a layer containing an organic compound between a pair of electrodes, in which the layer containing an organic compound contains a material having an N-carbazolyl group in which the 4-position of a dibenzothiophene skeleton or of a dibenzofuran skeleton is bonded to the 2- or 3-position of carbazole.

Another embodiment of the present invention is a light-emitting element including a layer containing an organic compound between a pair of electrodes, in which the layer containing an organic compound contains a material having an N-carbazolyl group in which the 4-position of a dibenzothiophene skeleton or of a dibenzofuran skeleton is bonded to the 2- or 3-position of and 6- or 7-position of carbazole.

Another embodiment of the present invention is a light-emitting element including a layer containing an organic compound between a pair of electrodes, in which the layer containing an organic compound contains a material having an N-carbazolyl group in which the 4-position of a dibenzothiophene skeleton or of a dibenzofuran skeleton is bonded to the 2- and 7-positions of or 3- and 6-positions of carbazole.

Another embodiment of the present invention is a light-emitting element including a layer containing an organic compound between a pair of electrodes, in which the layer containing an organic compound contains a carbazole derivative represented by the following general formula (G1).

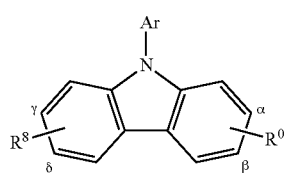

(G1)

In the formula, Ar represents an aryl group having 6 to 70 carbon atoms or a heteroaromatic group having 1 to 70 carbon atoms. In addition, $R^0$ represents a group represented by the following general formula (g1), and $R^8$ represents any one of hydrogen, an alkyl group having 1 to 6 carbon atoms, an aryl group having 6 to 15 carbon atoms, and a group represented by the following general formula (g2). Note that the substitution site of $R^0$ is a carbon atom represented by either α or β, and the substitution site of $R^8$ is a carbon atom represented by either γ or δ.

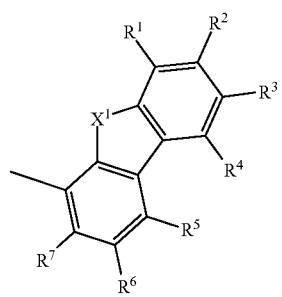

(g1)

(In the formula, $X^1$ represents oxygen or sulfur, and $R^1$ to $R^7$ individually represent any one of hydrogen, an alkyl group having 1 to 6 carbon atoms, and an aryl group having 6 to 15 carbon atoms.)

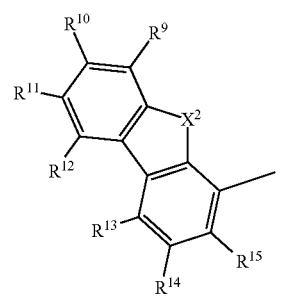

(g2)

(In the formula, $X^2$ represents oxygen or sulfur, and $R^9$ to $R^{15}$ individually represent any one of hydrogen, an aryl group having 6 to 15 carbon atoms, and an alkyl group having 1 to 6 carbon atoms.)

Another embodiment of the present invention is a light-emitting element having any of the above structures, in which $R^0$ is bonded to the position of α when a substituent $R^8$ represented by the general formula (g2) is bonded to the position of γ, or $R^0$ is bonded to the position of β when the substituent $R^8$ is bonded to the position of δ.

Another embodiment of the present invention is a light-emitting element including a layer containing an organic compound between a pair of electrodes, in which the layer containing an organic compound contains a carbazole derivative represented by the following general formula (G1).

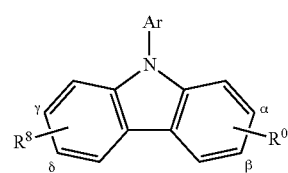

(G1)

In the formula, Ar represents an aryl group having 6 to 70 carbon atoms or a heteroaromatic group having 1 to 70 carbon atoms. In addition, $R^0$ represents a group represented by the following general formula (g3), and $R^8$ represents any one of hydrogen, an aryl group having 6 to 15 carbon atoms, an alkyl group having 1 to 6 carbon atoms, and a group represented by the following general formula (g4). Note that the substitution site of $R^0$ is a carbon atom represented by either α or β, and the substitution site of $R^8$ is a carbon atom represented by either γ or δ.

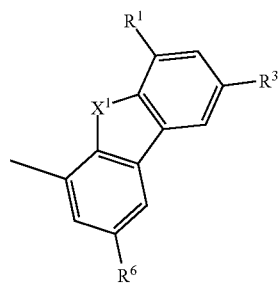

(g3)

In the formula, $X^1$ represents oxygen or sulfur, and $R^1$, $R^3$, and $R^6$ individually represent any one of hydrogen, an aryl group having 6 to 15 carbon atoms, and an alkyl group having 1 to 6 carbon atoms.

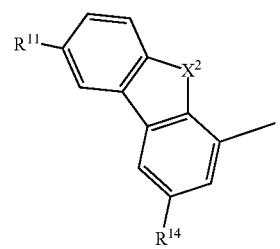

(g4)

Note that in the formula, $X^2$ represents oxygen or sulfur, and $R^9$, $R^{11}$, and $R^{14}$ individually represent any one of hydrogen, an aryl group having 6 to 15 carbon atoms, and an alkyl group having 1 to 6 carbon atoms.

Another embodiment of the present invention is a light-emitting element including a layer containing an organic compound between a pair of electrodes, in which the layer containing an organic compound contains a carbazole derivative represented by the following general formula (G1).

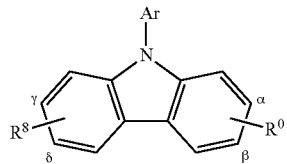
(G1)

In the formula, Ar represents an aryl group having 6 to 70 carbon atoms or a heteroaromatic group having 1 to 70 carbon atoms. Further, $R^0$ represents a group represented by the following general formula (g3), and $R^8$ represents any of hydrogen and a group represented by the following general formula (g4). Note that the substitution site of $R^0$ is a carbon atom represented by either α or β, and the substitution site of $R^8$ is a carbon atom represented by either γ or δ.

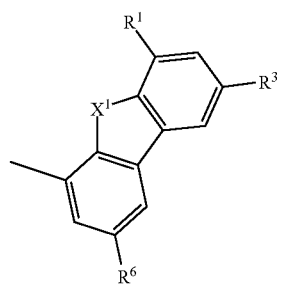
(g3)

In the formula, $X^1$ represents oxygen or sulfur, and $R^1$, $R^3$, and $R^6$ individually represent any one of hydrogen, an aryl group having 6 to 15 carbon atoms, and an alkyl group having 1 to 6 carbon atoms.

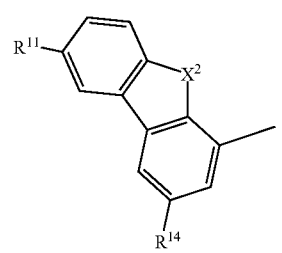
(g4)

Note that in the formula, $X^2$ represents oxygen or sulfur, and $R^9$, $R^{11}$, and $R^{14}$ individually represent any one of hydrogen, an aryl group having 6 to 15 carbon atoms, and an alkyl group having 1 to 6 carbon atoms.

Another embodiment of the present invention is a light-emitting element having any of the above structures, in which $R^0$ is bonded to the position of α when a substituent $R^8$ represented by the general formula (g4) is bonded to the position of γ, or $R^0$ is bonded to the position of β when the substituent $R^8$ is bonded to the position of δ.

Another embodiment of the present invention is a light-emitting element including a layer containing an organic compound between a pair of electrodes, in which the layer containing an organic compound contains a carbazole derivative represented by the following general formula (G3).

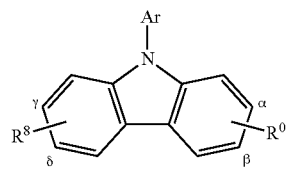
(G1)

In the formula, Ar represents an aryl group having 6 to 70 carbon atoms or a heteroaromatic group having 1 to 70 carbon atoms. Further, $R^0$ represents a group represented by the following general formula (g5), and $R^8$ represents any of hydrogen and a group represented by the following general formula (g6).

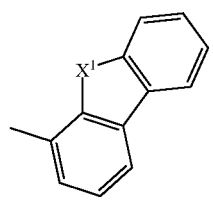
(g5)

In the formula, $X^1$ represents oxygen or sulfur.

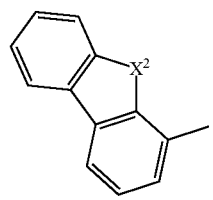
(g6)

In the formula, $X^2$ represents oxygen or sulfur.

Another embodiment of the present invention is a light-emitting element having any of the above structures, in which $R^0$ is bonded to the position of α when a substituent $R^8$ represented by the general formula (g6) is bonded to the position of γ, or $R^0$ is bonded to the position of β when the substituent $R^8$ is bonded to the position of δ.

Another embodiment of the present invention is a light-emitting element including a layer containing an organic compound between a pair of electrodes, in which the layer containing an organic compound contains a carbazole derivative represented by the following general formula (G4).

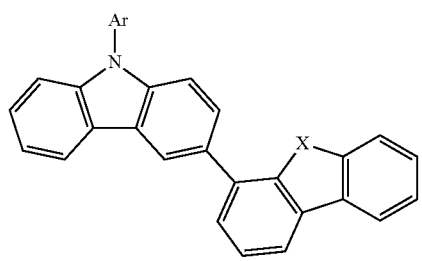
(G2)

Note that, in the formula, X represents oxygen or sulfur and Ar represents an aryl group having 6 to 70 carbon atoms or a heteroaromatic group having 1 to 70 carbon atoms.

Another embodiment of the present invention is a light-emitting element including a layer containing an organic compound between a pair of electrodes, in which the layer containing an organic compound contains a carbazole derivative represented by the following general formula (G5).

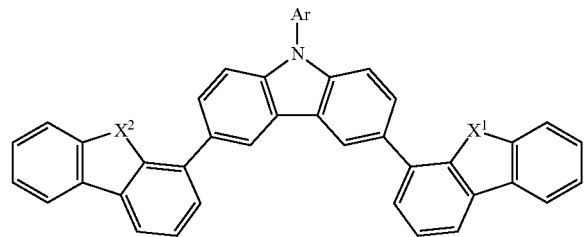

(G3)

Note that, in the formula, $X^1$ and $X^2$ individually represent oxygen or sulfur and Ar represents an aryl group having 6 to 70 carbon atoms or a heteroaromatic group having 1 to 70 carbon atoms.

Another embodiment of the present invention is a light-emitting element including a layer containing an organic compound between a pair of electrodes, in which the layer containing an organic compound contains a carbazole derivative represented by the following general formula (G6).

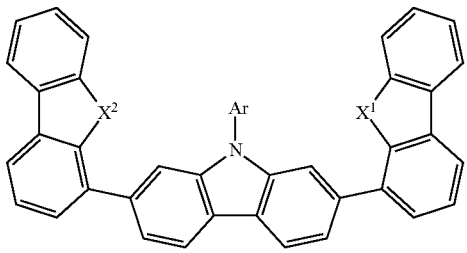

(G4)

Note that, in the formula, $X^1$ and $X^2$ individually represent oxygen or sulfur and Ar represents an aryl group having 6 to 70 carbon atoms or a heteroaromatic group having 1 to 70 carbon atoms.

A carbazole derivative having any of the above-described structures is a light-emitting element material having a wide energy gap, and can be used for a transport layer or as a host material in the light-emitting element. A light-emitting element using the carbazole derivative can be a light-emitting element having high emission efficiency. In addition, a light-emitting element using the carbazole derivative can be a light-emitting element driven with a low driving voltage. Further, a light-emitting element using the carbazole derivative can be a light-emitting element having a long lifetime.

BRIEF DESCRIPTION OF DRAWINGS

FIG. 154 shows an emission spectrum of the light-emitting element 19.

FIG. 155 shows normalized luminance versus time characteristics of the light-emitting element 19.

DETAILED DESCRIPTION OF THE INVENTION

Figure 1A:
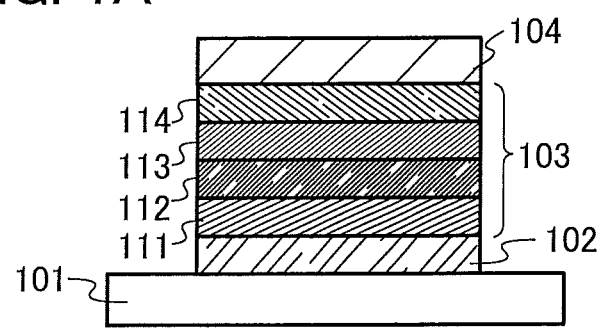
FIGS. 1A and 1B are conceptual diagrams of light-emitting elements.

Hereinafter, embodiments of the present invention are described. It is easily understood by those skilled in the art that modes and details disclosed herein can be modified in various ways without departing from the spirit and the scope of the present invention. Therefore, the present invention is not construed as being limited to description of the embodiments.

Embodiment 1

A light-emitting element in this embodiment is a light-emitting element including a substance having an N-carbazolyl group whose carbon atom at the 2- or 3-position of carbazole is bonded to the 4-position of a dibenzothiophene skeleton or the 4-position of a dibenzofuran skeleton. Note that the dibenzothiophene skeleton or dibenzofuran skeleton and the carbazole skeleton may or may not have a substituent.

In the case where the dibenzothiophene or dibenzofuran bonded to the N-carbazolyl group has a substituent, as the substituent, any of an aryl group having 6 to 15 carbon atoms and an alkyl group having 1 to 6 carbon atoms can be given.

In the case where the carbazole in the N-carbazolyl group has another substituent, the substitution site of the substituent is the 6- or 7-position of the carbazole, and the substituent can be any of an aryl group having 6 to 15 carbon atoms, an alkyl group having 1 to 6 carbon atoms, a dibenzothiophen-4-yl group, and a dibenzofuran-4-yl group. In the case where the dibenzothiophen-4-yl group or the dibenzofuran-4-yl group is selected as the substituent that is bonded to the 6- or 7-position of the carbazole, the dibenzothiophen-4-yl group or the dibenzofuran-4-yl group may further have a substituent that can be selected from an aryl group having 6 to 15 carbon atoms and an alkyl group having 1 to 6 carbon atoms. For easier synthesis, the dibenzothiophen-4-yl group or the dibenzofuran-4-yl group is preferably substituted at the 7-position of the carbazole when the dibenzothiophen-4-yl group or the dibenzofuran-4-yl group is selected as the substituent that is bonded to the 6- or 7-position of the carbazole and the dibenzothiophene or the dibenzofuran is bonded to the 2-position of the carbazole, and the dibenzothiophen-4-yl group or the dibenzofuran-4-yl group is preferably substituted at the 6-position of the carbazole when the dibenzothiophene or the dibenzofuran is bonded to the 3-position of the carbazole. Note that the dibenzothiophene or dibenzofuran which is bonded to the 2- or 3-position of the carbazole and the substituent bonded to the 6- or 7-position of the carbazole are preferably of the same type for easier synthesis.

By introduction of such an N-carbazolyl group, a hole-injection and hole-transport properties can be imparted to a substance into which the N-carbazolyl group is introduced without involving a reduction in band gap or triplet excitation energy: that is, a material for a light-emitting element having a wide band gap or high triplet excitation energy and an excellent carrier-transport property can be provided. Owing to the wide band gap or high triplet excitation energy, the loss of excitation energy is small in a light-emitting element including such a material, and accordingly, the light-emitting element can have high emission efficiency. In addition, a light-emitting element driven with a low driving voltage can be obtained owing to the excellent carrier mobility.

The above-described N-carbazolyl derivative has a rigid group such as dibenzothiophene or dibenzofuran, and thus the morphology is excellent and the film quality is stable. Further, the thermophysical property is also excellent. From the above, a light-emitting element that uses a substance having such an N-carbazolyl derivative can be a light-emitting element having a long lifetime.

Note that with the above-described N-carbazolyl group used by introduction into a substance that has an electron-transport property, a material having both the electron-transport property and a hole-transport property, i.e., a bipolar material, can be obtained. With the use of the bipolar material for a light-emitting layer in a light-emitting element, localization of an emission region can be prevented, concentration quenching or triplet-triplet annihilation (T-T annihilation) can be suppressed, and a light-emitting element having high emission efficiency can be obtained.

A substance having any of the above-described N-carbazolyl groups can also be represented by the following general formula (G1).

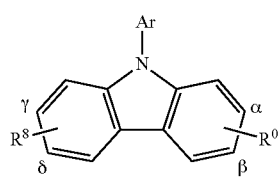

(G1)

In the formula (G1), Ar may be any group, but, in consideration of the use for the light-emitting element, it is preferably an aryl group having 6 to 70 carbon atoms or a heteroaromatic group having 1 to 70 carbon atoms. When Ar is such a group, the light-emitting element can be fabricated by use of a usual method, such as an evaporation method or a wet process, in the fabrication of the light-emitting element. Note that a structure in which the molecular weight of the carbazole derivative is 1200 or less is further preferred for easier evaporation.

$R^0$ represents a group represented by the following general formula (g1). Note that the substitution site of $R^0$ is a carbon atom represented by either α or β.

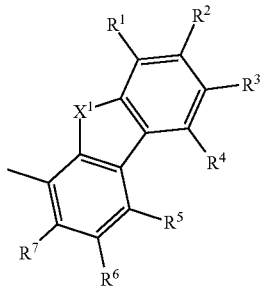

(g1)

In the formula (g1), $X^1$ represents oxygen or sulfur, and $R^1$ to $R^7$ individually represent any one of hydrogen, an alkyl group having 1 to 6 carbon atoms, and an aryl group having 6 to 15 carbon atoms.

A carbazole derivative having the above-described structure has a wide band gap or high triplet excitation energy, and a light-emitting element using the carbazole derivative can be a light-emitting element having high emission efficiency. Further, such a carbazole derivative has an excellent carrier-transport property, and a light-emitting element using the carbazole derivative can be a light-emitting element driven with a low driving voltage. In addition, the above-described carbazole derivative has a rigid group such as dibenzothiophene or dibenzofuran, and thus the morphology is excellent and the film quality is stable. Further, the thermophysical property is also excellent. From the above, the above carbazole derivative can realize a light-emitting element having a long lifetime.

Note that the carbazole derivative represented by the above general formula (G1) may have a substituent represented by $R^8$, as also illustrated in the above general formula (G1). $R^8$ represents any one of hydrogen, an alkyl group having 1 to 6 carbon atoms, an aryl group having 6 to 15 carbon atoms, and a group represented by the following general formula (g2). Note that the substitution site of $R^8$ is a carbon atom represented by either γ or δ.

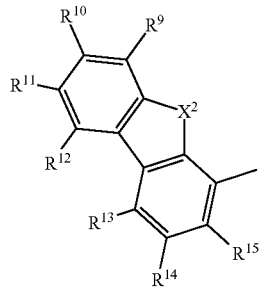

(g2)

In the formula (g2), $X^2$ represents oxygen or sulfur, and $R^9$ to $R^{15}$ individually represent any one of hydrogen, an aryl group having 6 to 15 carbon atoms, and an alkyl group having 1 to 6 carbon atoms.

In the case where $R^8$ is a substituent represented by the above general formula (g2), for easier synthesis, it is preferable that the substitution site of $R^8$ be γ when the substitution site of the substituent represented by the above general formula (g1) is α, or that the substitution site of $R^8$ be δ when the substitution site of the substituent represented by the above general formula (g1) is β. Further, in the case where $R^8$ is a substituent other than hydrogen, $R^8$ is preferably the same group as the above general formula (g1) for easier synthesis.

In the case where the group represented by the above general formula (g1) further includes a substituent, the substitution site of the substituent is preferably a site represented by $R^1$, $R^3$, or $R^6$ for a material cost reduction owing to availability of the material and to easiness of the synthesis. From the same point of view, it is further preferable that $R^1$ to $R^7$ be all hydrogen.

Also in the case where the group represented by (g2) is used as $R^8$, the substitution site of the substituent is preferably a site represented by $R^9$, $R^{11}$, or $R^{14}$, and further preferably, $R^9$ to $R^{15}$ are all hydrogen.

Examples of Ar in the formula are the groups represented by the following structural formulae (Ar-1) to (Ar-7), but no limitation is intended thereto as described above.

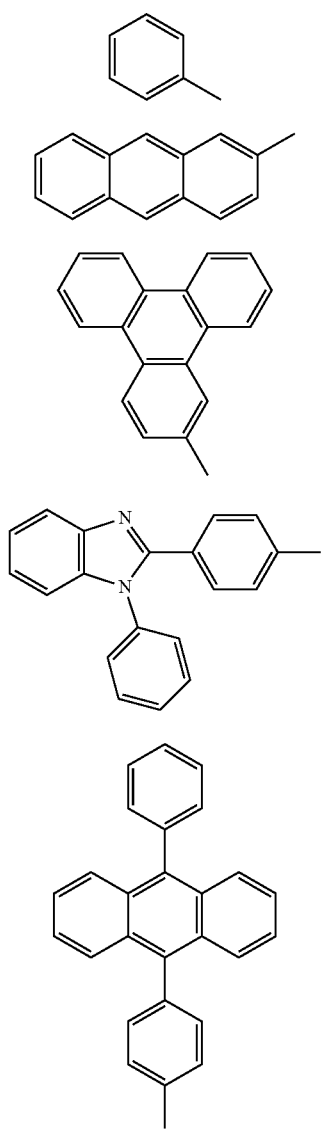

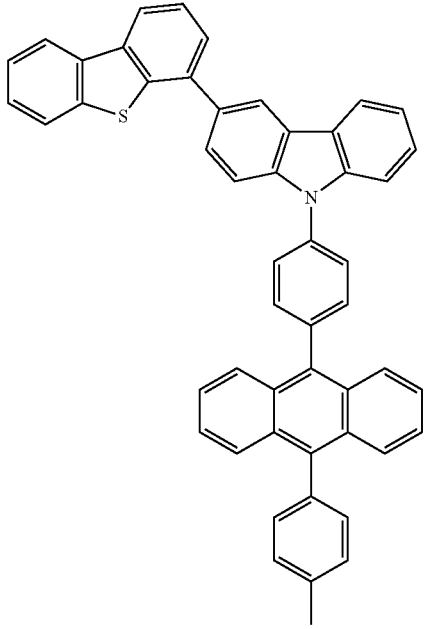

A carbazole derivative having the above-described structure has a wide band gap or high triplet excitation energy and enables efficient emission of even fluorescence or phosphorescence with high energy; therefore, such a carbazole derivative can be suitably used for a light-emitting element for emitting blue fluorescence or green phosphorescence, so that light-emitting element can be a light-emitting element having high emission efficiency. In addition, the carbazole derivative is suitable as a carrier-transport material as well owing to the excellent carrier-transport property, and thus a light-emitting element driven with a low driving voltage can also be provided. The carbazole derivative of this embodiment has a rigid group such as dibenzothiophene or dibenzofuran, and thus the morphology is excellent and the film quality is stable. Further, the thermophysical property is also excellent. From the above, a light-emitting element that uses such a carbazole derivative can be a light-emitting element having a long lifetime.

One embodiment of a light-emitting element using any of the carbazole derivatives is described with reference to FIG. 1A.

A light-emitting element of this embodiment includes a plurality of layers between a pair of electrodes. In this embodiment, the light-emitting element includes a first electrode 102, a second electrode 104, and an EL layer 103 provided between the first electrode 102 and the second electrode 104. In addition, in this embodiment, the first electrode 102 functions as an anode and the second electrode 104 functions as a cathode. In other words, when a voltage is applied between the first electrode 102 and the second electrode 104 such that the potential of the first electrode 102 is higher than that of the second electrode 104, light emission can be obtained.

The substrate 101 is used as a support of the light-emitting element. As the substrate 101, glass, plastic or the like can be used, for example. Note that a material other than glass or plastic can be used as far as it can function as a support of a light-emitting element.

The first electrode 102 is preferably formed using a metal, an alloy, a conductive compound, a mixture of them, or the like having a high work function (specifically, a work function of 4.0 eV or higher). Specifically, for example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like can be given. Films of these conductive metal oxides are usually formed by sputtering; however, a sol-gel method or the like may also be used. For example, indium zinc oxide (IZO) can be formed by a sputtering method using a target in which zinc oxide is added to indium oxide at 1 wt % to 20 wt %. Moreover, indium oxide containing tungsten oxide and zinc oxide (IWZO) can be formed by a sputtering method using a target in which tungsten oxide is added to indium oxide at 0.5 wt % to 5 wt % and zinc oxide is added to indium oxide at 0.1 wt % to 1 wt %. Besides, gold (Au), platinum (Pt), nickel (Ni), tungsten (W), chromium (Cr), molybdenum (Mo), iron (Fe), cobalt (Co), copper (Cu), palladium (Pd), graphene, nitride of a metal material (e.g., titanium nitride), and the like can be given.

There is no particular limitation on a stacked structure of the EL layer 103. The EL layer 103 may be formed as appropriate by combining a layer that contains a substance having a high electron-transport property, a layer that contains a substance having a high hole-transport property, a layer that contains a substance having a high electron-injection property, a layer that contains a substance having a high hole-injection property, a layer that contains a bipolar substance (a substance having a high electron- and hole-transport property), and the like. For example, the EL layer 103 can be formed as appropriate by combining a hole-injection layer, a hole-transport layer, a light-emitting layer, an electron-transport layer, an electron-injection layer, and the like. In this embodiment, described is a structure in which the EL layer 103 includes a hole-injection layer 111, a hole-transport layer 112, a light-emitting layer 113, and an electron-transport layer 114 stacked in that order over the first electrode 102. Specific materials to form each of the layers are given below.

The hole-injection layer 111 contains a substance having a high hole-injection property. Molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis[4-[bis(3-methylphenyl)amino]phenyl]-N,N'-diphenyl-[1,1'-biphenyl]-4,4'-diamine (abbreviation: DNTPD), a high molecular compound such as poly(ethylenedioxythiophene)/poly(styrenesulfonic acid) (PEDOT/PSS), or the like.

Alternatively, the hole-injection layer 111 can be formed using a composite material in which a substance having an acceptor property is mixed into a substance having a high hole-transport property. Note that, by using such a substance having an acceptor property into which a substance having a high hole-transport property is mixed, a material used to form an electrode may be selected regardless of its work function. In other words, besides a material having a high work function, a material having a low work function can also be used for the first electrode 102. As the acceptor substance, 7,7,8,8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air and its hygroscopic property is low and is easily treated.

As the substance having a high hole-transport property used for the composite material, any of various compounds such as an aromatic amine compound, a carbazole derivative, an aromatic hydrocarbon, and a high molecular compound (e.g., an oligomer, a dendrimer, or a polymer) can be used. The organic compound used for the composite material is preferably an organic compound having a high hole-transport property. Specifically, a substance having a hole mobility of $10^{-6}$ cm$^2$/Vs or higher is preferably used. Note that other than these substances, any substance that has a property of transporting more holes than electrons may be used. An organic compound which can be used as a substance having a high hole-transport property in the composite material is specifically given below.

Examples of the aromatic amine compound include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis[4-[bis(3-methylphenyl)amino]phenyl]-N,N'-diphenyl-[1,1'-biphenyl]-4,4'-diamine (abbreviation: DNTPD), 1,3,5-tris[N-(4-diphenylaminophenyl)-N-phenylamino]benzene (abbreviation: DPA3B), and the like.

Examples of the carbazole derivative which can be used for the composite material specifically include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Examples of the carbazole derivative which can be used for the composite material also include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon which can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,anthracene, tetracene, rubrene, perylene, and 2,5,8,11-tetra(tert-butyl)perylene. Besides, pentacene, coronene, or the like can also be used. Thus, an aromatic hydrocarbon having a hole mobility of $1 \times 10^{-6}$ cm$^2$/Vs or higher and having 14 to 42 carbon atoms is more preferably used.

The aromatic hydrocarbon which can be used for the composite material may have a vinyl skeleton. Examples of the aromatic hydrocarbon having a vinyl group include 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl) methacrylamide] (abbreviation: PTPDMA), or poly[N,N'-bis(4-butylphenyl)-N,N'-bis(phenyl)benzidine] (abbreviation: poly-TPD) can also be used.

Note that any of the carbazole derivatives represented by the general formula (G1) can also be used as the organic compound in the composite material. The carbazole derivative represented by the general formula (G1) is preferably contained in the hole-transport layer of the light-emitting element of this embodiment because in this case injection of holes from the hole-injection layer to the hole-transport layer can be smoothly performed, and thus, the driving voltage can be reduced. For the same reason, in the case where any of the carbazole derivatives represented by the general formula (G1) is used as an organic compound in the composite material, it is more preferable that the carbazole derivative and the substance used for the hole-transport layer be the same substance.

The hole-transport layer 112 contains a substance having a high hole-transport property. In this embodiment, any of the carbazole derivatives represented by the general formula (G1) is used for the hole-transport layer.

The light-emitting layer 113 contains a light-emitting substance. The light-emitting layer 113 may be formed using a film containing only a light-emitting substance or a film in which an emission center substance is dispersed in a host material.

There is no particular limitation on a material that can be used as the light-emitting substance or the emission center substance in the light-emitting layer 113, and light emitted from the material may be either fluorescence or phosphorescence. Examples of the light-emitting substance or the emission center substance include the following. Examples of a fluorescent substance include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N''-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM). Examples of a phosphorescent substance include bis[2-(3',5'-bistrifluoromethylphenyl)pyridinato-N,C$^{2'}$]iridium(III)picolinate (abbreviation: Ir(CF$_3$ppy)$_2$(pic)), bis[2-(4',6'-difluorophenyl)pyridinato-N,C$^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato)(monophenanthroline)terbium(III) (abbreviation: Tb(acac)$_3$(Phen)) bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)), bis[2-(2'-benzo[4,5-α]thienyl)pyridinato-N,C$^{3'}$]iridium (acetylacetonate) (abbreviation: Ir(btp)$_2$(acac)), bis(1-phenylisoquinolinato-N,C$^{2'}$)iridium(III)acetylacetonate (abbreviation: Ir(piq)$_2$(acac)), (acetylacetonato)bis[2,3-bis(4-fluorophenyl)quinoxalinato]iridium (III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphine platinum (II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

There is no particular limitation on a material that can be used as the above host material, and for example, a metal complex, a heterocyclic compound, or an aromatic amine compound can be used. Examples of the metal complex include tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), bis[2-(2-benzothiazolyl)phenolato]zinc(II) (abbreviation: ZnBTZ), and the like. Examples of the heterocyclic compounds include 2-(4-biphenylyl)-5(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), bathocuproine (abbreviation: BCP), 9-[4-(5-phenyl-1,3,4-oxadiazol-2-yl)phenyl]-9H-carbazole (abbreviation: CO11), and the like. Examples of the aromatic amine compound include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), and the like. In addition, a condensed polycyclic aromatic compound such as an anthracene derivative, a phenanthrene derivative, a pyrene derivative, a chrysene derivative, and a dibenzo[g,p]chrysene derivative can be used. Specific examples of the condensed polycyclic aromatic compound include 9,10-diphenylanthracene (abbreviation: DPAnth), N,N-diphenyl-9-[4-(10-phenyl-9-anthryl)phenyl]-9H-carbazol-3-amine (abbreviation: CzAlPA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N''',N''',N''''-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), and the like. One or more substances having a wider energy gap than the above-described emission center substance may be selected from these substances and known substances. Moreover, in the case where the emission center substance emits phosphorescence, a substance having higher triplet excitation energy (energy difference between a ground state and a triplet excitation state) than the emission center substance may be selected as the host material.

The light-emitting layer 113 may be a stack of two or more layers. For example, in the case where the light-emitting layer 113 is formed by stacking a first light-emitting layer and a second light-emitting layer in that order over the hole-transport layer, for example, the first light-emitting layer is formed using a substance having a hole-transport property as the host material and the second light-emitting layer is formed using a substance having an electron-transport property as the host material.

In the case where the light-emitting layer having the above-described structure is formed using a plurality of materials, the light-emitting layer can be formed using co-evaporation by a vacuum evaporation method; or an inkjet method, a spin coating method, a dip coating method, or the like as a method of mixing a solution.

The electron-transport layer 114 contains a substance having a high electron-transport property. For example, a layer containing a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), or the like can be used. Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here mainly have an electron mobility of $10^{-6}$ cm$^2$/Vs or higher. Note that other than these substances, any substance that has a property of transporting more electrons than holes may be used.

Furthermore, the electron-transport layer is not limited to a single layer, and two or more layers containing the above-described substances may be stacked.

Further, a layer that controls transport of electron carriers may be provided between the electron-transport layer and the light-emitting layer. Specifically, the layer that controls transport of electron carriers is a layer formed by adding a small amount of substance having a high electron-trapping property to the material having a high electron-transport property as described above, so that carrier balance can be adjusted. Such a structure is very effective in suppressing a problem (such as shortening of element lifetime) caused when electrons pass through the light-emitting layer.

In addition, an electron-injection layer may be provided between the electron-transport layer and the second electrode 104, in contact with the second electrode 104. As the electron-injection layer, an alkali metal, an alkaline earth metal, or a compound thereof such as lithium fluoride (LiF), cesium fluoride (CsF), or calcium fluoride (CaF$_2$) can be used. For example, a layer that is formed using a substance having an electron-transport property and contains an alkali metal, an alkaline earth metal, or a compound thereof, such as an Alq layer containing magnesium (Mg), may be used. A layer that is formed using a substance having an electron-transport property and contains an alkali metal or an alkaline earth metal is more preferably used as the electron-injection layer because electrons from the second electrode 104 is efficiently injected.

The second electrode 104 can be formed using a metal, an alloy, an electrically conductive compound, a mixture of them, or the like having a low work function (specifically, a work function of 3.8 eV or lower). Specific examples of such a cathode material include an element belonging to Group 1 or 2 in the periodic table, i.e., an alkali metal such as lithium (Li) or cesium (Cs), or an alkaline earth metal such as magnesium (Mg), calcium (Ca), or strontium (Sr); an alloy containing any of them (e.g., MgAg or AlLi); a rare earth metal such as europium (Eu) or ytterbium (Yb); an alloy containing such a rare earth metal; and the like. However, when the electron-injection layer is provided between the second electrode 104 and the electron-transport layer, the second electrode 104 can be formed using any of a variety of conductive materials such as Al, Ag, ITO, or indium oxide-tin oxide containing silicon or silicon oxide regardless of its work function. Films of these conductive materials can be formed by a sputtering method, an inkjet method, a spin coating method, or the like.

Further, any of a variety of methods can be employed for forming the EL layer 103 regardless of a dry process or a wet process. For example, a vacuum evaporation method, an inkjet method, a spin coating method or the like may be used. A different formation method may be employed for each electrode or each layer.

In addition, the electrode may be formed by a wet method using a sol-gel method, or by a wet method using paste of a metal material. Alternatively, the electrode may be formed by a dry method such as a sputtering method or a vacuum evaporation method.

In the light-emitting element having the above-described structure, a current flows due to a potential difference made between the first electrode 102 and the second electrode 104, a hole and an electron are recombined in the light-emitting layer 113, which contains a substance having a high light-emitting property, and light is emitted. That is, a light-emitting region is formed in the light-emitting layer 113.

The emitted light is extracted out through one or both of the first electrode 102 and the second electrode 104. Therefore, one or both of the first electrode 102 and the second electrode 104 are light-transmitting electrodes. In the case where only the first electrode 102 is a light-transmitting electrode, the emitted light is extracted from the substrate side through the first electrode 102. In the case where only the second electrode 104 is a light-transmitting electrode, the emitted light is extracted from the side opposite to the substrate side through the second electrode 104. In a case where each of the first electrode 102 and the second electrode 104 is a light-transmitting electrode, the emitted light is extracted from both the substrate side and the side opposite to the substrate through the first electrode 102 and the second electrode 104.

The structure of the layers provided between the first electrode 102 and the second electrode 104 is not limited to the above-described structure. However, a structure in which a light-emitting region for recombination of holes and electrons is positioned away from the first electrode 102 and the second electrode 104 so as to prevent quenching due to the proximity of the light-emitting region and a metal used for electrodes and carrier-injection layers is preferable. The order of stacking the layers is not limited thereto, and the following order, which is opposite to that in FIG. 1A, may be employed: the second electrode, the electron-injection layer, the electron-transport layer, the light-emitting layer, the hole-transport layer, the hole-injection layer, and the first electrode over the substrate.

In addition, as for the hole-transport layer or the electron-transport layer in direct contact with the light-emitting layer, particularly a carrier-transport layer in contact with a side closer to a light-emitting region in the light-emitting layer 113, in order to suppress energy transfer from an exciton which is generated in the light-emitting layer, it is preferable that the energy gap thereof be wider than the energy gap of the light-emitting substance contained in the light-emitting layer or the energy gap of the emission center substance contained in the light-emitting layer.

Since the light-emitting element of this embodiment uses any of the carbazole derivatives represented by the general formula (G1), which has a wide energy gap, for the hole-transport layer, the light-emitting element can emit light efficiently even when the light-emitting substance or the emission center substance is a substance that has a wide energy gap and emits blue fluorescence or a substance that has high triplet excitation energy (energy difference between a ground state and a triplet excited state) and emits green phosphorescence; thus, a light-emitting element with high emission efficiency can be provided. Accordingly, a light-emitting element having lower power consumption can be provided. In addition, a light-emitting element that emits light with high color purity can be provided. Further, any of the carbazole derivatives represented by the general formula (G1) is excellent in a carrier-transport property; therefore, a light-emitting element driven with a low driving voltage can be provided.

In this embodiment, the light-emitting element is formed over a substrate formed of glass, plastic, or the like. By fabricating a plurality of such light-emitting elements over one substrate, a passive matrix light-emitting device can be fabricated. In addition, for example, a thin film transistor (TFT) may be formed over a substrate formed of glass, plastic, or the like, and a light-emitting element may be fabricated over an electrode electrically connected to the TFT. In this way, an active matrix light-emitting device in which the TFT controls the drive of the light-emitting element can be fabricated. Note that there is no particular limitation on the structure of the TFT. Either a staggered TFT or an inverted staggered TFT may be employed. In addition, crystallinity of a semiconductor used for the TFT is not particularly limited either; an amorphous semiconductor or a crystalline semiconductor may be used. In addition, a driver circuit formed over a TFT substrate may be constructed from both n-channel and p-channel TFTs or from one of n-channel and p-channel TFTs.

Embodiment 2

In this embodiment, a light-emitting element having a different structure from that described in Embodiment 1 is described.

Described is a structure in which light is emitted from an emission center substance having a light-emitting property by forming a light-emitting layer 113 described in Embodiment 1 in such a way that the emission center substance having a light-emitting property is dispersed into any of the carbazole derivatives represented by the general formula (G1), i.e., a structure in which the carbazole derivative represented by the general formula (G1) is used as a host material of the light-emitting layer 113.

Each carbazole derivative represented by the general formula (G1) has a wide energy gap or high triplet excitation energy (energy difference between a ground state and a triplet excited state), and thus can make another light-emitting substance excited and emit light effectively; therefore, any of the carbazole derivatives represented by the general formula (G1) can be suitably used as the host material and light emission that originates from the light-emitting substance can be obtained. Thus, a light-emitting element having high emission efficiency with small energy loss can be provided. In addition, a light-emitting element that can easily provide light emission of a desired color that originates from the emission center substance can be provided. Accordingly, a light-emitting element capable of easily emitting light with high color purity can be provided. Further, any of the carbazole derivatives represented by the general formula (G1) is excellent in a carrier-transport property; therefore, a light-emitting element driven with a low driving voltage can also be provided.

Here, there is no particular limitation on the emission center substance dispersed into any of the carbazole derivatives represented by the general formula (G1), and any of various materials can be used. Specifically, it is possible to use 4-(dicyanomethylene)-2-methyl-6-(p-dimethylaminostyryl)-4H-pyran (abbreviation: DCM1), 4-(dicyanomethylene)-2-methyl-6-(julolidin-4-yl-vinyl)-4H-pyran (abbreviation: DCM2), N,N-dimethylquinacridone (abbreviation: DMQd), 9,10-diphenylanthracene (abbreviation: DPA), 5,12-diphenyltetracene (abbreviation: DPT), coumarin 6, perylene, rubrene, N,N'-bis[4-(9-phenyl-9H-fluoren-9-yl)phenyl]-N,N'-diphenylpyrene-1,6-diamine (abbreviation: 1,6FLPA-Prn), or another known fluorescent substance that emits fluorescence. Alternatively, it is possible to use bis(2-phenylbenzothiazolato-N,$C^{2'}$)iridium(III)acetylacetonate (abbreviation: Ir(bt)$_2$(acac)), tris(2-phenylquinolinato-N,$C^{2'}$) iridium(III) (abbreviation: Ir(pq)$_3$), bis(2-phenylquinolinato-N,$C^{2'}$)iridium(III)(acetylacetonate) (abbreviation: Ir(pq)$_2$ (acac)), bis[2-(2'-benzo[4,5-α]thienyl)pyridinato-N,$C^{3'}$] iridium(III)acetylacetonate (abbreviation: Ir(btp)$_2$(acac)), bis (1-phenylisoquinolinato-N,$C^{2'}$)iridium(III)acetylacetonate (abbreviation: Ir(piq)$_2$(acac)), (acetylacetonato)bis[2,3-bis (4-fluorophenyl)quinoxalinato]iridium(III) (abbreviation: Ir(Fdpq)$_2$(acac)), tris(2-phenylpyridinato-N,$C^{2'}$)iridium(III) (abbreviation: Ir(ppy)$_3$), or 2,3,7,8,12,13,17,18-octaethyl-21H,23H-porphine platinum(II) (abbreviation: PtOEP), or another known phosphorescent substance that emits phosphorescence. In the case where any of the carbazole derivatives represented by the general formula (G1) has a light-emitting property, the carbazole derivative can be used as the emission center substance. In that case, the carbazole derivative used as the host material and the carbazole derivative used as the emission center substance are preferably different from each other. Among the above-described substances or known substances, a substance that has a narrower band gap or lower triplet excitation energy than any of the carbazole derivatives represented by the general formula (G1), which is used as the host material, is selected as the emission center substance.

Further, another organic compound may be dispersed at the same time in the light-emitting layer, in addition to any of the carbazole derivatives represented by the general formula (G1) and the emission center substance dispersed into the carbazole derivative. In this case, a substance that improves carrier balance of the light-emitting layer is preferably used, such as the above-described substances having a high electron-transport property.

The carbazole derivative represented by the following general formula (G1) described in Embodiment 1 becomes a bipolar substance depending on the structure of Ar in the formula. By use of the bipolar carbazole derivative represented by the general formula (G1) as a host material for a light-emitting element, a light-emitting region can be dispersed, and a reduction in emission efficiency due to concentration quenching or T-T annihilation can be suppressed; thus, a light-emitting element having higher emission efficiency can be provided. Further, the light-emitting layer becomes a bipolar layer, so that the driving voltage can be more easily reduced in the light-emitting element than in a light-emitting element including a monopolar light-emitting layer.

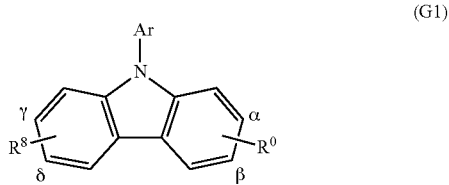

(G1)

In the formula, Ar represents an aryl group having 6 to 70 carbon atoms or a heteroaromatic group having 1 to 70 carbon atoms. In addition, $R^0$ represents a group represented by the following general formula (g1), and $R^8$ represents any one of hydrogen, an alkyl group having 1 to 6 carbon atoms, an aryl group having 6 to 15 carbon atoms, and a group represented by the following general formula (g2). Note that the substitution site of $R^0$ is a carbon atom represented by either α or β, and the substitution site of $R^8$ is a carbon atom represented by either γ or δ.

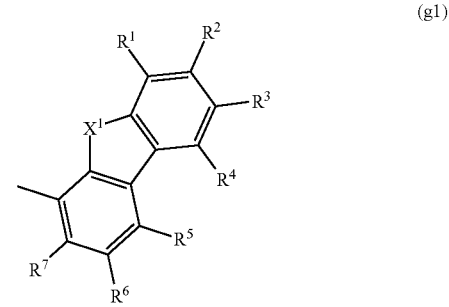

(g1)

(In the formula, $X^1$ represents oxygen or sulfur, and $R^1$ to $R^7$ individually represent any one of hydrogen, an alkyl group having 1 to 6 carbon atoms, and an aryl group having 6 to 15 carbon atoms.)

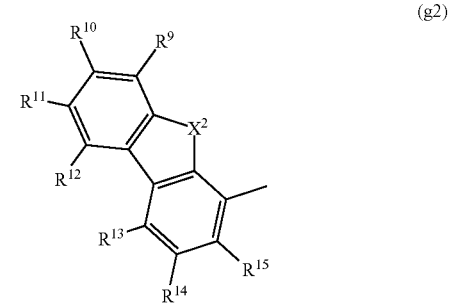

(g2)

(In the formula, $X^2$ represents oxygen or sulfur, and $R^9$ to $R^{15}$ individually represent any one of hydrogen, an aryl group having 6 to 15 carbon atoms, and an alkyl group having 1 to 6 carbon atoms.)

In order that any of the carbazole derivatives represented by the above general formula (G1) be bipolar, an aryl group having a π-electron deficient heteroaromatic ring group or a heteroaromatic ring group, for example, should be applied to a substituent represented by Ar above; that is, Ar should contain a skeleton having an electron-transport property. Specific examples thereof are an aryl group having a benzimidazolyl group, a heteroaromatic ring group having a benzimidazolyl group, an aryl group having a benzoxazolyl group, a heteroaromatic ring group having a benzoxazolyl group, an aryl group having an oxadiazolyl group, a heteroaromatic ring group having an oxadiazolyl group, and the like.

Note that, regarding the layers other than the light-emitting layer 113, the structure described in Embodiment 1 can be applied as appropriate. Further, the hole-transport layer 112 can be formed using any of the materials given as the substances having a high hole-transport property which can be used in a composite material in Embodiment 1. Besides, the hole-transport layer 112 can be formed using a substance having a high hole-transport property such as the following aromatic amine compounds: 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino) triphenylamine (abbreviation: TDATA), 4,4',4''-tris[N-(3-methylphenyl)-N-phenylamino]triphenylamine (abbreviation: MTDATA), or 4,4'-bis[N-(spiro-9,9'-bifluoren-2-yl)-N-phenylamino]biphenyl (abbreviation: BSPB); or the like. Needless to say, any of the carbazole derivatives represented by the general formula (G1) can also be used. The substances mentioned here mainly have a hole mobility of $10^{-6}$ cm$^2$/Vs or higher. Note that other than these substances, any substance that has a property of transporting more holes than electrons may be used. Note that the layer containing a substance having a high hole-transport property is not limited to a single layer, and two or more layers containing the above-described substances may be stacked.

Alternatively, a high molecular compound such as poly(N-vinylcarbazole) (abbreviation: PVK) or poly(4-vinyltriphenylamine) (abbreviation: PVTPA) can be used for the hole-transport layer 112.

Embodiment 3

In this embodiment, an embodiment of a light-emitting element with a structure in which a plurality of light-emitting units are stacked (hereinafter this type of light-emitting element is also referred to as a stacked element) is described with reference to FIG. 1B. This light-emitting element includes a plurality of light-emitting units between a first electrode and a second electrode. Each light-emitting unit can have a structure similar to that of an EL layer 103 described in Embodiment 1 or 2. That is, a light-emitting element described in Embodiment 1 or 2 includes a single light-emitting unit; the light-emitting element in this embodiment includes a plurality of light-emitting units.

Figure 1B:
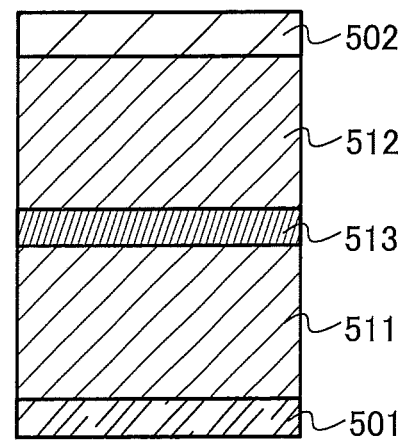

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond to a first electrode 102 and a second electrode 104 in Embodiment 1, respectively, and electrodes similar to those described in Embodiment 1 can be applied to the first electrode 501 and the second electrode 502. Further, the first light-emitting unit 511 and the second light-emitting unit 512 may have the same structure or different structures.

The charge generation layer 513 contains a composite material of an organic compound and a metal oxide. This composite material of an organic compound and a metal oxide is described in Embodiment 1 and contains an organic compound and a metal oxide such as vanadium oxide, molybdenum oxide, or tungsten oxide. As the organic compound, any of various compounds such as an aromatic amine compound, a carbazole derivative, an aromatic hydrocarbon, and a high molecular compound (e.g., oligomer, dendrimer, or polymer) can be used. As the organic compound, an organic compound having a hole-transport property and a hole mobility of $10^{-6}$ cm$^2$/Vs or higher is preferably used. Note that other than these substances, any substance that has a property of transporting more holes than electrons may be used. The composite of an organic compound and a metal oxide is excellent in carrier-injection property and carrier-transport property, and hence, low-voltage driving and low-current driving can be achieved.

The charge generation layer 513 may be formed by combining a layer containing the composite material of an organic compound and metal oxide with a layer containing another material. For example, the layer containing the composite material of an organic compound and a metal oxide may be combined with a layer containing a compound of a substance selected from substances having an electron-donating property and a compound having a high electron-transport property. Moreover, the layer containing the composite material of an organic compound and a metal oxide may be combined with a transparent conductive film.

The charge generation layer 513 interposed between the first light-emitting unit 511 and the second light-emitting unit 512 may have any structure as far as electrons can be injected to a light-emitting unit on one side and holes can be injected to a light-emitting unit on the other side when a voltage is applied between the first electrode 501 and the second electrode 502. For example, in FIG. 1B, any layer can be employed as the charge generation layer 513 as far as the layer injects electrons into the first light-emitting unit 511 and holes into the second light-emitting unit 512 when a voltage is applied such that the potential of the first electrode is higher than that of the second electrode.

Although the light-emitting element having two light-emitting units is described in this embodiment, the present invention can be similarly applied to a light-emitting element in which three or more light-emitting units are stacked. When the charge generation layer is provided between the pair of electrodes so as to partition the plural light-emitting units like the light-emitting element of this embodiment, the element can have a long lifetime with high luminance while keeping low current density. When the light-emitting element is applied for illumination, voltage drop due to resistance of an electrode material can be reduced, thereby achieving homogeneous light emission in a large area. Moreover, the light-emitting device can be driven with a low driving voltage and consume less power.

By making emission colors of the light-emitting units different from each other, light of a desired color can be obtained from the light-emitting element as a whole. For example, in a light-emitting element including two light-emitting units, the emission colors of the first light-emitting unit and the second light-emitting unit are made complementary, so that the light-emitting element which emits white light as the whole element can be obtained. Note that the word "complementary" means color relationship in which an achromatic color is obtained when colors are mixed. In other words, when light of complementary colors is mixed, white light emission can be obtained. The same can be applied to a light-emitting element including three light-emitting units. For example, when the first light-emitting unit emits red light, the second light-emitting unit emits green light, and the third light-emitting unit emits blue light, white light can be emitted from the light-emitting element as a whole.

Since the light-emitting element of this embodiment contains any of the carbazole derivatives represented by the general formula (G1), a light-emitting element having high emission efficiency can be provided. In addition, a light-emitting element driven with a low driving voltage can be provided. Further, a light-emitting element having a long lifetime can be provided. In addition, the light-emitting unit containing the carbazole derivative can provide light that originates from the emission center substance with high color purity; therefore, it is easy to adjust the color of light emitted from the light-emitting element as a whole.

Note that this embodiment can be combined with any of the other embodiments as appropriate.

Embodiment 4

Next, in this embodiment, a method of synthesizing the carbazole derivative represented by the following general formula (G1) is described.

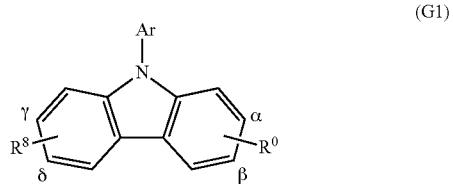
(G1)

In the formula, Ar represents an aryl group having 6 to 70 carbon atoms or a heteroaromatic group having 1 to 70 carbon atoms. In addition, $R^0$ is a substituent represented by the following general formula (g1) which is bonded to a carbon atom represented by either α or β. $R^8$ represents any one of hydrogen, an alkyl group having 1 to 6 carbon atoms, an aryl group having 6 to 15 carbon atoms, and a group represented by the following general formula (g2), which is bonded to a carbon atom represented by either γ or δ.

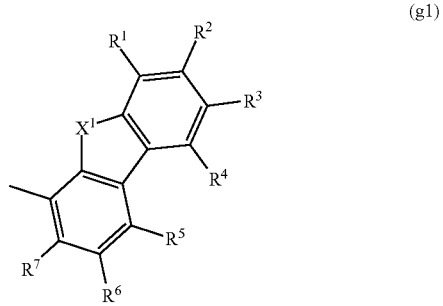
(g1)

In the formula, $X^1$ represents oxygen or sulfur, and $R^1$ to $R^7$ individually represent any one of hydrogen, an alkyl group having 1 to 6 carbon atoms, and an aryl group having 6 to 15 carbon atoms.

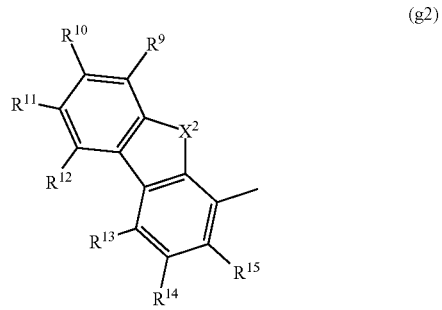
(g2)

In the formula (g2), $X^2$ represents oxygen or sulfur, and $R^9$ to $R^{15}$ individually represent any one of hydrogen, an aryl group having 6 to 15 carbon atoms, and an alkyl group having 1 to 6 carbon atoms.

Here, and $R^0$ in the formula is a substituent represented by the above general formula (g1); therefore, the above general formula (G1) can also be represented by the following general formula (G1'). In the general formula (G1'), the substitution site of the substituent corresponding to the above general formula (g1) is a carbon atom represented by either α or β in the general formula (G1). Hereinafter, the substitution sites of substituents or elements represented by Ar, $R^1$ to $R^{16}$, $X^1$, and $X^2$, and substituents corresponding to $R^8$ and the above general formula (g1) are the same as those in the above explanation unless otherwise explained.

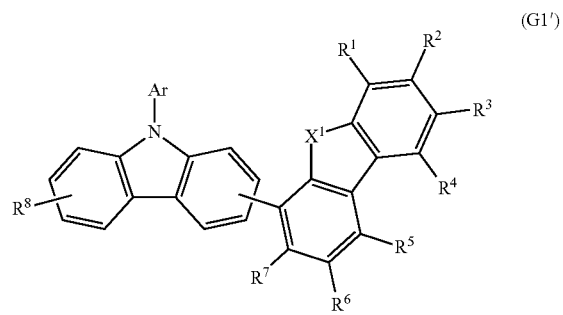
(G1')

Instead of the above general formula (G1), the above general formula (G1') is used to explain a synthesis method of thereof in this embodiment.

<Synthesis Method 1>

In Synthesis Method 1, a method of synthesizing a substance represented by the general formula (G1') in which $R^8$ is hydrogen (the following general formula (G1'-1)) is described.

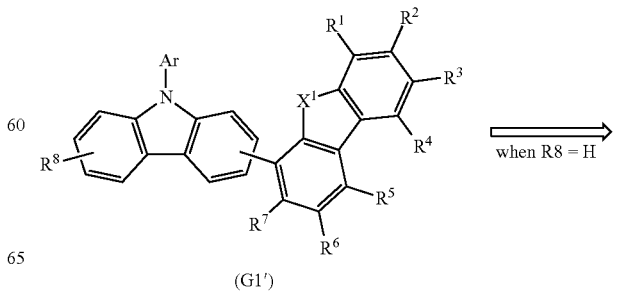
when R8 = H
(G1')

First, a compound having a halogen group or a triflate group at the 2- or 3-position of 9H-carbazole (a compound 1) is coupled with a boronic acid compound of dibenzothiophene or a boronic acid compound of dibenzofuran (a compound 2), so that a 9H-carbazole derivative having a structure in which the 2- or 3-position of 9H-carbazole is bonded to the 4-position of dibenzothiophene or the 4-position of dibenzofuran (a compound 3) can be obtained (a reaction formula (A-1)).

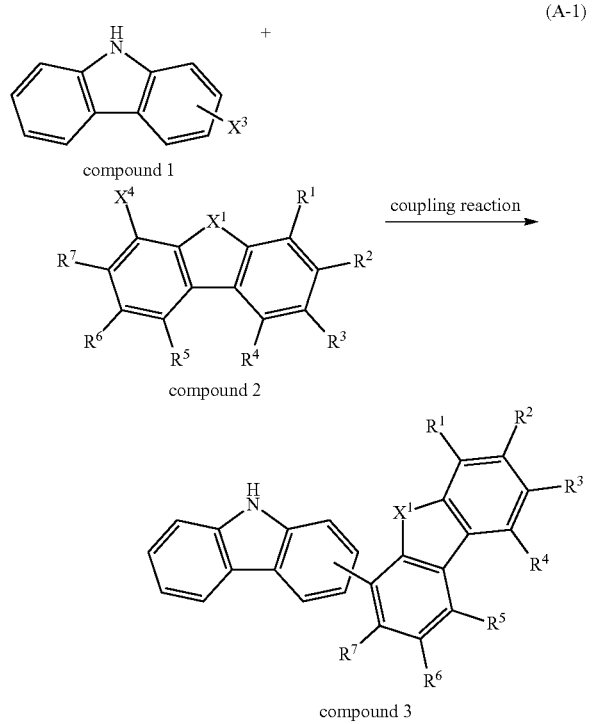

In the reaction formula (A-1), $X^1$ represents oxygen or sulfur, $X^3$ represents a halogen group, a triflate group, or the like, $X^4$ represents a boronic acid (the boronic acid may be protected by ethylene glycol or the like), $R^1$ to $R^7$ individually represent any one of hydrogen, an alkyl group having 1 to 6 carbon atoms, and an aryl group having 6 to 15 carbon atoms. As the coupling reaction in the reaction formula (A-1), a Suzuki-Miyaura coupling reaction using a palladium catalyst or the like can be given.

Next, the obtained 9H-carbazole derivative (the compound 3) is coupled with a halogenated aryl (a compound 4), so that a compound (G1-1), which is the object of the synthesis, can be obtained (a reaction formula (A-2)).

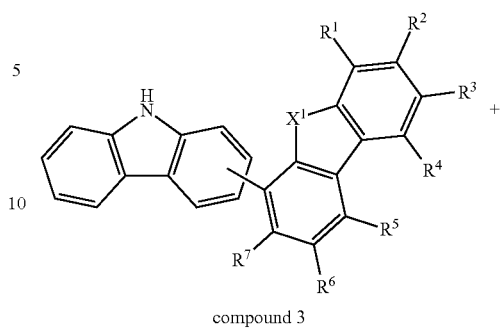

In the reaction formula (A-2), $X^1$ represents oxygen or sulfur, $X^5$ represents a halogen group or the like, $R^1$ to $R^7$ individually represent any one of hydrogen, an alkyl group having 1 to 6 carbon atoms, and an aryl group having 6 to 15 carbon atoms, and Ar represents an aryl group having 6 to 70 carbon atoms or a heteroaromatic group having 1 to 70 carbon atoms. As the coupling reaction in the reaction formula (A-2), a Buchwald-Hartwig reaction using a palladium catalyst, an Ullmann reaction using copper or a copper compound, or the like can be given.

<Synthesis Method 2>

In Synthesis Method 2, a method of synthesizing a substance in which $R^8$ in the above general formula (G1') is a substituent represented by the above general formula (g2) (the following general formula (G1'-2)) is described.

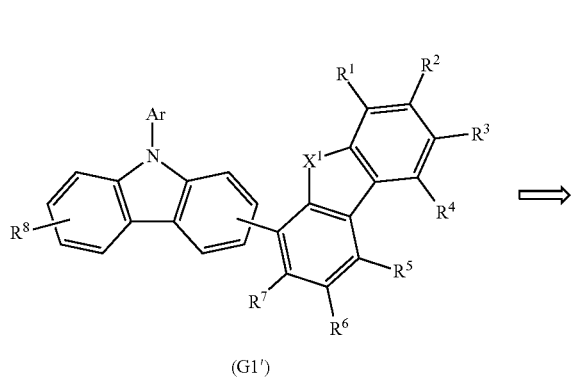

-continued

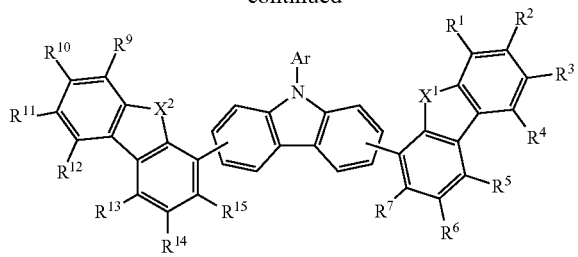

(G1'-2)

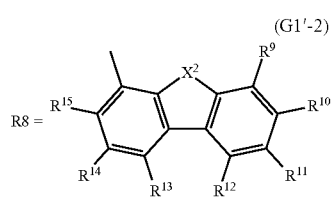

First, a carbazole derivative having halogen groups at the 2- and 7-positions of, the 3- and 6-positions of, or the 2- and 6-positions of 9H-carbazole (a compound 5) is coupled with a boronic acid compound of dibenzothiophene or a boronic acid compound of dibenzofuran (a compound 2), so that a carbazole derivative (a compound 6) can be obtained (a reaction formula (B-1)).

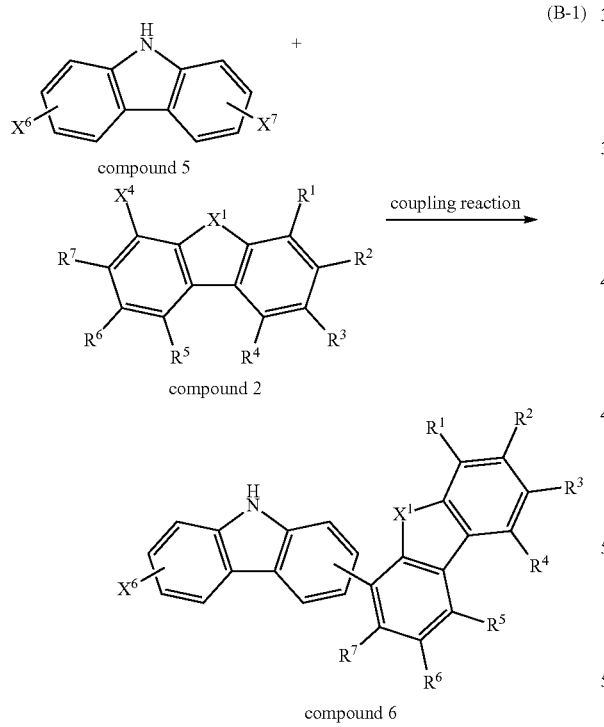

In the reaction formula (B-1), $X^6$ and $X^7$ individually represent a halogen group or the like, $X^4$ represents a boronic acid (the boronic acid may be protected by ethylene glycol or the like), $R^1$ to $R^7$ individually represent any of hydrogen, an alkyl group having 1 to 6 carbon atoms, and an aryl group having 6 to 15 carbon atoms. $X^6$ and $X^7$ may the same or different. As the coupling reaction in the reaction formula (B-1), a Suzuki-Miyaura coupling reaction using a palladium catalyst or the like can be given.

Next, the monohalide of 9H-carbazole (the compound 6) is coupled with a boronic acid compound of dibenzothiophene or a boronic acid compound of dibenzofuran (a compound 7), so that a carbazole derivative (a compound 8) can be obtained (a reaction formula (B-2)).

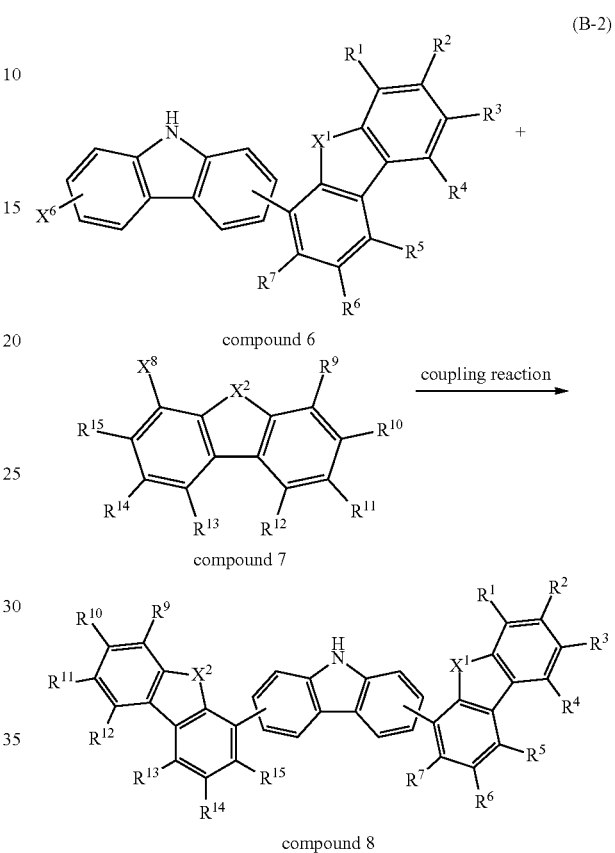

In the reaction formula (B-2), $X^6$ represents a halogen group or the like, $X^4$ represents a boronic acid (the boronic acid may be protected by ethylene glycol or the like), $R^1$ to $R^7$ individually represent any of hydrogen, an alkyl group having 1 to 6 carbon atoms, and an aryl group having 6 to 15 carbon atoms. As the coupling reaction in the reaction formula (B-1), a Suzuki-Miyaura coupling reaction using a palladium catalyst or the like can be given.

Lastly, the 9H-carbazole derivative (the compound 8) is coupled with a halogenated aryl (a compound 4), so that a compound (G1-2), which is the object of the synthesis, can be obtained (a reaction formula (B-3)).

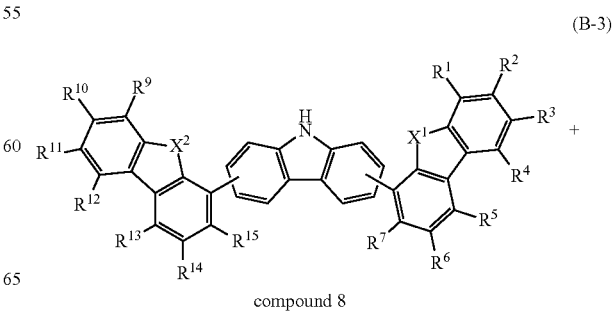

-continued

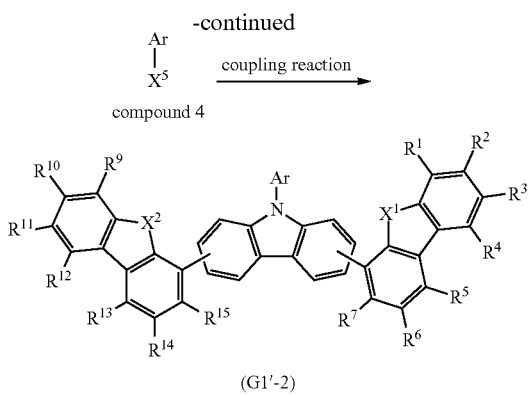

(G1'-2)

In the reaction formula (B-3), $X^1$ represents oxygen or sulfur, $X^5$ represents a halogen group, $R^1$ to $R^7$ individually represent any one of hydrogen, an alkyl group having 1 to 6 carbon atoms, and an aryl group having 6 to 15 carbon atoms, and Ar represents an aryl group having 6 to 70 carbon atoms or a heteroaromatic group having 1 to 70 carbon atoms. As the coupling reaction in the reaction formula (B-3), a Buchwald-Hartwig reaction using a palladium catalyst, an Ullmann reaction using copper or a copper compound, or the like can be given. With the above reaction formulae (B-1) to (B-3), a method in which a dibenzothiophene skeleton or a dibenzofuran skeleton is coupled by one equivalent is described. However, when the compounds 2 and 7 have the same structure, two equivalents of the dibenzothiophene derivative or dibenzofuran derivative may be coupled with the 9H-carbazole derivative at the same time.

<Synthesis Method 3>

In Synthesis Method 3, a method of synthesizing a substance in which $R^8$ in the above general formula (G1') is an aryl group having 6 to 15 carbon atoms or an alkyl group having 1 to 6 carbon atoms (the following general formula (G1'-3)) is described.

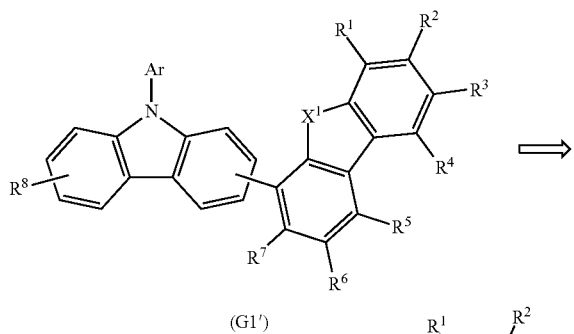

(G1')

⇒

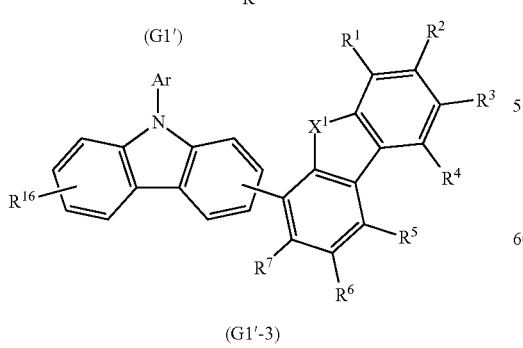

(G1'-3)

R8 = aryl group or alkyl group

First, a 9H-carbazole derivative in which the 2- or 3-position of 9H-carbazole is substituted with an alkyl group or an aryl group and the 3- or 6-position of 9H-carbazole is substituted with a halogen group (a compound 9) is coupled with a boronic acid compound of dibenzothiophene or a boronic acid compound of dibenzofuran (a compound 2), so that a 9H-carbazole derivative (a compound 10) can be obtained (a reaction formula (C-1)).

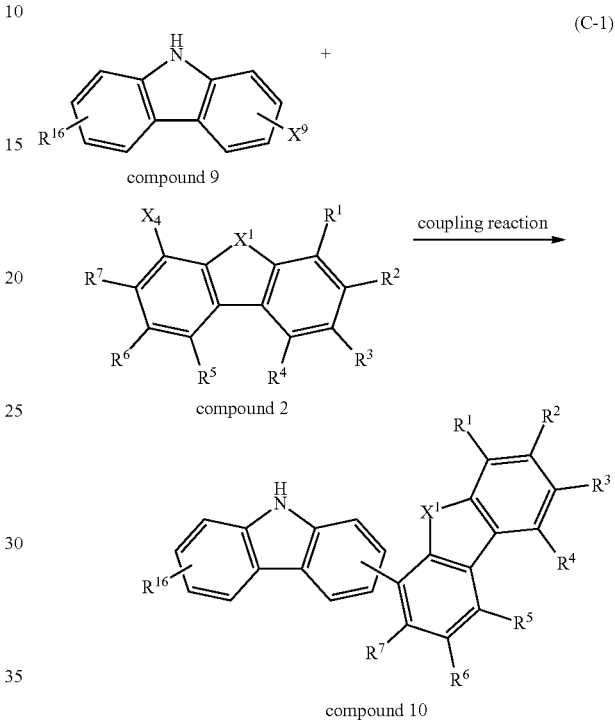

(C-1)

In the reaction formula (C-1), $X^1$ represents oxygen or sulfur, $X^9$ represents a halogen group, a triflate group, or the like, $R^1$ to $R^7$ individually represent any one of hydrogen, an alkyl group having 1 to 6 carbon atoms, and an aryl group having 6 to 15 carbon atoms, and $R^{16}$ represents any of an alkyl group having 1 to 6 carbon atoms and an aryl group having 6 to 15 carbon atoms. As the coupling reaction in the reaction formula (C-1), a Suzuki-Miyaura coupling reaction using a palladium catalyst or the like can be given.

Next, the 9H-carbazole derivative (the compound 10) is coupled with a halogenated aryl (a compound 4), so that a compound (G1'-3), which is the object of the synthesis, can be obtained (a reaction formula (C-2)).

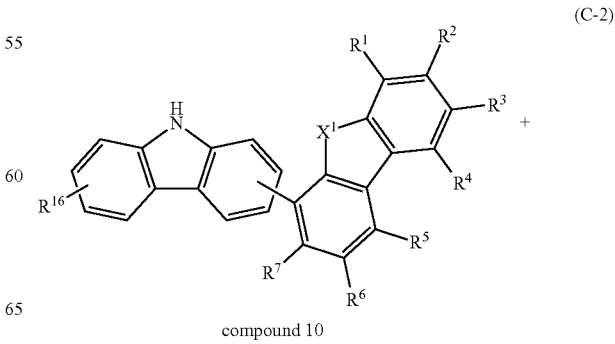

(C-2)

compound 10

-continued

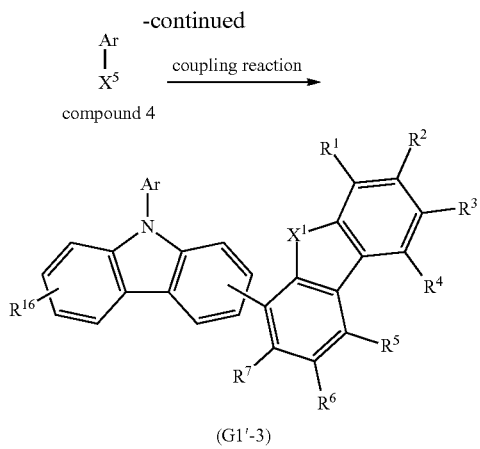

(G1'-3)

In the reaction formula (C-2), $X^1$ represents oxygen or sulfur, $X^5$ represents a halogen group, $R^1$ to $R^7$ individually represent any one of hydrogen, an alkyl group having 1 to 6 carbon atoms, and an aryl group having 6 to 15 carbon atoms, $R^{16}$ represents any of an alkyl group having 1 to 6 carbon atoms and an aryl group having 6 to 15 carbon atoms, and Ar represents an aryl group having 6 to 70 carbon atoms or a heteroaromatic group having 1 to 70 carbon atoms.

Embodiment 5

In this embodiment, a light-emitting device including a light-emitting element containing any of the carbazole derivatives represented by the general formula (G1) is described.

Figure 2A:
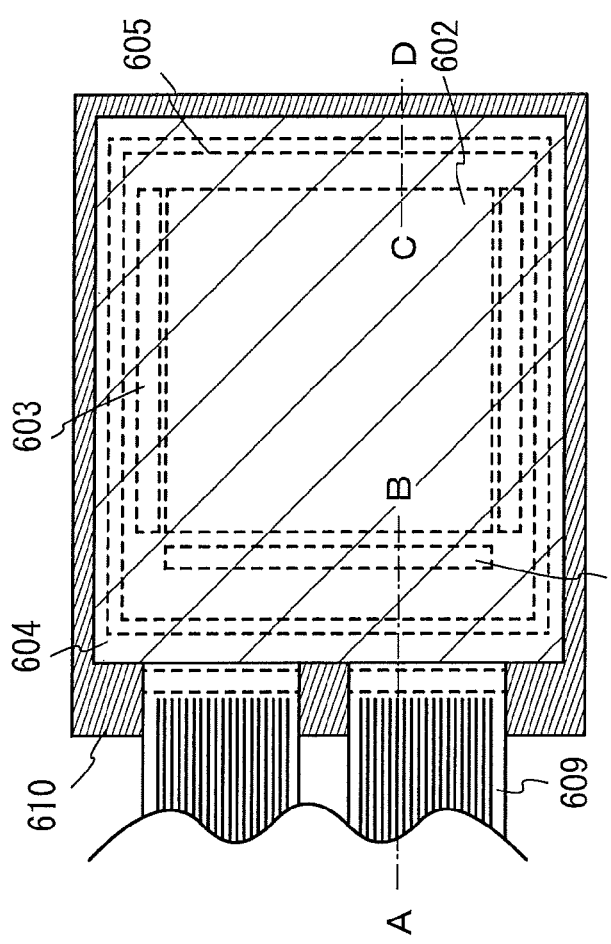
FIGS. 2A and 2B are conceptual diagrams of an active matrix light-emitting device.
Figure 2B:
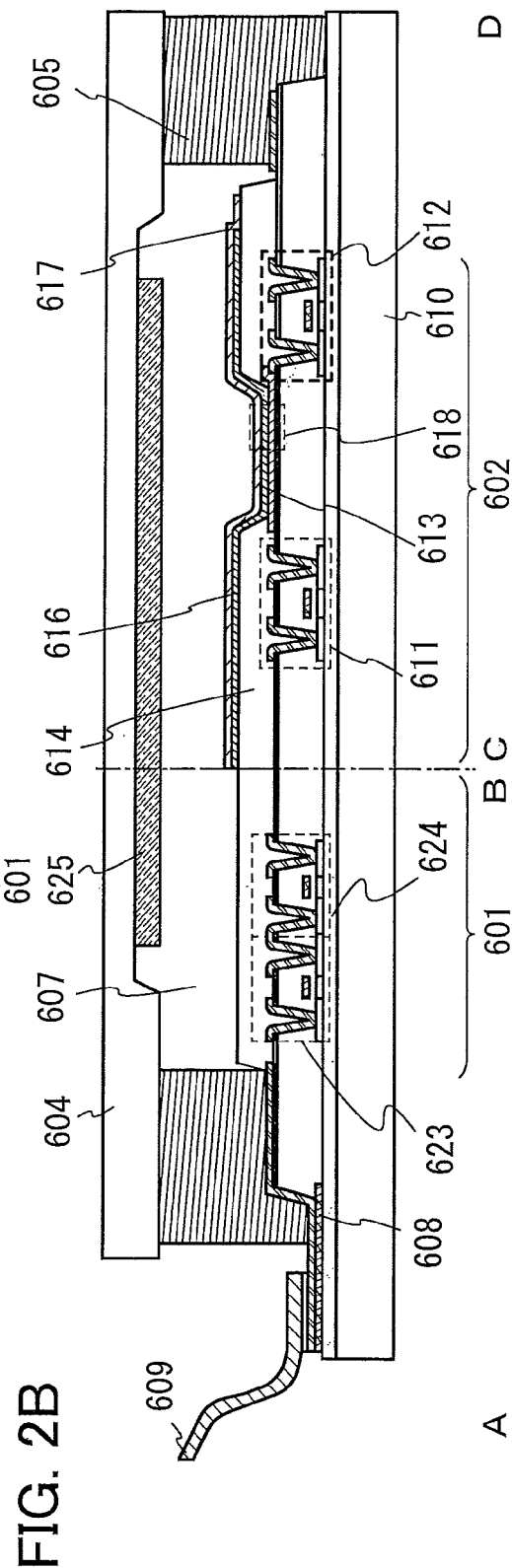

In this embodiment, the light-emitting device including a light-emitting element containing any of the carbazole derivatives represented by the general formula (G1) is described with reference to FIGS. 2A and 2B. Note that FIG. 2A is a top view illustrating the light-emitting device and FIG. 2B is a cross-sectional view of FIG. 2A taken along lines A-B and C-D. The light-emitting device includes a driver circuit portion (source-side driver circuit) 601, a pixel portion 602, and a driver circuit portion (gate-side driver circuit) 603 which are illustrated with dotted lines. These units control light emission of the light-emitting element. Moreover, a reference numeral 604 denotes a sealing substrate; 605, a sealing material; and 607, a space surrounded by the sealing material 605.

Reference numeral 608 denotes a wiring for transmitting signals to be inputted into the source-side driver circuit 601 and the gate-side driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, the cross-sectional structure is described with reference to FIG. 2B. Although the driving circuit portion and the pixel portion are formed on an element substrate 610, the source-side driving circuit 601 that is the driving circuit portion, and one of the pixels in the pixel portion 602 are illustrated here In the source-side driver circuit 601, a CMOS circuit is formed in which an n-channel TFT 623 and a p-channel TFT 624 are combined. Such a driver circuit may be formed by using various circuits such as a CMOS circuit, a PMOS circuit, or an NMOS circuit. Although this embodiment shows a driver-integrated type where the driver circuit is formed over the substrate, the present invention is not limited to this, and the driver circuit may be formed outside the substrate, not over the substrate.

The pixel portion 602 is formed with a plurality of pixels including a switching TFT 611, a current controlling TFT 612, and a first electrode 613 electrically connected to a drain of the current controlling TFT. An insulator 614 is formed so as to cover the end portions of the first electrode 613; here, the insulator 614 is formed using a positive type photosensitive acrylic resin film.

In order to improve the coverage, the insulator 614 is formed to have a curved surface with curvature at its upper or lower end portion. For example, in the case of using positive photosensitive acrylic for the insulator 614, only the upper end portion of the insulator 614 preferably has a curved surface with a radius of curvature of 0.2 μm to 0.3 μm. As the insulator 614, either a negative type which becomes insoluble in etchant by irradiation with light or a positive type which becomes soluble in etchant by irradiation with light can be used.

A layer 616 containing an organic compound and a second electrode 617 are formed over the first electrode 613. As a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like can be used. Alternatively, a stack of a titanium nitride film and a film containing aluminum as its main component, a stack of three layers of a titanium nitride film, a film containing aluminum as its main component, and a titanium nitride film, or the like can be used. Note that when a stacked structure is employed, the first electrode 613 has low resistance as a wiring, forms a favorable ohmic contact, and can function as an anode.

In addition, the layer 616 containing an organic compound is formed by any of a variety of methods such as an evaporation method using an evaporation mask, an inkjet method, and a spin coating method. The layer 616 containing an organic compound contains any of the carbazole derivatives described in Embodiment 1. Further, the layer 616 containing an organic compound may be formed using another material such as a low molecular compound or a high molecular compound (the category of the high molecular compound includes an oligomer and a dendrimer).

As a material used for the second electrode 617, which is formed over the layer 616 containing an organic compound and functions as a cathode, a material having a low work function (e.g., Al, Mg, Li, Ca, or an alloy or compound thereof, such as MgAg, MgIn, AlLi, LiF, or $CaF_2$) is preferably used. In the case where light generated in the layer 616 containing an organic compound passes through the second electrode 617, the second electrode 617 is preferably formed using a stack of a thin metal film and a transparent conductive film (ITO, indium oxide containing zinc oxide at 2 wt % to 20 wt %, indium tin oxide containing silicon, zinc oxide (ZnO), or the like).

Note that the light-emitting element is formed by the first electrode 613, the layer 616 containing an organic compound, and the second electrode 617. The light-emitting element has any of the structures described in Embodiments 1 to 3. The pixel portion, which includes a plurality of light-emitting elements, in the light-emitting device of this embodiment may include both the light-emitting element with any of the structures described in Embodiments 1 to 3 and the light-emitting element with a structure other than those.

Further, a light-emitting element 618 is provided in the space 607 surrounded by the element substrate 610, the sealing substrate 604, and the sealing material 605 by pasting the sealing substrate 604 and the element substrate 610 using the sealing material 605. The space 607 may be filled with filler, and may be filled with an inert gas (such as nitrogen or argon), the sealing material 605, or the like.

An epoxy based resin is preferably used for the sealing material 605. It is desirable that such a material do not transmit moisture or oxygen as much as possible. As a material for the sealing substrate 604, a plastic substrate formed of FRP (fiberglass-reinforced plastics), PVF (polyvinyl fluoride), polyester, acrylic, or the like can be used besides a glass substrate or a quartz substrate.

In this way, the light-emitting device manufactured using the light-emitting element containing any of the carbazole derivatives represented by the general formula (G1) can be obtained.

Since the light-emitting device in this embodiment uses the light-emitting element containing any of the carbazole derivatives represented by the general formula (G1), a light-emitting device having favorable characteristics can be provided. Specifically, since any of the carbazole derivatives described in Embodiment 1 has a wide energy gap and high triplet excitation energy and can suppress energy transfer from a light-emitting substance, a light-emitting element having high emission efficiency can be provided; thus, a light-emitting device having less power consumption can be provided. In addition, since a light-emitting element driven with a low driving voltage can be provided, a light-emitting device driven with a low driving voltage can be provided. Further, since the light-emitting element using any of the carbazole derivatives represented by the general formula (G1) has a long lifetime, a light-emitting device having high reliability can be provided.

Figure 3A:
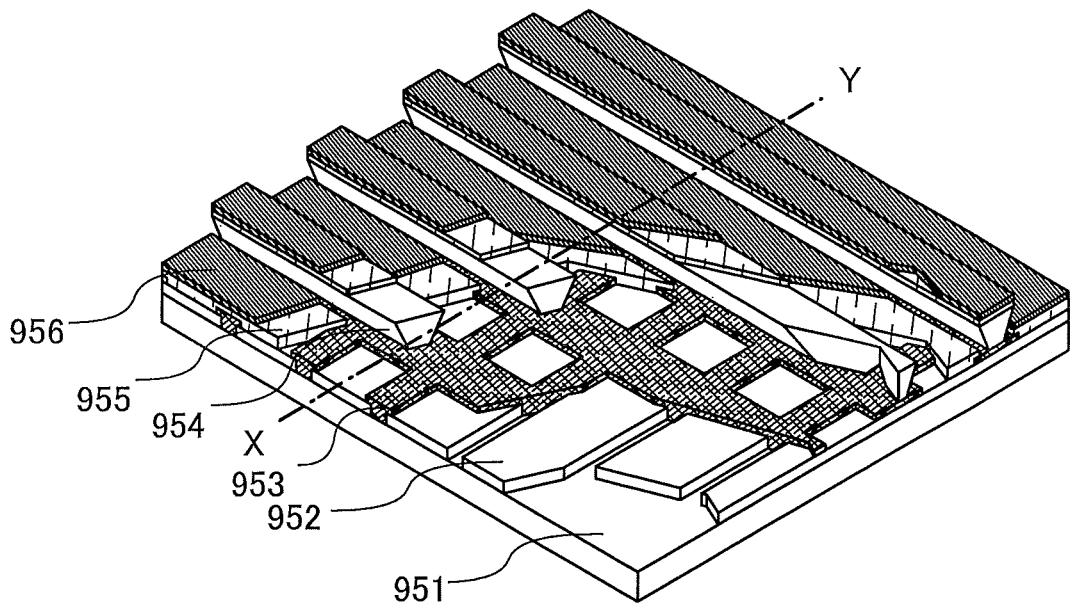
FIGS. 3A and 3B are conceptual diagrams of a passive matrix light-emitting device.
Figure 3B:
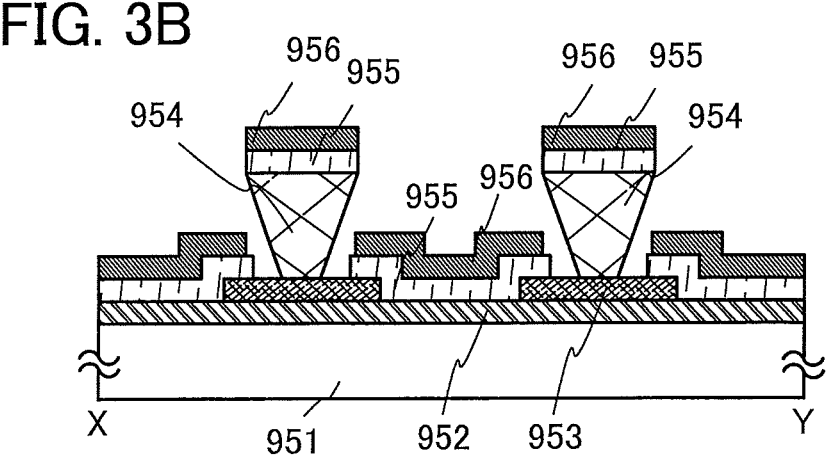

Although an active matrix light-emitting device is described in this embodiment as described above, a passive matrix light-emitting device may be alternatively fabricated. FIGS. 3A and 3B illustrate a passive matrix light-emitting device fabricated according to the present invention. FIG. 3A is a perspective view of the light-emitting device, and FIG. 3B is a cross-sectional view taken along line X-Y in FIG. 3A. In FIGS. 3A and 3B, an electrode 952 and an electrode 956 are provided over a substrate 951, and a layer 955 containing an organic compound is provided between the electrodes 952 and 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. That is, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). By providing the partition layer 954 in this way, defects of the light-emitting element due to static charge and the like can be prevented. The passive matrix light-emitting device can also be operated with low power consumption by including the light-emitting element according to any of Embodiments 1 to 3 which is driven with a low driving voltage. In addition, the light-emitting device can be driven with low power consumption by including the light-emitting element according to any of Embodiments 1 to 3 which has high emission efficiency. Further, the light-emitting device can have high reliability by including the light-emitting element according to any of Embodiments 1 to 3.

Embodiment 6

In this embodiment, electronic devices of one embodiment of the present invention, each including the light-emitting device described in Embodiment 5, are described. The electronic devices of the present invention each include a light-emitting element containing any of any of the carbazole derivatives represented by the general formula (G1) and thus electronic devices each having a display portion which consumes less power can be obtained. In addition, electronic devices driven with a low driving voltage can be provided. Further, electronic devices having high reliability can be provided.

As examples of the electronic devices each including the light-emitting element containing any of the carbazole derivatives represented by the general formula (G1), the following can be given: cameras such as video cameras and digital cameras, goggle type displays, navigation systems, audio replay devices (e.g., car audio systems and audio systems), computers, game machines, portable information terminals (e.g., mobile computers, mobile phones, portable game machines, and electronic book readers), image replay devices in which a recording medium is provided (specifically, devices that are capable of replaying recording media, such as digital versatile discs (DVDs), and equipped with a display device that can display an image), and the like. Specific examples of these electronic devices are illustrated in FIGS. 4A to 4D.

Figure 4A:
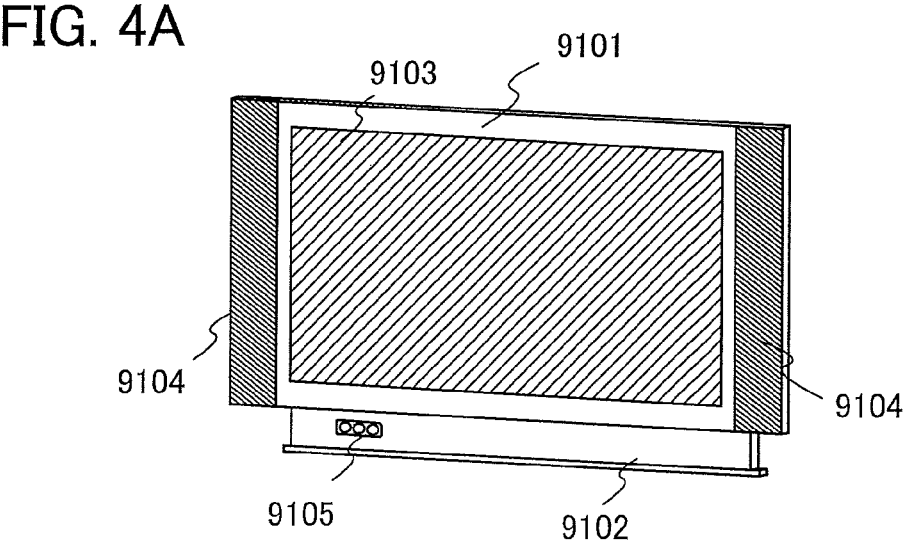
FIGS. 4A to 4D each illustrate an electronic device.

FIG. 4A illustrates a television device which includes a housing 9101, a support 9102, a display portion 9103, speaker portions 9104, video input terminals 9105, and the like. In the display portion 9103 of this television device, light-emitting elements similar to those described in any of Embodiments 1 to 3 are arranged in matrix. The light-emitting elements can have high emission efficiency. In addition, a light-emitting element driven with a low driving voltage can be provided. Further, a light-emitting element having high reliability can be provided. Therefore, this television device having the display portion 9103 which is formed using the light-emitting elements consumes less power. In addition, a television device driven with a low driving voltage can be provided. Further, a television device having high reliability can be provided.

Figure 4B:
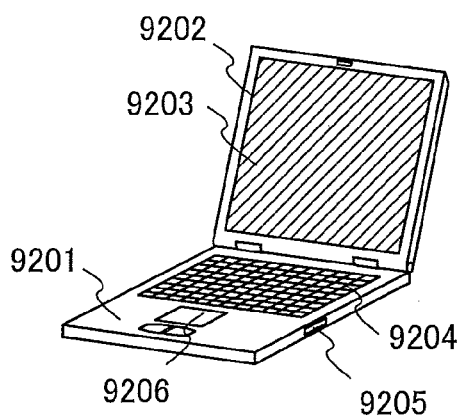

FIG. 4B illustrates a computer according to one embodiment of the present invention. The computer includes a main body 9201, a housing 9202, a display portion 9203, a keyboard 9204, an external connection port 9205, a pointing device 9206, and the like. In the display portion 9203 of this computer, light-emitting elements similar to those described in any of Embodiments 1 to 3 are arranged in matrix. The light-emitting elements can have high emission efficiency. In addition, a light-emitting element driven with a low driving voltage can be provided. Further, a light-emitting element having high reliability can be provided. Therefore, this computer having the display portion 9203 which is formed using the light-emitting elements consumes less power. In addition, a computer driven with a low driving voltage can be provided. Further, a computer having high reliability can be provided.

Figure 4C:
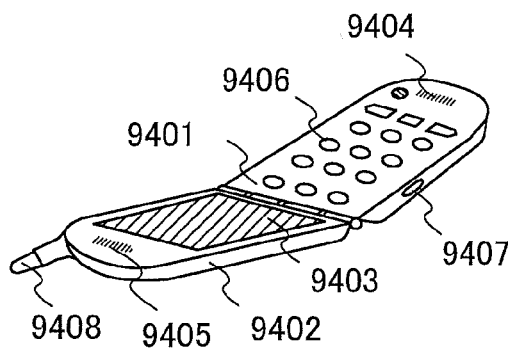

FIG. 4C illustrates a mobile phone according to one embodiment of the present invention. The mobile phone includes a main body 9401, a housing 9402, a display portion 9403, an audio input portion 9404, an audio output portion 9405, operation keys 9406, an external connection port 9407, an antenna 9408, and the like. In the display portion 9403 of this mobile phone, light-emitting elements similar to those described in any of Embodiments 1 to 3 are arranged in matrix. The light-emitting elements can have high emission efficiency. In addition, a light-emitting element driven with a low driving voltage can be provided. Further, a light-emitting element having high reliability can be provided. Therefore, this mobile phone having the display portion 9403 which is formed using the light-emitting elements consumes less power. In addition, a mobile phone driven with a low driving voltage can be provided. Further, a mobile phone having high reliability can be provided.

Figure 4D:
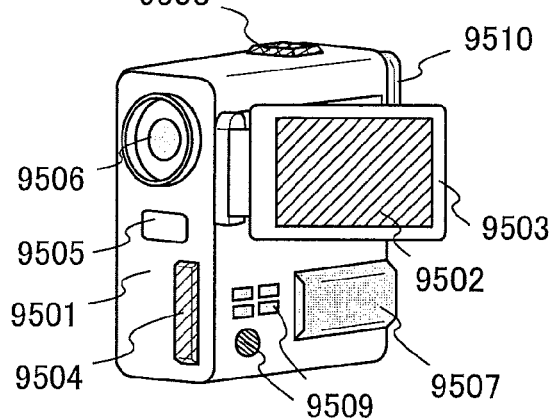

FIG. 4D illustrates a camera according to one embodiment of the present invention which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the display portion 9502 of this camera, light-emitting elements similar to those described in any of Embodiments 1 to 3 are arranged in matrix. The light-emitting elements can have high emission efficiency. In addition, a light-emitting element driven with a low driving voltage can be provided. Further, a light-emitting element having high reliability can be provided. Therefore, this camera having the display portion 9502 which is formed using the light-emitting elements consumes less power. In addition, a camera driven with a low driving voltage can be provided. Further, a camera having high reliability can be provided.

As described above, the application range of the light-emitting device described in Embodiment 5 is so wide that the light-emitting device can be applied to electronic devices of every field. An electronic device which consumes less power can be obtained by using any of the carbazole derivatives represented by the general formula (G1). In addition, an electronic device having a display portion capable of providing high-quality display with excellent color reproducibility can be obtained.

The light-emitting device described in Embodiment 5 can also be used as a lighting device. One embodiment in which the light-emitting device described in Embodiment 5 is used as a lighting device is described with reference to FIG. 5.

Figure 5:
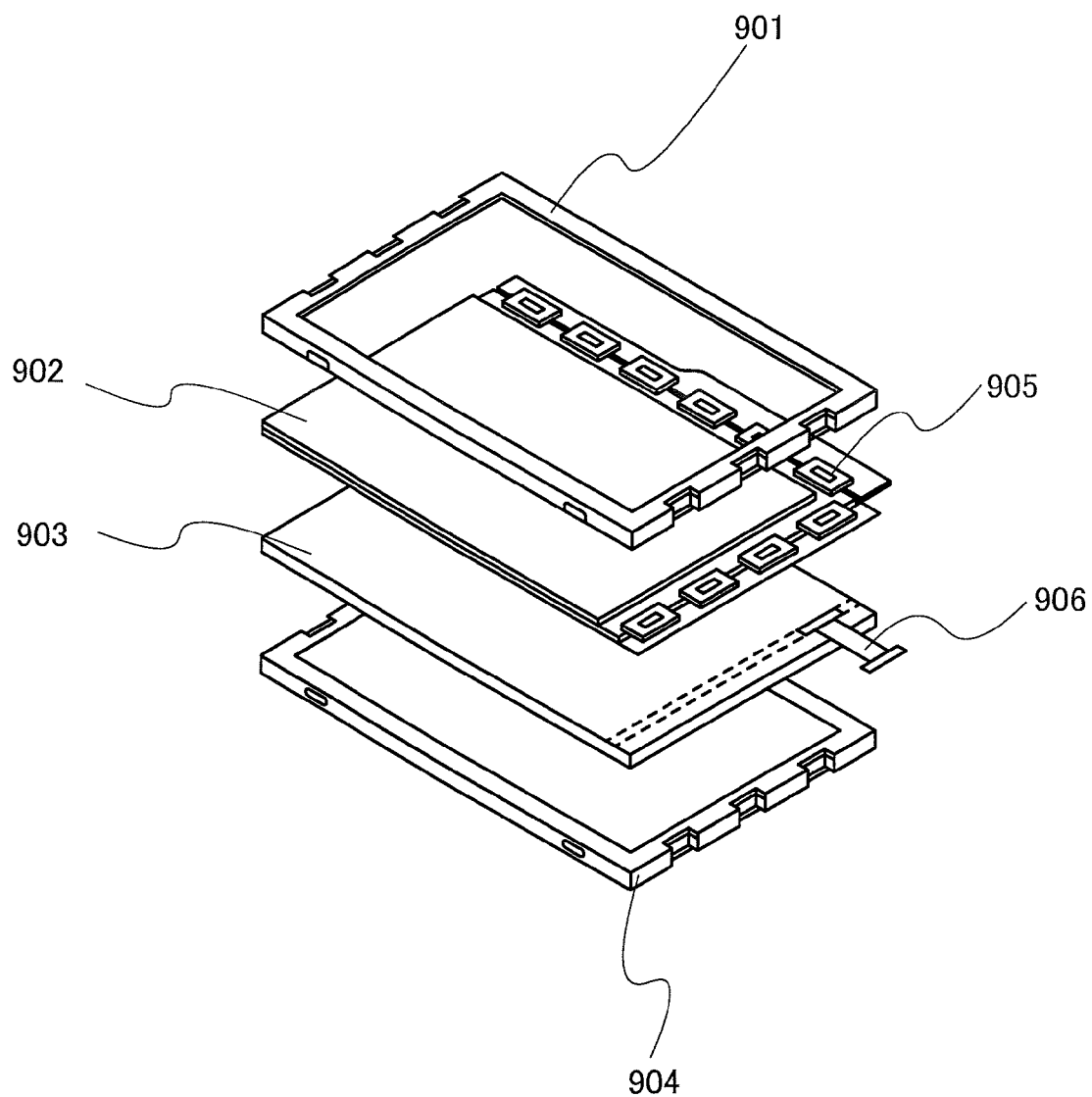
FIG. 5 illustrates an electronic device.

FIG. 5 illustrates an example of a liquid crystal display device using the light-emitting device described in Embodiment 5 as a backlight. The liquid crystal display device illustrated in FIG. 5 includes a housing 901, a liquid crystal layer 902, a backlight unit 903, and a housing 904. The liquid crystal layer 902 is connected to a driver IC 905. The light-emitting device described in Embodiment 5 is used as the backlight unit 903, to which a current is supplied through a terminal 906.

With the use of the light-emitting device described in Embodiment 5 as the backlight of the liquid crystal display device, a backlight having less power consumption can be provided. Further, the light-emitting device described in Embodiment 5 is a lighting device with plane light emission and can have a large area. Therefore, the backlight can have a large area, and a liquid crystal display device having a large area can be obtained. Furthermore, since the light-emitting device described in Embodiment 5 is thin, it becomes possible to reduce the thickness of a display device.

Figure 6:
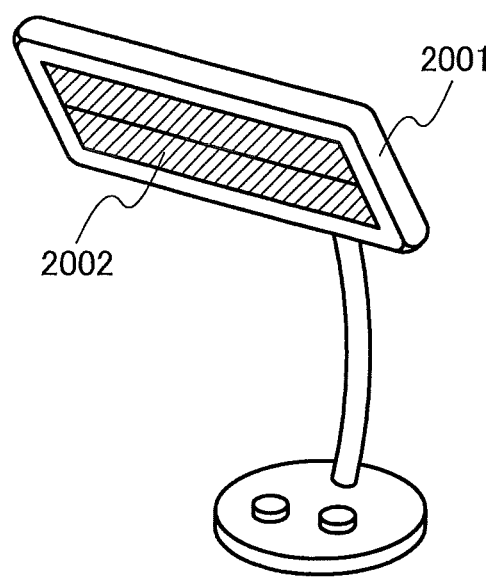
FIG. 6 illustrates a lighting device.

FIG. 6 illustrates an example in which the light-emitting device described in Embodiment 5 is used as a table lamp which is a lighting device. The table lamp illustrated in FIG. 6 includes a housing 2001 and a light source 2002, and the light-emitting device described in Embodiment 5 is used as the light source 2002.

Figure 7:
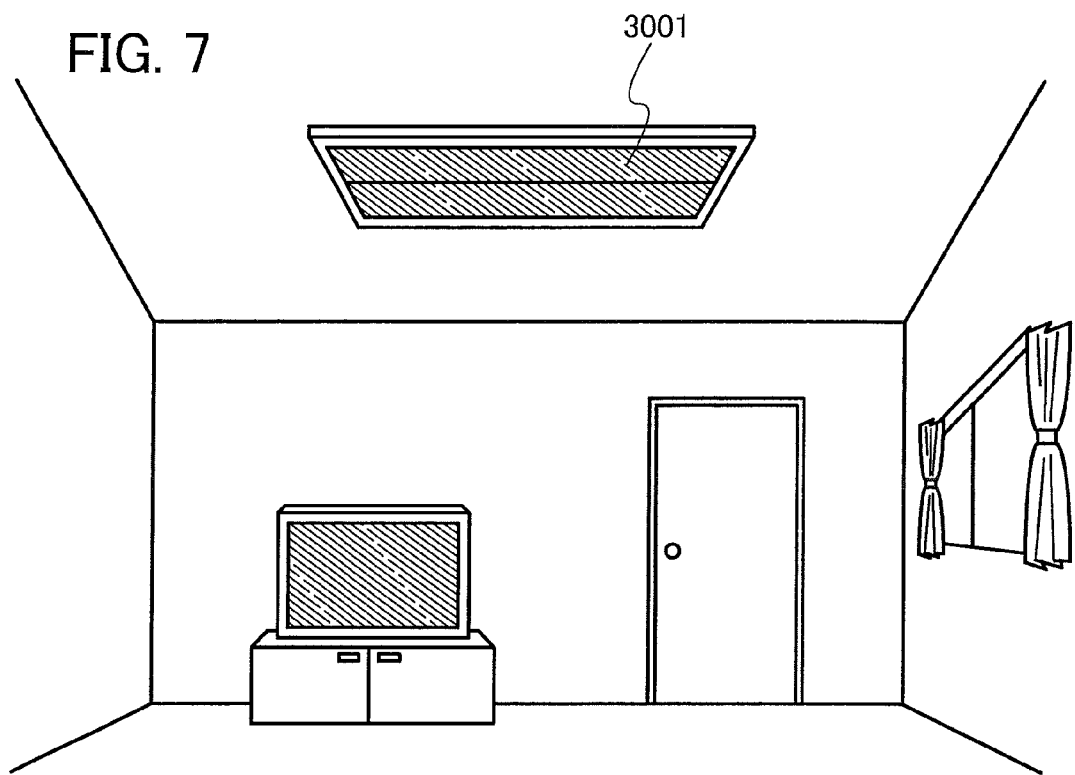
FIG. 7 illustrates lighting devices.

FIG. 7 illustrates an example in which the light-emitting device described in Embodiment 5 is used as an indoor lighting device 3001. Since the light-emitting device described in Embodiment 5 consumes less power, a lighting device that consumes less power can be obtained. Further, since the light-emitting device described in Embodiment 5 can have a large area, the light-emitting device can be used as a large-area lighting device. Further, since the light-emitting device described in Embodiment 5 is thin, the light-emitting device can be used for a lighting device having reduced thickness.

Example 1

In this example are described light-emitting elements according to Embodiment 1, in which an emission center substance that emits green phosphorescence is used for light-emitting layers and 2-[4-{3-(dibenzothiophen-4-yl)-9H-carbazol-9-yl}phenyl]-1-phenylbenzimidazole (abbreviation: DBTCzBIm-II, a structural formula (1)) and 2-[4-{3-(dibenzofuran-4-yl)-9H-carbazol-9-yl}phenyl]-1-phenylbenzimidazole (abbreviation: DBFCzBIm-II, a structural formula (3)), which are carbazole derivatives, are used as host materials for the respective light-emitting layers.

The molecular structures of organic compounds used in this example are represented by the structural formulae (i) to (iv), (1), and (3) below. In the element structure in FIG. 1A, an electron-injection layer is provided between an electron-transport layer 114 and a second electrode 104.

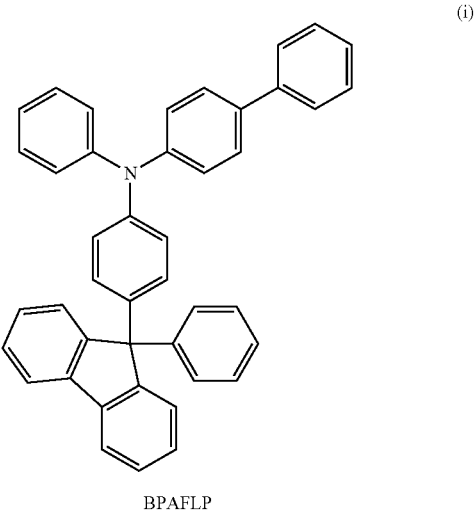

(i)

BPAFLP

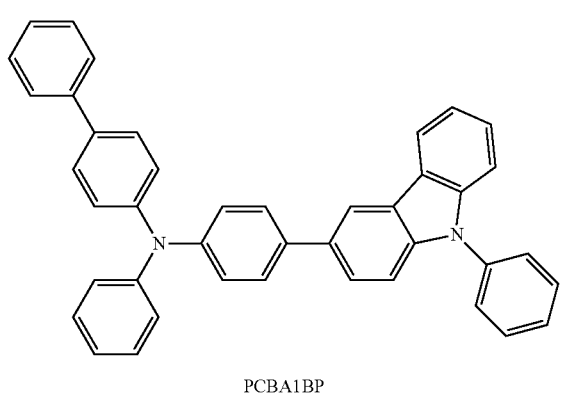

(ii)

PCBA1BP

-continued

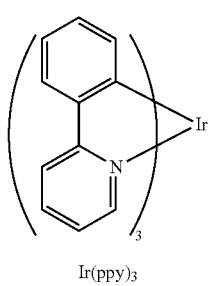
Ir(ppy)₃ (iii)

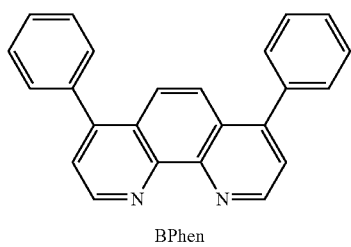
BPhen (iv)

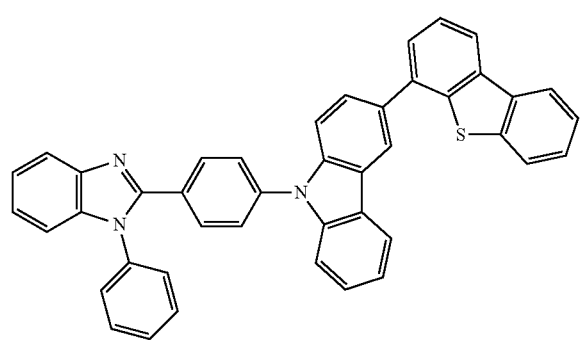
DBTCzBIm-II (1)

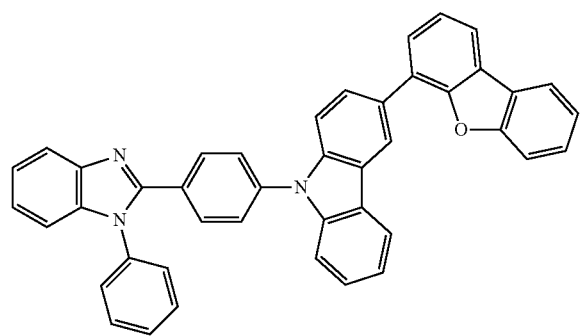
DBFCzBIm-II (3)

[Fabrication of Light-Emitting Element 1 and Light-Emitting Element 2]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 4-phenyl-4'-(9-phenylfluoren-9-yl) triphenylamine (abbreviation: BPAFLP) represented by the above structural formula (1) and molybdenum(VI) oxide such that the ratio of BPAFLP:molybdenum(VI) oxide was 2:1 (weight ratio). The thickness of was the layer was get to 50 nm. Note that the co-evaporation is an evaporation method in which a plurality of different substances is concurrently vaporized from the respective different evaporation sources.

Next, BPAFLP was evaporated to a thickness of 10 nm, so that a hole-transport layer 112 was formed.

Further, for the light-emitting element 1, the light-emitting layer 113 was formed on the hole-transport layer 112 in such a way that DBTCzBIm-II, which is the carbazole derivative represented by the above structural formula (1) and described in Embodiment 1,4-phenyl-4'-(9-phenyl-9H-carbazol-3-yl) triphenylamine (abbreviation: PCBA1BP) represented by the above structural formula (ii), and tris(2-phenylpyridinato-N, $C^{2'}$)iridium(III) (abbreviation: Ir(ppy)₃) represented by the above structural formula (iii) were evaporated to form a 20-nm-thick film so that the ratio of DBTCzBIm-II to PCBA1BP and Ir(ppy)₃ was 1:0.25:0.06 (weight ratio), DBTCzBIm-II and Ir(ppy)₃ were then evaporated to form a 20-nm-thick film so that the ratio of DBTCzBIm-II to Ir(ppy)₃ was 1:0.06 (weight ratio), and lastly DBTCzBIm-II was evaporated to form a 15-nm-thick film.

For the light-emitting element 2, the light-emitting layer 113 was formed on the hole-transport layer 112 in such a way that DBFCzBIm-II, which is the carbazole derivative represented by the above structural formula (2) and described in Embodiment 1, PCBA1BP, and Ir(ppy)₃ were evaporated to form a 20-nm-thick film in which the ratio of DBFCzBIm-II to PCBA1BP and Ir(ppy)₃ was 1:0.25:0.06 (weight ratio), DBFCzBIm-II to Ir(ppy)₃ were then evaporated to form a 20-nm-thick film in which the ratio of DBFCzBIm-II to Ir(ppy)₃ was 1:0.06 (weight ratio), and lastly DBFCzBIm-II was evaporated to form a 15-nm-thick film.

Next, bathophenanthroline (abbreviation: BPhen) represented by the above structural formula (iv) was evaporated to a thickness of 15 nm, so that an electron-transport layer 114 was formed. Further, lithium fluoride was evaporated to a thickness of 1 nm on the electron-transport layer 114, so that the electron-injection layer was fruited. Lastly, an aluminum film was formed to a thickness of 200 nm as the second electrode 104 functioning as a cathode, so that the light-emitting elements 1 and 2 were completed. Note that in the above evaporation processes, evaporation was all performed by a resistance heating method.

[Operation Characteristics of Light-Emitting Elements 1 and 2]

The light-emitting elements 1 and 2 thus obtained were sealed in a glove box under a nitrogen atmosphere without being exposed to the air. Then, the operation characteristics of these light-emitting elements were measured. Note that the measurements were carried out at room temperature (in an atmosphere kept at 25° C.).

Figure 8:
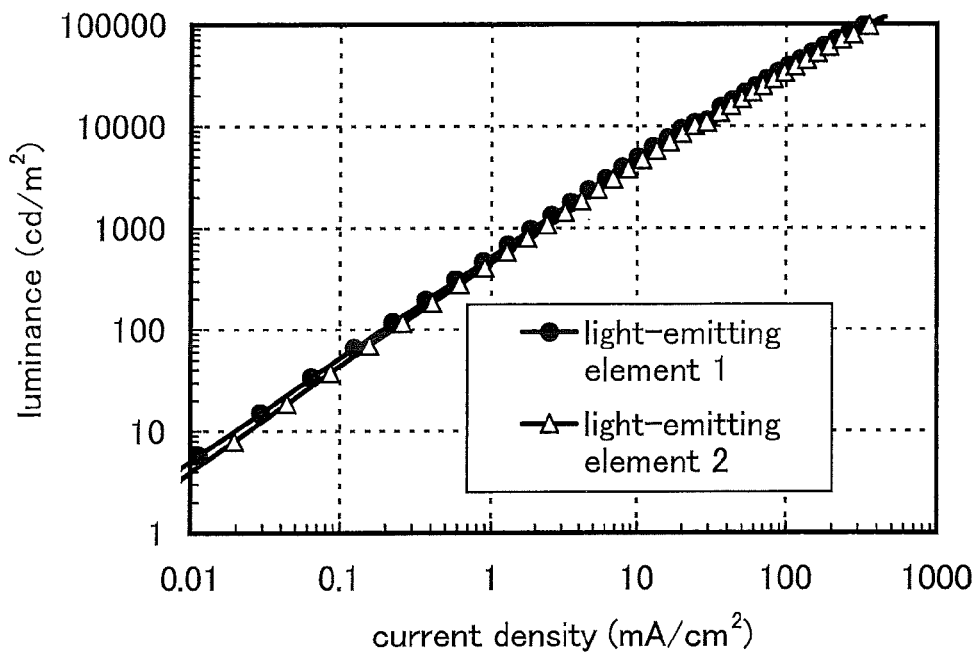
FIG. 8 shows luminance versus current density characteristics of a light-emitting element 1 and a light-emitting element 2.
Figure 9:
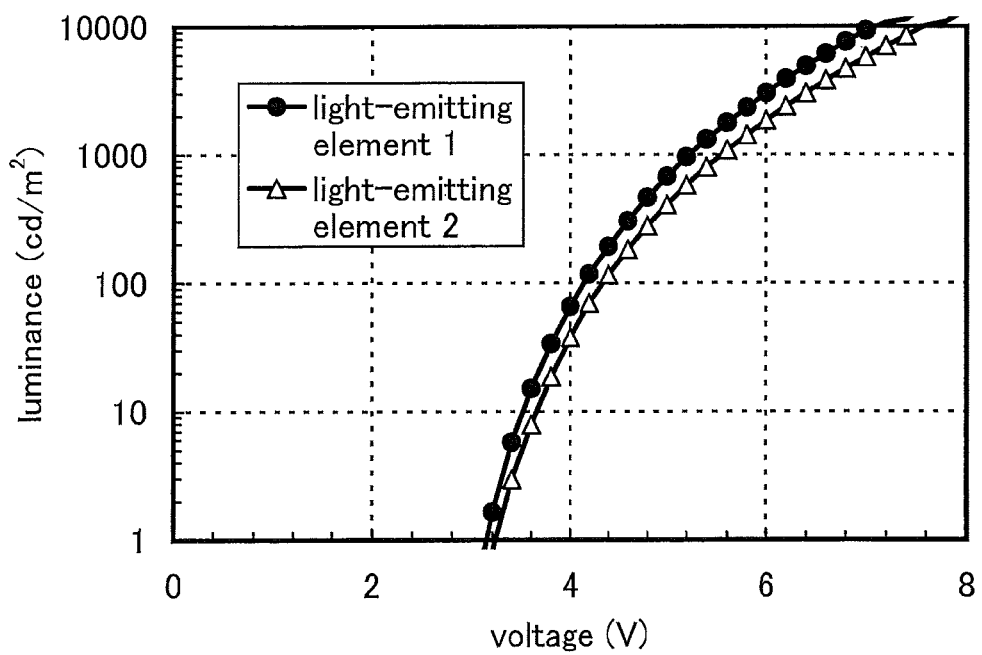
FIG. 9 shows luminance versus voltage characteristics of the light-emitting element 1 and the light-emitting element 2.
Figure 10:
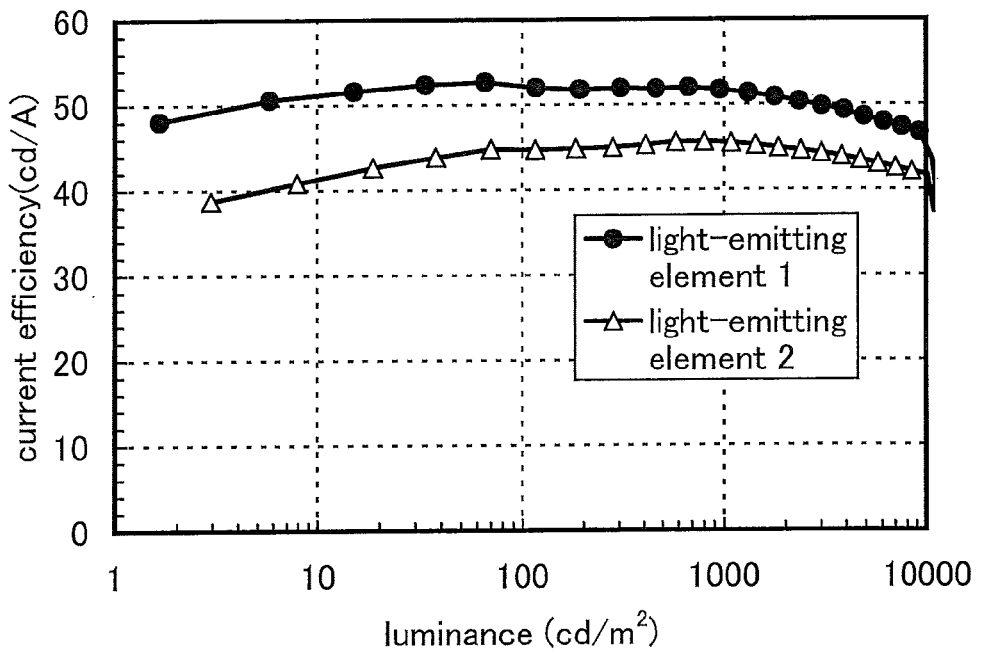
FIG. 10 shows current efficiency versus luminance characteristics of the light-emitting element 1 and the light-emitting element 2.

FIG. 8 shows luminance versus current density characteristics of the light-emitting elements, FIG. 9 shows luminance versus voltage characteristics thereof, and FIG. 10 shows current efficiency versus luminance characteristics thereof. In FIG. 8, the vertical axis represents luminance (cd/m$^2$), and the horizontal axis represents current density (mA/cm$^2$). In FIG. 9, the vertical axis represents luminance (cd/m$^2$), and the horizontal axis represents voltage (V). In FIG. 10, the vertical axis represents current efficiency (cd/A), and the horizontal axis represents luminance (cd/m$^2$).

FIG. 10 reveals that the light-emitting elements in each of which the carbazole derivative represented by the general formula (G1) is used as a host material of a light-emitting layer for emitting green phosphorescence, has favorable luminance versus emission efficiency characteristics and high emission efficiency. This is because each carbazole derivative represented by the general formula (G1) has a wide energy gap and high triplet excitation energy, and thus even a light-emitting substance that emits green phosphorescence gap can be efficiently excited. In addition, FIG. 8 reveals that the light-emitting elements in each of which the carbazole derivative represented by the general formula (G1) is used as a host material of a light-emitting layer for emitting green phosphorescence, has favorable luminance versus voltage characteristics and can be driven with a low voltage. This indicates that each carbazole derivative represented by the general formula (G1) has an excellent carrier-transport property.

Figure 11:
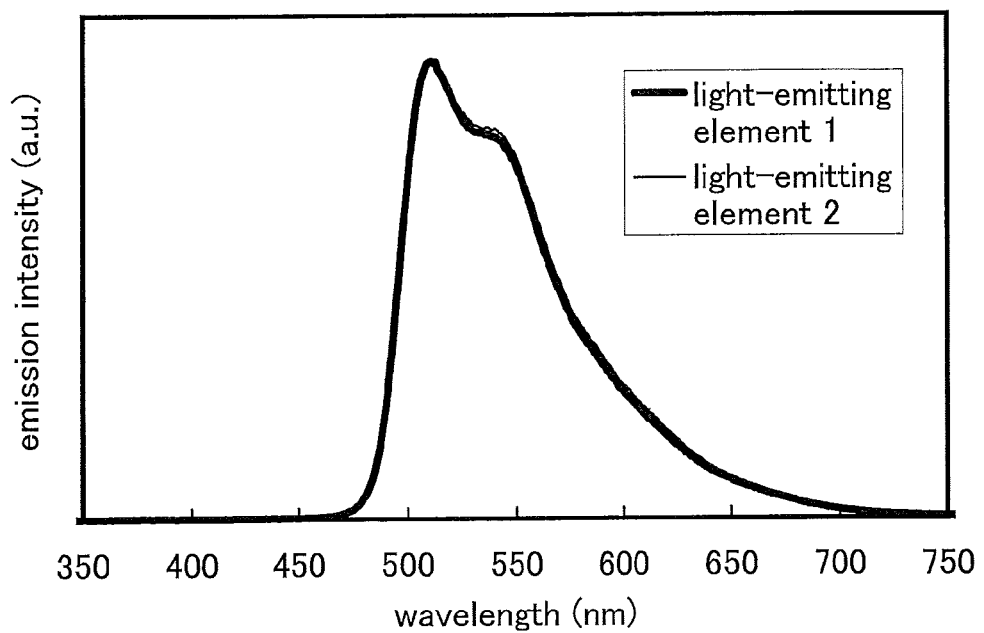
FIG. 11 shows emission spectra of the light-emitting element 1 and the light-emitting element 2.

FIG. 11 shows emission spectra when a current of 1 mA was made to flow in the fabricated light-emitting elements 1 and 2. In FIG. 11, the horizontal axis represents emission wavelength (nm), and the vertical axis represents emission intensity. The emission intensity is shown as a value relative to the greatest emission intensity assumed to be 1. FIG. 11 reveals that the light-emitting elements 1 and 2 each emit green light due to Ir(ppy)$_3$, which is the emission center substance.

Figure 12:
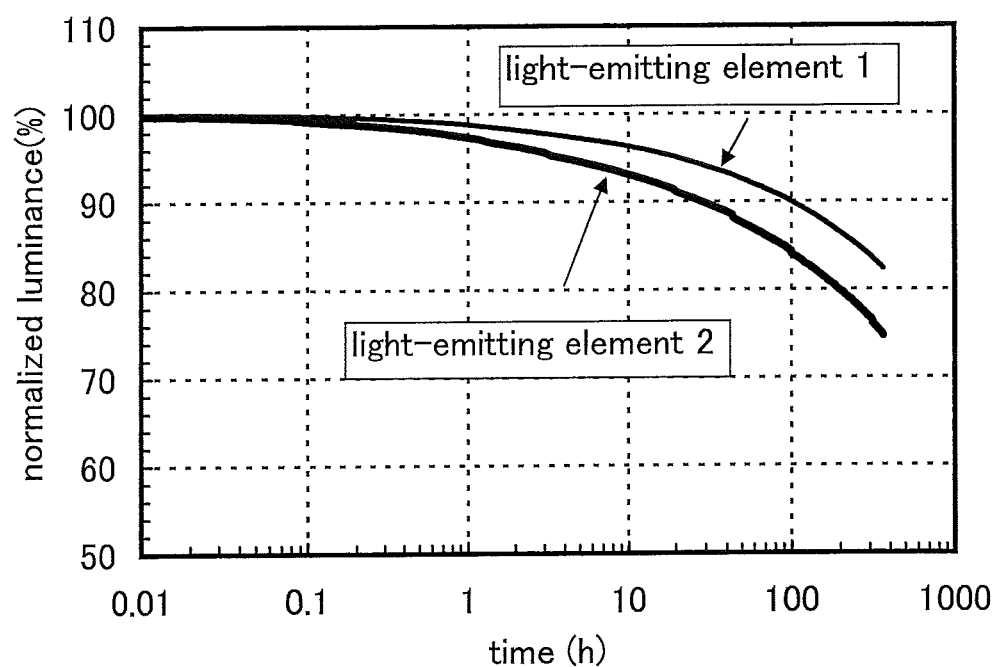
FIG. 12 shows normalized luminance versus time characteristics of the light-emitting element 1 and the light-emitting element 2.

Next, the initial luminance is set at 1000 cd/m$^2$, these elements were driven under a condition where the current density was constant, and changes in luminance with respect to the driving time were examined. FIG. 12 shows normalized luminance versus time characteristics. From FIG. 12, it is found that each of the light-emitting elements 1 and 2 shows favorable characteristics and has high reliability.

Example 2

In this example described are light-emitting elements according to Embodiment 1, in which an emission center substance that emits green phosphorescence is used for light-emitting layers and 3-(dibenzothiophen-4-yl)-9-(triphenylen-2-yl)-9H-carbazole (abbreviation: DBTCzTp-II, a structural formula (5)) and 3-(dibenzofuran-4-yl)-9-(triphenylen-2-yl)-9H-carbazole (abbreviation: DBFCzTp-II, a structural formula (6)), which are carbazole derivatives, are used as host materials for the respective light-emitting layers.

The molecular structures of organic compounds used in this example are represented by the structural formulae (i), (iv), (5), and (6) below. In the element structure in FIG. 1A, an electron-injection layer is provided between an electron-transport layer 114 and a second electrode 104.

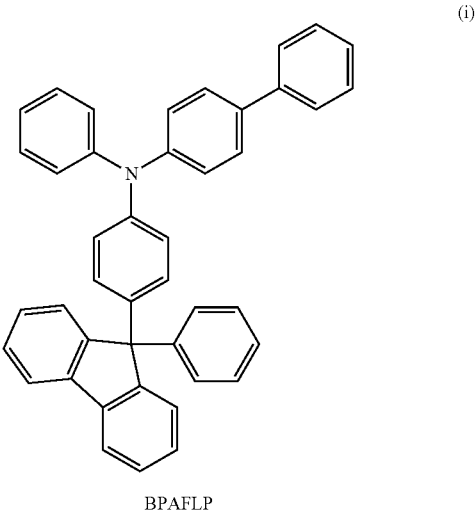

BPAFLP (i)

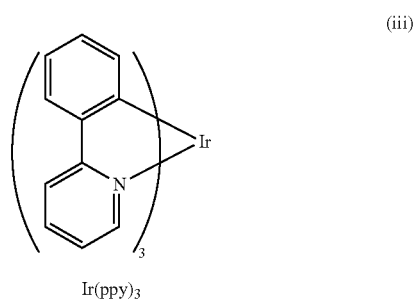

Ir(ppy)$_3$ (iii)

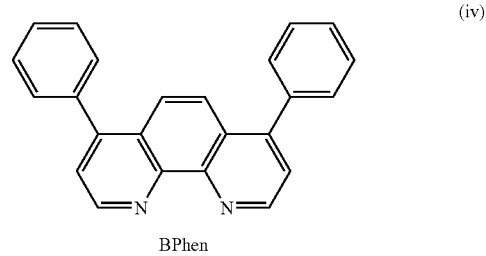

BPhen (iv)

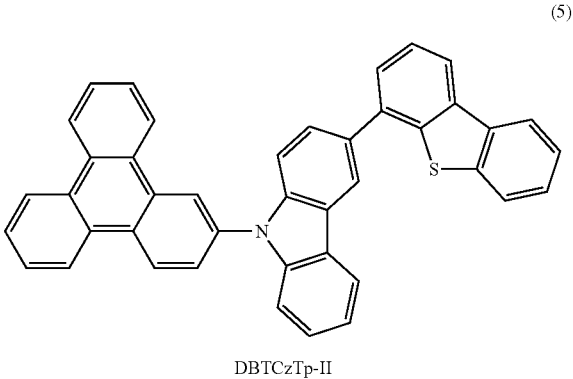 [SMILES: c1ccc2c(c1)oc1c(-c3ccc4c(c3)c3ccccc3n4-c3ccc4c5ccccc5c5ccccc5c4c3)cccc12]

DBTCzTp-II (5)

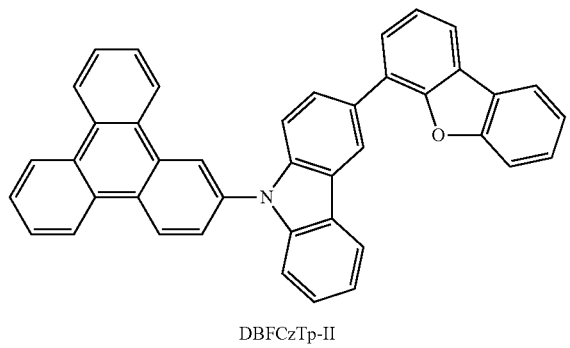

DBFCzTp-II (6)

[Fabrication of Light-Emitting Element 3 and Light-Emitting Element 4]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 4-phenyl-4'-(9-phenylfluoren-9-yl) triphenylamine (abbreviation: BPAFLP) represented by the above structural formula (1) and molybdenum(VI) oxide such that the ratio of BPAFLP:molybdenum(VI) oxide was 2:1 (weight ratio). The thickness of was the layer was set to 50 nm. Note that the co-evaporation is an evaporation method in which a plurality of different substances is concurrently vaporized from the respective different evaporation sources.

Next, BPAFLP was evaporated to a thickness of 10 nm, so that a hole-transport layer 112 was formed.

Further, for the light-emitting element 3, the light-emitting layer 113 was formed on the hole-transport layer 112 in such a way that DBTCzTp-II, which is the carbazole derivative represented by the above structural formula (5) and described in Embodiment 1, and tris(2-phenylpyridinato-N,$C^{2'}$)iridium (III) (abbreviation: Ir(ppy)$_3$) represented by the above structural formula (iii) were evaporated to form a 40-nm-thick film so that the ratio of DBTCzTp-II to Ir(ppy)$_3$ was 1:0.06 (weight ratio) and then a 15-nm-thick DBTCzTp-II film.

For the light-emitting element 4, the light-emitting layer 113 was formed on the hole-transport layer 112 in such a way that DBFCzTp-II, which is the carbazole derivative represented by the above structural formula (6) and described in Embodiment 1, and Ir(ppy)$_3$ were evaporated to form a 40-nm-thick film so that the ratio of DBFCzTp-II to Ir(ppy)$_3$ was 1:0.06 (weight ratio) and then DBFCzTp-II was evaporated to form a 15-nm-thick film.

Next, on the light-emitting layer 113, bathophenanthroline (abbreviation: BPhen) represented by the above structural formula (iv) was evaporated to a thickness of 15 nm, so that the electron-transport layer 114 was formed. Further, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting elements 3 and 4 were completed. Note that in the above evaporation processes, evaporation was all performed by a resistance heating method.

[Operation Characteristics of Light-Emitting Elements 3 and 4]

The light-emitting elements 3 and 4 thus obtained were sealed in a glove box under a nitrogen atmosphere without being exposed to the air. Then, the operation characteristics of these light-emitting elements were measured. Note that the measurements were carried out at room temperature (in an atmosphere kept at 25° C.).

Figure 13:
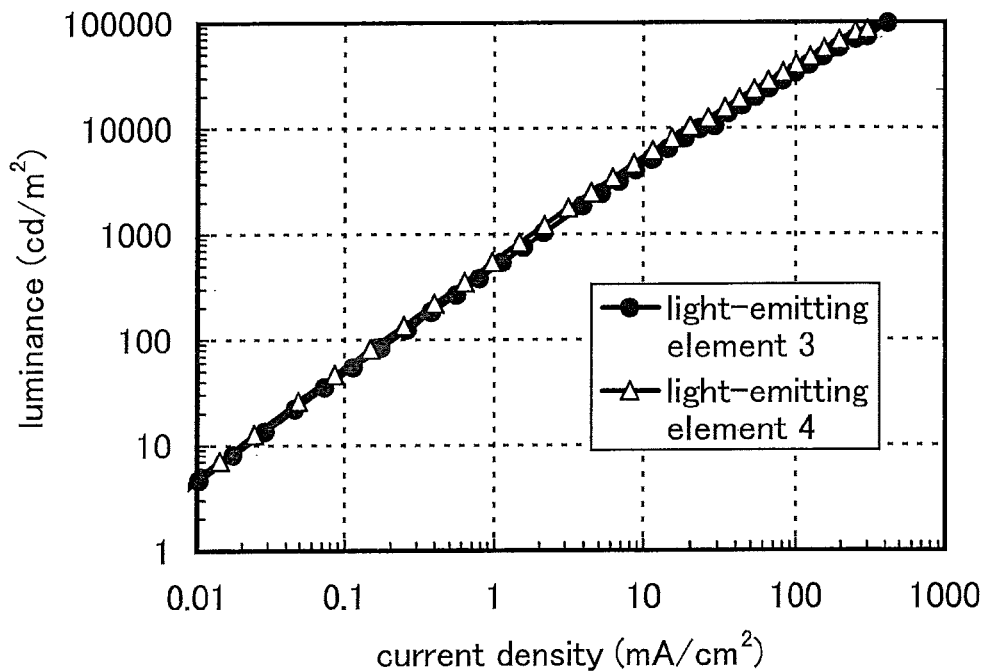
FIG. 13 shows luminance versus current density characteristics of a light-emitting element 3 and a light-emitting element 4.
Figure 14:
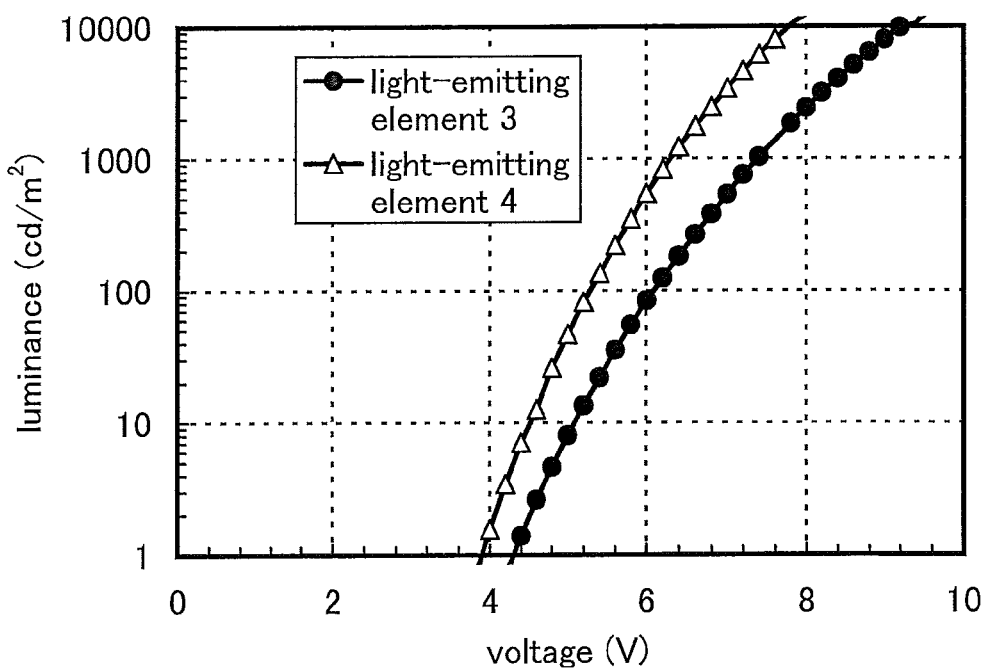
FIG. 14 shows luminance versus voltage characteristics of the light-emitting element 3 and the light-emitting element 4.
Figure 15:
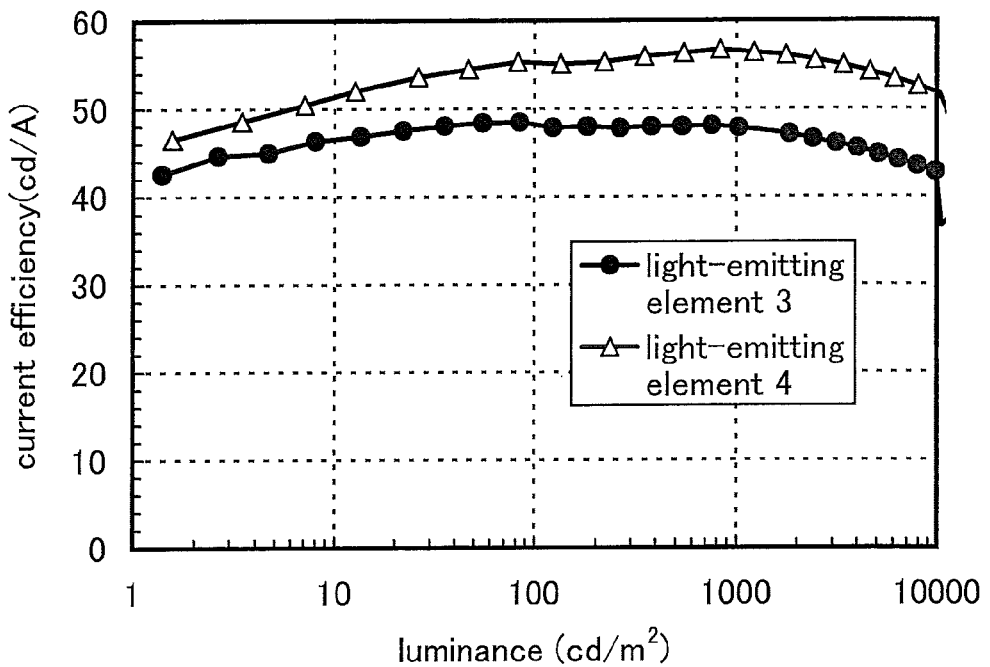
FIG. 15 shows current efficiency versus luminance characteristics of the light-emitting element 3 and the light-emitting element 4.

FIG. 13 shows luminance versus current density characteristics of the light-emitting elements, FIG. 14 shows luminance versus voltage characteristics thereof, and FIG. 15 shows current efficiency versus luminance characteristics thereof. In FIG. 13, the vertical axis represents luminance (cd/m$^2$), and the horizontal axis represents current density (mA/cm$^2$). In FIG. 14, the vertical axis represents luminance (cd/m$^2$), and the horizontal axis represents voltage (V). In FIG. 15, the vertical axis represents current efficiency (cd/A), and the horizontal axis represents luminance (cd/m$^2$).

FIG. 15 reveals that the light-emitting elements in each of which the carbazole derivative represented by the general formula (G1) is used as a host material of a light-emitting layer for emitting green phosphorescence, has favorable luminance versus emission efficiency characteristics and high emission efficiency. This is because each carbazole derivative represented by the general formula (G1) has a wide energy gap and high triplet excitation energy, and thus even a light-emitting substance that emits green phosphorescence gap can be efficiently excited. In addition, FIG. 13 reveals that the light-emitting elements in each of which the carbazole derivative represented by the general formula (G1) is used as a host material of a light-emitting layer for emitting green phosphorescence, has favorable luminance versus voltage characteristics and can be driven with a low voltage. This indicates that each carbazole derivative represented by the general formula (G1) has an excellent carrier-transport property.

Figure 16:
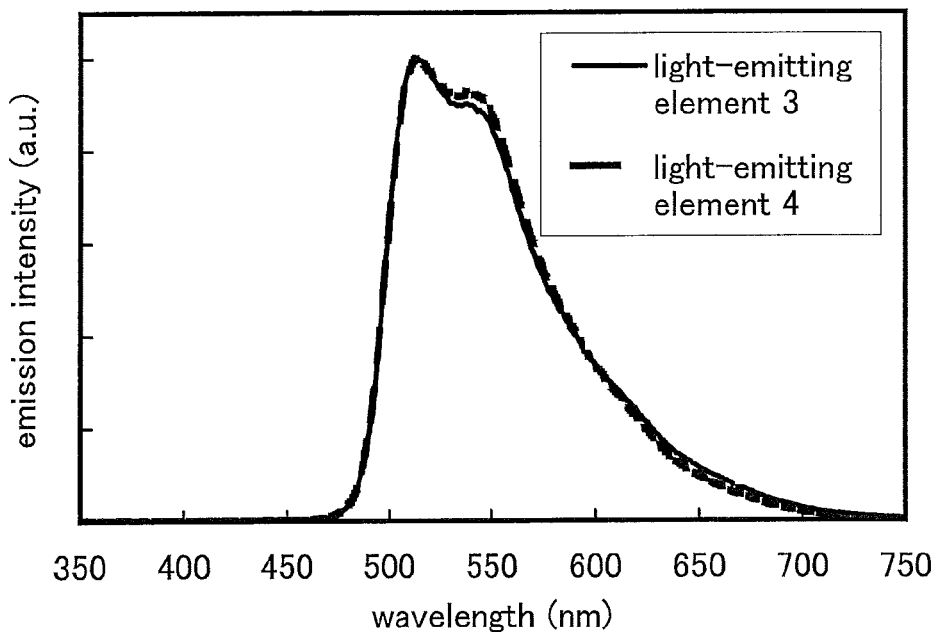
FIG. 16 shows emission spectra of the light-emitting element 3 and the light-emitting element 4.

FIG. 16 shows emission spectra when a current of 1 mA was made to flow in the fabricated light-emitting elements 3 and 4. In FIG. 16, the horizontal axis represents emission wavelength (nm), and the vertical axis represents emission intensity. The emission intensity is shown as a value relative to the greatest emission intensity assumed to be 1. FIG. 16 reveals that the light-emitting elements 3 and 4 each emit green light due to Ir(ppy)$_3$, which is the emission center substance.

Figure 17:
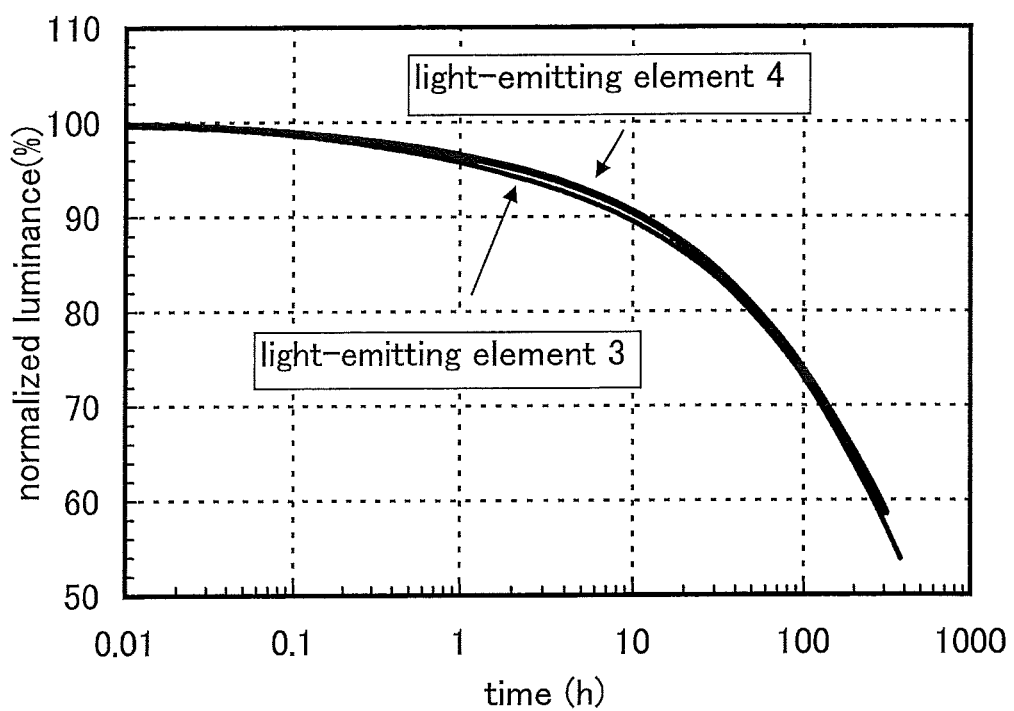
FIG. 17 shows normalized luminance versus time characteristics of the light-emitting element 3 and the light-emitting element 4.

Next, the initial luminance is set at 1000 cd/m$^2$, these elements were driven under a condition where the current density was constant, and changes in luminance with respect to the driving time were examined FIG. 17 shows normalized luminance versus time characteristics. From FIG. 17, it is found that each of the light-emitting elements 3 and 4 shows favorable characteristics and has high reliability.

Example 3

In this example described are light-emitting elements in which an emission center substance that emits blue fluorescence is used for light-emitting layers and 3-(dibenzothiophen-4-yl)-9-[4-(10-phenyl-9-anthryl)phenyl]-9H-carbazole (abbreviation: DBTCzPA-II, a structural formula (7)) and 3-(dibenzofuran-4-yl)-9-[4-(10-phenyl-9-anthryl)phenyl]-9H-carbazole (abbreviation: DBFCzPA-II, a structural formula (8)), which are carbazole derivatives represented by the general formula (G1), are used as host materials for the respective light-emitting layers.

The molecular structures of organic compounds used in this example are represented by the structural formulae (iv) to (vi), (7), and (8) below. In the element structure in FIG. 1A, an electron-injection layer is provided between an electron-transport layer 114 and a second electrode 104.

(v)

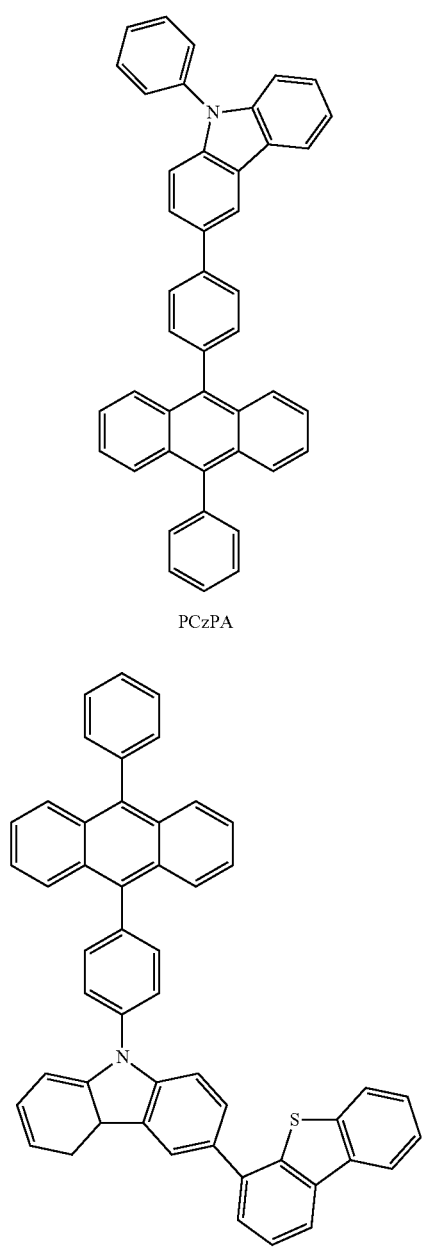

PCzPA (7)

DBTCzPA-II

-continued (8)

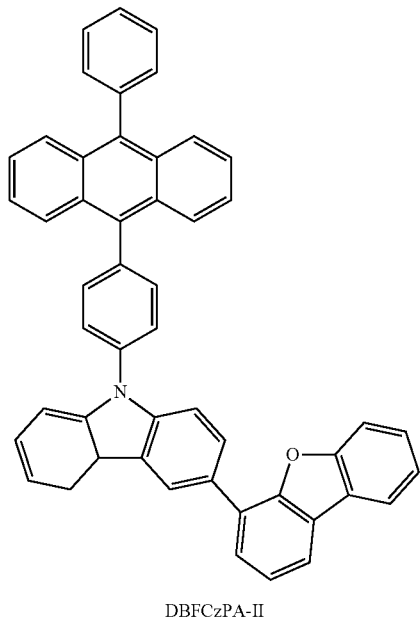

DBFCzPA-II (vi)

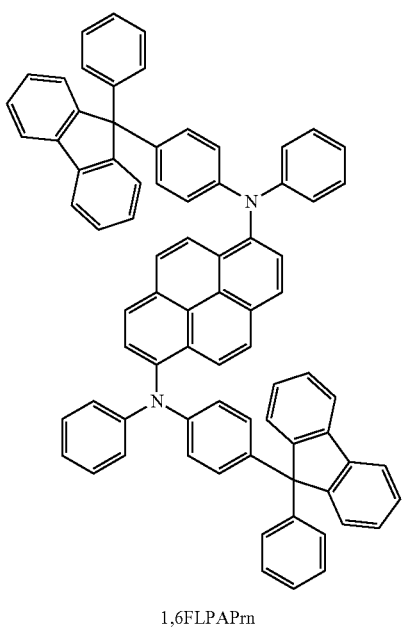

1,6FLPAPrn (vii)

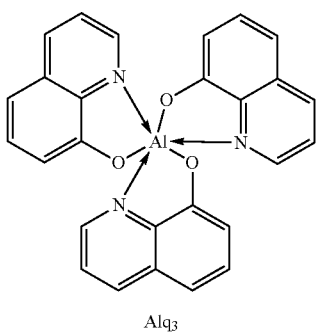

Alq$_3$

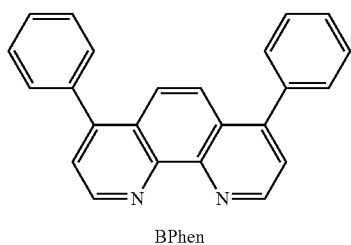

BPhen (iv)

[Fabrication of Light-Emitting Element 5 and Light-Emitting Element 6]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 9-[4-(9-phenylcarbazol-3-yl)]phenyl-10-phenylanthracene (abbreviation: PCzPA) represented by the above structural formula (v) and molybdenum(VI) oxide such that the ratio of PCzPA:molybdenum(VI) oxide was 2:1 (weight ratio). The thickness of was the layer was set to 50 nm. Note that the co-evaporation is an evaporation method in which a plurality of different substances is concurrently vaporized from the respective different evaporation sources.

Next, PCzPA was evaporated to a thickness of 10 nm, so that a hole-transport layer 112 was formed.

Further, for the light-emitting element 5, the light-emitting layer 113 was formed on the hole-transport layer 112 in such a way that DBTCzPA-II, which is the carbazole derivative represented by the above structural formula (7) and described in Embodiment 1, and N,N'-bis[4-(9-phenyl-9H-fluoren-9-yl)phenyl]-N,N'-diphenyl-pyrene-1,6-diamine (abbreviation: 1,6FLPAPrn) represented by the above structural formula (vi) were evaporated to form a 30-nm-thick film so that the ratio of DBTCzPA-II to 1,6FLPAPrn was 1:0.05 (weight ratio).

For the light-emitting element 6, the light-emitting layer 113 was formed on the hole-transport layer 112 in such a way that DBFCzPA-II, which is the carbazole derivative represented by the above structural formula (8) and described in Embodiment 1, and 1,6FLPAPrn were evaporated to form a 30-nm-thick film so that the ratio of DBFCzPA-II to 1,6FL-PAPrn was 1:0.05 (weight ratio).

Next, on the light-emitting layer 113, tris(8-quinolinolato) aluminum(III) (abbreviation: Alq) represented by the above structural formula (vii) was evaporated to a thickness of 10 nm, and then bathophenanthroline (abbreviation: BPhen) represented by the above structural formula (iv) was evaporated to a thickness of 15 nm, so that the electron-transport layer 114 was formed. Further, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting elements 5 and 6 were completed. Note that in the above evaporation processes, evaporation was all performed by a resistance heating method.

[Operation Characteristics of Light-Emitting Elements 5 and 6]

The light-emitting elements 5 and 6 thus obtained were sealed in a glove box under a nitrogen atmosphere without being exposed to the air. Then, the operation characteristics of these light-emitting elements were measured. Note that the measurements were carried out at room temperature (in an atmosphere kept at 25° C.).

Figure 18:
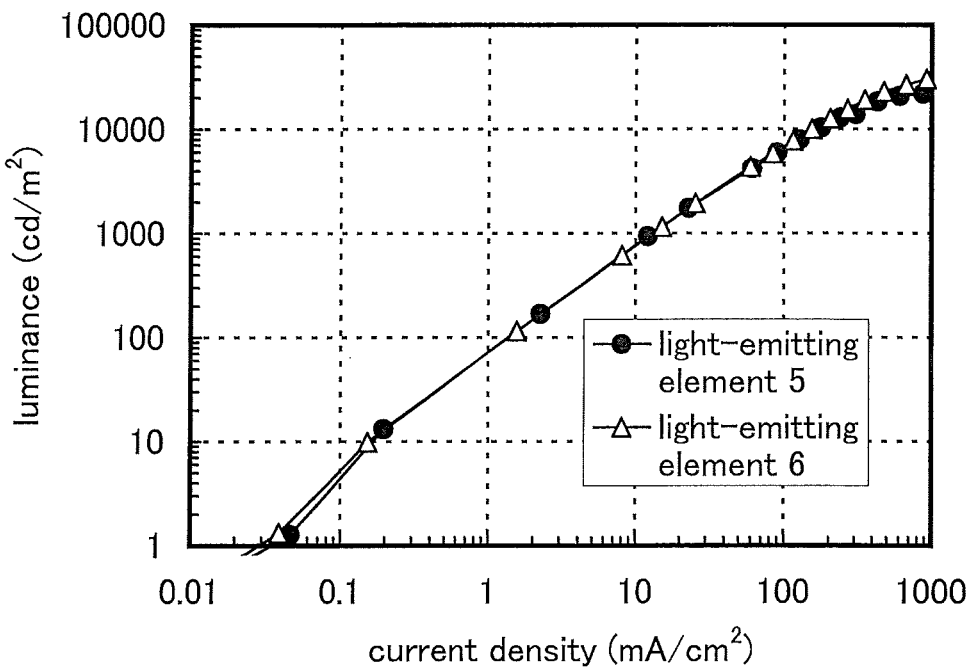
FIG. 18 shows luminance versus current density characteristics of a light-emitting element 5 and a light-emitting element 6.
Figure 19:
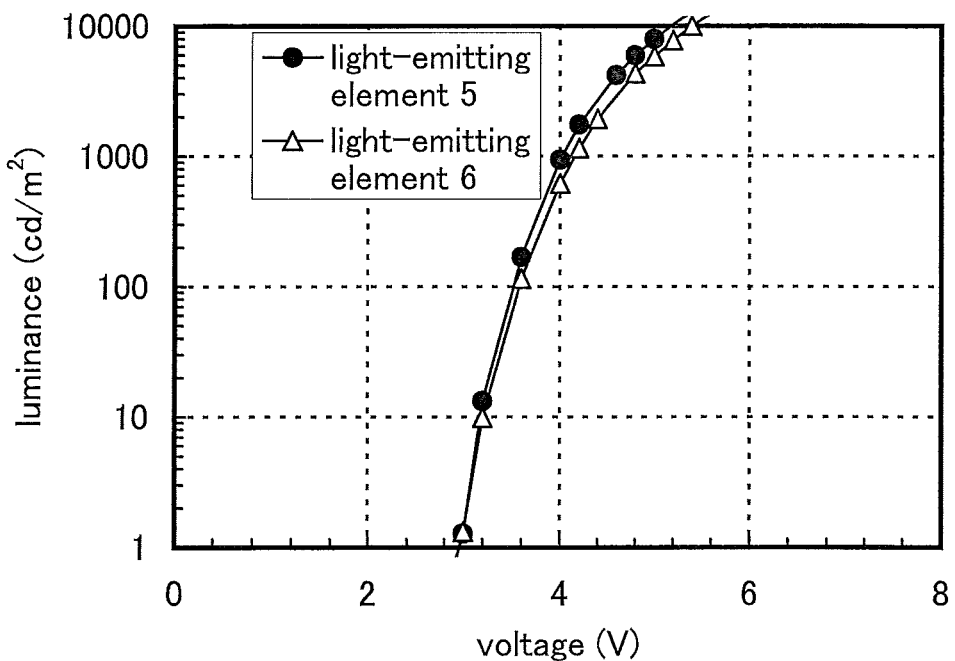
FIG. 19 shows luminance versus voltage characteristics of the light-emitting element 5 and the light-emitting element 6.
Figure 20:
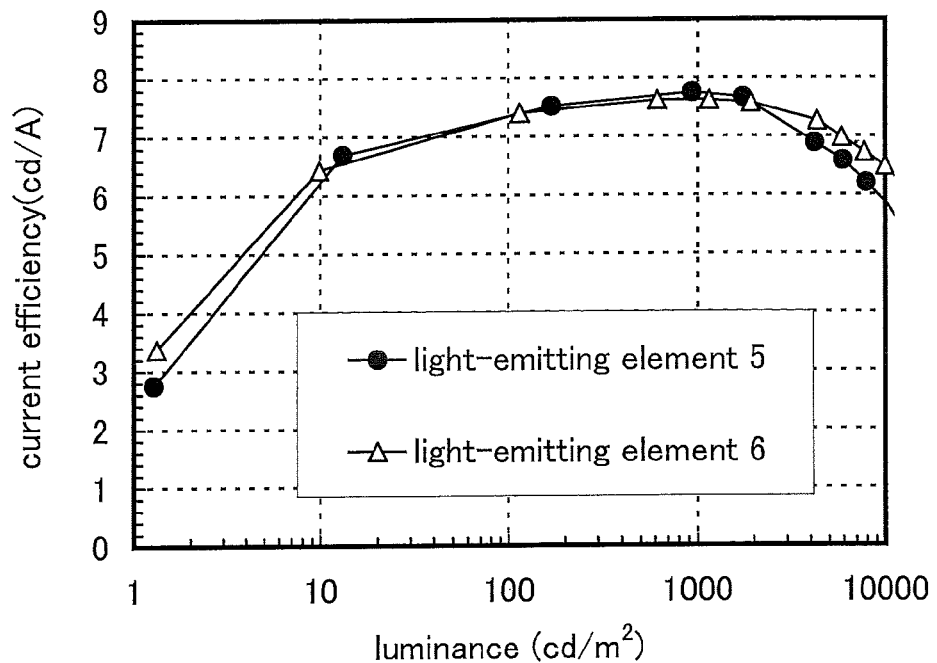
FIG. 20 shows current efficiency versus luminance characteristics of the light-emitting element 5 and the light-emitting element 6.

FIG. 18 shows luminance versus current density characteristics of the light-emitting elements, FIG. 19 shows luminance versus voltage characteristics thereof, and FIG. 20 shows current efficiency versus luminance characteristics thereof. In FIG. 18, the vertical axis represents luminance ($cd/m^2$), and the horizontal axis represents current density ($mA/cm^2$). In FIG. 19, the vertical axis represents luminance ($cd/m^2$), and the horizontal axis represents voltage (V). In FIG. 20, the vertical axis represents current efficiency (cd/A), and the horizontal axis represents luminance ($cd/m^2$).

FIG. 20 reveals that the light-emitting elements in each of which the carbazole derivative represented by the general formula (G1) is used as a host material of a light-emitting layer for emitting blue fluorescence, has favorable luminance versus emission efficiency characteristics and high emission efficiency. This is because each carbazole derivative represented by the general formula (G1) has a wide energy gap, and thus even a light-emitting substance that emits blue fluorescence and has a wide energy gap can be efficiently excited. In addition, FIG. 18 reveals that the light-emitting elements in each of which the carbazole derivative represented by the general formula (G1) is used as a host material of a light-emitting layer for emitting blue fluorescence, has favorable luminance versus voltage characteristics and can be driven with a low voltage. This indicates that each carbazole derivative represented by the general formula (G1) has an excellent carrier-transport property.

Figure 21:
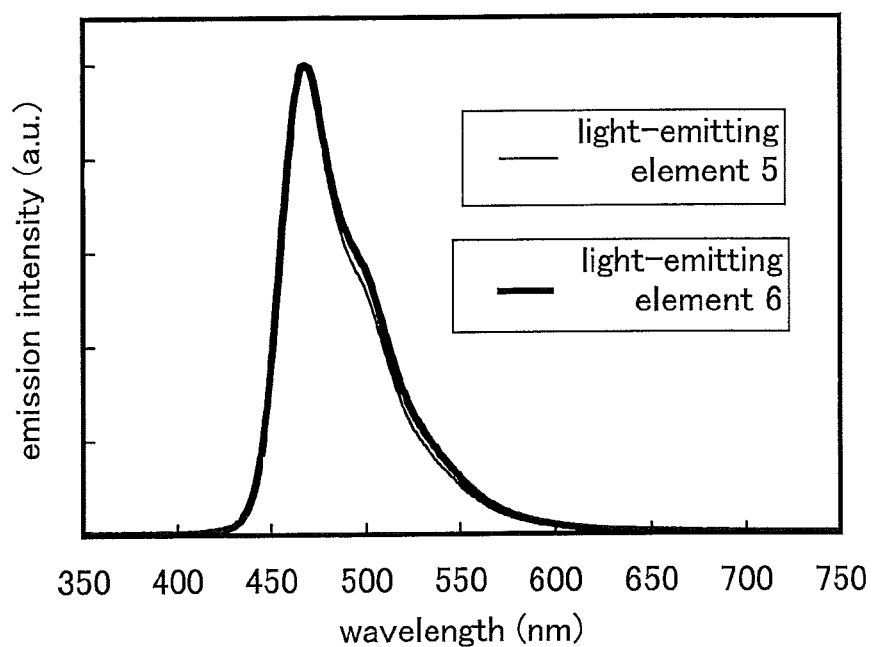
FIG. 21 shows emission spectra of the light-emitting element 5 and the light-emitting element 6.

FIG. 21 shows emission spectra when a current of 1 mA was made to flow in the fabricated light-emitting elements. In FIG. 21, the horizontal axis represents emission wavelength (nm), and the vertical axis represents emission intensity. The emission intensity is shown as a value relative to the greatest emission intensity assumed to be 1. FIG. 21 reveals that the light-emitting elements 5 and 6 each emit blue light due to 1,6FLPAPrn, which is the emission center substance.

Figure 22:
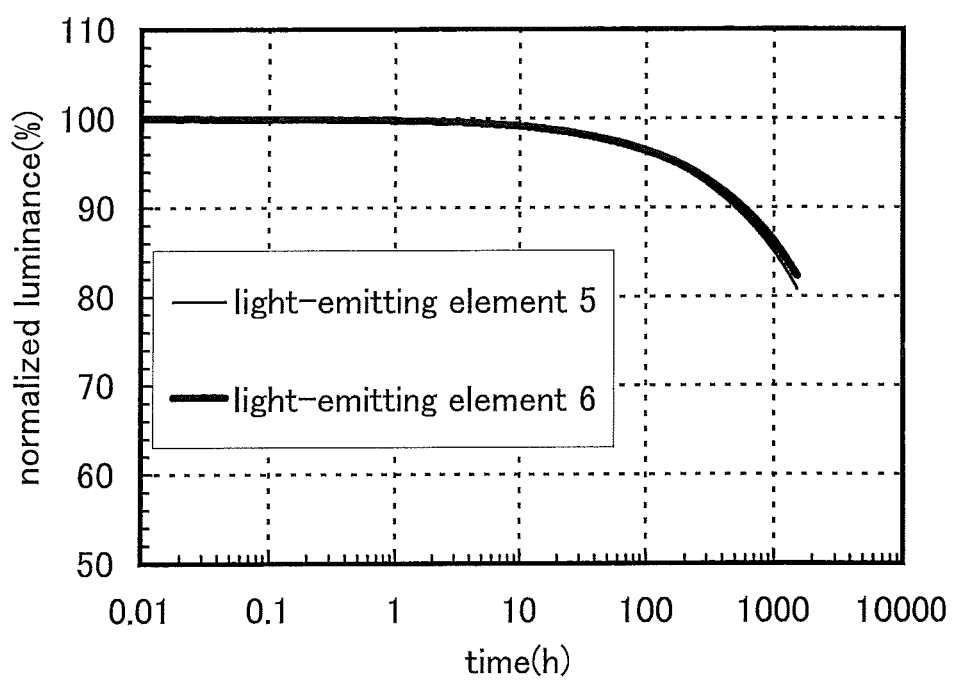
FIG. 22 shows normalized luminance versus time characteristics of the light-emitting element 5 and the light-emitting element 6.

Next, the initial luminance is set at 1000 $cd/m^2$, these elements were driven under a condition where the current density was constant, and changes in luminance with respect to the driving time were examined. FIG. 22 shows normalized luminance versus time characteristics of the light-emitting elements. From FIG. 22, it is found that each of the light-emitting elements 5 and 6 shows favorable characteristics and has high reliability.

Example 4

In this example described is a light-emitting element in which 3,6-di-(dibenzothiophen-4-yl)-9-phenyl-9H-carbazole (abbreviation: DBT2PC-II, a structural formula (9)), which is a carbazole derivative represented by the general formula (G1), is used as a material for a hole-transport layer adjacent to a light-emitting layer using an emission center substance that emits blue fluorescence.

The molecular structures of organic compounds used in this example are represented by the structural formulae (iv), (vi), (viii), and (9) below. In the element structure in FIG. 1A, an electron-injection layer is provided between an electron-transport layer 114 and a second electrode 104.

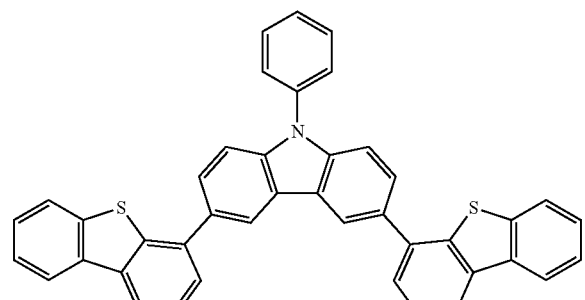

DBT2PC-II (9)

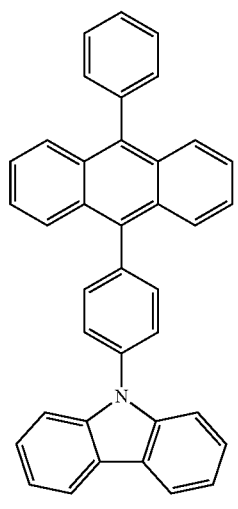

CzPA (viii)

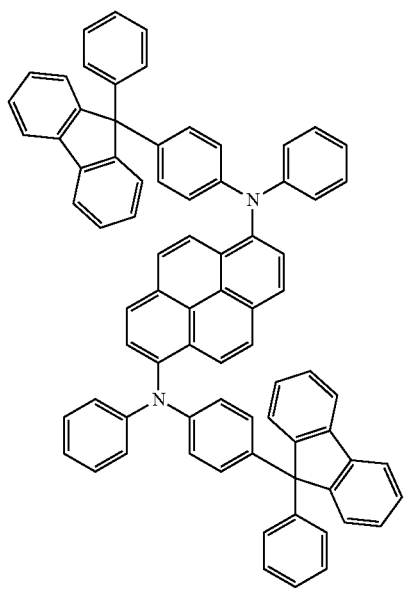

1,6FLPAPrn (vi)

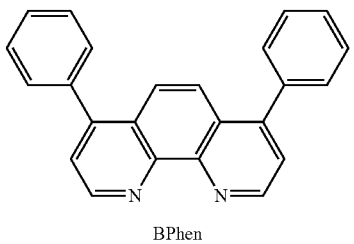

BPhen (iv)

[Fabrication of Light-Emitting Element 7]

First, a glass substrate 101 over which indium tin oxide containing silicon (ITSO) with a thickness of 110 nm was faulted as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of DBT2PC-II represented by the above structural formula (9), which is described in Embodiment 1, and molybdenum(VI) oxide such that the ratio of DBT2PC-II:molybdenum(VI) oxide was 2:1 (weight ratio). The thickness of was the layer was set to 50 nm. Note that the co-evaporation is an evaporation method in which a plurality of different substances is concurrently vaporized from the respective different evaporation sources.

Next, DBT2PC-II was evaporated to a thickness of 10 nm, so that the hole-transport layer 112 was formed.

Further, the light-emitting layer 113 was formed on the hole-transport layer 112 in such a way that 9-[4-(10-phenyl-9-anthryl)phenyl]-9H-carbazole (abbreviation: CzPA) represented by the above structural formula (viii) and N,N'-bis[4-(9-phenyl-9H-fluoren-9-yl)phenyl]-N,N'-diphenyl-pyrene-1,6-diamine (abbreviation: 1,6FLPAPrn) represented by the above structural formula (vi) were evaporated to form a 30-nm-thick film so that the ratio of CzPA to 1,6FLPAPrn was 1:0.05 (weight ratio).

Next, on the light-emitting layer 113, CzPA represented by the above structural formula (viii) was evaporated to a thickness of 10 nm, and then bathophenanthroline (abbreviation: BPhen) represented by the above structural formula (iv) was evaporated to a thickness of 15 nm, so that the electron-transport layer 114 was formed. Further, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 7 was completed. Note that in the above evaporation processes, evaporation was all performed by a resistance heating method.

[Operation Characteristics of Light-Emitting Element 7]

The light-emitting element 7 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 23:
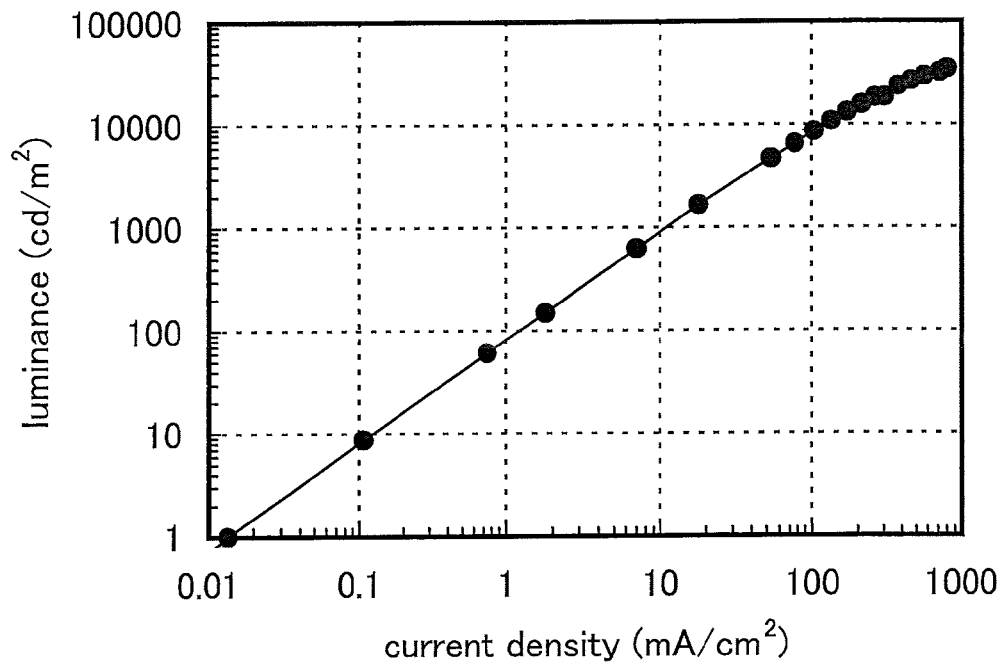
FIG. 23 shows luminance versus current density characteristics of a light-emitting element 7.
Figure 24:
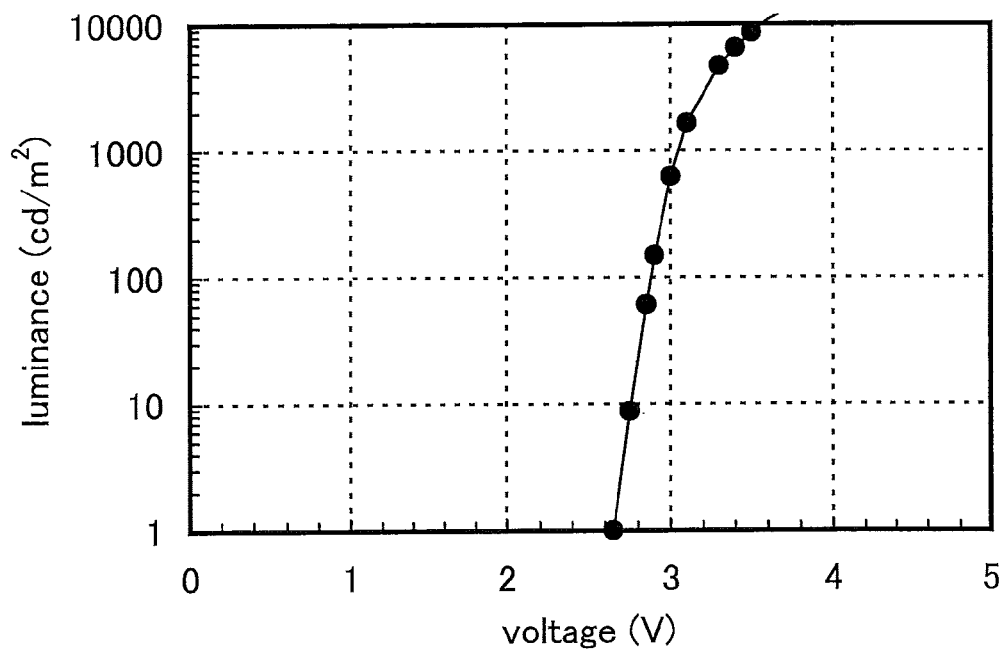
FIG. 24 shows luminance versus voltage characteristics of the light-emitting element 7.
Figure 25:
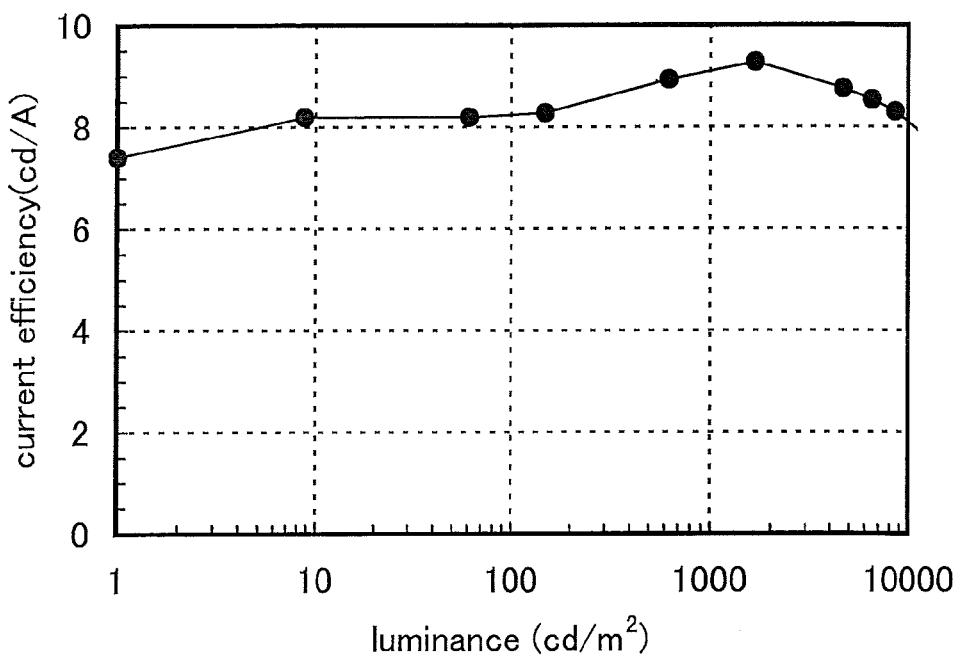
FIG. 25 shows current efficiency versus luminance characteristics of the light-emitting element 7.

FIG. 23 shows luminance versus current density characteristics of the light-emitting element 7, FIG. 24 shows luminance versus voltage characteristics thereof, and FIG. 25 shows current efficiency versus luminance characteristics thereof. In FIG. 23, the vertical axis represents luminance (cd/m$^2$), and the horizontal axis represents current density (mA/cm$^2$). In FIG. 24, the vertical axis represents luminance (cd/m$^2$), and the horizontal axis represents voltage (V). In FIG. 25, the vertical axis represents current efficiency (cd/A), and the horizontal axis represents luminance (cd/m$^2$).

FIG. 25 reveals that the light-emitting element, in which the carbazole derivative represented by the general formula (G1) is used as a material for a hole-transport layer in contact with a light-emitting layer for emitting blue fluorescence, has favorable luminance versus emission efficiency characteristics and high emission efficiency. This is because the carbazole derivative represented by the general formula (G1) has a wide energy gap, and thus transfer of excitation energy can be suppressed despite the adjacency to a light-emitting substance that emits blue fluorescence and has a wide energy gap. In addition, FIG. 23 reveals that the light-emitting element, in which the carbazole derivative represented by the general formula (G1) is used as a material for a hole-transport layer adjacent to a light-emitting layer for emitting blue fluorescence, has favorable luminance versus voltage characteristics and can be driven with a low voltage. This indicates that any of the carbazole derivatives represented by the general formula (G1) has an excellent carrier-transport property.

Figure 26:
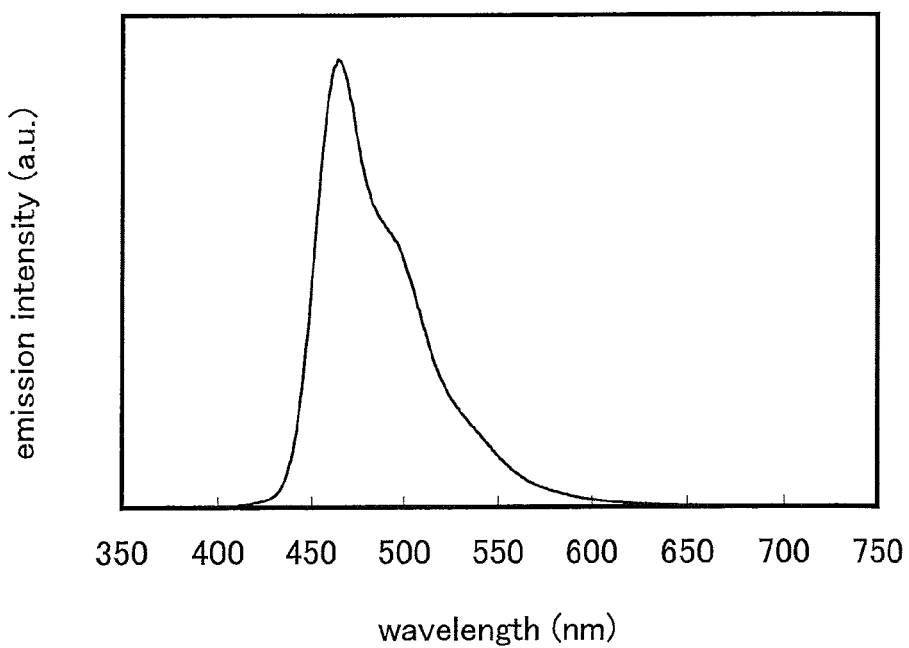
FIG. 26 shows an emission spectrum of the light-emitting element 7.

FIG. 26 shows an emission spectrum when a current of 1 mA was made to flow in the fabricated light-emitting element 7. In FIG. 26, the horizontal axis represents emission wavelength (nm), and the vertical axis represents emission intensity. The emission intensity is shown as a value relative to the greatest emission intensity assumed to be 1. FIG. 26 reveals that the light-emitting element 7 emits blue light due to 1,6FLPAPrn, which is the emission center substance.

Example 5

In this example described is a light-emitting element in which 2,7-di-(dibenzothiophen-4-yl)-9-phenyl-9H-carbazole (abbreviation: 2,7DBT2PC-II, a structural formula (10)), which is a carbazole derivative represented by the general formula (G1), is used as a material for a hole-transport layer adjacent to a light-emitting layer using an emission center substance that emits blue fluorescence.

The molecular structures of organic compounds used in this example are represented by the structural formulae (iv), (vi), (viii), and (10) below. In the element structure in FIG. 1A, an electron-injection layer is provided between an electron-transport layer 114 and a second electrode 104.

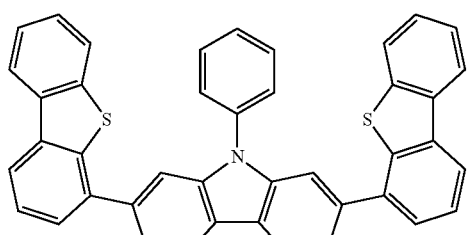

2,7DBT2PC-II (10)

-continued

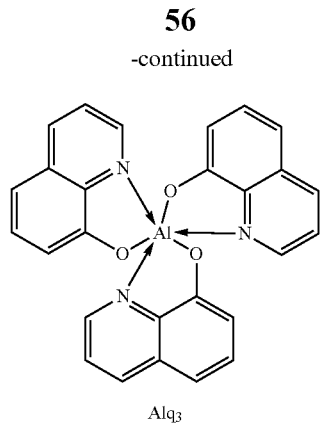

Alq$_3$ (vii)

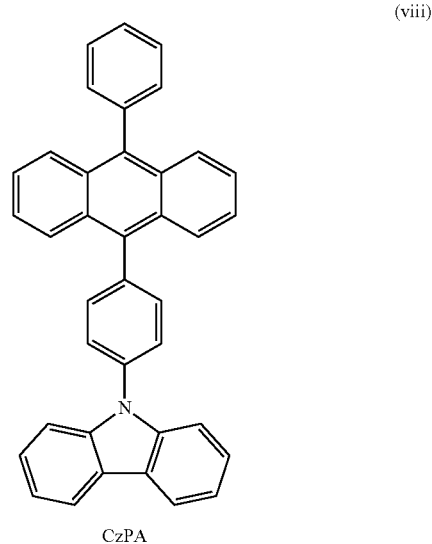

CzPA (viii)

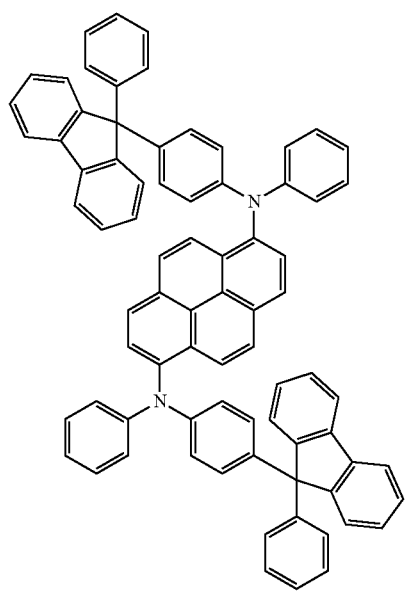

1,6FLPAPrn (vi)

-continued

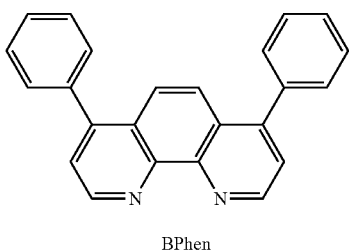

BPhen

[Fabrication of Light-Emitting Element 8]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 2,7DBT2PC-II represented by the above structural formula (10), which is described in Embodiment 1, and molybdenum(VI) oxide such that the ratio of 2,7DBT2PC-II:molybdenum(VI) oxide was 2:1 (weight ratio). The thickness of was the layer was set to 50 nm Note that the co-evaporation is an evaporation method in which a plurality of different substances is concurrently vaporized from the respective different evaporation sources.

Next, 2,7DBT2PC-II was evaporated to a thickness of 10 nm, so that the hole-transport layer 112 was formed.

Further, the light-emitting layer 113 was formed on the hole-transport layer 112 in such a way that 9-[4-(10-phenyl-9-anthryl)phenyl]-9H-carbazole (abbreviation: CzPA) represented by the above structural formula (viii) and N,N'-bis[4-(9-phenyl-9H-fluoren-9-yl)phenyl]-N,N'-diphenyl-pyrene-1,6-diamine (abbreviation: 1,6FLPAPrn) represented by the above structural formula (vi) were evaporated to form a 30-nm-thick film so that the ratio of CzPA to 1,6FLPAPrn was 1:0.05 (weight ratio).

Next, on the light-emitting layer 113, Alq represented by the above structural formula (vii) was evaporated to a thickness of 10 nm, and then bathophenanthroline (abbreviation: BPhen) represented by the above structural formula (iv) was evaporated to a thickness of 15 nm, so that the electron-transport layer 114 was formed. Further, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 8 was completed. Note that in the above evaporation processes, evaporation was all performed by a resistance heating method.

[Operation Characteristics of Light-Emitting Element 8]

The light-emitting element 8 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 27:
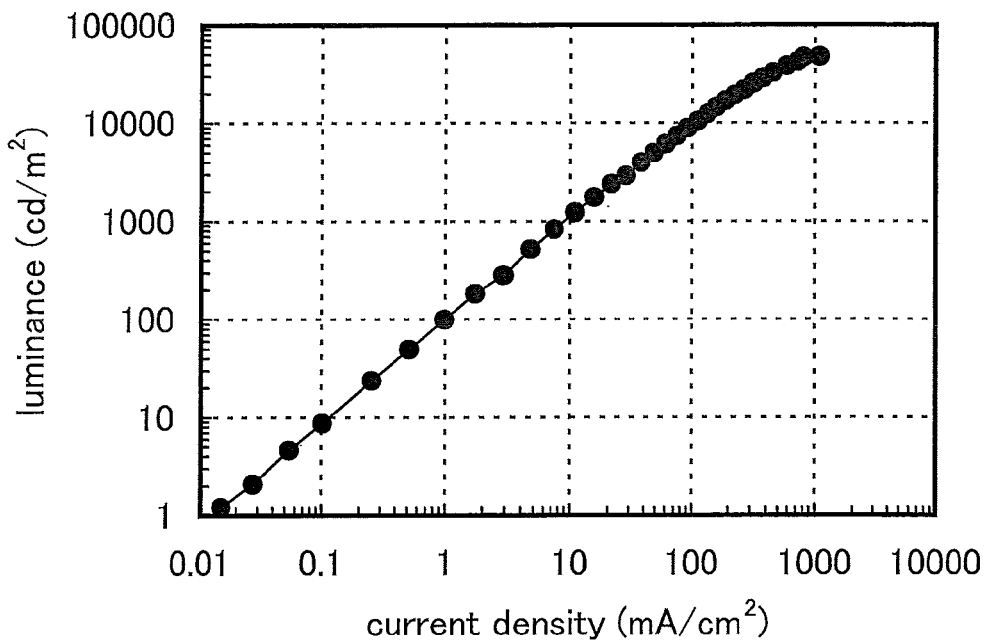
FIG. 27 shows luminance versus current density characteristics of a light-emitting element 8.
Figure 28:
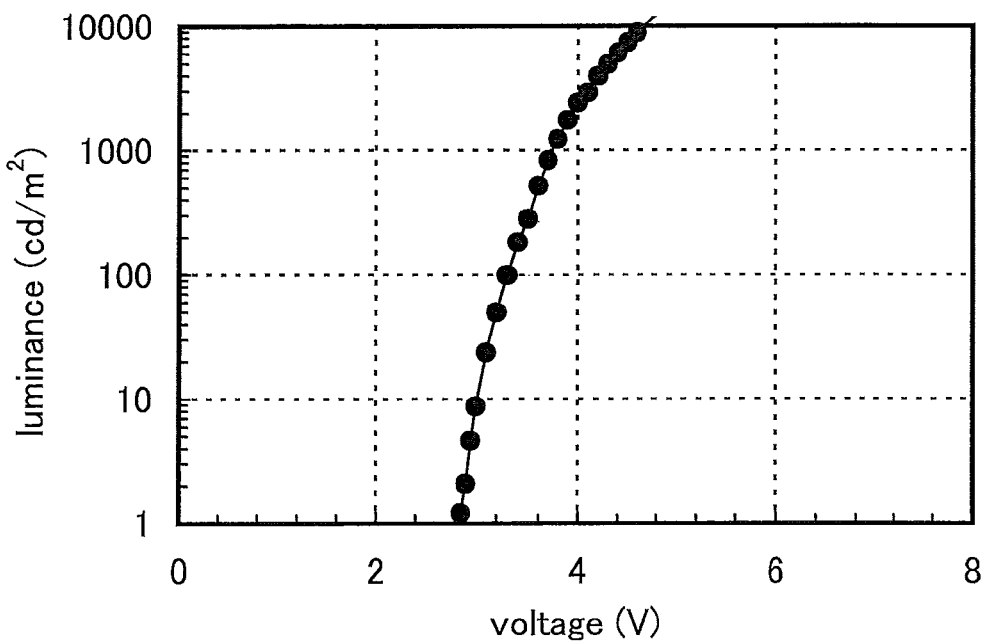
FIG. 28 shows luminance versus voltage characteristics of the light-emitting element 8.
Figure 29:
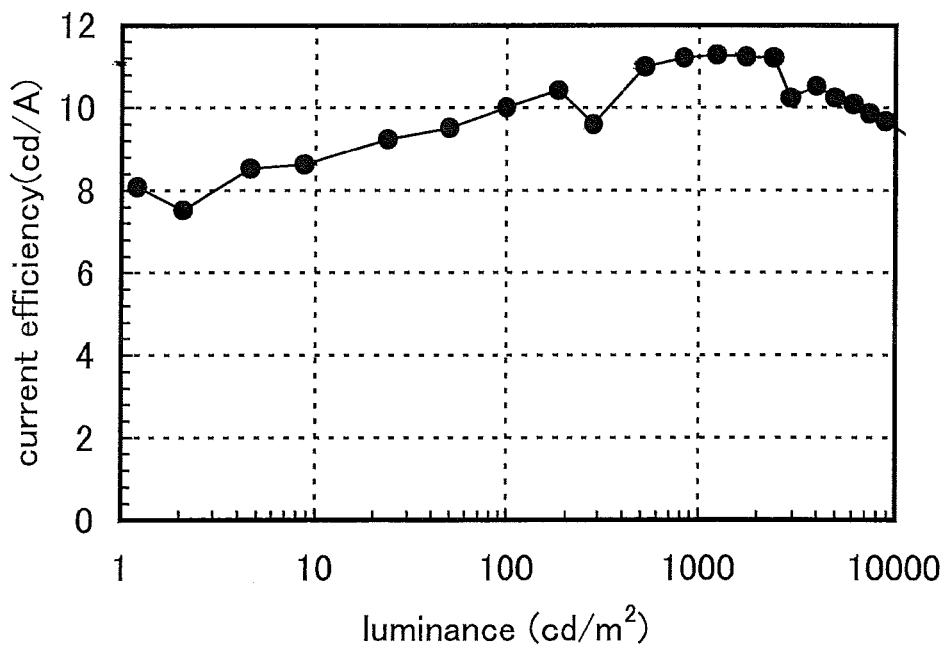
FIG. 29 shows current efficiency versus luminance characteristics of the light-emitting element 8.

FIG. 27 shows luminance versus current density characteristics of the light-emitting element 8, FIG. 28 shows luminance versus voltage characteristics thereof, and FIG. 29 shows current efficiency versus luminance characteristics thereof. In FIG. 27, the vertical axis represents luminance (cd/m²), and the horizontal axis represents current density (mA/cm²). In FIG. 28, the vertical axis represents luminance (cd/m²), and the horizontal axis represents voltage (V). In FIG. 29, the vertical axis represents current efficiency (cd/A), and the horizontal axis represents luminance (cd/m²).

FIG. 29 reveals that the light-emitting element, in which the carbazole derivative represented by the general formula (G1) is used as a material for a hole-transport layer in contact with a light-emitting layer for emitting blue fluorescence, has favorable luminance versus emission efficiency characteristics and high emission efficiency. This is because the carbazole derivative represented by the general formula (G1) has a wide energy gap, and thus transfer of excitation energy can be suppressed despite the adjacency to a light-emitting substance that emits blue fluorescence and has a wide energy gap. In addition, FIG. 27 reveals that the light-emitting element, in which the carbazole derivative represented by the general formula (G1) is used as a material for a hole-transport layer adjacent to a light-emitting layer for emitting blue fluorescence, has favorable luminance versus voltage characteristics and can be driven with a low voltage. This indicates that any of the carbazole derivatives represented by the general formula (G1) has an excellent carrier-transport property.

Figure 30:
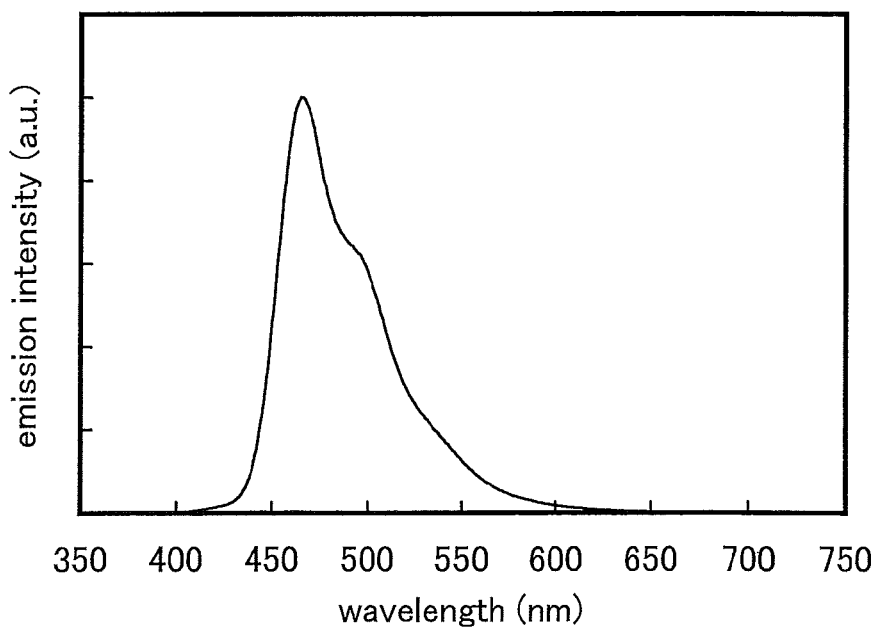
FIG. 30 shows an emission spectrum of the light-emitting element 8.

FIG. 30 shows an emission spectrum when a current of 1 mA was made to flow in the fabricated light-emitting element 8. In FIG. 30, the horizontal axis represents emission wavelength (nm), and the vertical axis represents emission intensity. The emission intensity is shown as a value relative to the greatest emission intensity assumed to be 1. FIG. 30 reveals that the light-emitting element 8 emits blue light due to 1,6FLPAPrn, which is the emission center substance.

Example 6

Synthesis Example 1

In this example is described a method of synthesizing 2-[4-{3-(dibenzothiophen-4-yl)-9H-carbazol-9-yl}phenyl]-1-phenylbenzimidazole (abbreviation: DBTCzBIm-II), which is the carbazole derivative represented by the general formula (G1). A structure of DBTCzBIm-II is illustrated in the following structural formula (1).

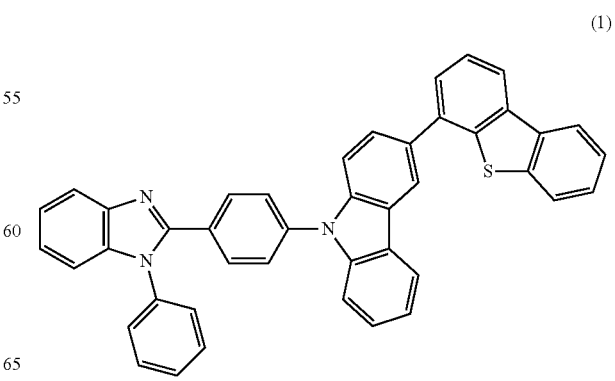

First, a method of synthesizing 3-(dibenzothiophen-4-yl)-9H-carbazole, which is a synthetic intermediate of DBTCzBIm-II, will be described. 3-(Dibenzothiophen-4-yl)-9H-carbazole is a carbazole derivative represented by a structural formula below. A structure of 3-(dibenzothiophen-4-yl)-9H-carbazole is shown in the following structural formula (2).

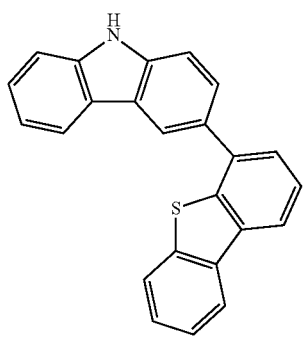

(2)

Step 1: Synthesis of 3-(Dibenzothiophen-4-yl)-9H-carbazole

In a 200-mL three-neck flask were put 3.0 g (12 mmol) of 3-bromocarbazole, 2.8 g (12 mmol) of dibenzothiophene-4-boronic acid, and 150 mg (0.5 mol) of tri(ortho-tolyl)phosphine, and the air in the flask was replaced with nitrogen. To this mixture were added 40 mL of toluene, 40 mL of ethanol, and 15 mL (2.0 mol/L) of an aqueous potassium carbonate solution. In the flask, the mixture was degassed by being stirred under reduced pressure. After the degassing, replacement with nitrogen was performed, and 23 mg (0.10 mmol) of palladium(II) acetate was added to this mixture, and then the mixture was refluxed at 110° C. for 3 hours. After the reflux, the mixture was cooled to room temperature, and then the obtained solid was collected by suction filtration. The collected solid was dissolved in 100 mL of toluene, and this solution was filtered through Celite (produced by Wako Pure Chemical Industries, Ltd., Catalog No. 531-16855), Florisil (produced by Wako Pure Chemical Industries, Ltd., Catalog No. 540-00135), and alumina. The solid obtained by concentration of the obtained filtrate was recrystallized from toluene/hexane, so that 1.4 g of a white solid was obtained in 32% yield. The synthesis scheme of Step 1 is illustrated in (a-1).

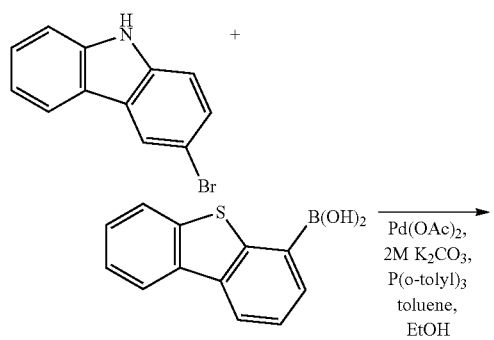

(a-1)

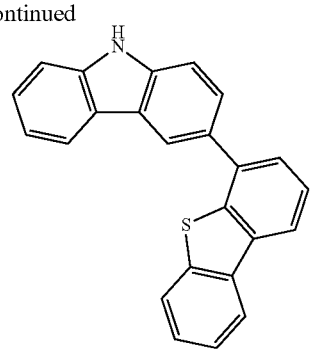

Step 2: Synthesis of N-Phenyl-2-{4-[3-(dibenzothiophen-4-yl)-9H-carbazol-9-yl]phenyl}benzimidazole (abbreviation: DBTCzBIm-II)

In a 100-mL three-neck flask were put 0.36 g (1.0 mmol) of N-phenyl-2-(4-bromophenyl)benzimidazole and 0.36 g (1.0 mmol) of 3-(dibenzothiophen-4-yl)-9H-carbazole, and the air in the flask was replaced with nitrogen. To this mixture were added 10 mL of toluene, 0.10 mL of tri(tert-butyl)phosphine (a 10 wt % hexane solution), 0.15 g (4.3 mmol) of sodium tert-butoxide. This mixture was degassed while being stirred under reduced pressure. After this mixture was heated to 80° C., 5.0 mg (0.025 mmol) of bis(dibenzylideneacetone)palladium(0) was added thereto, and then the mixture was stirred at 80° C. for 3 hours. After the stirring, 14 mg (0.025 mmol) of bis(dibenzylideneacetone)palladium(0) was added to this mixture, and then it was further stirred at 110° C. for 7.5 hours. After the stirring, about 30 mL of toluene was added to the mixture, and then it was stirred at 80° C. This mixture was subjected to hot filtration with ethyl acetate through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give a white solid. The obtained solid was dissolved in toluene. The mixture was purified by silica gel column chromatography (a developing solvent in which the hexane/ethyl acetate ratio was 4:1), and further recrystallized from toluene/hexane, so that 0.41 g of a white solid was obtained in 65% yield. The synthesis scheme of Step 2 is illustrated in (b-1).

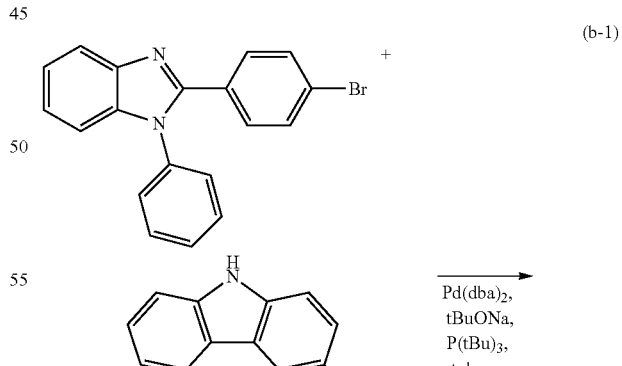

(b-1)

-continued

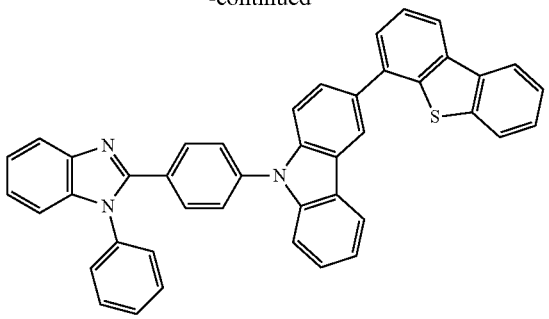

Then, 0.40 g of the obtained white solid was purified. Using a train sublimation method, the purification was conducted by heating of the white solid at 290° C. under a pressure of 2.3 Pa with a flow rate of argon gas 5.0 of mL/min. After the purification, 0.32 g of a colorless transparent solid was obtained in 78% yield.

Figure 31A:
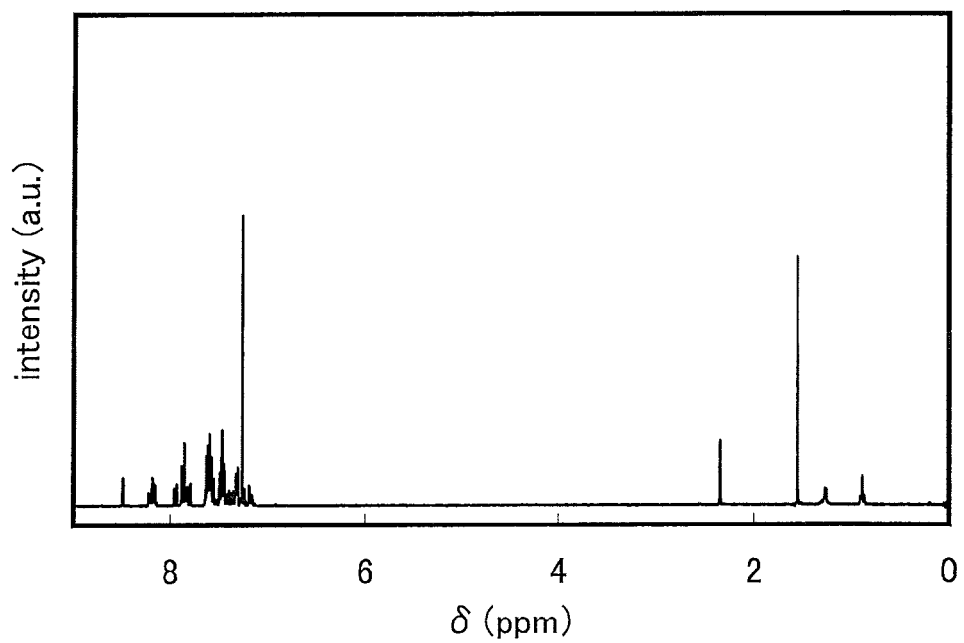
FIGS. 31A and 31B are $^1$H NMR charts of DBTCzBIm-II.
Figure 31B:
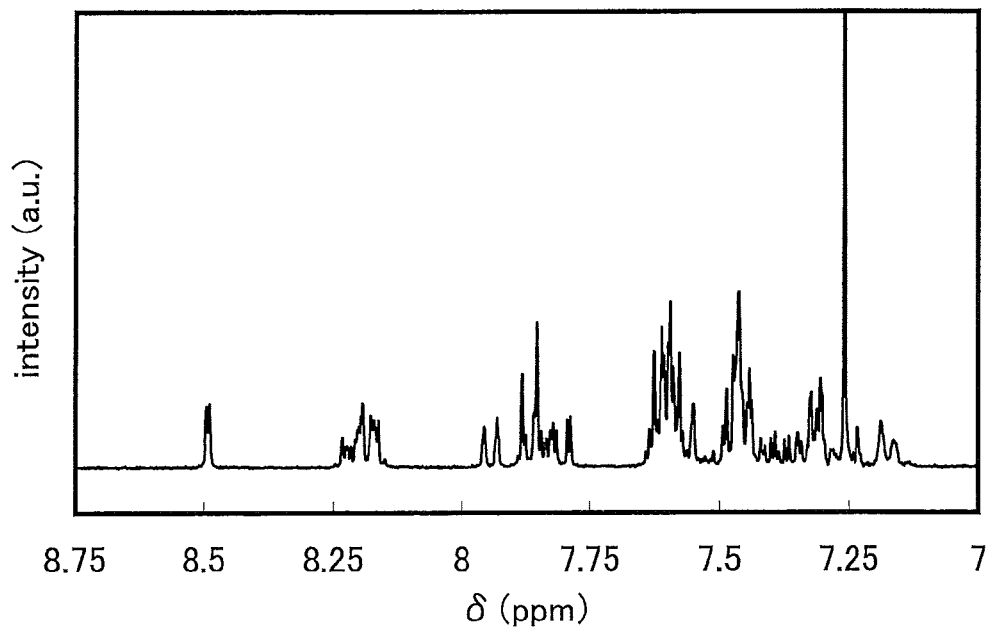

The colorless and transparent solid after the purification was subjected to nuclear magnetic resonance ($^1$H NMR) spectroscopy. The measurement data are shown below. In addition, $^1$H NMR charts are shown in FIGS. 31A and 31B. Note that FIG. 31B is a chart where the range of from 7 ppm to 8.75 ppm in FIG. 31A is enlarged.

$^1$H NMR (CDCl$_3$, 300 MHz): δ=7.31-7.42 (m, 4H), 7.44-7.49 (m, 6H), 7.51-7.64 (m, 8H), 7.79-7.89 (m, 4H), 7.94 (d, J=7.8 Hz, 1H), 8.45-8.23 (m, 3H), 8.49 (d, J=2.1 Hz, 1H)

The measurement results showed that DBTCzBIm-II, which is the carbazole derivative represented by the above structural formula (1), was obtained.

Figure 32:
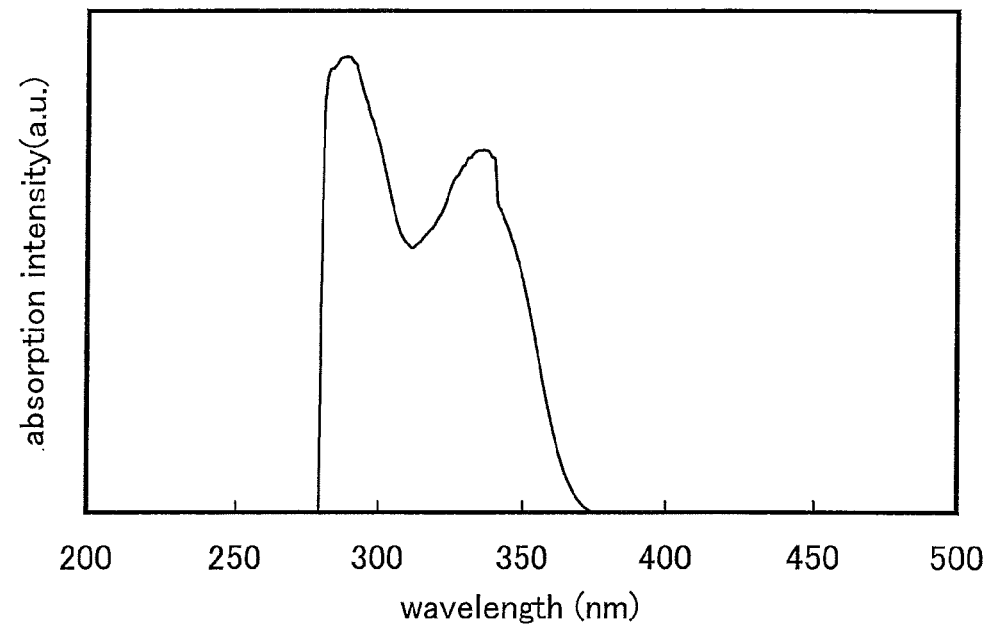
FIG. 32 shows an absorption spectrum of DBTCzBIm-II in a solution of DBTCzBIm-II (the solvent of which is toluene).
Figure 33:
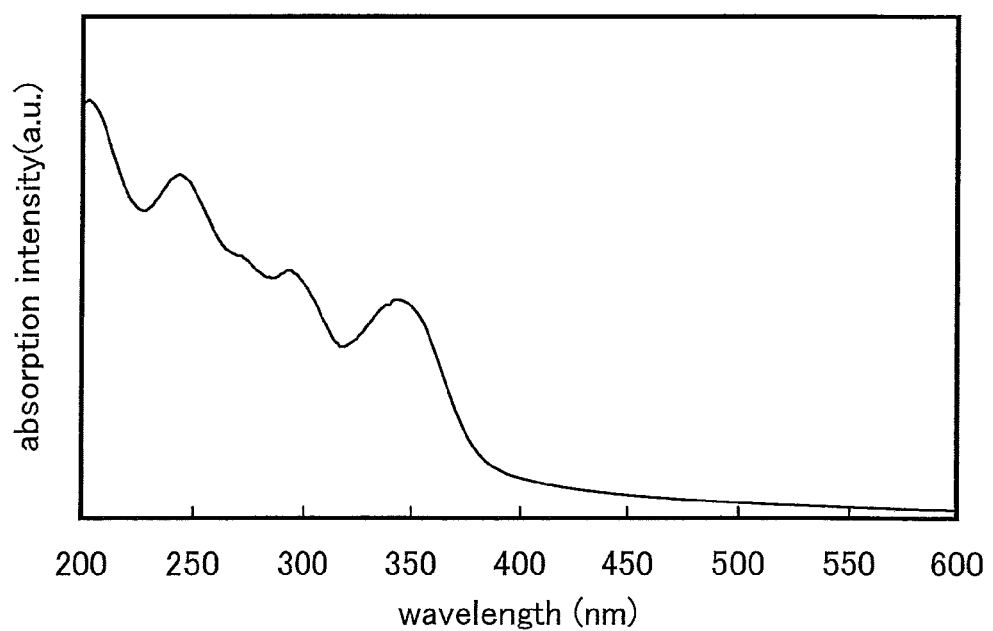
FIG. 33 shows an absorption spectrum of DBTCzBIm-II in a thin film state.

Further, an absorption spectrum of DBTCzBIm-II in a toluene solution of DBTCzBIm-II is shown in FIG. 32, and an absorption spectrum of a thin film of DBTCzBIm-II is shown in FIG. 33. An ultraviolet-visible spectrophotometer (V-550, manufactured by JASCO Corporation) was used for the measurements of the absorption spectra. In the case of the toluene solution, the measurements were made with the toluene solution of DBTCzBIm-II put in a quartz cell, and the absorption spectrum obtained by subtraction of the absorption spectra of quartz and toluene from the measured spectra is shown in the drawing. In addition, as for the absorption spectrum of the thin film, a sample was prepared by evaporation of DBTCzBIm-II on a quartz substrate, and the absorption spectrum obtained by subtraction of that of quartz from the measured spectra is shown in the drawing. In FIG. 32 and FIG. 33, the horizontal axis represents wavelength (nm) and the vertical axis represents absorption intensity (arbitrary unit).

Figure 34:
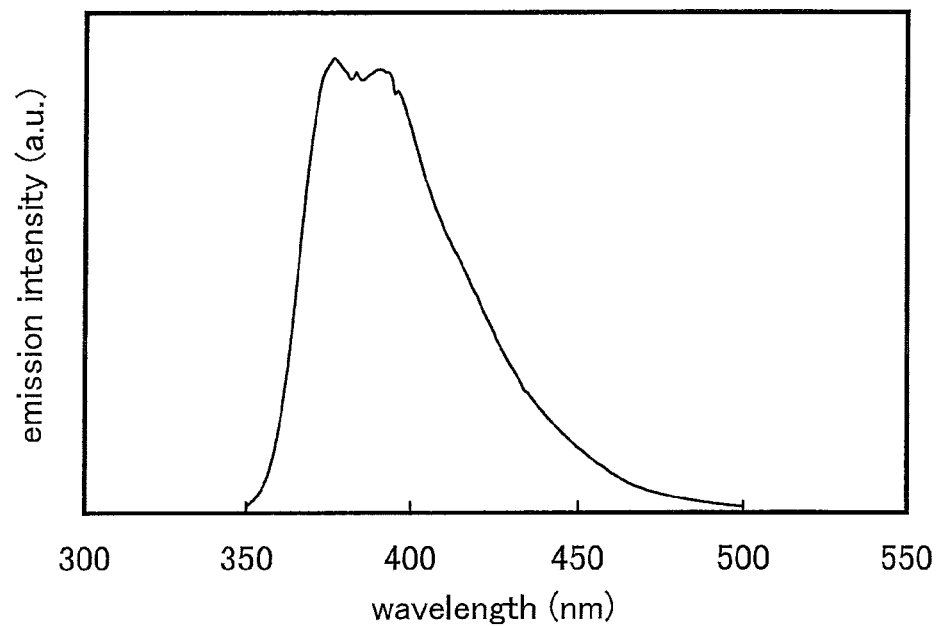
FIG. 34 shows an emission spectrum of DBTCzBIm-II in the solution of DBTCzBIm-II (the solvent of which is toluene).
Figure 35:
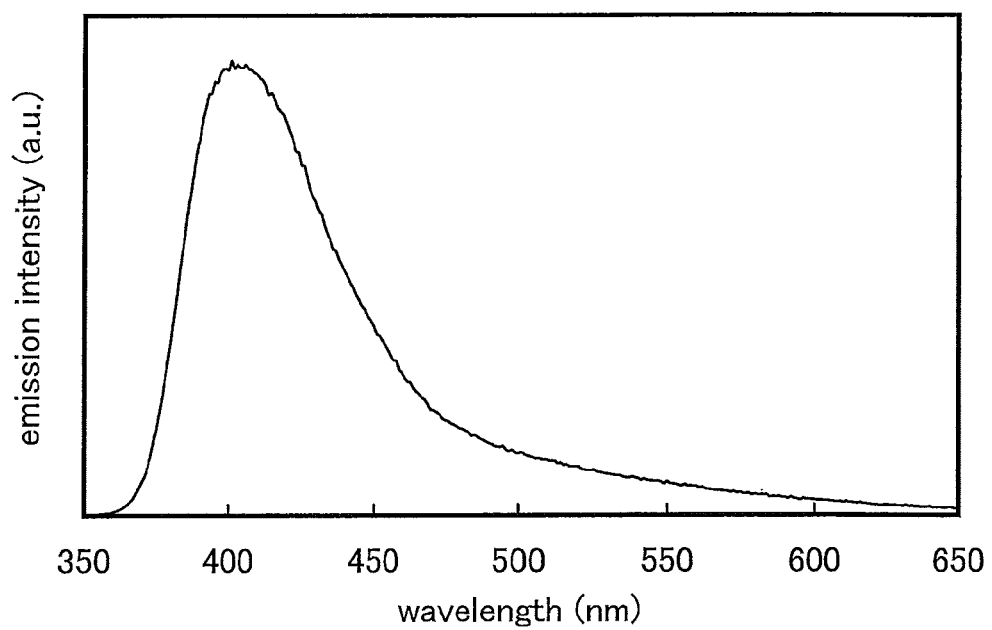
FIG. 35 shows an emission spectrum of DBTCzBIm-II in a thin film state.

An emission spectrum of DBTCzBIm-II in the toluene solution of DBTCzBIm-II is shown in FIG. 34, and an emission spectrum of the thin film of DBTCzBIm-II is shown in FIG. 35. As in the measurements of the absorption spectra, an ultraviolet-visible spectrophotometer (V-550, manufactured by JASCO Corporation) was used for the measurements. The emission spectrum in the case of the toluene solution was measured with the toluene solution of DBTCzBIm-II put in a quartz cell, and the emission spectrum of the thin film was measured with a sample prepared by evaporation of DBTCzBIm-II on a quartz substrate. FIG. 34 shows that the greatest emission wavelength of DBTCzBIm-II in the toluene solution of DBTCzBIm-II was around 377 nm (at an excitation wavelength of 340 nm) and FIG. 35 shows that the greatest emission wavelength of the thin film of DBTCzBIm-II was around 402 nm (at an excitation wavelength of 339 nm).

Further, the ionization potential of DBTCzBIm-II in a thin film state was measured by a photoelectron spectrometer (AC-2, manufactured by Riken Keiki, Co., Ltd.) in air. The obtained value of the ionization potential was converted to a negative value, so that the HOMO level of DBTCzBIm-II was −5.68 eV. From the data of the absorption spectra of the thin film in FIG. 33, the absorption edge of DBTCzBIm-II, which was obtained from Tauc plot with an assumption of direct transition, was 3.31 eV. Therefore, the optical energy gap of DBTCzBIm-II in the solid state was estimated at 3.31 eV; from the values of the HOMO level obtained above and this energy gap, the LUMO level of DBTCzBIm-II was able to be estimated at −2.37 eV. It was thus found that DBTCzBIm-II had a wide energy gap of 3.31 eV in the solid state.

Further, the oxidation reaction characteristics of DBTCzBIm-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.00 V to 1.10 V and then changed from 1.10 V to 0.00 V was one cycle, and 100 cycles were performed.

The measurement results revealed that DBTCzBIm-II showed properties effective against repetition of redox reactions between an oxidized state and a neutral state without a large variation in oxidation peak even after the 100 cycles in the measurements.

Further, the HOMO level of DBTCzBIm-II was determined also by calculation from the CV measurement results.

First, the potential energy of the reference electrode with respect to the vacuum level used was found to be −4.94 eV. The oxidation peak potential $E_{pa}$ of DBTCzBIm-II was 1.03 V. In addition, the reduction peak potential $E_{pc}$ thereof was 0.90 V. Therefore, a half-wave potential (an intermediate potential between $E_{pa}$ and $E_{pc}$) can be calculated at 0.97 V. This means that DBTCzBIm-II is oxidized by an electric energy of 0.97 [V versus Ag/Ag$^+$], and this energy corresponds to the HOMO level. Here, since the potential energy of the reference electrode, which was used in this example, with respect to the vacuum level is −4.94 [eV] as described above, the HOMO level of DBTCzBIm-II was calculated as follows: −4.94−0.97=−5.91 [eV].

Note that the potential energy of the reference electrode (Ag/Ag$^+$ electrode) with respect to the vacuum level corresponds to the Fermi level of the Ag/Ag$^+$ electrode, and should be calculated from a value obtained by measuring a substance whose potential energy with respect to the vacuum level is known, with the use of the reference electrode (Ag/Ag$^+$ electrode).

How the potential energy (eV) of the reference electrode (Ag/Ag$^+$ electrode), which was used in this example, with respect to the vacuum level is determined by calculation will be specifically described. It is known that the oxidation-reduction potential of ferrocene in methanol is +0.610 V [vs. SHE] with respect to a standard hydrogen electrode (Reference: Christian R. Goldsmith et al., *J. Am. Chem. Soc.*, Vol. 124, No. 1, pp. 83-96, 2002). In contrast, using the reference electrode used in this example, the oxidation-reduction potential of ferrocene in methanol was calculated at +0.11 V [vs. Ag/Ag$^+$]. Thus, it was found that the potential energy of the reference electrode used in this example was lower than that of the standard hydrogen electrode by 0.50 [eV].

Here, it is known that the potential energy of the standard hydrogen electrode with respect to the vacuum level is −4.44 eV (Reference: Toshihiro Ohnishi and Tamami Koyama, *High molecular EL material*, Kyoritsu shuppan, pp. 64-67). Therefore, the potential energy of the reference electrode used in this example with respect to the vacuum level can be calculated at −4.44−0.50=−4.94 [eV].

Example 7

Synthesis Example 2

In this example is described a method of synthesizing 2-[4-{3-(dibenzofuran-4-yl-9H-carbazol-9-yl}phenyl]-1-phenylbenzimidazole (abbreviation: DBFCzBIm-II), which is one of the carbazole derivatives described in Embodiment 1. A structure of DBFCzBIm-II is illustrated in the following structural formula (3).

(3)

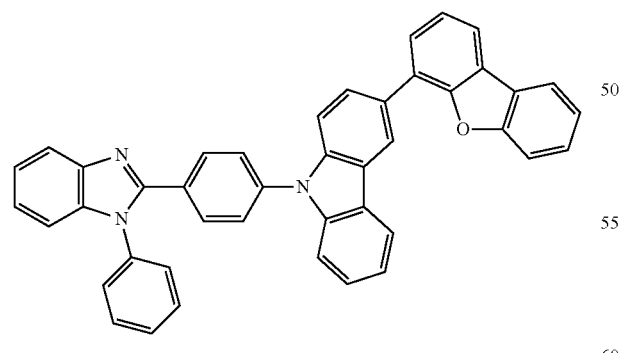

First, a method of synthesizing 4-(9H-carbazol-3-yl) dibenzofuran, which is a synthetic intermediate of DBFCzBIm-II, will be described. 4-(9H-Carbazol-3-yl)dibenzofuran is a carbazole derivative represented by the following structural formula (4).

(4)

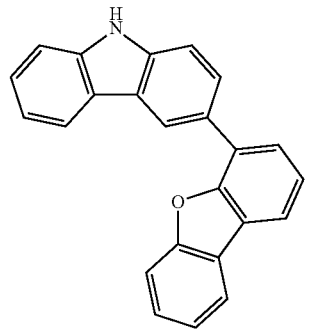

Step 1: Synthesis of 4-(9H-Carbazol-3-yl)dibenzofuran

In a 200-mL three-neck flask were put 2.0 g (8.1 mmol) of 3-bromocarbazole, 1.7 g (8.1 mmol) of dibenzofuran-4-boronic acid, and 150 mg (0.5 mol) of tri(ortho-tolyl)phosphine, and the air in the flask was replaced with nitrogen. To this mixture were added 20 mL of toluene, 20 mL of ethanol, and 15 mL (0.2 mol) of an aqueous potassium carbonate solution (2.0 mol/L). In the flask, the mixture was degassed by being stirred under reduced pressure. After 23 mg (0.10 mmol) of palladium(II) acetate was added to this mixture, the mixture was refluxed at 80° C. After the reflux, the mixture was cooled to room temperature, and then the obtained solid was collected by suction filtration. The collected solid was dissolved in 100 mL of toluene, and this solution was filtered through Celite (produced by Wako Pure Chemical Industries, Ltd., Catalog No. 531-16855), alumina, and Florisil (produced by Wako Pure Chemical Industries, Ltd., Catalog No. 540-00135). The solid obtained by concentration of the obtained filtrate was recrystallized from toluene/hexane, so that 2.3 g of a white solid was obtained in 85% yield. The synthesis scheme of Step 1 is illustrated in (a-2).

(a-2)

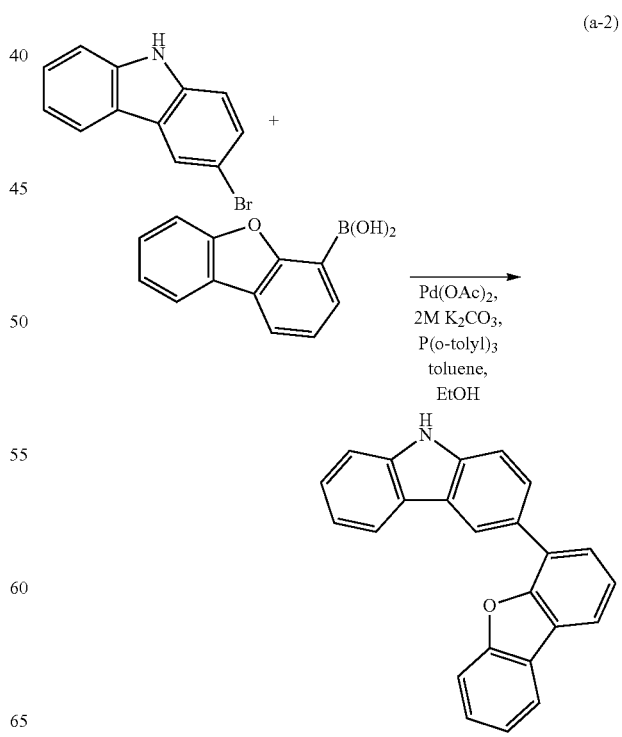

Step 2: Synthesis of 2-[4-{3-(Dibenzofuran-4-yl)-9H-carbazol-9-yl}phenyl]-1-phenylbenzimidazole (abbreviation: DBFCzBIm-II)

To a 100-mL three-neck flask were added 0.70 g (1.0 mmol) of 2-(4-bromophenyl)-3-phenylbenzimidazole and 0.67 g (1.0 mmol) of 4-(9H-carbazol-3-yl)dibenzofuran, and the air in the flask was replaced with nitrogen. To this mixture were added 15 mL of toluene, 0.10 mL of tri(tert-butyl) phosphine (a 10 wt % hexane solution), 0.48 g (4.3 mmol) of sodium tert-butoxide. This mixture was degassed while being stirred under reduced pressure. This mixture was stirred at 110° C. for 20 hours. After the stirring, the mixture was washed twice with about 30 mL of water, and the mixture was separated into an organic layer and an aqueous layer. Then, the aqueous layer was subjected to extraction twice with about 30 mL of toluene. The organic layer and the solution of the extract were combined and washed once with about 100 mL of saturated brine. The obtained organic layer was dried over magnesium sulfate, and this mixture was subjected to filtration through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give a brown solid. The obtained brown solid was purified by silica gel column chromatography (a developing solvent in which the ethyl acetate/toluene ratio was 5:95), and further recrystallized from hexane/toluene, so that 0.86 g of a pale brown solid was obtained in 71% yield. The synthesis scheme of Step 2 is illustrated in (b-2).

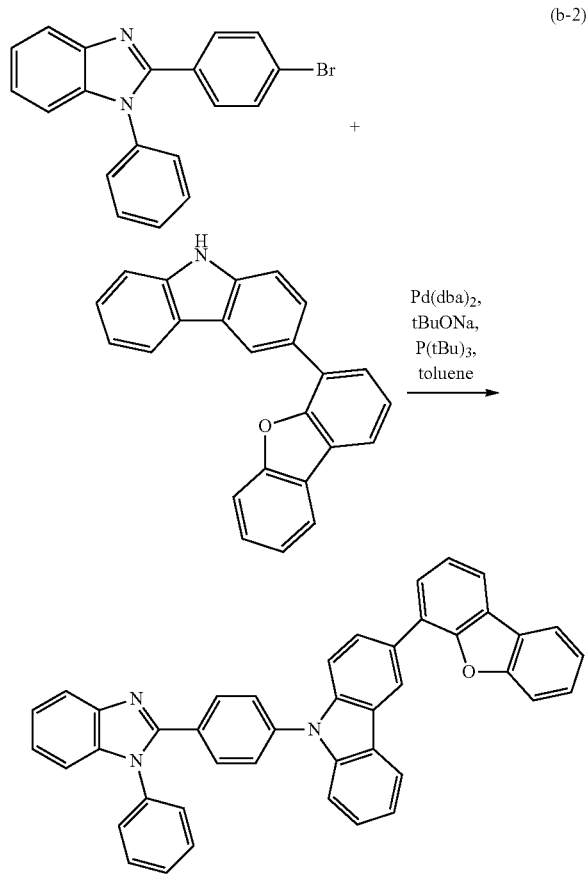

(b-2)

By a train sublimation method, 854 mg of the obtained pale brown solid was purified. In the purification, the pressure was 1.8 Pa, the flow rate of argon gas was 5.0 mL/min, and the temperature of the heating was 290° C. After the purification, 0.64 g of a pale brown solid of the substance which was the object of the synthesis was obtained in a yield of 75%.

Figure 36A:
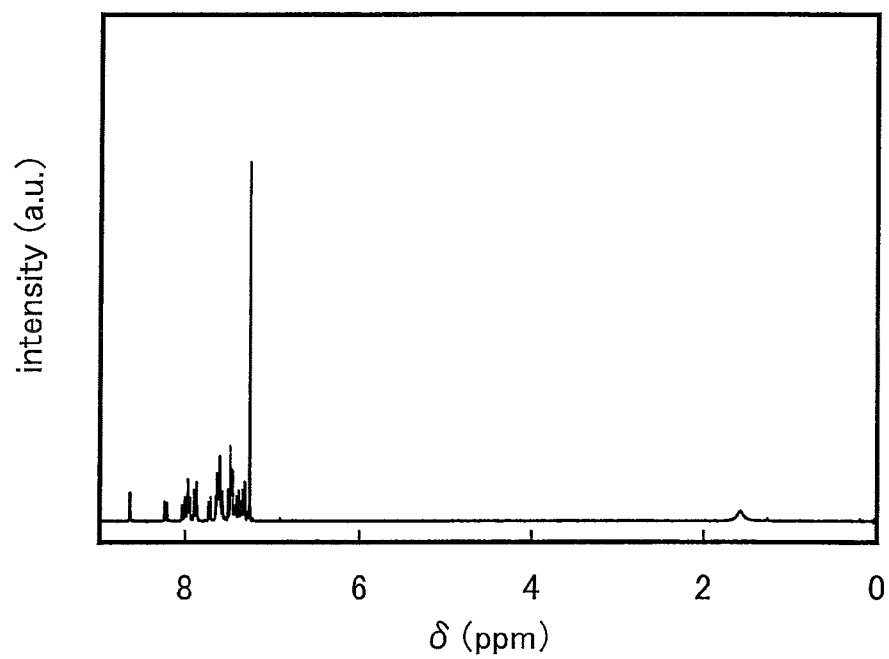
FIGS. 36A and 36B are $^1$H NMR charts of DBFCzBIm-II.
Figure 36B:
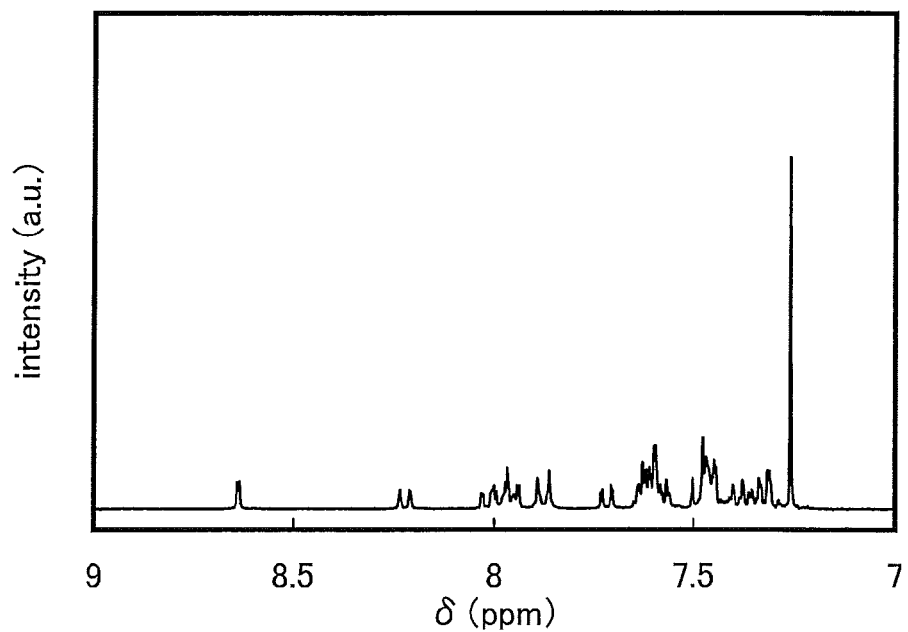

The pale brown solid after the purification was subjected to nuclear magnetic resonance ($^1$H NMR) spectroscopy. The measurement data are shown below. In addition, $^1$H NMR charts are shown in FIGS. 36A and 36B. Note that FIG. 36B is a chart where the range of from 7 ppm to 9 ppm in FIG. 36A is enlarged.

$^1$H NMR (CDCl$_3$, 300 MHz): δ=7.31-7.50 (m, 11H), 7.54-7.65 (m, 7H), 7.72 (dd, J$_1$=1.5 Hz, J$_2$=7.5 Hz, 1H), 7.88 (d, J=8.7 Hz, 2H), 7.34-8.03 (m, 4H), 8.22 (d, J=7.5 Hz, 1H), 8.63 (d, J=1.5 Hz, 1H)

The measurement results showed that DBFCzBIm-II, which is the carbazole derivative represented by the above structural formula (3), was obtained.

Figure 37:
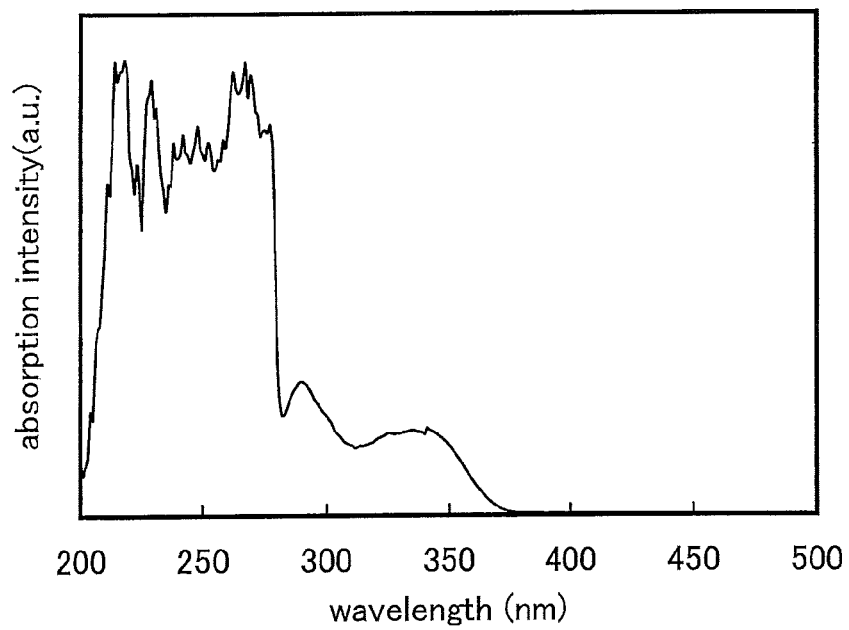
FIG. 37 shows an absorption spectrum of DBFCzBIm-II in a solution of DBFCzBIm-II (the solvent of which is toluene).
Figure 38:
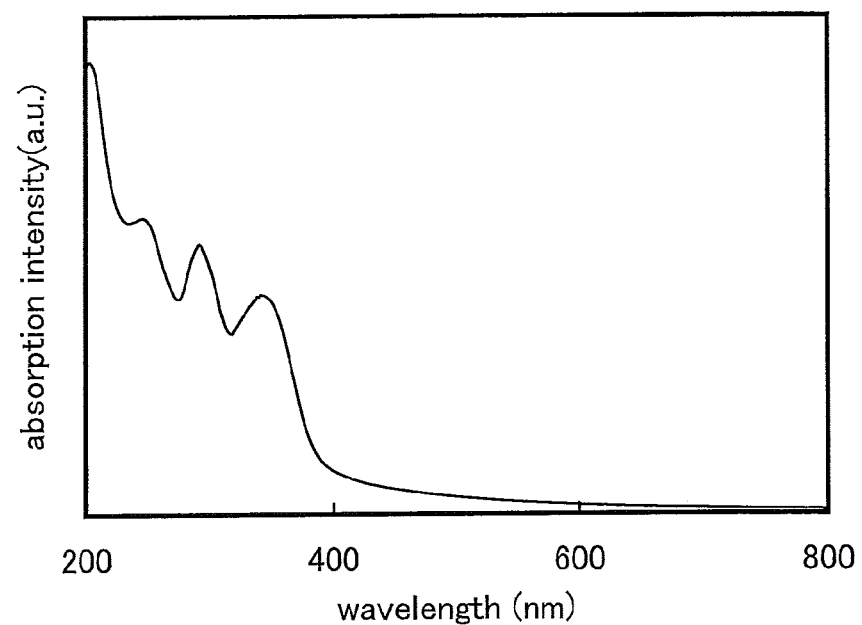
FIG. 38 shows an absorption spectrum of DBFCzBIm-II in a thin film state.

Further, an absorption spectrum of DBFCzBIm-II in a toluene solution of DBFCzBIm-II is shown in FIG. 37, and an absorption spectrum of a thin film of DBFCzBIm-II is shown in FIG. 38. An ultraviolet-visible spectrophotometer (V-550, manufactured by JASCO Corporation) was used for the measurements of the absorption spectra. In the case of the toluene solution, the measurements were made with the toluene solution of DBFCzBIm-II put in a quartz cell, and the absorption spectrum obtained by subtraction of the absorption spectra of quartz and toluene from the measured spectra is shown in the drawing. In addition, as for the absorption spectrum of the thin film, a sample was prepared by evaporation of DBFCzBIm-II on a quartz substrate, and the absorption spectrum obtained by subtraction of that of quartz from the measured spectra is shown in the drawing. In FIG. 37 and FIG. 38, the horizontal axis represents wavelength (nm) and the vertical axis represents absorption intensity (arbitrary unit).

Figure 39:
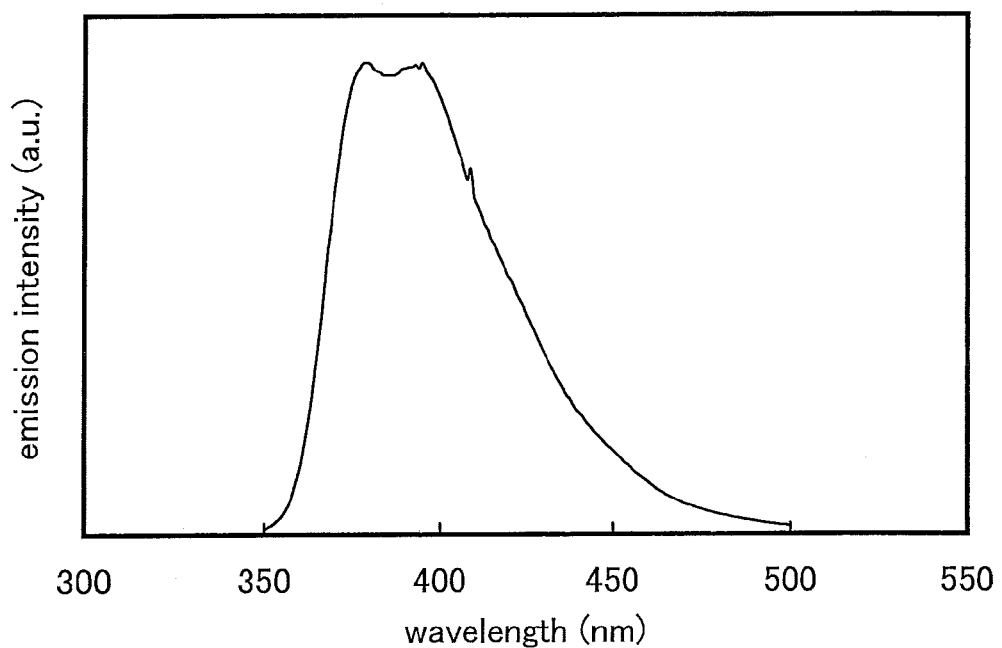
FIG. 39 shows an emission spectrum of DBFCzBIm-II in the solution of DBFCzBIm-II (the solvent of which is toluene).
Figure 40:
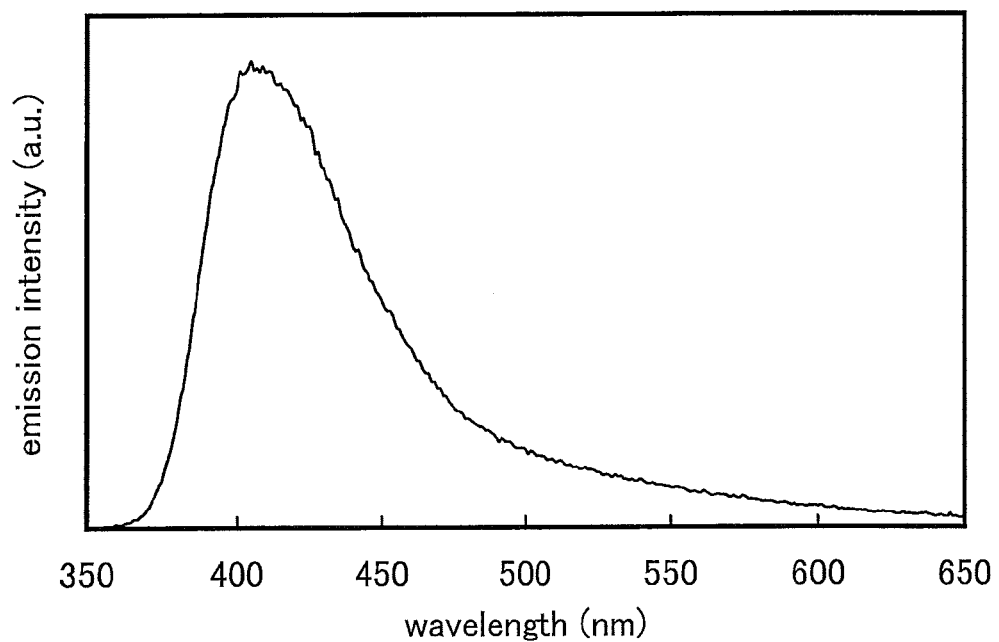
FIG. 40 shows an emission spectrum of DBFCzBIm-II in a thin film state.

An emission spectrum of DBFCzBIm-II in the toluene solution of DBFCzBIm-II is shown in FIG. 39, and an emission spectrum of the thin film of DBFCzBIm-II is shown in FIG. 40. As in the measurements of the absorption spectra, an ultraviolet-visible spectrophotometer (V-550, manufactured by JASCO Corporation) was used for the measurements. The emission spectrum was measured with the toluene solution of DBFCzBIm-II put in a quartz cell, and the emission spectrum of the thin film was measured with a sample prepared by evaporation of DBFCzBIm-II on a quartz substrate. FIG. 39 shows that the maximum emission wavelengths of DBFCzBIm-II in a toluene solution of DBFCzBIm-II were around 380 nm and 395 nm (at an excitation wavelength of 340 nm) and FIG. 40 shows that the greatest emission wavelength of the thin film of DBFCzBIm-II was around 405 nm (at an excitation wavelength of 332 nm).

Further, the ionization potential of DBFCzBIm-II in a thin film state was measured by a photoelectron spectrometer (AC-2, manufactured by Riken Keiki, Co., Ltd.) in air. The obtained value of the ionization potential was converted to a negative value, so that the HOMO level of DBFCzBIm-II was −5.71 eV. From the data of the absorption spectra of the thin film in FIG. 38, the absorption edge of DBFCzBIm-II, which was obtained from Tauc plot with an assumption of direct transition, was 3.28 eV. Therefore, the optical energy gap of DBFCzBIm-II in the solid state was estimated at 3.28 eV;

from the values of the HOMO level obtained above and this energy gap, the LUMO level of DBFCzBIm-II was able to be estimated at −2.43 eV. It was thus found that DBFCzBIm-II had a wide energy gap of 3.28 eV in the solid state.

Further, the oxidation reaction characteristics of DBFCzBIm-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.00 V to 1.12 V and then changed from 1.12 V to 0.00 V was one cycle, and 100 cycles were performed.

The measurement results revealed that DBFCzBIm-II showed properties effective against repetition of redox reactions between an oxidized state and a neutral state without a large variation in oxidation peak even after the 100 cycles in the measurements.

Further, the HOMO level of DBFCzBIm-II was determined also by calculation from the CV measurement results.

First, the potential energy of the reference electrode with respect to the vacuum level used was found to be −4.94 eV, as determined in Example 6. The oxidation peak potential $E_{pa}$ of DBFCzBIm-II was 1.04 V. In addition, the reduction peak potential was 0.89 V. Therefore, a half-wave potential (an intermediate potential between $E_{pa}$ and $E_{pc}$) can be calculated at 0.97 V. This means that DBFCzBIm-II is oxidized by an electric energy of 0.97 [V versus Ag/Ag$^+$], and this energy corresponds to the HOMO level. Here, since the potential energy of the reference electrode, which was used in this example, with respect to the vacuum level is −4.94 [eV] as described above, the HOMO level of DBFCzBIm-II was calculated as follows: −4.94−0.97=−5.91 [eV].

Example 8

Synthesis Example 3

In this example is described a method of synthesizing 3-(dibenzothiophen-4-yl)-9-(triphenylen-2-yl)-9H-carbazole (abbreviation: DBTCzTp-II), which is one of the carbazole derivatives described in Embodiment 1. A structure of DBTCzTp-II is illustrated in the following structural formula (5).

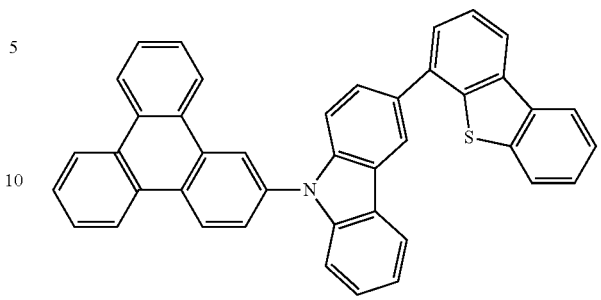

(5)

Step 1: Synthesis of 3-(Dibenzothiophen-4-yl)-9H-carbazole

This was synthesized as in Step 1 in Synthesis Example 1.

Step 2: Synthesis of DBTCzTp-II

In a 100-mL three-neck flask were put 1.0 g (2.9 mmol) of 2-bromotriphenylene and 0.88 g (2.9 mmol) of 3-(dibenzothiophen-4-yl)-9H-carbazole, and the air in the flask was replaced with nitrogen. To this mixture were added 15 mL of toluene, 0.10 mL of tri(tert-butyl)phosphine (a 10 wt % hexane solution), 0.45 g (4.3 mmol) of sodium tert-butoxide. This mixture was degassed while being stirred under reduced pressure. After the degassing, replacement with nitrogen was performed, this mixture was heated to 80° C., and then 14 mg (0.025 mmol) of bis(dibenzylideneacetone)palladium(0) was added thereto. This mixture was stirred at 80° C. for 4 hours. After the stirring, 15 mg (0.025 mmol) of bis(dibenzylideneacetone)palladium(0) was added to this mixture, and then it was further stirred at 110° C. for 8 hours. After the stirring, about 30 mL of toluene was added to the mixture, and then it was stirred at 80° C. The mixture was subjected to hot filtration through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give a white solid. The obtained solid was dissolved in toluene. The mixture was purified by silica gel column chromatography (a developing solvent in which the hexane/ethyl acetate ratio was 9:1), and further recrystallized from toluene/hexane, so that 500 mg of a white solid was obtained in 27% yield. The synthesis scheme of Step 2 is illustrated in (b-3).

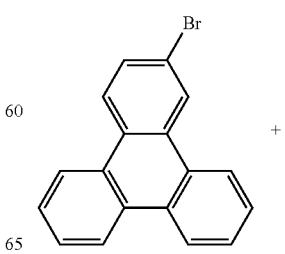

(b-3)

-continued

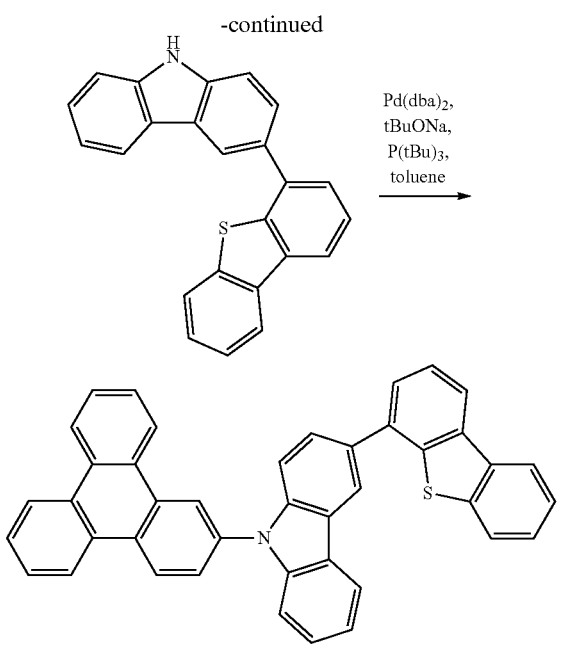

By a train sublimation method, 0.50 g of the obtained white solid was purified. In the purification, the pressure was 2.1 Pa, the flow rate of argon gas was 5.0 mL/min, and the temperature of the heating was 310° C. After the purification, 0.40 g of a colorless transparent solid was obtained in a yield of 78%.

Figure 41A:
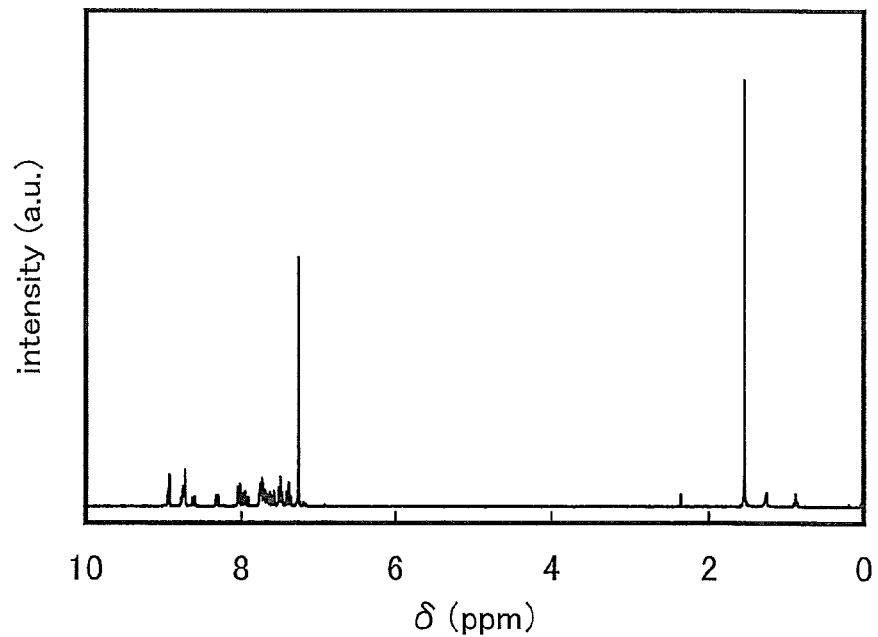
FIGS. 41A and 41B are $^1$H NMR charts of DBTCzTp-II.
Figure 41B:
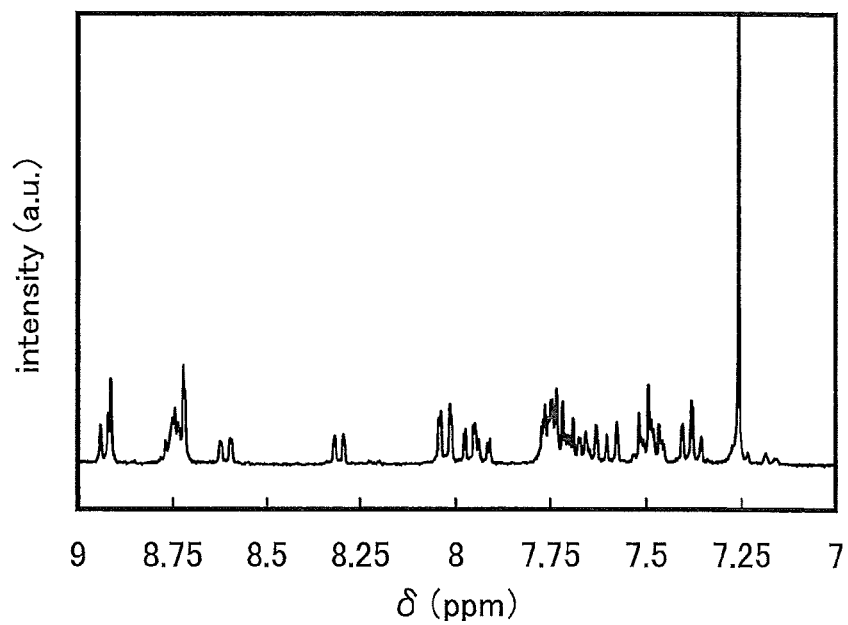

The colorless and transparent solid after the purification was subjected to nuclear magnetic resonance ($^1$H NMR) spectroscopy. The measurement data are shown below. In addition, $^1$H NMR charts are shown in FIGS. 41A and 41B.

$^1$H NMR (CDCl$_3$, 300 MHz): δ=7.37-7.41 (m, 2H), 7.45-7.52 (m, 3H), 7.58-7.77 (m, 8H), 7.93 (dd, J$_1$=2.1 Hz, J$_1$=8.7 Hz, 1H), 7.96 (dd, J$_1$=1.5 Hz, J$_1$=7.8 Hz, 1H), 8.03 (dd, J$_1$=1.5 Hz, J$_1$=8.2 Hz, 1H), 8.31 (d, J=7.5 Hz, 1H), 8.61 (dd, J$_1$=1.5 Hz, J$_2$=8.0 Hz 1H), 8.72-8.77 (m, 4H), 8.91-8.94 (m, 2H)

The measurement results showed that DBTCzTp-II, which is the carbazole derivative represented by the above structural formula (5), was obtained.

Figure 42:
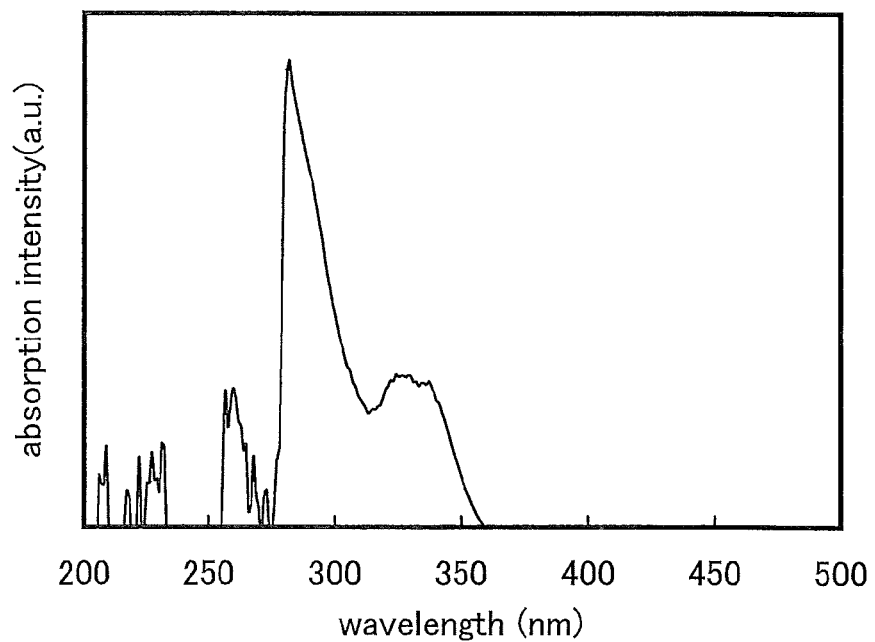
FIG. 42 shows an absorption spectrum of DBTCzTp-II in a solution of DBTCzTp-II (the solvent of which is toluene).
Figure 43:
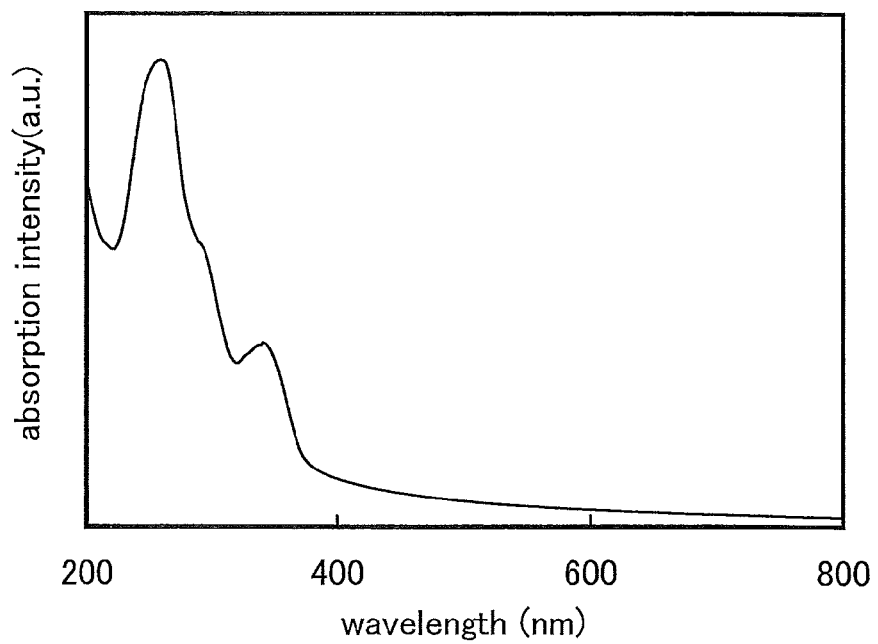
FIG. 43 shows an absorption spectrum of DBTCzTp-II in a thin film state.

Further, an absorption spectrum of DBTCzTp-II in a toluene solution of DBTCzTp-II is shown in FIG. 42, and an absorption spectrum of a thin film is shown in FIG. 43. An ultraviolet-visible spectrophotometer (V-550, manufactured by JASCO Corporation) was used for the measurements of the absorption spectra. In the case of the toluene solution, the measurements were made with the toluene solution of DBTCzTp-II put in a quartz cell, and the absorption spectrum obtained by subtraction of the absorption spectra of quartz and toluene from the measured spectra is shown in the drawing. In addition, as for the absorption spectrum of the thin film, a sample was prepared by evaporation of DBTCzTp-II on a quartz substrate, and the absorption spectrum obtained by subtraction of that of quartz from the measured spectra is shown in the drawing. In FIG. 42 and FIG. 43, the horizontal axis represents wavelength (nm) and the vertical axis represents absorption intensity (arbitrary unit).

Figure 44:
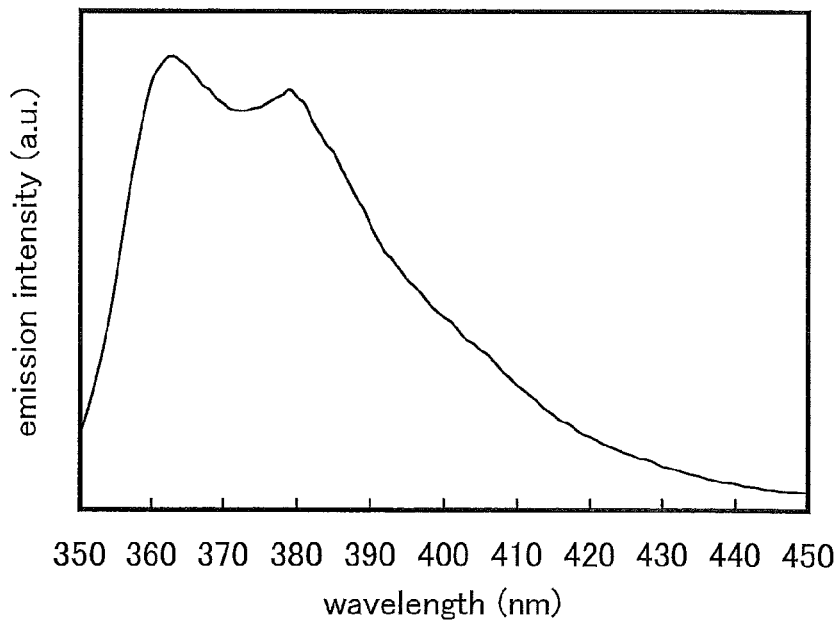
FIG. 44 shows an emission spectrum of DBTCzTp-II in the solution of DBTCzTp-II (the solvent of which is toluene).
Figure 45:
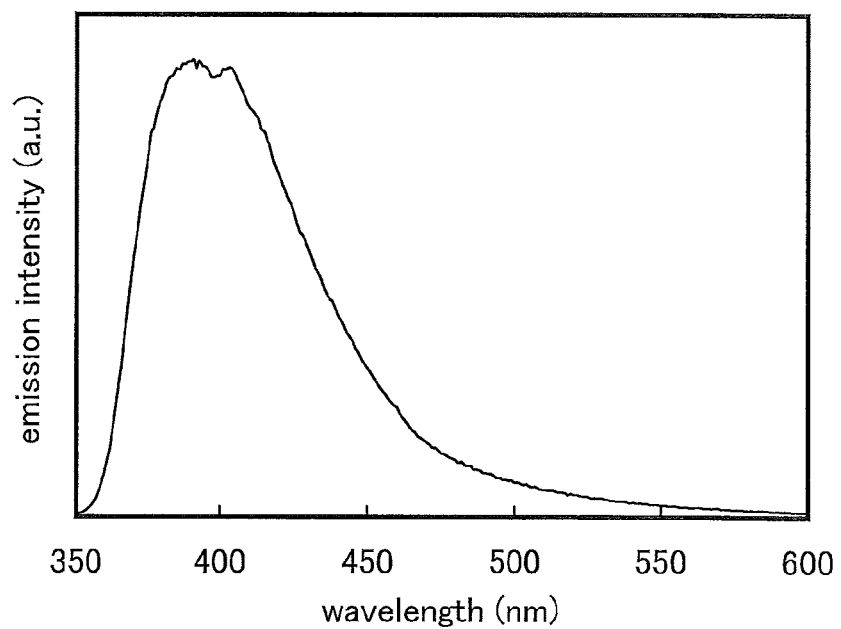
FIG. 45 shows an emission spectrum of DBTCzTp-II in a thin film state.

An emission spectrum of DBTCzTp-II in the toluene solution of DBTCzTp-II is shown in FIG. 44, and an emission spectrum of a thin film of DBTCzTp-II is shown in FIG. 45. As in the measurements of the absorption spectra, an ultraviolet-visible spectrophotometer (V-550, manufactured by JASCO Corporation) was used for the measurements. The emission spectrum was measured with the toluene solution of DBTCzTp-II put in a quartz cell, and the emission spectrum of the thin film was measured with a sample prepared by evaporation of DBTCzTp-II on a quartz substrate. FIG. 44 shows that the maximum emission wavelengths of DBTCzTp-II in the toluene solution of DBTCzTp-II were around 363 nm and 379 nm (at an excitation wavelength of 340 nm) and FIG. 45 shows that the greatest emission wavelength of the thin film of DBTCzTp-II was around 390 nm (at an excitation wavelength of 336 nm).

Further, the ionization potential of DBTCzTp-II in a thin film state was measured by a photoelectron spectrometer (AC-2, manufactured by Riken Keiki, Co., Ltd.) in air. The obtained value of the ionization potential was converted to a negative value, so that the HOMO level of DBTCzTp-II was −5.84 eV. From the data of the absorption spectra of the thin film in FIG. 43, the absorption edge of DBTCzTp-II, which was obtained from Tauc plot with an assumption of direct transition, was 3.34 eV. Therefore, the optical energy gap of DBTCzTp-II in the solid state was estimated at 3.34 eV; from the values of the HOMO level obtained above and this energy gap, the LUMO level of DBTCzTp-II was able to be estimated at −2.50 eV. It was thus found that DBTCzTp-II had a wide energy gap of 3.34 eV in the solid state.

Further, the oxidation reaction characteristics of DBTCzTp-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.05 V to 1.10 V and then changed from 1.10 V to −0.05 V was one cycle, and 100 cycles were performed.

The measurement results revealed that DBTCzTp-II showed properties effective against repetition of redox reactions between an oxidized state and a neutral state without a large variation in oxidation peak even after the 100 cycles in the measurements.

Further, the HOMO level of DBTCzTp-II was determined also by calculation from the CV measurement results.

First, the potential energy of the reference electrode with respect to the vacuum level used was found to be −4.94 eV, as determined in Example 6. The oxidation peak potential E$_{pa}$ of DBTCzTp-II was 1.01 V. In addition, the reduction peak potential E$_{pc}$ thereof was 0.86 V. Therefore, a half-wave potential (an intermediate potential between E$_{pa}$ and E$_{pc}$) can be calculated at 0.94 V. This means that DBTCzTp-II is oxidized by an electric energy of 0.94 [V versus Ag/Ag$^+$], and this energy corresponds to the HOMO level. Here, since the potential energy of the reference electrode, which was used in this example, with respect to the vacuum level is −4.94 [eV] as described above, the HOMO level of DBTCzTp-II was calculated as follows: −4.94−0.94=−5.88 [eV].

Example 9

Synthesis Example 4

In this example is described a method of synthesizing 3-(dibenzofuran-4-yl)-9-(triphenylen-2-yl)-9H-carbazole (abbreviation: DBFCzTp-II), which is one of the carbazole derivatives described in Embodiment 1. A structure of DBFC-zTp-II is illustrated in the following structural formula (6).

(6)

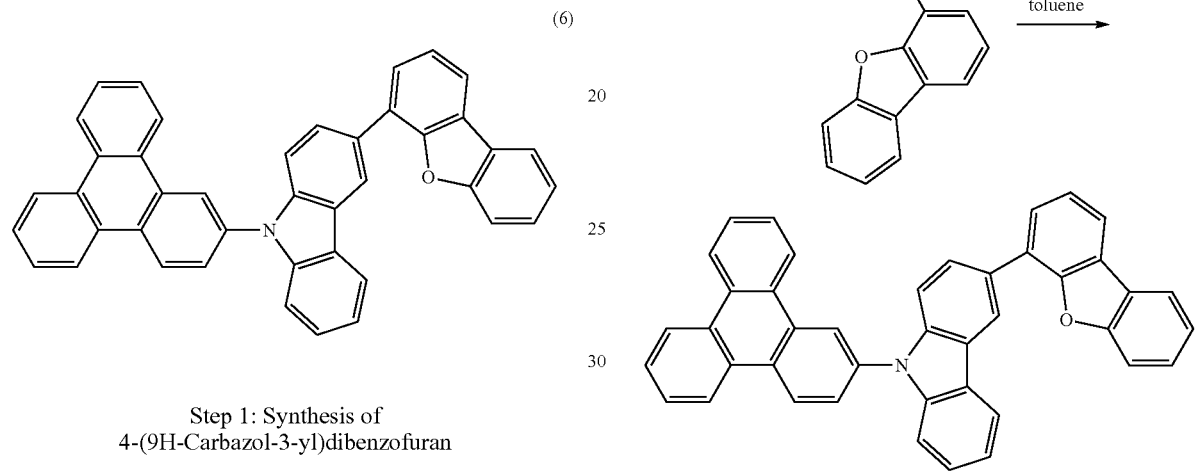

Step 1: Synthesis of 4-(9H-Carbazol-3-yl)dibenzofuran

This was synthesized as in Step 1 in Example 2.

Step 2: Synthesis of DBFCzTp-II

In a 50-mL three-neck flask were put 0.62 g (2.0 mmol) of 2-bromotriphenylene and 0.67 g (2.0 mmol) of 4-(9H-carbazol-3-yl)dibenzofuran, and the air in the flask was replaced with nitrogen. To this mixture were added 15 mL of toluene, 0.10 mL of tri(tert-butyl)phosphine (a 10 wt % hexane solution), 0.48 g (4.3 mmol) of sodium tert-butoxide. This mixture was degassed while being stirred under reduced pressure. After this mixture was heated at 80° C., 14 mg (0.025 mmol) of bis(dibenzylideneacetone)palladium(0) was added thereto. This mixture was stirred at 110° C. for 15.5 hours. After the stirring, the mixture was washed twice with about 30 mL of water, and the mixture was separated into an organic layer and an aqueous layer that was subjected to extraction. Then, the aqueous layer was subjected to extraction twice with about 30 mL of toluene. The organic layer and the solution of the extract were combined and washed once with about 100 mL of saturated brine, and the mixture was separated into an organic layer and an aqueous layer. The obtained organic layer was dried over magnesium sulfate, and this mixture was subjected to filtration through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give a brown solid. The obtained brown solid was purified by silica gel column chromatography (a developing solvent in which the hexane/toluene was 2:1), and further recrystallized from hexane/toluene, so that 0.73 g of a white solid was obtained in 65% yield. The synthesis scheme of Step 2 is illustrated in (b-4).

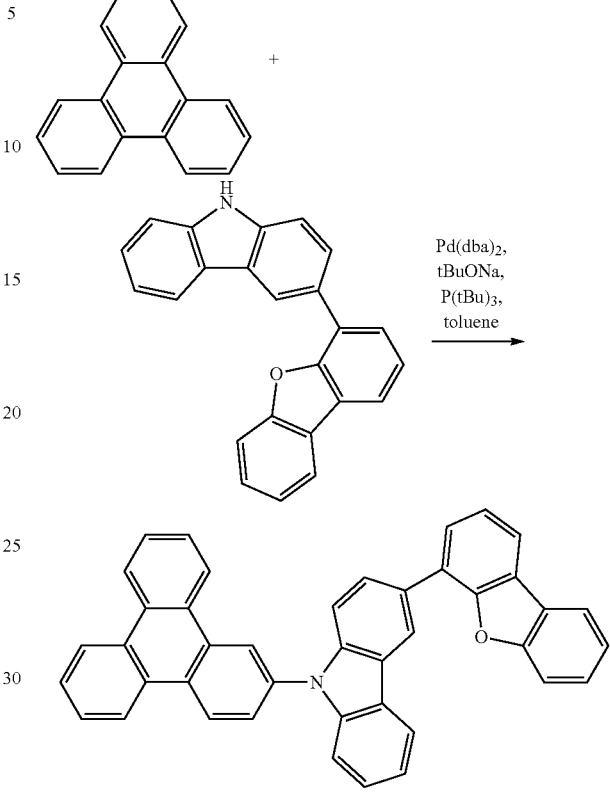

(b-4)

By a train sublimation method, 0.73 g of the obtained white solid was purified. In the purification, the pressure was 2.2 Pa, the flow rate of argon gas was 5.0 mL/min, and the temperature of the heating was 310° C. After the purification, 0.59 g of a colorless transparent solid was obtained in a yield of 81%.

Figure 46A:
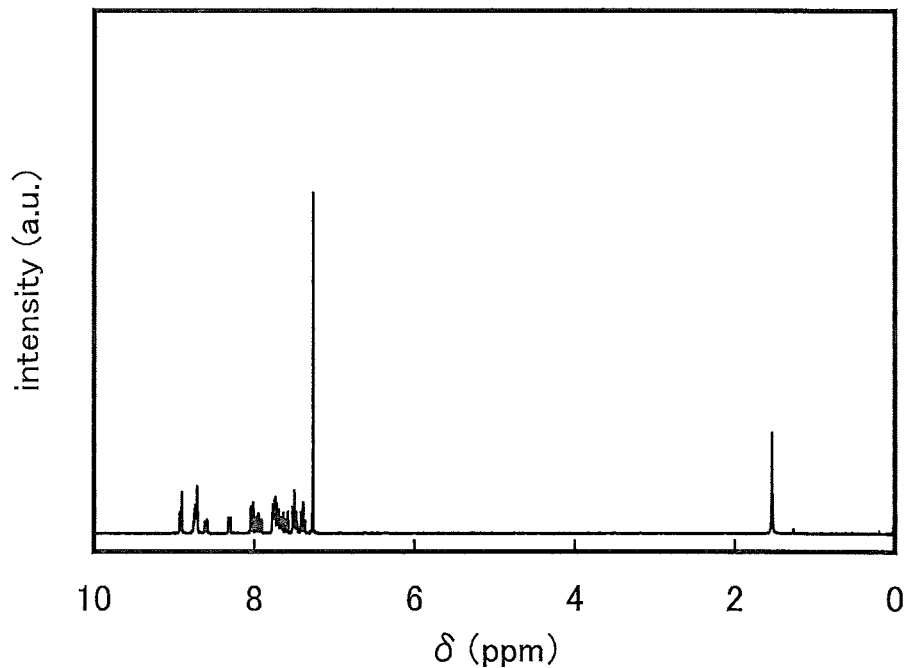
FIGS. 46A and 46B are $^1$H NMR charts of DBFCzTp-II.
Figure 46B:
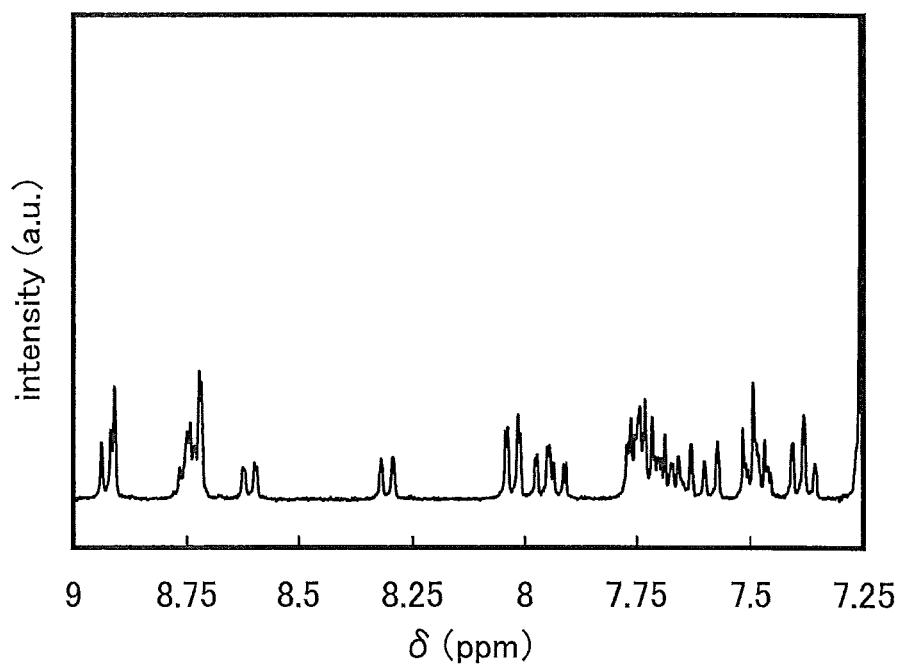

The colorless and transparent solid after the purification was subjected to nuclear magnetic resonance ($^1$H NMR) spectroscopy. The measurement data are shown below. In addition, $^1$H NMR charts are shown in FIGS. 46A and 46B. Note that FIG. 46B is a chart where the range of from 7.25 ppm to 9 ppm in FIG. 46A is enlarged.

$^1$H NMR (CDCl$_3$, 300 MHz): δ=7.37-7.41 (m, 2H), 7.45-7.52 (m, 3H), 7.58-7.77 (m, 8H), 7.93 (dd, J$_1$=2.1 Hz, J$_1$=8.7 Hz, 1H), 7.96 (dd, J$_1$=1.5 Hz, J$_1$=7.8 Hz, 1H), 8.03 (dd, J$_1$=1.5 Hz, J$_1$=8.2 Hz, 1H), 8.31 (d, J=7.5 Hz, 1H), 8.61 (dd, J$_1$=1.5 Hz, J$_2$=8.0 Hz 1H), 8.72-8.77 (m, 4H), 8.91-8.94 (m, 2H)

The measurement results showed that DBFCzTp-II, which is the carbazole derivative represented by the above structural formula (6), was obtained.

Figure 47:
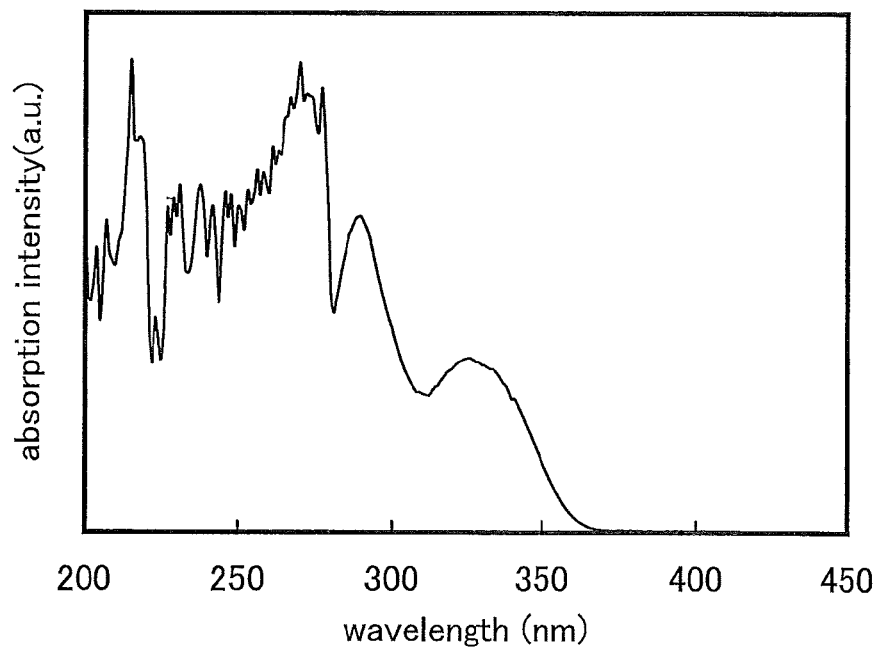
FIG. 47 shows an absorption spectrum of DBFCzTp-II in a solution of DBFCzTp-II (the solvent of which is toluene).
Figure 48:
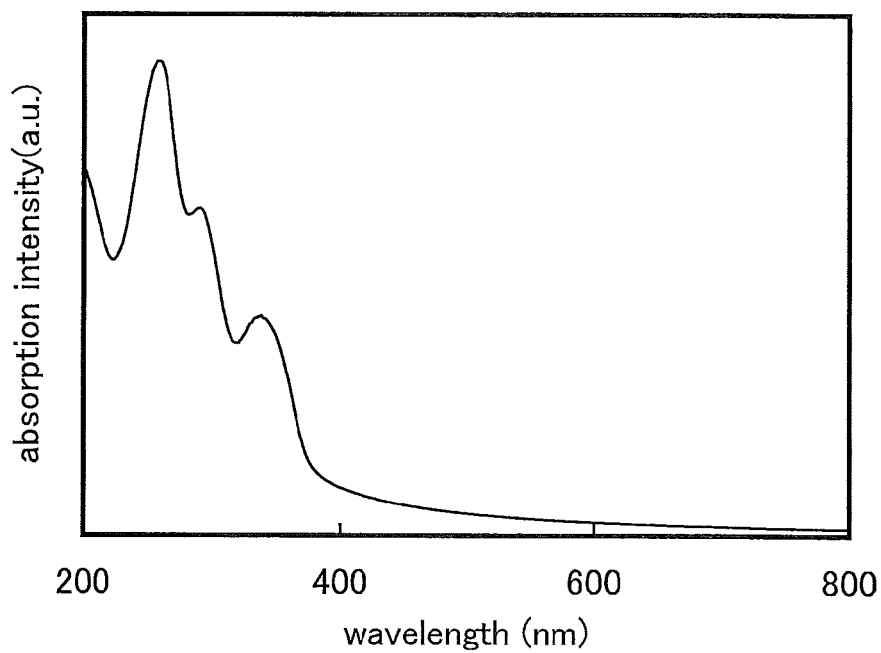
FIG. 48 shows an absorption spectrum of DBFCzTp-II in a thin film state.

Further, an absorption spectrum of DBFCzTp-II in a toluene solution of DBFCzTp-II is shown in FIG. 47, and an absorption spectrum of a thin film of DBFCzTp-II is shown in FIG. 48. An ultraviolet-visible spectrophotometer (V-550, manufactured by JASCO Corporation) was used for the measurements of the absorption spectra. In the case of the toluene solution, the measurements were made with the toluene solution of DBFCzTp-II put in a quartz cell, and the absorption spectrum obtained by subtraction of the absorption spectra of quartz and toluene from the measured spectra is shown in the drawing. In addition, as for the absorption spectrum of the thin film, a sample was prepared by evaporation of DBFCzTp-II on a quartz substrate, and the absorption spectrum obtained by subtraction of that of quartz from the measured spectra is shown in the drawing. In FIG. 47 and FIG. 48, the horizontal axis represents wavelength (nm) and the vertical axis represents absorption intensity (arbitrary unit).

Figure 49:
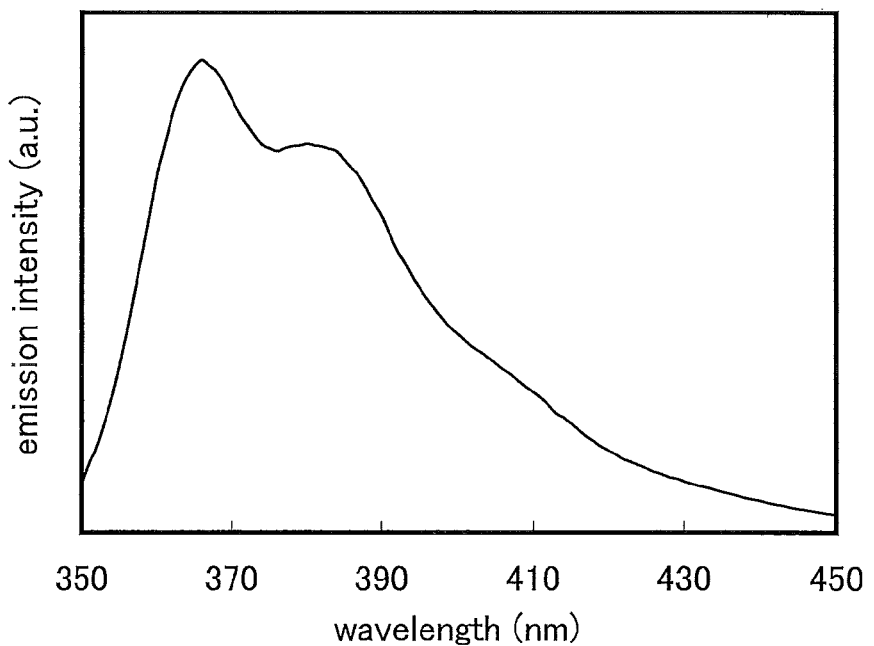
FIG. 49 shows an emission spectrum of DBFCzTp-II in the solution of DBFCzTp-II (the solvent of which is toluene).
Figure 50:
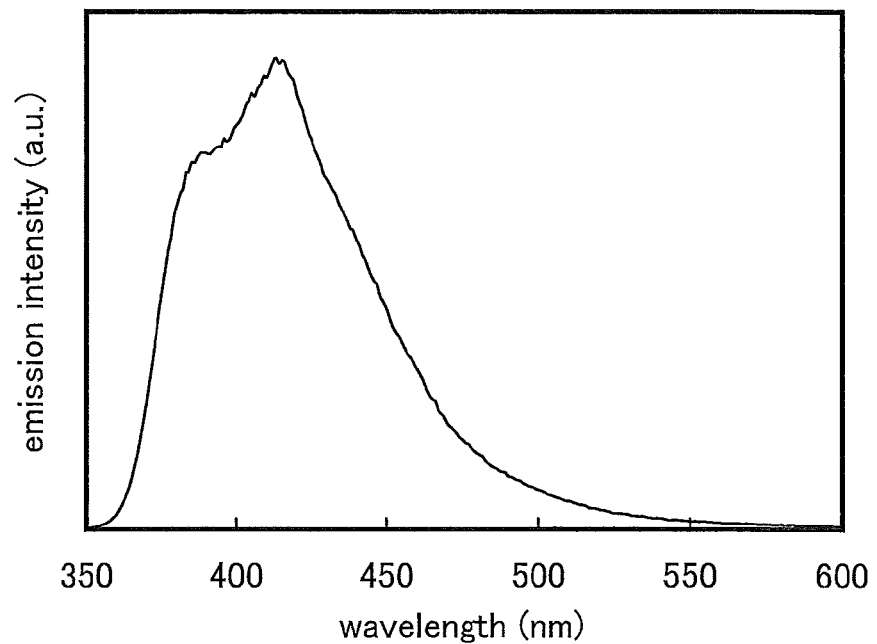
FIG. 50 shows an emission spectrum of DBFCzTp-II in a thin film state.

An emission spectrum of DBFCzTp-II in the toluene solution of DBFCzTp-II is shown in FIG. 49, and an emission spectrum of a thin film is shown in FIG. 50. As in the measurements of the absorption spectra, an ultraviolet-visible spectrophotometer (V-550, manufactured by JASCO Corporation) was used for the measurements. The emission spectrum was measured with the toluene solution of DBFCzTp-II put in a quartz cell, and the emission spectrum of the thin film was measured with a sample prepared by evaporation of DBFCzTp-II on a quartz substrate. FIG. 49 shows that the maximum emission wavelengths of DBFCzTp-II in the toluene solution of DBFCzTp-II were around 380 nm and 395 nm (at an excitation wavelength of 340 nm) and FIG. 50 shows that the greatest emission wavelength of the thin film of DBFCzTp-II was around 413 nm (at an excitation wavelength of 334 nm).

Further, the ionization potential of DBFCzTp-II in a thin film state was measured by a photoelectron spectrometer (AC-2, manufactured by Riken Keiki, Co., Ltd.) in air. The obtained value of the ionization potential was converted to a negative value, so that the HOMO level of DBFCzTp-II was −5.79 eV. From the data of the absorption spectra of the thin film in FIG. 48, the absorption edge of DBFCzTp-II, which was obtained from Tauc plot with an assumption of direct transition, was 3.33 eV. Therefore, the optical energy gap of DBFCzTp-II in the solid state was estimated at 3.33 eV; from the values of the HOMO level obtained above and this energy gap, the LUMO level of DBFCzTp-II was able to be estimated at −2.46 eV. It was thus found that DBFCzTp-II had a wide energy gap of 3.33 eV in the solid state.

Further, the oxidation reaction characteristics of DBFCzTp-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.00 V to 1.10 V and then changed from 1.10 V to 0.00 V was one cycle, and 100 cycles were performed.

The measurement results revealed that DBFCzTp-II showed properties effective against repetition of redox reactions between an oxidized state and a neutral state without a large variation in oxidation peak even after the 100 cycles in the measurements.

Further, the HOMO level of DBFCzTp-II was determined also by calculation from the CV measurement results.

First, the potential energy of the reference electrode with respect to the vacuum level used was found to be −4.94 eV, as determined in Example 6. The oxidation peak potential $E_{pa}$ was 1.00 V. In addition, the reduction peak potential $E_{pc}$ was 0.83 V. Therefore, a half-wave potential (an intermediate potential between $E_{pa}$ and $E_{pc}$) can be calculated at 0.92 V. This means that DBFCzTp-II is oxidized by an electric energy of 0.92 [V versus Ag/Ag$^+$], and this energy corresponds to the HOMO level. Here, since the potential energy of the reference electrode, which was used in this example, with respect to the vacuum level is −4.94 [eV] as described above, the HOMO level of DBFCzTp-II was calculated as follows: −4.94−0.92=−5.86 [eV].

Example 10

Synthesis Example 5

In this example is described a method of synthesizing 3-(dibenzothiophen-4-yl)-9-[4-(10-phenyl-9-anthryl)phenyl]-9H-carbazole (abbreviation: DBTCzPA-II), which is one of the carbazole derivatives described in Embodiment 1. A structure of DBTCzPA-II is illustrated in the following structural formula (7).

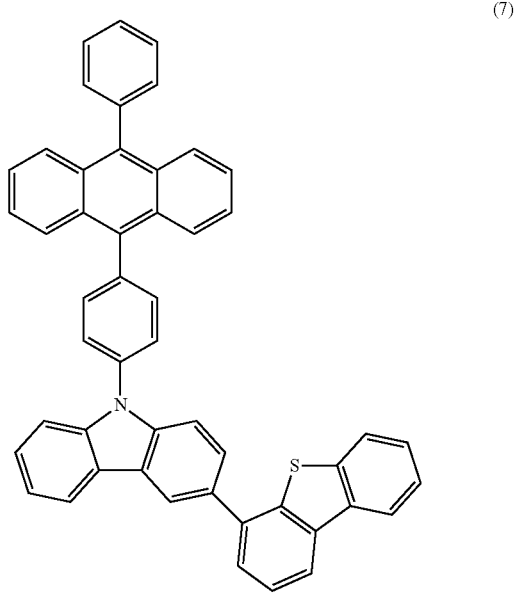 [SMILES: c1ccc(-c2c3ccccc3c(-c3ccc(-n4c5ccccc5c5cc(-c6cccc7c6sc6ccccc67)ccc54)cc3)c3ccccc23)cc1]

(7)

Step 1: Synthesis of 3-(Dibenzothiophen-4-yl)-9H-carbazole

This was synthesized as in Step 1 in Synthesis Example 1.

Step 2: Synthesis of DBTCzPA-II

To a 100-mL three-neck flask were added 1.8 g (4.4 mmol) of 9-(4-bromophenyl)-10-phenylanthracene, 1.5 g (4.4 mmol) of 3-(dibenzothiophen-4-yl)-9H-carbazole, and 0.85 g (8.8 mmol) of sodium tert-butoxide. After the air in the flask was replaced with nitrogen, to this mixture were added 25 mL of toluene and 2.2 mL of tri(tert-butyl)phosphine (a 10 wt % hexane solution). This mixture was degassed by being stirred while the pressure was reduced. After the degassing, 0.12 g (0.22 mmol) of bis(dibenzylideneacetone)palladium(0) was added to the mixture. This mixture was stirred at 110° C. for 18 hours under a nitrogen stream, so that a solid was precipitated. After the stirring, this mixture was cooled to room temperature, and the obtained solid was collected by suction filtration. The collected solid was dissolved in about 60 mL of toluene, and the obtained solution was suction-filtered through Celite, alumina, and Florisil. The obtained filtrate was concentrated to give a solid and the solid was recrystallized from toluene, so that 1.1 g of a white powder was obtained in 36% yield. The synthesis scheme of Step 2 is illustrated in (b-6).

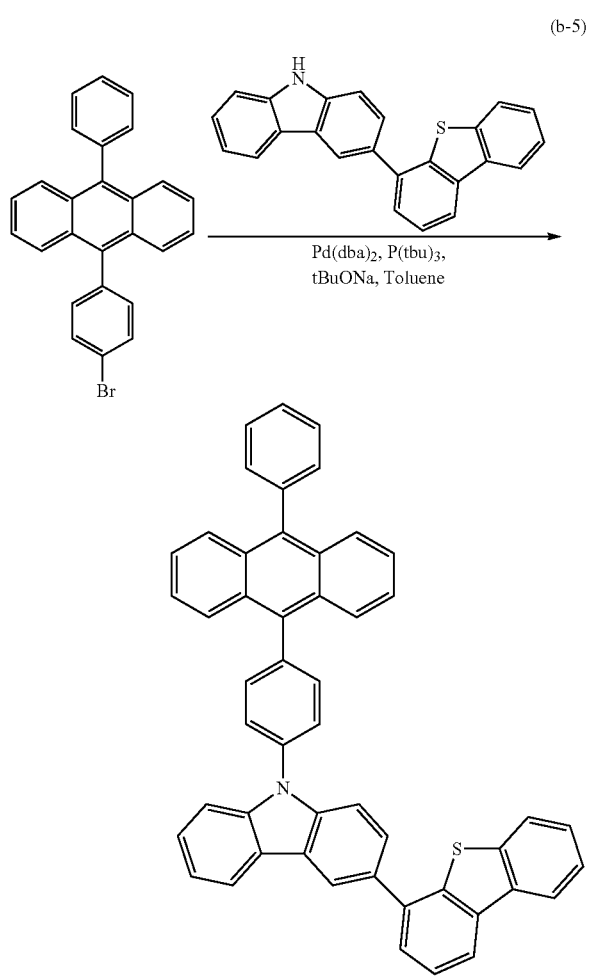

(b-5)

Then, 1.1 g of the obtained white powder was purified. Using a train sublimation method, the purification was conducted by heating of the white powder at 300° C. under a pressure of 3.0 Pa with a flow rate of argon gas of 4.0 mL/min. After the purification, 1.0 g of a pale yellow solid was obtained in 90% yield.

The pale yellow solid after the above purification was subjected to nuclear magnetic resonance ($^1$H NMR) spectroscopy. The measurement data are shown below.

$^1$H NMR (CDCl$_3$, 300 MHz): δ=7.36-7.68 (m, 15H), 7.72-7.93 (m, 12H), 8.19-8.286 (m, 3H), 8.57 (sd, J$_1$=1.5 Hz, 1H).

Figure 51:
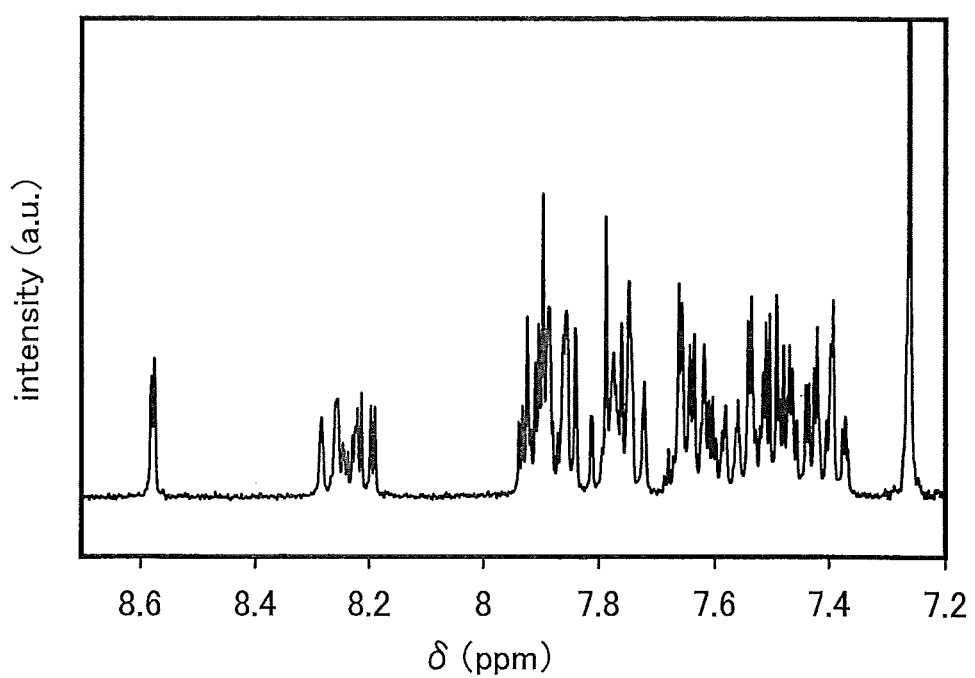
FIG. 51 is a $^1$H NMR chart of DBTCzPA-II.

Further, a $^1$H NMR chart is shown in FIG. 51. The measurement results showed that DBTCzPA-II, which is the carbazole derivative represented by the above structural formula (7), was obtained.

Figure 52:
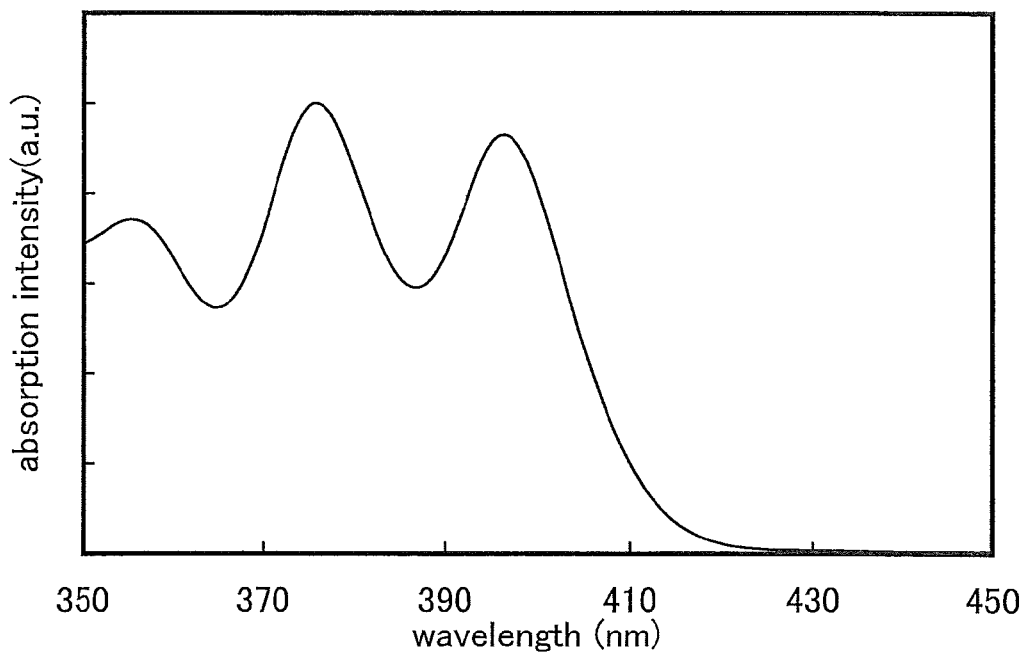
FIG. 52 shows an absorption spectrum of DBTCzPA-II in a solution of DBTCzPA-II (the solvent of which is toluene).
Figure 53:
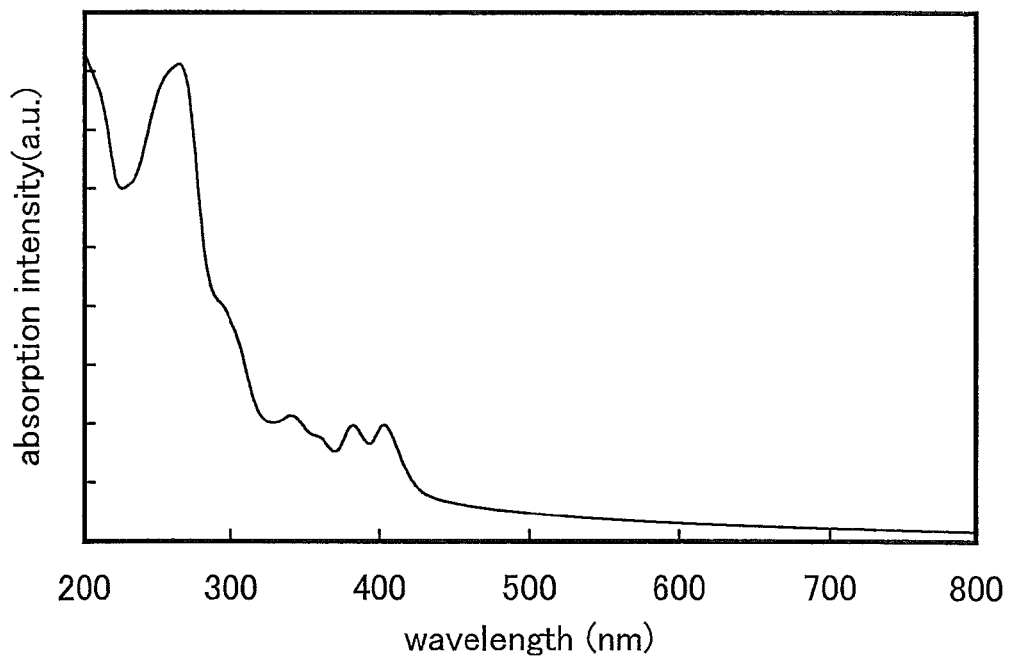
FIG. 53 shows an absorption spectrum of DBTCzPA-II in a thin film state.

Further, an absorption spectrum of DBTCzPA-II in a toluene solution of DBTCzPA-II is shown in FIG. 52, and an absorption spectrum of a thin film of DBTCzPA-II is shown in FIG. 53. An ultraviolet-visible spectrophotometer (V-550, manufactured by JASCO Corporation) was used for the measurements of the absorption spectra. In the case of the toluene solution, the measurements were made with the toluene solution of DBTCzPA-II put in a quartz cell, and the absorption spectrum obtained by subtraction of the absorption spectra of quartz and toluene from the measured spectra is shown in the drawing. In addition, as for the absorption spectrum of the thin film, a sample was prepared by evaporation of DBTCzPA-II on a quartz substrate, and the absorption spectrum obtained by subtraction of that of quartz from the measured spectra is shown in the drawing. In FIG. 52 and FIG. 53, the horizontal axis represents wavelength (nm) and the vertical axis represents absorption intensity (arbitrary unit).

Figure 54:
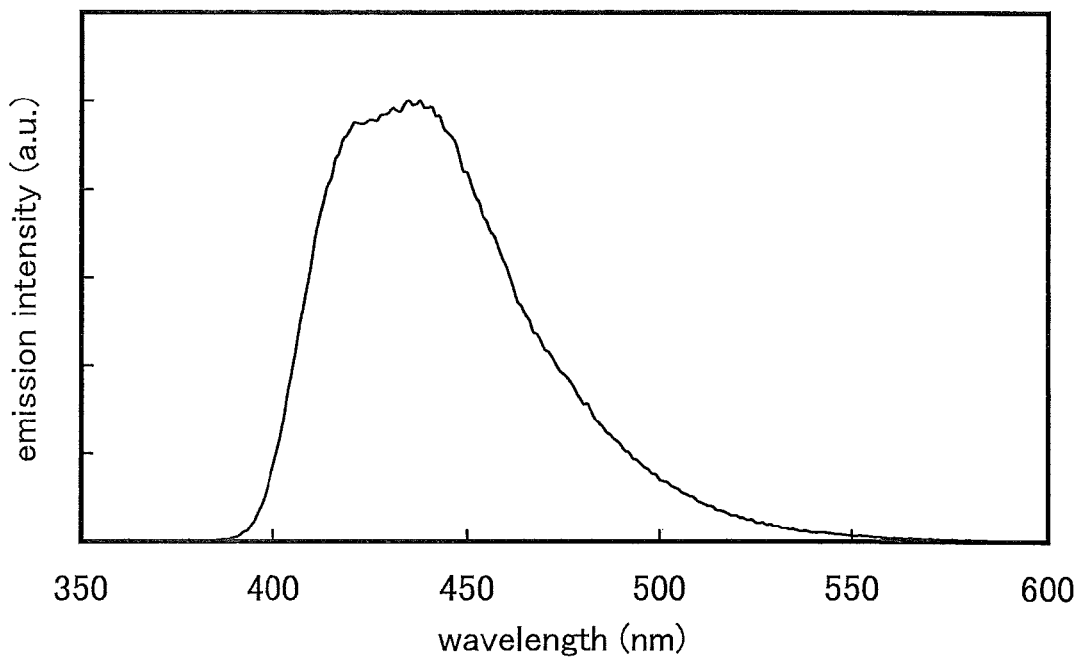
FIG. 54 shows an emission spectrum of DBTCzPA-II in the solution of DBTCzPA-II (the solvent of which is toluene).
Figure 55:
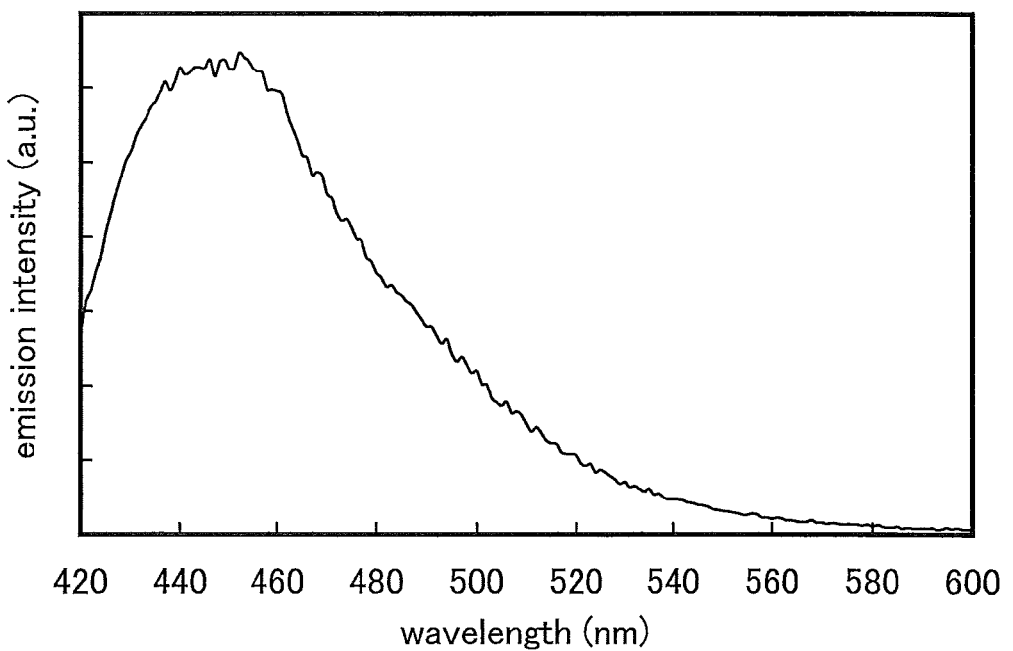
FIG. 55 shows an emission spectrum of DBTCzPA-II in a thin film state.

An emission spectrum of DBTCzPA-II in the toluene solution of DBTCzPA-II is shown in FIG. 54, and an emission spectrum of a thin film is shown in FIG. 55. As in the measurements of the absorption spectra, an ultraviolet-visible spectrophotometer (V-550, manufactured by JASCO Corporation) was used for the measurements. The emission spectrum was measured with the toluene solution of DBTCzPA-II put in a quartz cell, and the emission spectrum of the thin film was measured with a sample prepared by evaporation of DBTCzPA-II on a quartz substrate. FIG. 54 shows that the greatest emission wavelength of DBTCzPA-II in the toluene solution of DBTCzPA-II was around 436 nm (at an excitation wavelength of 376 nm) and FIG. 55 shows that the greatest emission wavelength of the thin film of DBTCzPA-II was around 447 nm (at an excitation wavelength of 400 nm).

Further, the ionization potential of DBTCzPA-II in a thin film state was measured by a photoelectron spectrometer (AC-2, manufactured by Riken Keiki, Co., Ltd.) in air. The obtained value of the ionization potential was converted to a negative value, so that the HOMO level of DBTCzPA-II was −5.73 eV. From the data of the absorption spectra of the thin film in FIG. 53, the absorption edge of DBTCzPA-II, which was obtained from Tauc plot with an assumption of direct transition, was 2.92 eV. Therefore, the optical energy gap of DBTCzPA-II in the solid state was estimated at 2.92 eV; from the values of the HOMO level obtained above and this energy gap, the LUMO level of DBTCzPA-II was able to be estimated at −2.81 eV. It was thus found that DBTCzPA-II had a wide energy gap of 2.92 eV in the solid state.

Further, the oxidation reaction characteristics of DBTCzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.05 V to 1.10 V and then changed from 1.1 V to −0.05 V was one cycle, and 100 cycles were performed.

The measurement results revealed that DBTCzPA-II showed properties effective against repetition of redox reactions between an oxidized state and a neutral state without a large variation in oxidation peak even after the 100 cycles in the measurements.

Further, the HOMO level of DBTCzPA-II was determined also by calculation from the CV measurement results.

First, the potential energy of the reference electrode with respect to the vacuum level used was found to be −4.94 eV, as determined in Example 6. The oxidation peak potential $E_{pa}$ of DBTCzPA-II was 1.01 V. In addition, the reduction peak potential $E_{pc}$ thereof was 0.86 V. Therefore, a half-wave potential (an intermediate potential between $E_{pa}$ and $E_{pc}$) can be calculated at 0.94 V. This means that DBTCzPA-II is oxidized by an electric energy of 0.94 [V versus Ag/Ag$^+$], and this energy corresponds to the HOMO level. Here, since the potential energy of the reference electrode, which was used in this example, with respect to the vacuum level is −4.94 [eV] as described above, the HOMO level of DBTCzPA-II was calculated as follows: −4.94−0.94=−5.88 [eV].

Example 11

Synthesis Example 6

In this example is described a method of synthesizing 3-(dibenzofuran-4-yl)-9-[4-(10-phenyl-9-anthryl)phenyl]-9H-carbazole (abbreviation: DBFCzPA-II), which is one of the carbazole derivatives described in Embodiment 1. A structure of DBFCzPA-II is illustrated in the following structural formula (8).

(8)

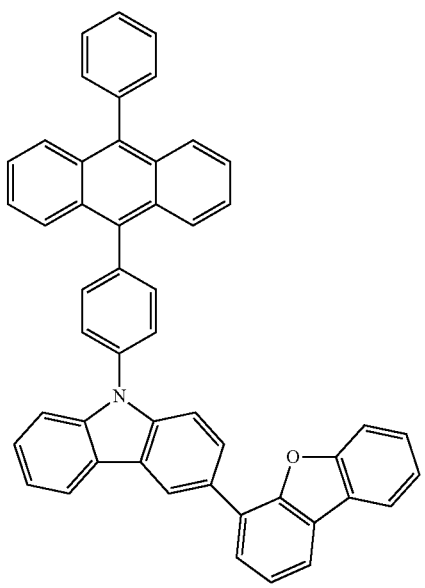

Step 1: Synthesis of 3-(Dibenzofuran-4-yl)-9H-carbazole

This was synthesized as in Step 1 in Synthesis Example 2.

Step 2: Synthesis of DBFCzPA-II

To a 50-mL three-neck flask were added 0.61 g (1.5 mmol) of 9-(4-bromophenyl)-10-phenylanthracene, 0.50 g (1.5 mmol) of 3-(dibenzofuran-4-yl)-9H-carbazole, and 0.29 g (3.0 mmol) of sodium tert-butoxide. After the air in the flask was replaced with nitrogen, to this mixture were added 8.0 mL of toluene and 0.76 mL of tri(tert-butyl)phosphine (a 10 wt % hexane solution). This mixture was degassed by being stirred while the pressure was reduced. After the degassing, 43 mg (0.075 mmol) of bis(dibenzylideneacetone)palladium (0) was added to the mixture. This mixture was stirred at 110° C. for 10 hours under a nitrogen stream. After the stirring, the obtained mixture was suction-filtered through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give an oily substance. The obtained oily substance was purified by silica gel column chromatography (a developing solvent in which the hexane/toluene ratio was 5:1), and the obtained solid was recrystallized from toluene/hexane, so that 0.63 g of a white powder was obtained in 63% yield. The synthesis scheme of Step 2 is illustrated in (b-6).

(b-6)

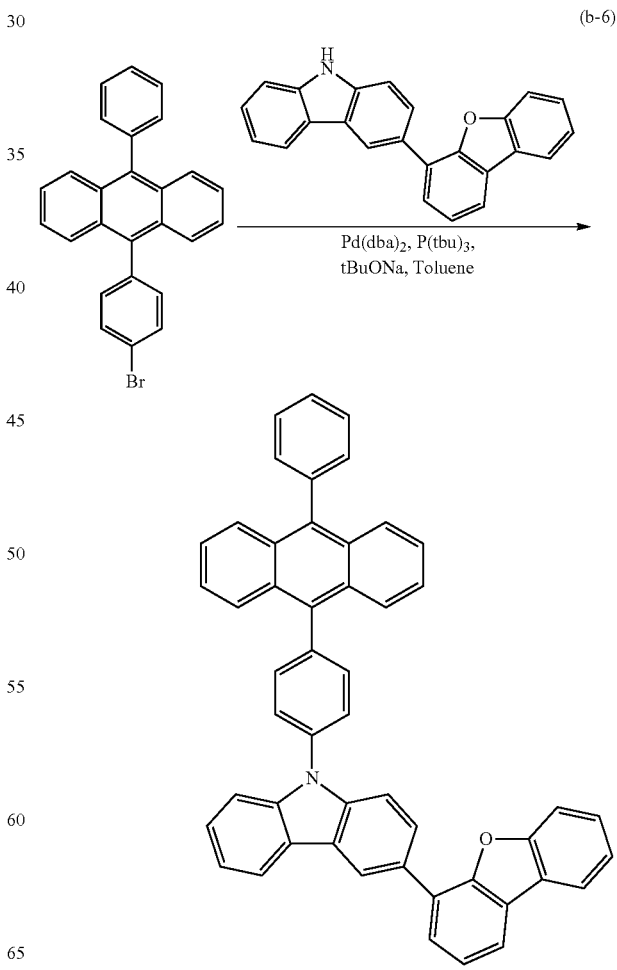

Then, 0.63 g of the obtained white powder was purified. Using a train sublimation method, the purification was conducted by heating of the white powder at 300° C. under a pressure of 3.0 Pa with a flow rate of argon gas of 4.0 mL/min. After the purification, 0.55 g of a pale yellow solid was obtained in 87% yield.

The pale yellow solid after the above purification was subjected to nuclear magnetic resonance ($^1$H NMR) spectroscopy. The measurement data are shown below.

$^1$H NMR (CDCl$_3$, 300 M Hz): δ=7.30-7.66 (m, 15H), 7.71-7.79 (m, 6H), 7.83-7.91 (m, 5H), 7.97 (dd, J$_1$=1.2 Hz, J$_2$=7.2 Hz, 1H), 8.04 (dd, J$_1$=0.90 Hz, J$_2$=7.8 Hz, 1H), 8.10 (dd, J$_1$=1.8 Hz, J$_2$=8.4 Hz, 1H), 8.31 (d, J$_1$=7.5 Hz, 1H), 8.72 (sd, J$_1$=0.90 Hz, 1H).

Figure 56:
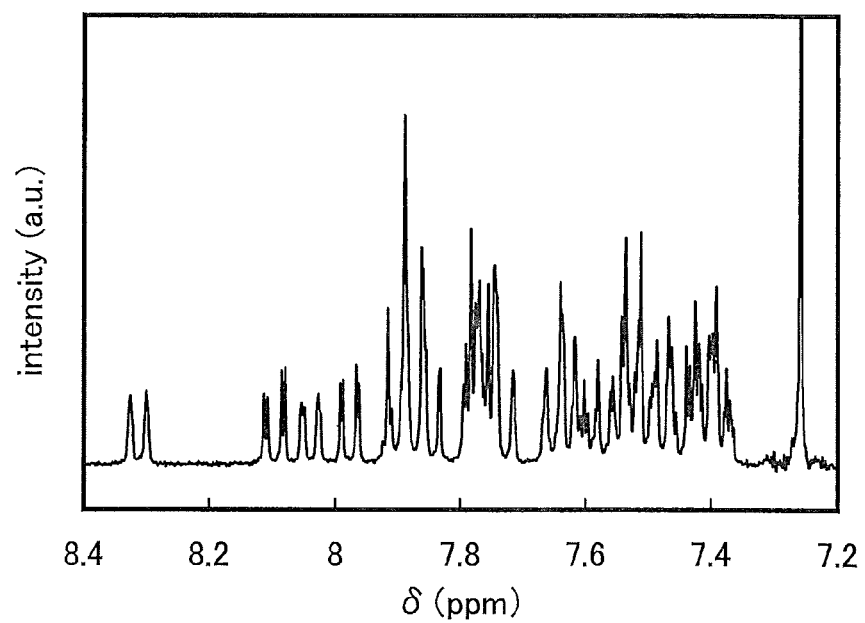
FIG. 56 is a $^1$H NMR chart of DBFCzPA-II.

Further, a $^1$H NMR chart is shown in FIG. 56. The measurement results showed that DBFCzPA-II, which is the carbazole derivative represented by the above structural formula (8), was obtained.

Figure 57:
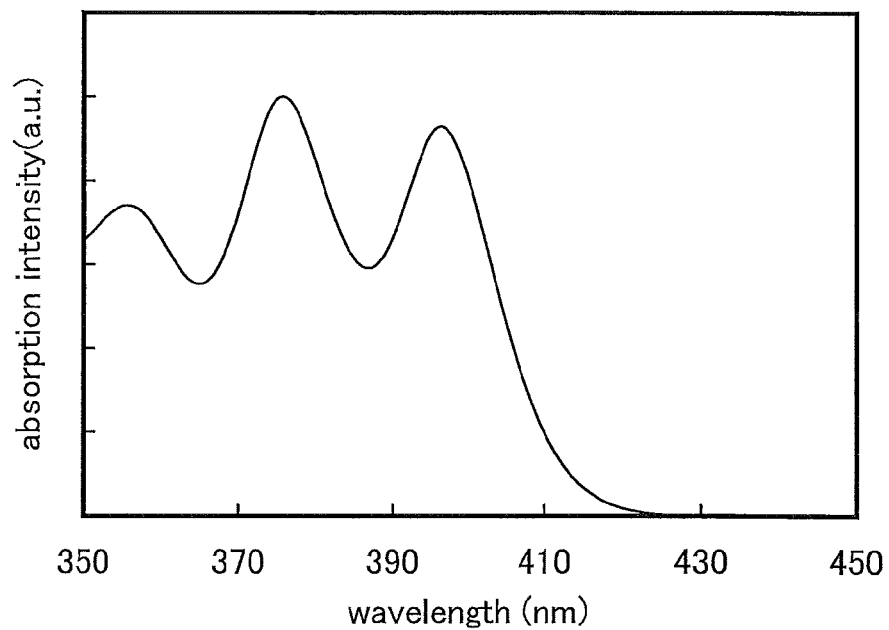
FIG. 57 shows an absorption spectrum of DBFCzPA-II in a solution of DBFCzPA-II (the solvent of which is toluene).
Figure 58:
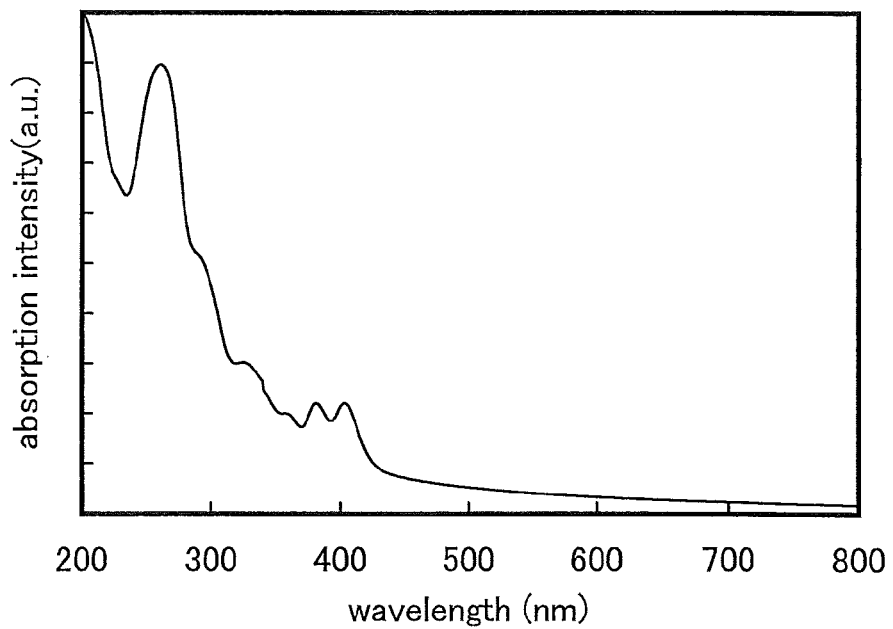
FIG. 58 shows an absorption spectrum of DBFCzPA-II in a thin film state.

Further, an absorption spectrum of DBFCzPA-II in a toluene solution of DBFCzPA-II is shown in FIG. 57, and an absorption spectrum of a thin film of DBFCzPA-II is shown in FIG. 58. An ultraviolet-visible spectrophotometer (V-550, manufactured by JASCO Corporation) was used for the measurements of the absorption spectra. In the case of the toluene solution, the measurements were made with the toluene solution of DBFCzPA-II put in a quartz cell, and the absorption spectrum obtained by subtraction of the absorption spectra of quartz and toluene from the measured spectra is shown in the drawing. In addition, as for the absorption spectrum of the thin film, a sample was prepared by evaporation of DBFCzPA-II on a quartz substrate, and the absorption spectrum obtained by subtraction of that of quartz from the measured spectra is shown in the drawing. In FIG. 57 and FIG. 58, the horizontal axis represents wavelength (nm) and the vertical axis represents absorption intensity (arbitrary unit).

Figure 59:
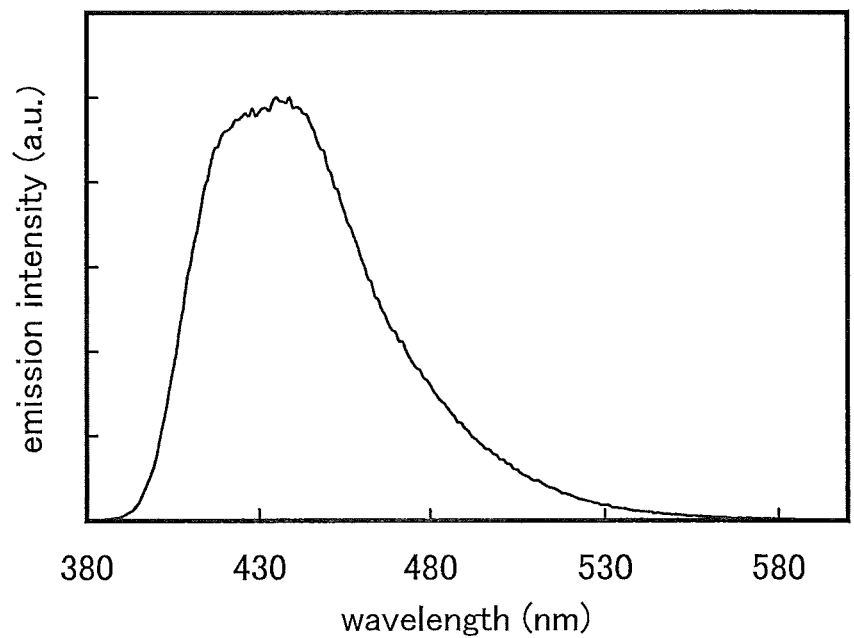
FIG. 59 shows an emission spectrum of DBFCzPA-II in the solution of DBFCzPA-II (the solvent of which is toluene).
Figure 60:
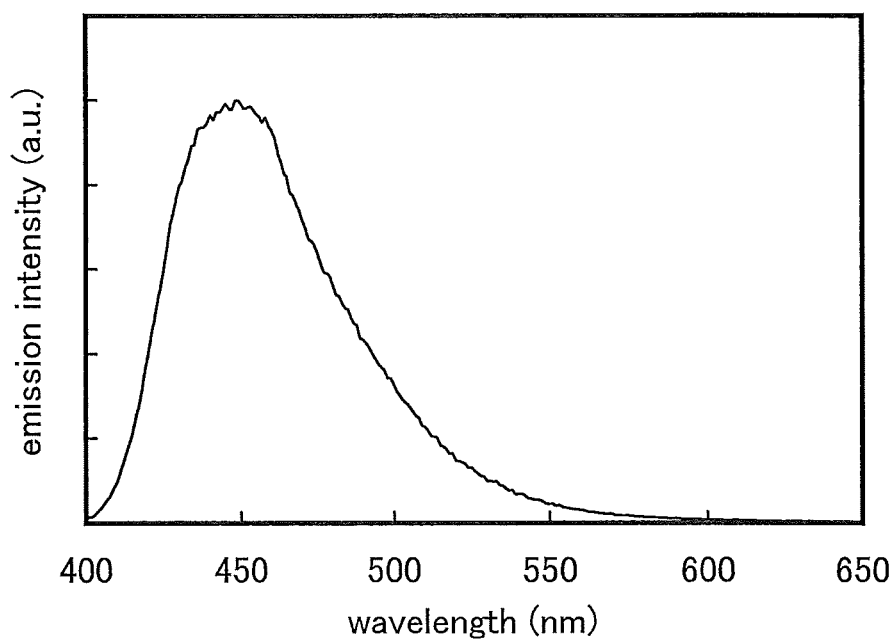
FIG. 60 shows an emission spectrum of DBFCzPA-II in a thin film state.

An emission spectrum of DBFCzPA-II in the toluene solution of DBFCzPA-II is shown in FIG. 59, and an emission spectrum of a thin film is shown in FIG. 60. As in the measurements of the absorption spectra, an ultraviolet-visible spectrophotometer (V-550, manufactured by JASCO Corporation) was used for the measurements. The emission spectrum was measured with the toluene solution of DBFCzPA-II put in a quartz cell, and the emission spectrum of the thin film was measured with a sample prepared by evaporation of DBFCzPA-II on a quartz substrate. FIG. 59 shows that the greatest emission wavelength of DBFCzPA-II in the toluene solution of DBFCzPA-II was around 435 nm (at an excitation wavelength of 376 nm) and FIG. 60 shows that the greatest emission wavelength of the thin film of DBFCzPA-II was around 449 nm (at an excitation wavelength of 380 nm).

Further, the ionization potential of DBFCzPA-II in a thin film state was measured by a photoelectron spectrometer (AC-2, manufactured by Riken Keiki, Co., Ltd.) in air. The obtained value of the ionization potential was converted to a negative value, so that the HOMO level of DBFCzPA-II was −5.64 eV. From the data of the absorption spectra of the thin film in FIG. 58, the absorption edge of DBFCzPA-II, which was obtained from Tauc plot with an assumption of direct transition, was 2.93 eV. Therefore, the optical energy gap of DBFCzPA-II in the solid state was estimated at 2.93 eV; from the values of the HOMO level obtained above and this energy gap, the LUMO level of DBFCzPA-II was able to be estimated at −2.71 eV. It was thus found that DBFCzPA-II had a wide energy gap of 2.93 eV in the solid state.

Further, the oxidation reaction characteristics of DBFCzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.35 V to 0.95 V and then changed from 0.95 V to 0.35 V was one cycle, and 100 cycles were performed.

The measurement results revealed that DBFCzPA-II showed properties effective against repetition of redox reactions between an oxidized state and a neutral state without a large variation in oxidation peak even after the 100 cycles in the measurements.

Further, the HOMO level of DBFCzPA-II was determined also by calculation from the CV measurement results.

First, the potential energy of the reference electrode with respect to the vacuum level used was found to be −4.94 eV, as determined in Example 6. The oxidation peak potential $E_{pa}$ of DBFCzPA-II was 0.91 V. In addition, the reduction peak potential $E_{pc}$ thereof was 0.78 V. Therefore, a half-wave potential (an intermediate potential between $E_{pa}$ and $E_{pc}$) can be calculated at 0.85 V. This means that DBFCzPA-II is oxidized by an electric energy of 0.85 [V versus Ag/Ag$^+$], and this energy corresponds to the HOMO level. Here, since the potential energy of the reference electrode, which was used in this example, with respect to the vacuum level is −4.94 [eV] as described above, the HOMO level of DBFCzPA-II was calculated as follows: −4.94−0.85=−5.79 [eV].

Example 12

Synthesis Example 7

In this example is described a method of synthesizing 3,6-di-(dibenzothiophen-4-yl)-9-phenyl-9H-carbazole (abbreviation: DBT2PC-II), which is one of the carbazole derivatives described in Embodiment 1. A structure of DBT2PC-II is illustrated in the following structural formula (9).

(9)

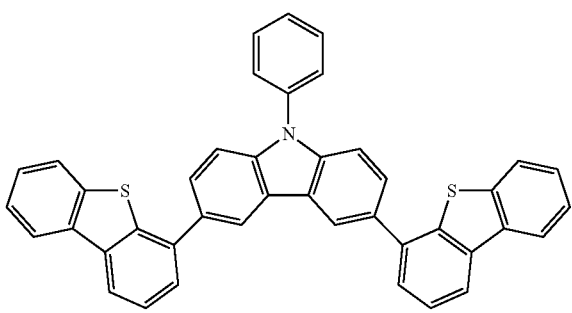

Step 1: Synthesis of 3,6-Di-(dibenzothiophen-4-yl)-9-phenyl-9H-carbazole (abbreviation: DBT2PC-II)

To a 200-mL three-neck flask were added 2.0 g (5.0 mmol) 3,6-dibromo-9-phenyl-9H-carbazole, 3.2 g (11 mmol) of dibenzothiophene-4-boronic acid, 10 mg (0.1 mmol) of palladium(II) acetate, 30 mg (0.1 mmol) of tri(ortho-tolyl)phosphine, 50 mL of toluene, 5 mL of ethanol, and 7.5 mL of a 2 mol/L aqueous potassium carbonate solution. This mixture was degassed while being stirred under reduced pressure, and then heated and stirred at 90° C. for 6 hours in a nitrogen atmosphere to be reacted. After the reaction, this reaction mixture solution was cooled to room temperature, and then filtered to give a residue while being washed with water, ethanol, toluene, and hexane in this order. The residue was purified by silica gel column chromatography (a developing solvent in which the toluene/hexane ratio was 1:3). The fraction thus obtained was concentrated, acetone and ethanol were added thereto, and the mixture was irradiated with ultrasonic waves. Then, recrystallization gave 1.4 g of a white powder in 47% yield. The synthesis scheme of Step 1 is illustrated in (C-7).

(C-7)

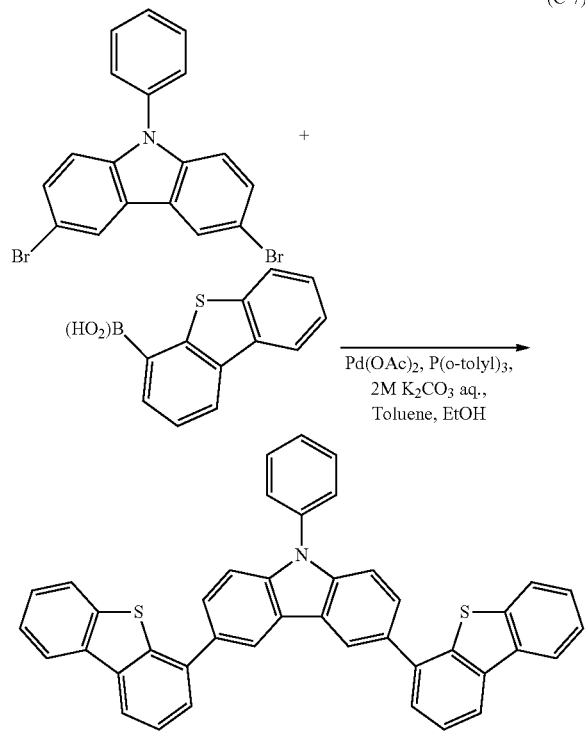

The obtained white powder was subjected to nuclear magnetic resonance (NMR) spectroscopy. The measurement data are shown below.

$^1$H NMR (CDCl$_3$, 300 M Hz): δ=7.44-7.70 (m, 15H), 7.82-7.86 (m, 4H), 8.15-8.22 (m, 4H), 8.57 (d, J=1.5, 2H)

Figure 61A:
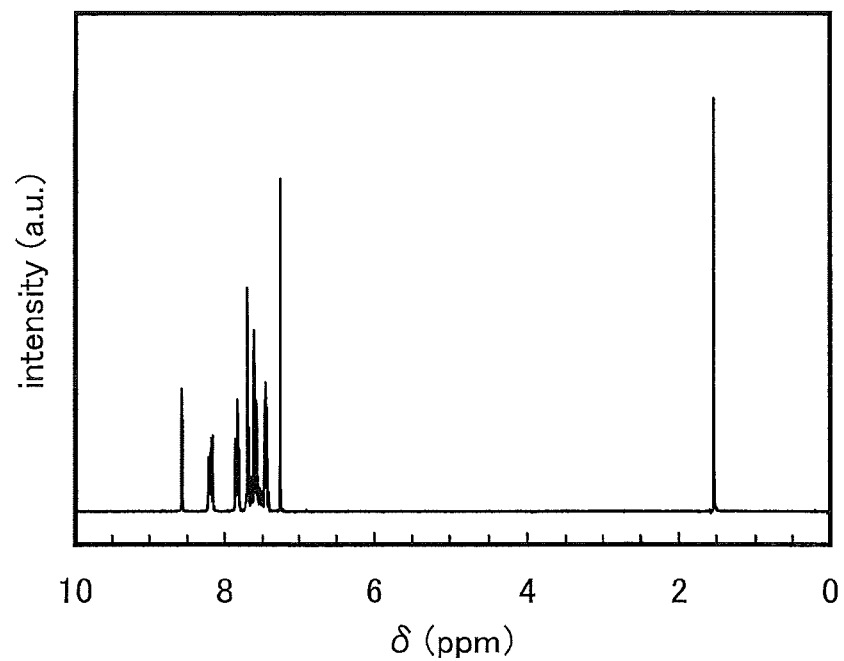
FIGS. 61A and 61B are $^1$H NMR charts of DBT2PC-II.
Figure 61B:
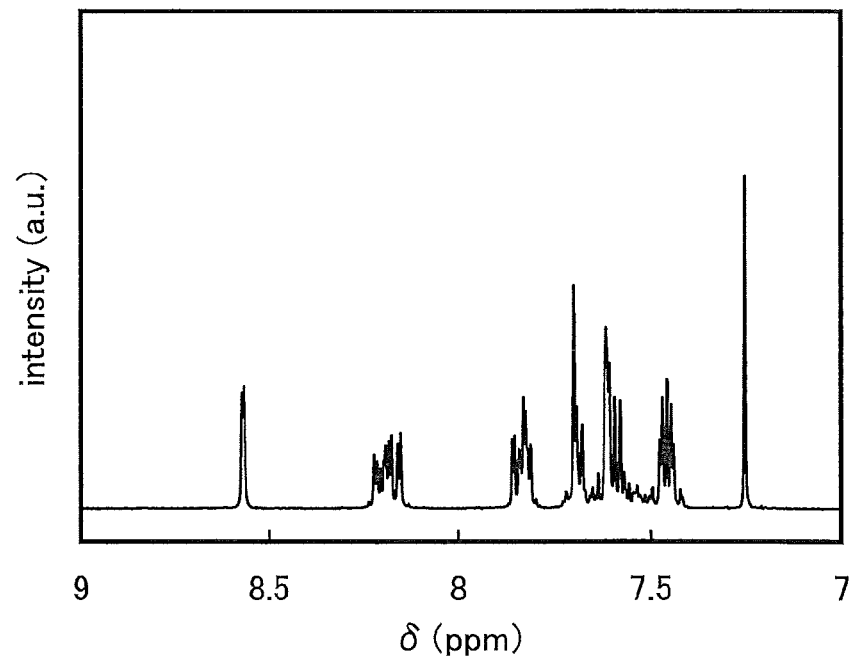

In addition, $^1$H NMR charts are shown in FIGS. 61A and 61B. Note that FIG. 61B is a chart where the range of from 7 ppm to 9 ppm in FIG. 61A is enlarged. The measurement results showed that DBT2PC-II, which is the carbazole derivative represented by the above structural formula (9), was obtained. Note that the Rf values of DBT2PC-II and 3,6-dibromo-9-phenyl-9H-carbazole were respectively 0.41 and 0.51, which were found by silica gel thin layer chromatography (TLC) (a developing solvent in which the ethyl acetate/hexane ratio was 1:10).

Figure 62:
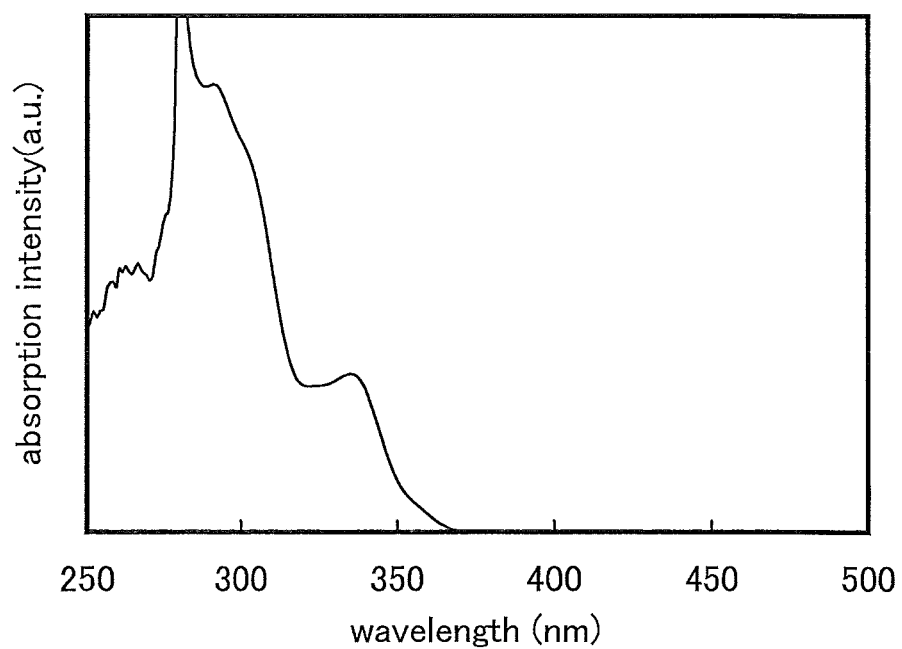
FIG. 62 shows an absorption spectrum of DBT2PC-II in a solution of DBT2PC-II (the solvent of which is toluene).
Figure 63:
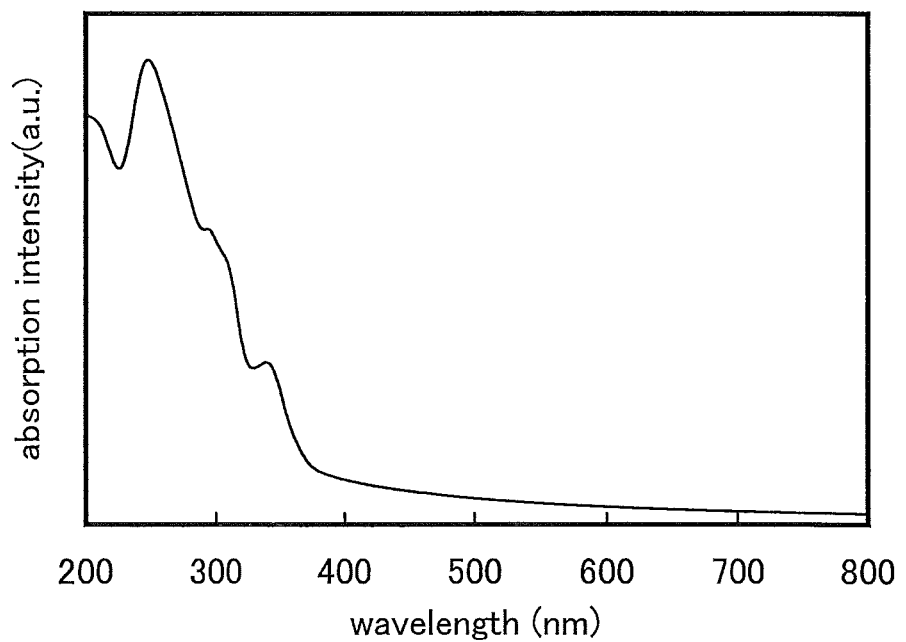
FIG. 63 shows an absorption spectrum of DBT2PC-II in a thin film state.

Further, an absorption spectrum of DBT2PC-II in a toluene solution of DBT2PC-II is shown in FIG. 62, and an absorption spectrum of a thin film of DBT2PC-II is shown in FIG. 63. An ultraviolet-visible spectrophotometer (V-550, manufactured by JASCO Corporation) was used for the measurements of the absorption spectra. In the case of the toluene solution, the measurements were made with the toluene solution of DBT2PC-II put in a quartz cell, and the absorption spectrum obtained by subtraction of the absorption spectra of quartz and toluene from the measured spectra is shown in the drawing. In addition, as for the absorption spectrum of the thin film, a sample was prepared by evaporation of DBT2PC-II on a quartz substrate, and the absorption spectrum obtained by subtraction of that of quartz from the measured spectra is shown in the drawing. In FIG. 62 and FIG. 63, the horizontal axis represents wavelength (nm) and the vertical axis represents absorption intensity (arbitrary unit).

Figure 64:
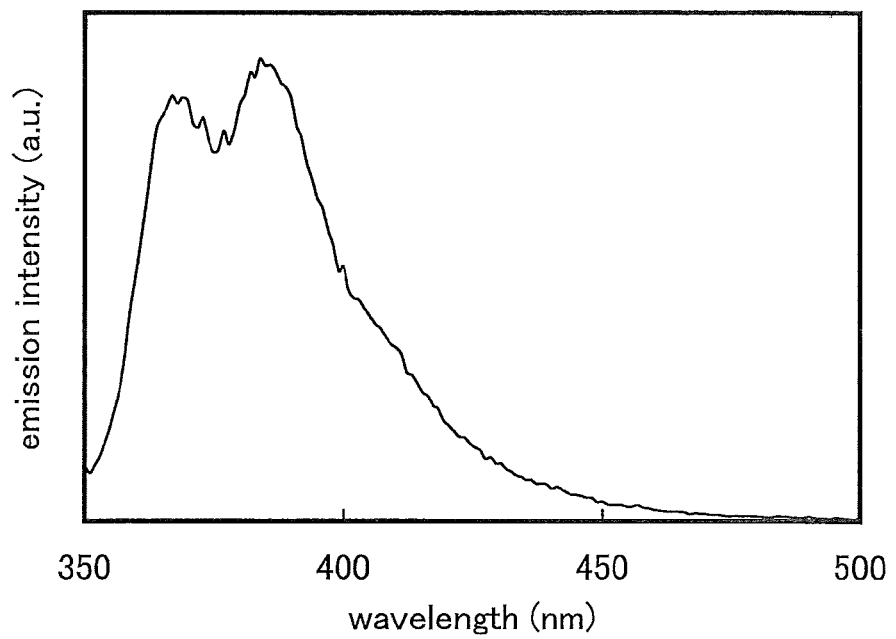
FIG. 64 shows an emission spectrum of DBT2PC-II in the solution of DBT2PC-II (the solvent of which is toluene).
Figure 65:
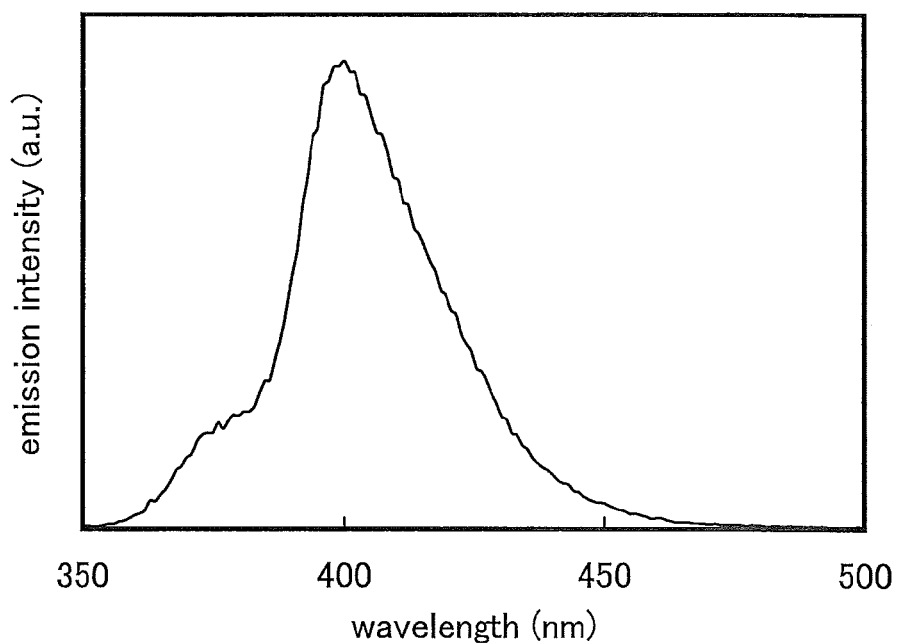
FIG. 65 shows an emission spectrum of DBT2PC-II in a thin film state.

An emission spectrum of DBT2PC-II in the toluene solution of DBT2PC-II is shown in FIG. 64, and an emission spectrum of a thin film is shown in FIG. 65. As in the measurements of the absorption spectra, an ultraviolet-visible spectrophotometer (V-550, manufactured by JASCO Corporation) was used for the measurements. The emission spectrum was measured with the toluene solution of DBT2PC-II put in a quartz cell, and the emission spectrum of the thin film was measured with a sample prepared by evaporation of DBT2PC-II on a quartz substrate. FIG. 64 shows that the maximum emission wavelengths of DBT2PC-II in the toluene solution of DBT2PC-II were around 368 nm and 385 nm (at an excitation wavelength of 300 nm) and FIG. 65 shows that the greatest emission wavelength of the thin film of DBT2PC-II was around 400 nm (at an excitation wavelength of 341 nm).

Further, the ionization potential of DBT2PC-II in a thin film state was measured by a photoelectron spectrometer (AC-2, manufactured by Riken Keiki, Co., Ltd.) in air. The obtained value of the ionization potential was converted to a negative value, so that the HOMO level of DBT2PC-II was −5.72 eV. From the data of the absorption spectra of the thin film in FIG. 63, the absorption edge of DBT2PC-II, which was obtained from Tauc plot with an assumption of direct transition, was 3.40 eV. Therefore, the optical energy gap of DBT2PC-II in the solid state was estimated at 3.40 eV; from the values of the HOMO level obtained above and this energy gap, the LUMO level of DBT2PC-II was able to be estimated at −2.32 eV. It was thus found that DBT2PC-II had a wide energy gap of 3.40 eV in the solid state.

Further, the oxidation reaction characteristics of DBT2PC-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.35 V to 1.50 V and then changed from 1.50 V to −0.35 V was one cycle, and 100 cycles were performed.

The measurement results revealed that DBT2PC-II showed properties effective against repetition of redox reactions between an oxidized state and a neutral state without a large variation in oxidation peak even after the 100 cycles in the measurements.

Further, the HOMO level of DBT2PC-II was determined also by calculation from the CV measurement results.

First, the potential energy of the reference electrode with respect to the vacuum level used was found to be −4.94 eV, as determined in Example 6. The oxidation peak potential E$_{pa}$ of DBT2PC-II was 1.20 V. In addition, the reduction peak potential E$_{pc}$ thereof was 0.81 V. Therefore, a half-wave potential (an intermediate potential between E$_{pa}$ and E$_{pc}$) can be calculated at 1.01 V. This means that DBT2PC-II is oxidized by an electric energy of 1.01 [V versus Ag/Ag$^+$], and this energy corresponds to the HOMO level. Here, since the potential energy of the reference electrode, which was used in this example, with respect to the vacuum level is −4.94 [eV] as described above, the HOMO level of DBT2PC-II was calculated as follows: −4.94−1.01=−5.95 [eV].

Example 13

Synthesis Example 8

In this example is described a method of synthesizing 2,7-di-(dibenzothiophen-4-yl)-9-phenyl-9H-carbazole (abbreviation: 2,7DBT2PC-II), which is one of the carbazole derivatives described in Embodiment 1. A structure of 2,7DBT2PC-II is illustrated in the following structural formula (10).

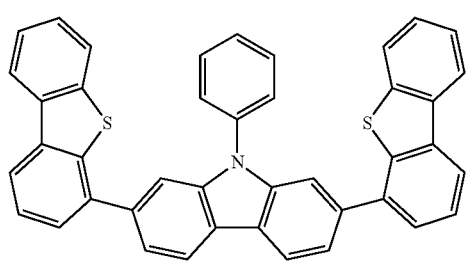

(10)

Step 1: Synthesis of
2,7-Di-(dibenzothiophen-4-yl)-9H-carbazole

In a 200-mL three-neck flask were mixed 3.3 g (10 mmol) of 2,7-dibromo-9H-carbazole, 6.0 g (21 mmol) of dibenzofuran-4-boronic acid, 11 mg (0.1 mmol) of palladium(II) acetate, 30 mg (0.1 mmol) of tris(ortho-tolyl)phosphine, 50 mL of toluene, 5 mL of ethanol, and 7.5 mL of a 2 mol/L aqueous potassium carbonate solution. This mixture was degassed while being stirred under reduced pressure, and then heated and stirred at 90° C. for 4.5 hours in a nitrogen atmosphere to be reacted. After the reaction, this reaction mixture solution was cooled to room temperature, and then filtered to give a residue. This residue was heated and stirred in a mixed solution of ethanol/water, and was filtered to give 4.9 g of a white powder in 92% yield. The synthesis scheme of Step 1 is illustrated in (D-8).

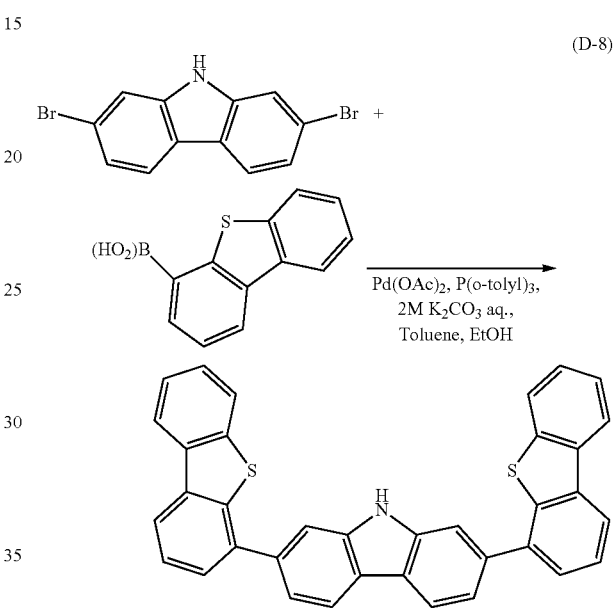

(D-8)

Step 2: Synthesis of 2,7-Di-(dibenzothiophen-4-yl)-
9-phenyl-9H-carbazole (abbreviation:
2,7DBT2PC-II)

In a 200-mL three-neck flask were mixed 0.7 g (4.3 mmol) of iodobenzene, 1.7 g (3.2 mmol) of 2,7-di-(dibenzothiophen-4-yl)-9H-carbazole, 0.6 g (5.5 mmol) of sodium tert-butoxide, and 36 mg (0.1 mmol) of bis(dibenzylideneacetone)palladium(0), and the air in the flask was replaced with nitrogen. Then, 5 mL of dehydrated xylene was added to this mixture. After the mixture was degassed while being stirred under reduced pressure, 0.7 mL (0.3 mmol) of tri(tert-butyl)phosphine (10 wt % hexane solution) was added to the mixture. This mixture was stirred at 120° C. for 5 hours in a nitrogen atmosphere to be reacted. After the reaction, 300 mL of toluene was added to this reaction mixture solution, and this suspension was filtered through Florisil and Celite. The resulting filtrate was concentrated, followed by purification by silica gel column chromatography (toluene as the developing solvent). The fraction thus obtained was concentrated, acetone and methanol were added thereto, and the mixture was irradiated with ultrasonic waves. Then, recrystallization gave 1.9 g of a white powder in 93% yield. The above synthesis method is illustrated in (E-8) below.

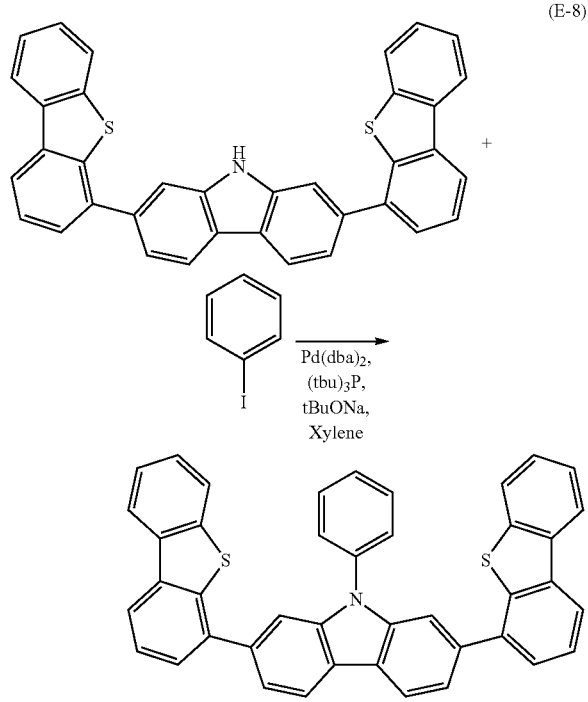

(E-8)

The obtained white powder was subjected to nuclear magnetic resonance (NMR) spectroscopy. The measurement data are shown below.

$^1$H NMR (CDCl$_3$, 300 M Hz): δ (ppm)=7.39-7.50 (m, 5H), 7.53-7.62 (m, 6H), 7.70-7.74 (m, 4H), 7.81-7.87 (m, 4H), 8.12-8.21 (m, 4H), 8.32 (d, J=8.1, 2H)

Figure 66A:
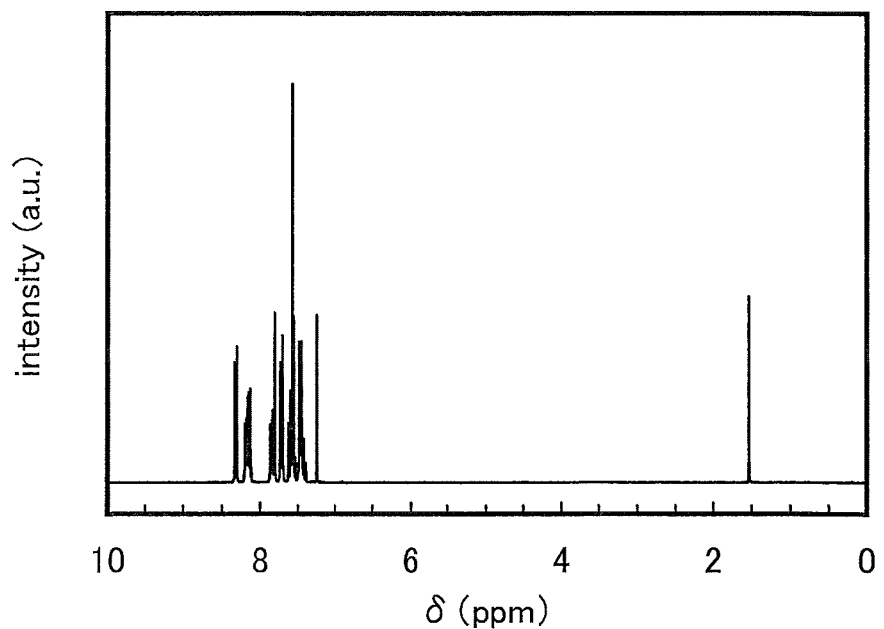
FIGS. 66A and 66B are $^1$H NMR charts of 2,7DBT2PC-II.
Figure 66B:
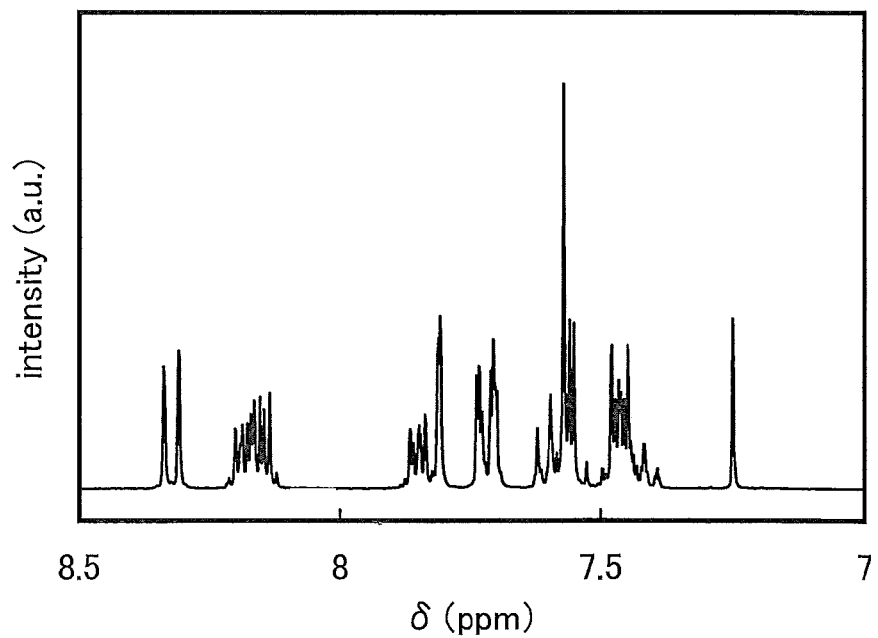

In addition, $^1$H NMR charts are shown in FIGS. 66A and 66B. The measurement results showed that 2,7DBT2PC-II, which is the carbazole derivative represented by the above structural formula (910 was obtained. Note that the Rf values of 2,7DBT2PC-II and 2,7-di-(dibenzothiophen-4-yl)-9H-carbazole were respectively 0.41 and 0.22, which were found by silica gel thin layer chromatography (TLC) (a developing solvent in which the ethyl acetate/hexane ratio was 1:5).

Figure 67:
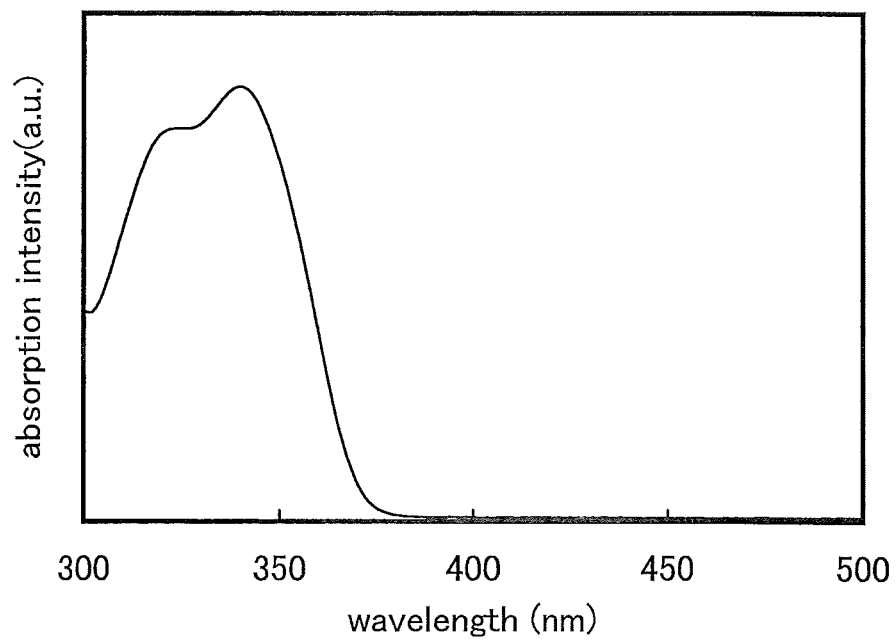
FIG. 67 shows an absorption spectrum of 2,7DBT2PC-II in a solution of 2,7DBT2PC-II (the solvent of which is toluene).
Figure 68:
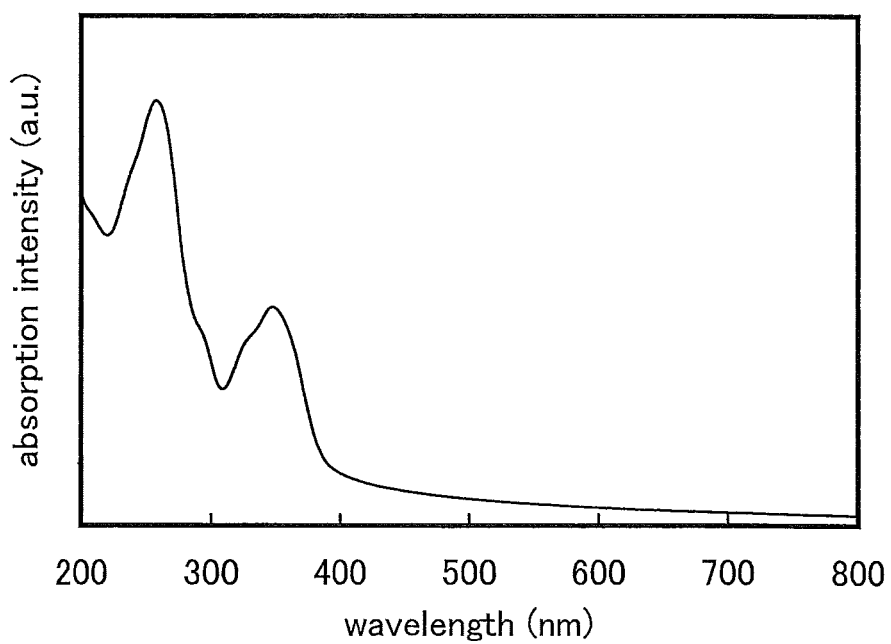
FIG. 68 shows an absorption spectrum of 2,7DBT2PC-II in a thin film state.

Further, an absorption spectrum of 2,7DBT2PC-II in a toluene solution of 2,7DBT2PC-II is shown in FIG. 67, and an absorption spectrum of a thin film of 2,7DBT2PC-II is shown in FIG. 68. An ultraviolet-visible spectrophotometer (V-550, manufactured by JASCO Corporation) was used for the measurements of the absorption spectra. In the case of the toluene solution, the measurements were made with the toluene solution of 2,7DBT2PC-II put in a quartz cell, and the absorption spectrum obtained by subtraction of the absorption spectra of quartz and toluene from the measured spectra is shown in the drawing. In addition, as for the absorption spectrum of the thin film, a sample was prepared by evaporation of 2,7DBT2PC-II on a quartz substrate, and the absorption spectrum obtained by subtraction of that of quartz from the measured spectra is shown in the drawing. In FIG. 67 and FIG. 68, the horizontal axis represents wavelength (nm) and the vertical axis represents absorption intensity (arbitrary unit).

Figure 69:
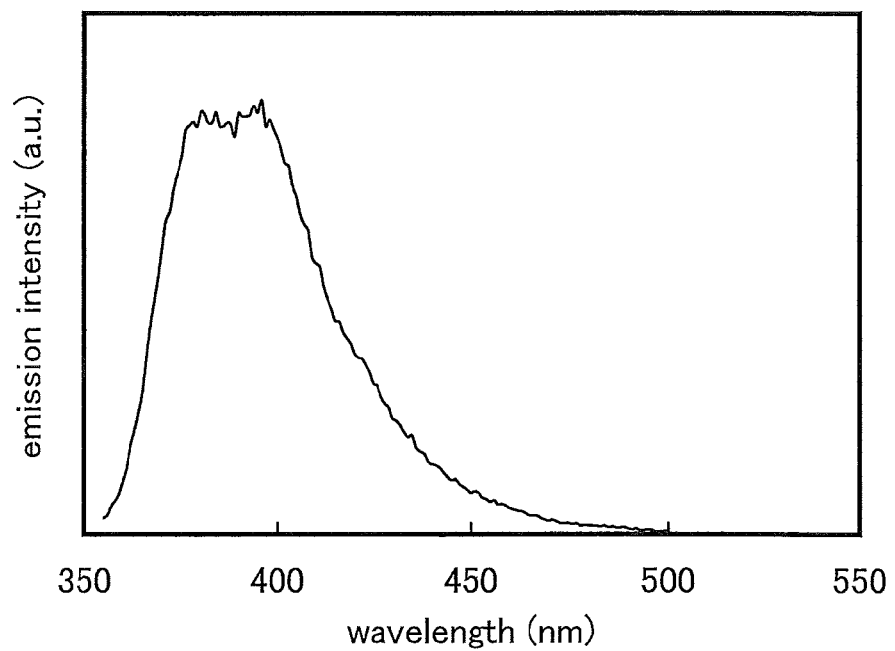
FIG. 69 shows an emission spectrum of 2,7DBT2PC-II in the solution of 2,7DBT2PC-II (the solvent of which is toluene).
Figure 70:
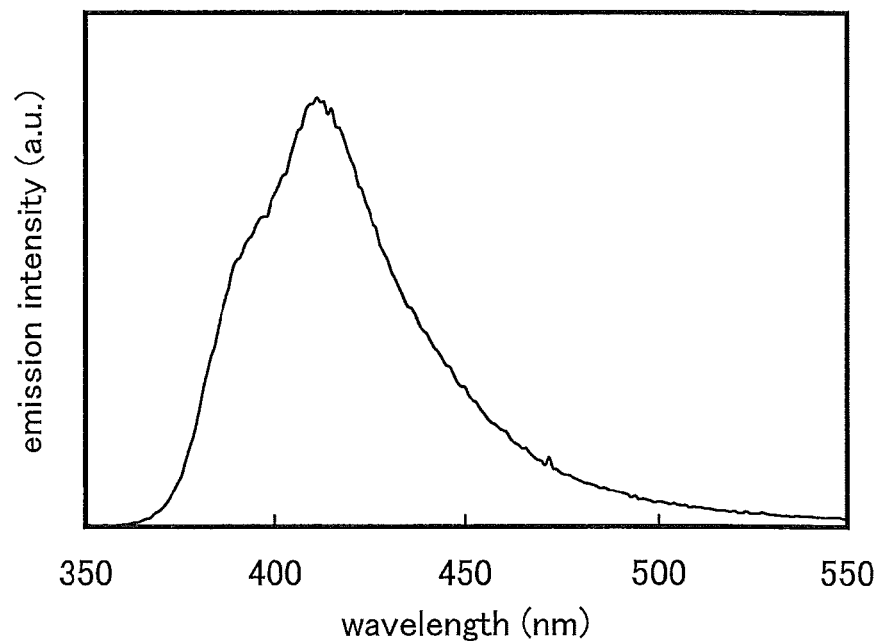
FIG. 70 shows an emission spectrum of 2,7DBT2PC-II in a thin film state.

An emission spectrum of 2,7DBT2PC-II in the toluene solution of 2,7DBT2PC-II is shown in FIG. 69, and an emission spectrum of the thin film of 2,7DBT2PC-II is shown in FIG. 70. As in the measurements of the absorption spectra, an ultraviolet-visible spectrophotometer (V-550, manufactured by JASCO Corporation) was used for the measurements. The emission spectrum was measured with the toluene solution of 2,7DBT2PC-II put in a quartz cell, and the emission spectrum of the thin film was measured with a sample prepared by evaporation of 2,7DBT2PC-II on a quartz substrate. FIG. 69 shows that the maximum emission wavelengths of 2,7DBT2PC-II in the toluene solution of 2,7DBT2PC-II were around 381 nm and 395 nm (at an excitation wavelength of 345 nm) and FIG. 70 shows that the greatest emission wavelength of the thin film of 2,7DBT2PC-II was around 411 nm (at an excitation wavelength of 347 nm).

Further, the ionization potential of 2,7DBT2PC-II in a thin film state was measured by a photoelectron spectrometer (AC-2, manufactured by Riken Keiki, Co., Ltd.) in air. The obtained value of the ionization potential was converted to a negative value, so that the HOMO level of 2,7DBT2PC-II was −5.79 eV. From the data of the absorption spectra of the thin film in FIG. 68, the absorption edge of 2,7DBT2PC-II, which was obtained from Tauc plot with an assumption of direct transition, was 3.25 eV. Therefore, the optical energy gap of 2,7DBT2PC-II in the solid state was estimated at 3.25 eV; from the values of the HOMO level obtained above and this energy gap, the LUMO level of 2,7DBT2PC-II was able to be estimated at −2.54 eV. It was thus found that 2,7DBT2PC-II had a wide energy gap of 3.25 eV in the solid state.

Further, the oxidation reaction characteristics of 2,7DBT2PC-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.13 V to 1.50 V and then changed from 1.50 V to −0.13 V was one cycle, and 100 cycles were performed.

The measurement results revealed that 2,7DBT2PC-II showed properties effective against repetition of redox reactions between an oxidized state and a neutral state without a large variation in oxidation peak even after the 100 cycles in the measurements.

Further, the HOMO level of 2,7DBT2PC-II was determined also by calculation from the CV measurement results.

First, the potential energy of the reference electrode with respect to the vacuum level used was found to be −4.94 eV, as determined in Example 6. The oxidation peak potential $E_{pa}$ of 2,7DBT2PC-II was 1.23 V. In addition, the reduction peak potential $E_{pc}$ thereof was 0.93 V. Therefore, a half-wave potential (an intermediate potential between $E_{pa}$ and $E_{pc}$) can be calculated at 1.08 V. This means that 2,7DBT2PC-II is oxidized by an electric energy of 1.01 [V versus Ag/Ag$^+$], and this energy corresponds to the HOMO level. Here, since the potential energy of the reference electrode, which was used in this example, with respect to the vacuum level is −4.94 [eV] as described above, the HOMO level of 2,7DBT2PC-II was calculated as follows: −4.94−1.08=−6.02 [eV].

Example 14

Synthesis Example 9

In this example is described a method of synthesizing 3,6-di-(dibenzofuran-4-yl)-9-phenyl-9H-carbazole (abbreviation: DBF2PC-II), which is one of the carbazole derivatives described in Embodiment 1. A structure of DBF2PC-II is illustrated in the following structural formula (11).

(11)

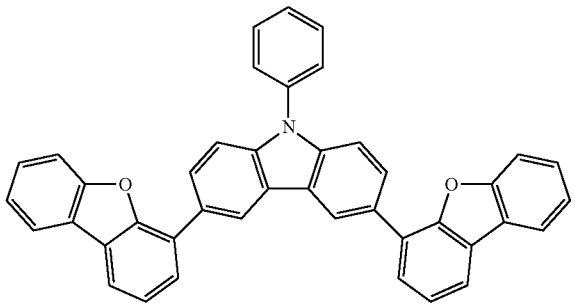

Synthesis of 3,6-Di(dibenzofuran-4-yl)-9-phenyl-9H-carbazole (abbreviation: DBF2PC-II)

To a 200-mL three-neck flask were added 2.0 g (5.0 mmol) of 3,6-dibromo-9-phenyl-9H-carbazole, 3.2 g (11 mmol) of dibenzofuran-4-boronic acid, 10 mg (0.1 mmol) of palladium (II) acetate, 30 mg (0.1 mmol) of tris(o-tolyl)phosphine, 50 mL of toluene, 5 mL of ethanol, and 7.5 mL of a 2 mol/L aqueous potassium carbonate solution. This mixture was degassed while being stirred under reduced pressure, and then heated and stirred at 90° C. for 6.5 hours under a nitrogen stream to be reacted.

After the reaction, 250 mL of toluene was added to this reaction mixture and the mixture was heated. The mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135) in this order to give a filtrate. The resulting filtrate was purified by silica gel column chromatography (a developing solvent in which the toluene/hexane ratio was 1:3). The obtained fraction was concentrated, acetone, methanol, and water were added thereto, and the mixture was irradiated with ultrasonic waves. Then, acetone and methanol were added to the obtained precipitate and the mixture was washed while being irradiated with ultrasonic waves, so that 2.8 g of a white powder which was the object of the synthesis was obtained in 69% yield. The synthesis scheme of the above synthesis method is illustrated in (c-9) below.

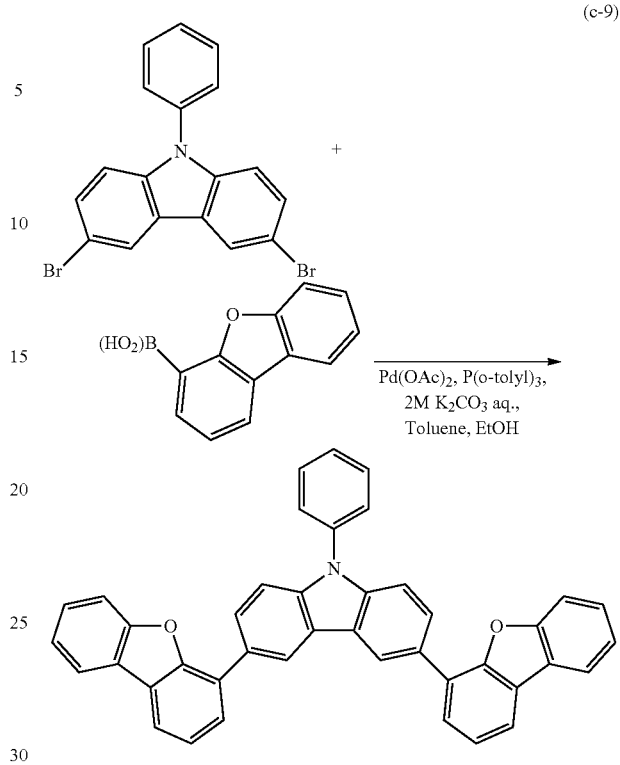

(c-9)

The Rf values of the white powder obtained through the above reaction and 3,6-dibromo-9-phenyl-9H-carbazole were respectively 0.32 and 0.55, which were found by silica gel thin layer chromatography (TLC) (a developing solvent in which the ethyl acetate/hexane ratio was 1:10).

Figure 71A:
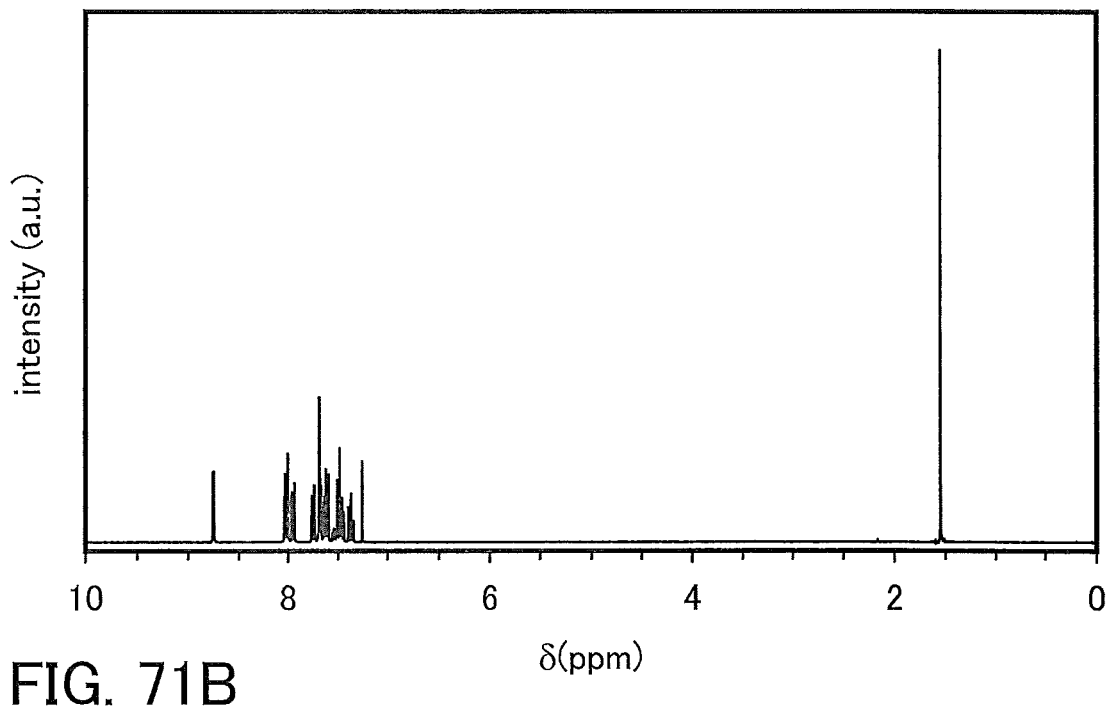
FIGS. 71A and 71B are NMR charts of DBF2PC-II.
Figure 71B:
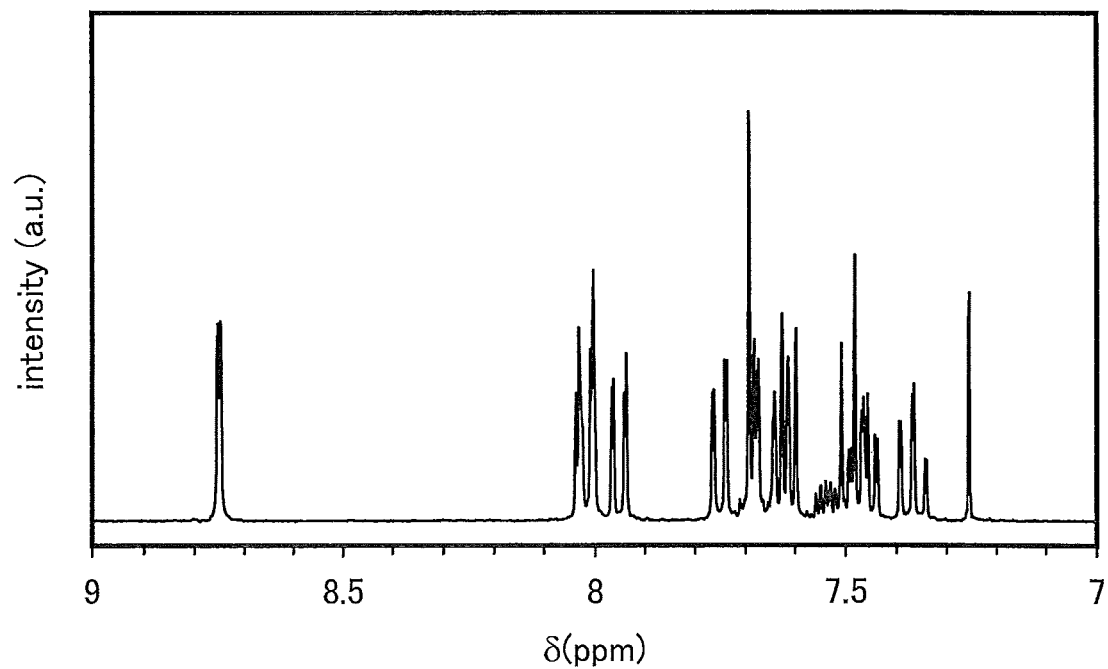

The white powder obtained by the above Step 1 was subjected to nuclear magnetic resonance (NMR) spectroscopy. The measurement data are shown below. In addition, $^1$H NMR charts are shown in FIGS. 71A and 71B. Note that FIG. 71B is an enlarged chart of FIG. 71A. The measurement results confirmed that the white powder obtained by the above Step 1 was DBF2PC-II, which is represented by the above structural formula (11).

$^1$H NMR (CDCl$_3$, 300 MHz): δ (ppm)=7.37 (dt, J=7.8 Hz, J=1.2 Hz, 2H), 7.44-7.56 (m, 5H), 7.60-7.69 (m, 8H), 7.75 (dd, J=7.2 Hz, J=1.5 Hz, 2H), 7.95 (dd, J=7.8 Hz, J=1.5 Hz, 2H), 8.00-8.04 (m, 4H), 8.75 (d, J=1.5 Hz, 2H).

Figure 72A:
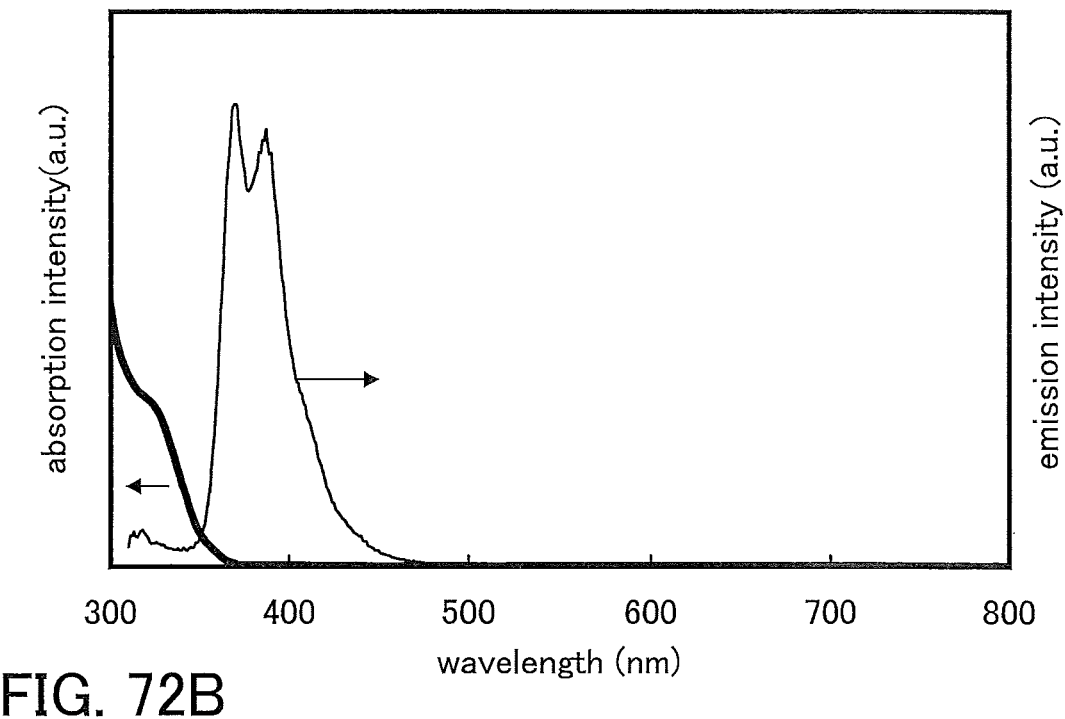
FIGS. 72A and 72B show an absorption and emission spectra of DBF2PC-II.
Figure 72B:
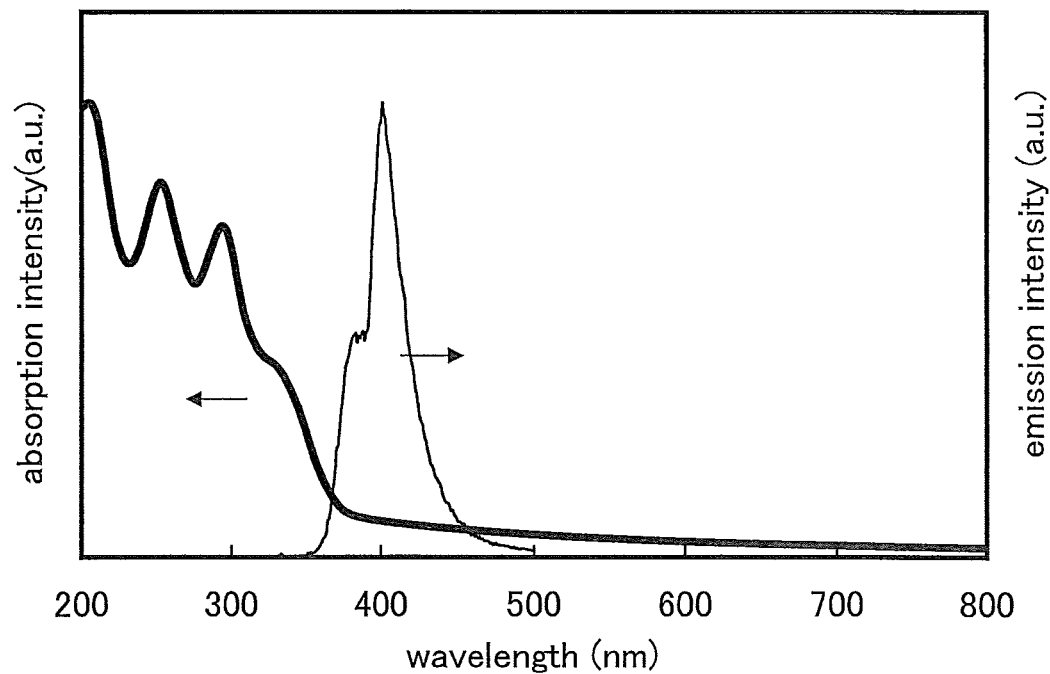

Further, an absorption and emission spectra of DBF2PC-II in a toluene solution of DBF2PC-II are shown in FIG. 72A, and an absorption and emission spectra of a thin film of DBF2PC-II are shown in FIG. 72B. An ultraviolet-visible spectrophotometer (V-550, manufactured by JASCO Corporation) was used for the measurements of the spectra. The spectra of the toluene solution were measured with a toluene solution of DBF2PC-II put in a quartz cell. The spectra of the thin film were measured with a sample prepared by evaporation of DBF2PC-II on a quartz substrate. Note that as the absorption spectrum of the toluene solution, the absorption spectrum obtained by subtraction of the absorption spectra of quartz and toluene from the measured spectra is shown in the drawing, and as the absorption spectrum of the thin film, the absorption spectrum obtained by subtraction of that of quartz from the measured spectra is shown in the drawing.

FIGS. 72A and 72B show that the maximum absorption wavelength of DBF2PC-II in the toluene solution of DBF2PC-II was around 320 nm, the maximum emission wavelengths thereof were around 370 nm and 387 nm (at an excitation wavelength of 290 nm), the maximum absorption wavelengths of the thin film of DBF2PC-II were around 325 nm, 294 nm, 253 nm, and 205 nm, and the maximum emission wavelengths thereof were around 401 nm and 382 nm (at an excitation wavelength of 325 nm).

The absorption spectra reveal that DBF2PC-II described in this example is a material that shows almost no absorption in the visible region. Further, the emission spectra reveal that the light emission is bluish violet.

Further, the ionization potential of DBF2PC-II in a thin film state was measured by a photoelectron spectrometer (AC-2, manufactured by Riken Keiki, Co., Ltd.) in air. The obtained value of the ionization potential was converted to a negative value, so that the HOMO level of DBF2PC-II was −5.67 eV. From the data of the absorption spectra of the thin film in FIG. 72, the absorption edge of DBF2PC-II, which was obtained from Tauc plot with an assumption of direct transition, was 3.40 eV. Therefore, the optical band gap of DBF2PC-II in the solid state was estimated at 3.40 eV; from the values of the HOMO level obtained above and this band gap, the LUMO level of DBF2PC-II was able to be estimated at −2.27 eV. It was thus found that DBF2PC-II had a wide band gap of 3.40 eV in the solid state and also had a relatively deep HOMO level.

Further, thermophysical properties of DBF2PC-II were measured with a differential scanning calorimeter (DSC, manufactured by PerkinElmer, Inc., Pyris 1). First, a sample was heated from −10° C. up to 350° C. at a temperature rising rate of 40° C./min, and then it was cooled to −10° C. at 40° C./min. After that, heating was performed up to 290° C. at a temperature rising rate of 10° C./min, and thus a DSC chart was obtained. As can be seen from the DSC chart, a peak indicating the glass transition temperature of DBF2PC-II was observed, which showed the glass transition temperature (Tg) was 131° C. Thus, DBF2PC-II has a high glass transition point. Therefore, it was confirmed that DBF2PC-II of this synthesis example had high heat resistance.

Example 15

In this example described is a light-emitting element in which 3,6-di(dibenzofuran-4-yl)-9-phenyl-9H-carbazole (abbreviation: DBF2PC-II, a structural formula (11)), which is one of the carbazole derivatives represented by the general formula (G1), is used as a material for a hole-transport layer adjacent to a light-emitting layer using an emission center substance that emits blue fluorescence.

The molecular structures of organic compounds used in this example are represented by the structural formulae (11), (iv), (viii), and (ix) below.

(11)

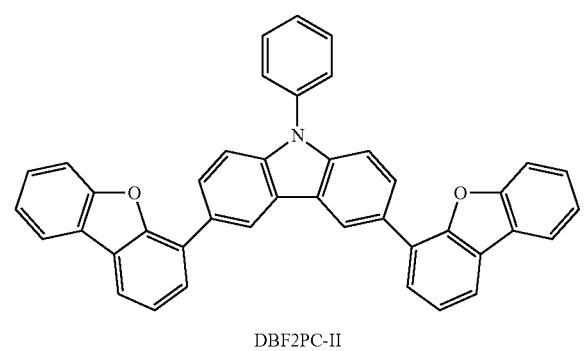

DBF2PC-II

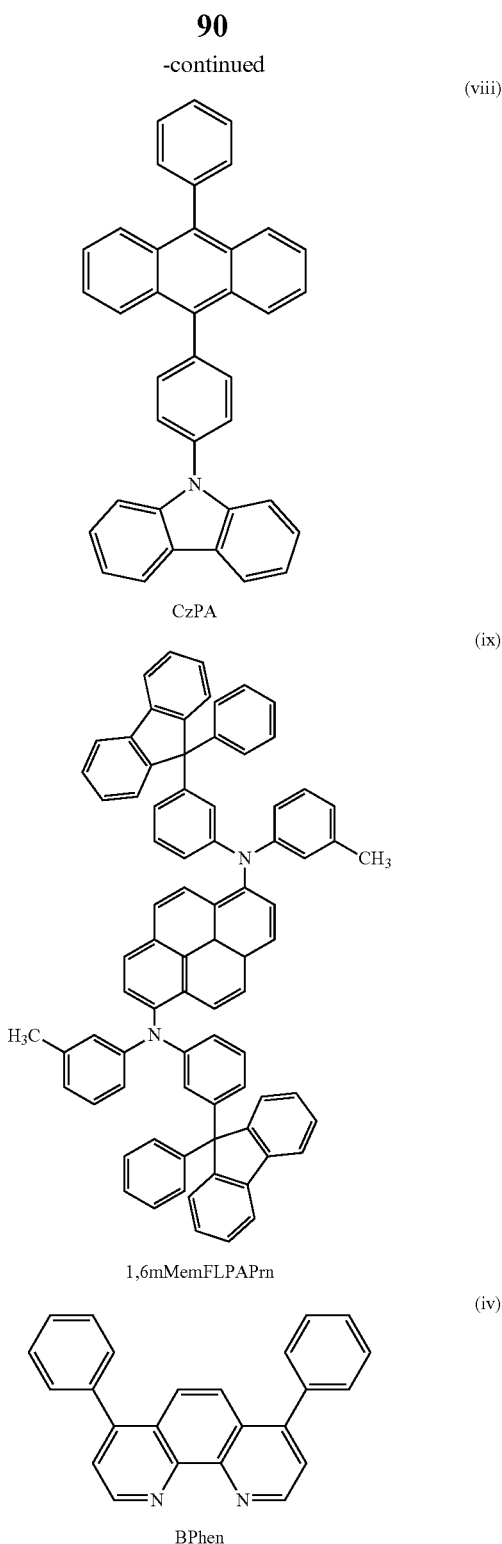

In the element structure in FIG. 1A, an electron-injection layer is provided between an electron-transport layer 114 and a second electrode 104.

[Fabrication of Light-Emitting Element 9]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 3,6-di(dibenzofuran-4-yl)-9-phenyl-9H-carbazole (abbreviation: DBF2PC-II) represented by the above structural formula (11) and molybdenum(VI) oxide such that the ratio of DBF2PC-II:molybdenum(VI) oxide was 2:1 (weight ratio). The thickness of was the layer was set to 50 nm. Note that the co-evaporation is an evaporation method in which a plurality of different substances is concurrently vaporized from the respective different evaporation sources.

Next, DBF2PC-II was evaporated to a thickness of 10 nm, so that the hole-transport layer 112 was formed.

Further, the light-emitting layer 113 was formed on the hole-transport layer 112 in such a way that 9-[4-(10-phenyl-9-anthryl)phenyl]-9H-carbazole (abbreviation: CzPA) represented by the above structural formula (viii) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (ix) were evaporated to form a 30-nm-thick film so that the ratio of CzPA to 1,6mMemFLPAPrn was 1:0.05 (weight ratio).

Next, on the light-emitting layer 113, CzPA was evaporated to a thickness of 10 nm, and then bathophenanthroline (abbreviation: BPhen) represented by the above structural formula (iv) was evaporated to a thickness of 15 nm, so that the electron-transport layer 114 was formed. Then, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 9 was completed. Note that in the above evaporation processes, evaporation was all performed by a resistance heating method.

[Operation Characteristics of Light-Emitting Element 9]

The light-emitting element 9 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 73:
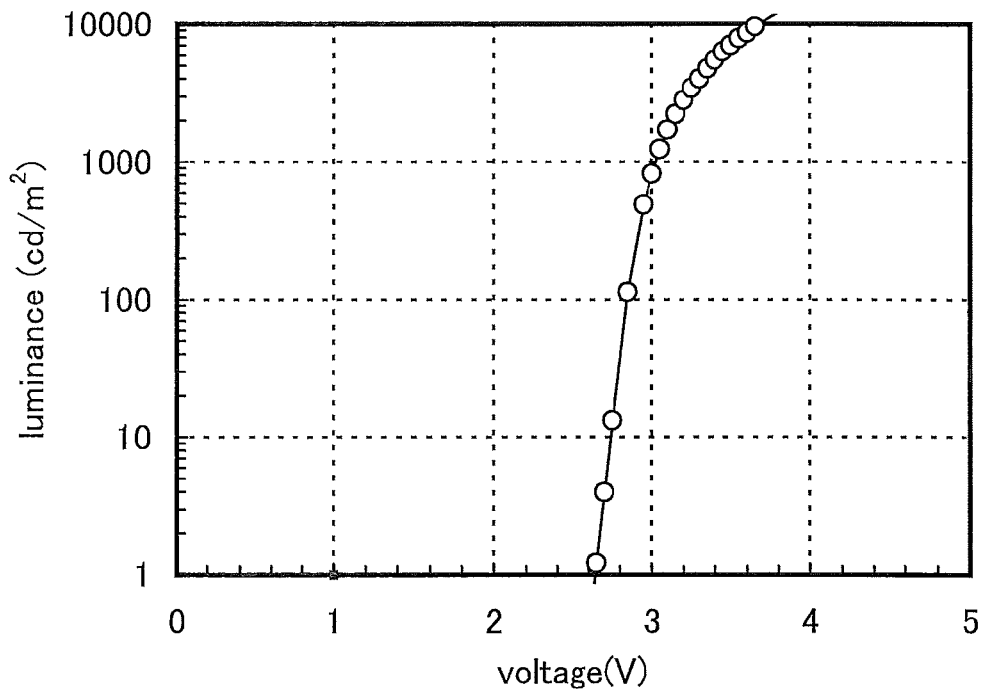
FIG. 73 shows luminance versus voltage characteristics of a light-emitting element 9.
Figure 74:
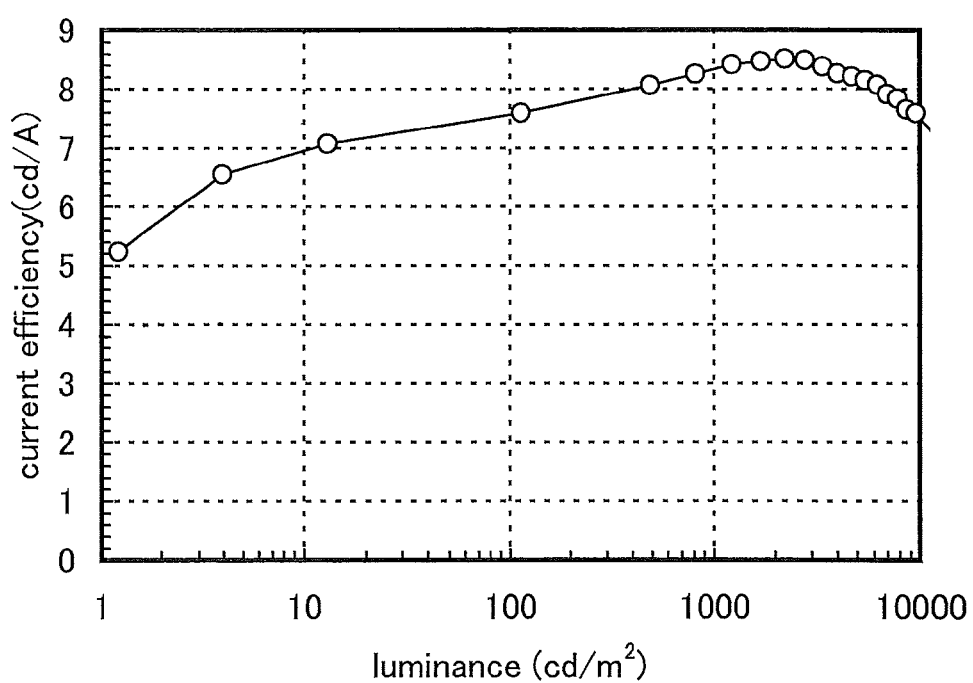
FIG. 74 shows current efficiency versus luminance characteristics of the light-emitting element 9.
Figure 75:
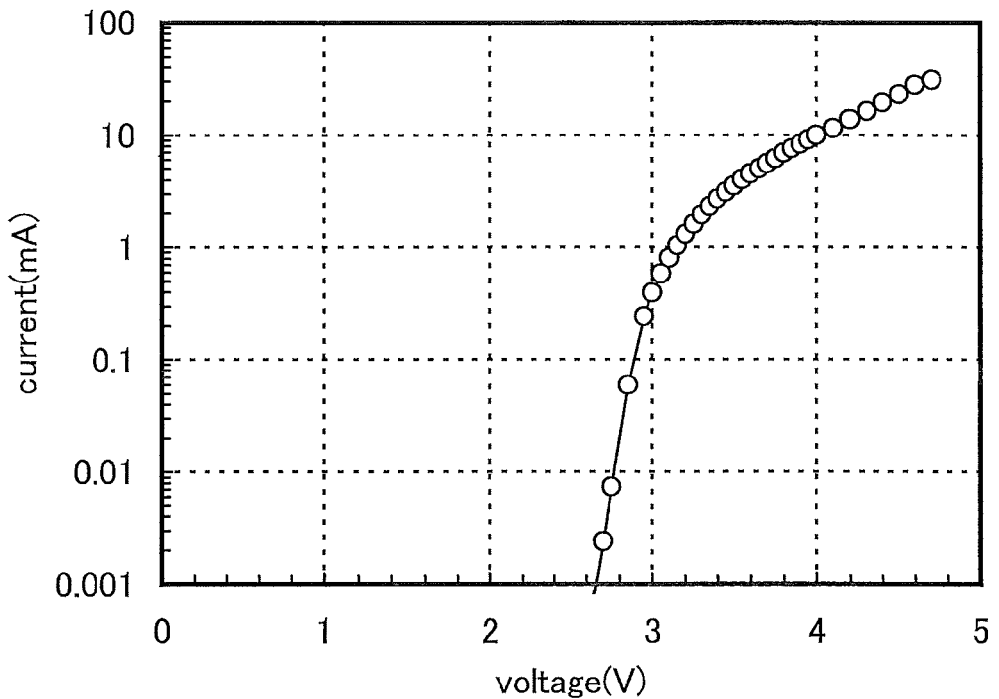
FIG. 75 shows current versus voltage characteristics of the light-emitting element 9.
Figure 76:
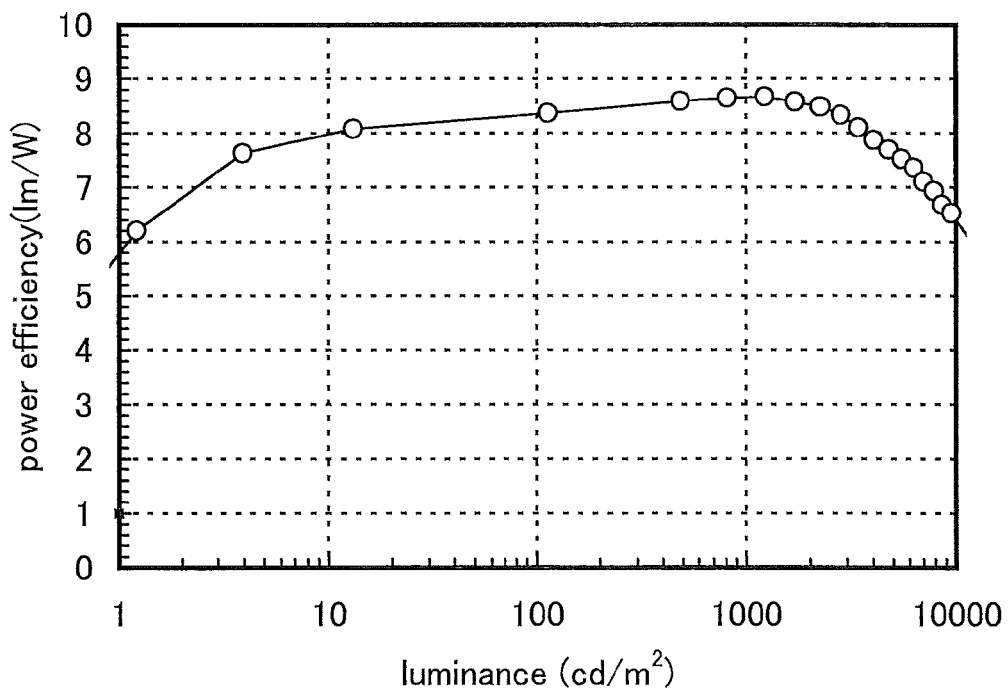
FIG. 76 shows power efficiency versus luminance characteristics of the light-emitting element 9.
Figure 77:
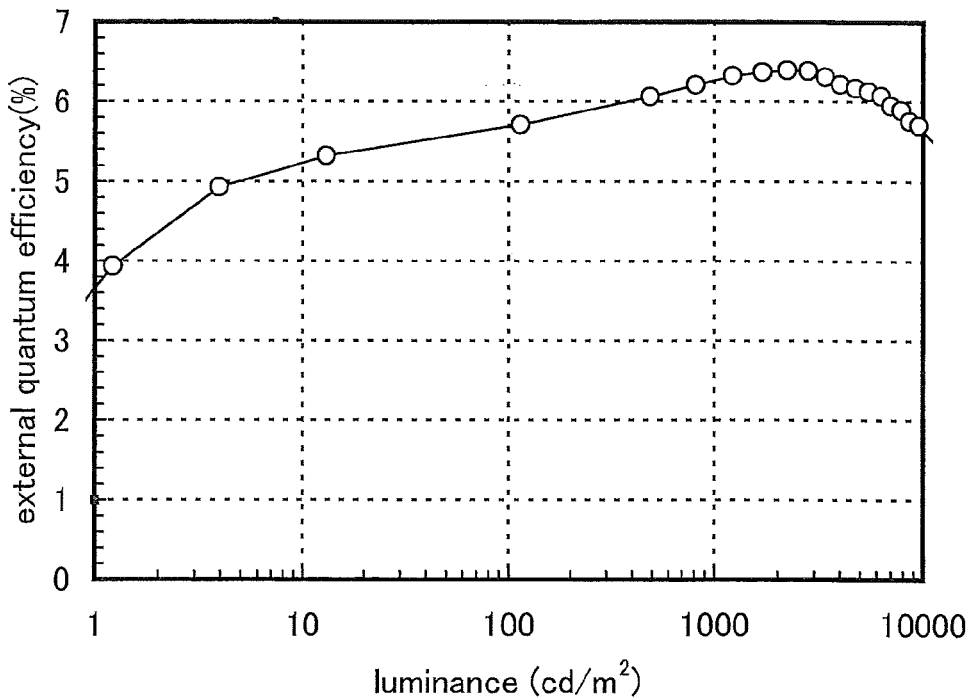
FIG. 77 shows external quantum efficiency-luminance characteristics of the light-emitting element 9.

FIG. 73 shows luminance versus voltage characteristics of the light-emitting element 9, FIG. 74 shows current efficiency versus luminance characteristics thereof, FIG. 75 shows current versus voltage characteristics thereof, FIG. 76 shows power efficiency versus luminance characteristics thereof, and FIG. 77 shows external quantum efficiency-luminance characteristics thereof.

FIG. 74 reveals that the light-emitting element, in which the carbazole derivative represented by the general formula (G1) is used as a material for a hole-transport layer in contact with a light-emitting layer for emitting blue fluorescence, has favorable current efficiency versus luminance characteristics and high emission efficiency. This is because the carbazole derivative represented by the general formula (G1) has a high T1 level, and thus transfer of excitation energy can be suppressed despite the adjacency to a light-emitting substance that emits blue fluorescence and has a wide energy gap. In addition, FIG. 73 reveals that the light-emitting, in which the carbazole derivative represented by the general formula (G1) is used as a material for a hole-transport layer adjacent to a light-emitting layer for emitting blue phosphorescence, has favorable luminance versus voltage characteristics and can be driven with a low voltage. This indicates that any of the carbazole derivatives represented by the general formula (G1) has an excellent carrier-transport property. Further, FIG. 76 and FIG. 77 reveal that light-emitting element 9 has excellent power efficiency versus luminance characteristics and excellent external quantum efficiency-luminance characteristics.

Figure 78:
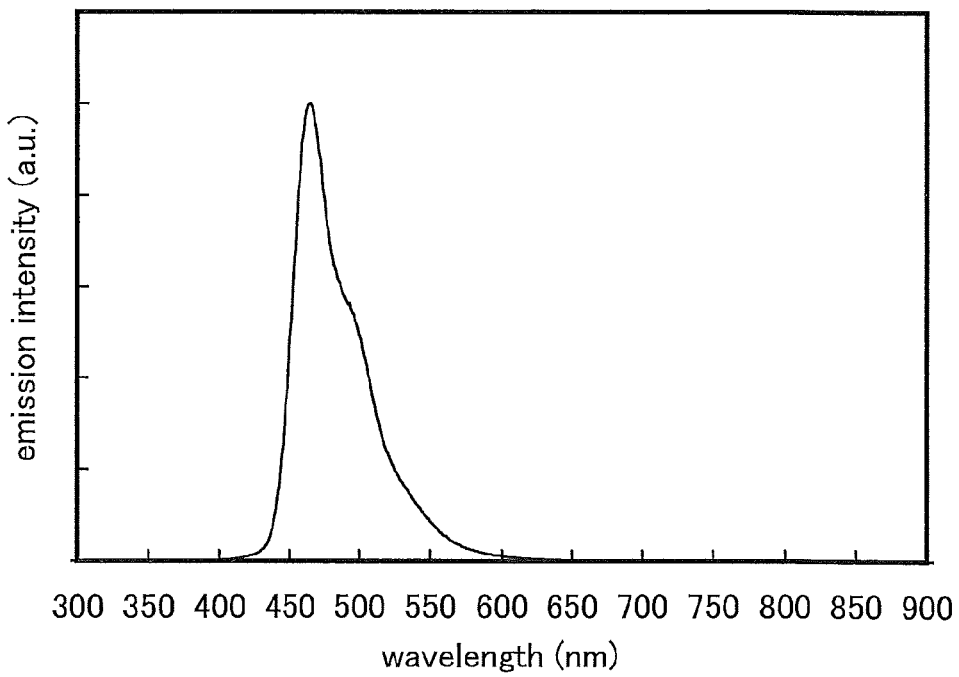
FIG. 78 shows an emission spectrum of the light-emitting element 9.

FIG. 78 shows an emission spectrum when a current of 1 mA was made to flow in the fabricated light-emitting element 9. The emission intensity is shown as a value relative to the greatest emission intensity assumed to be 1. FIG. 78 reveals that the light-emitting element 9 emits blue light due to 1,6mMemFLPAPrn, which is the emission center substance.

Figure 79:
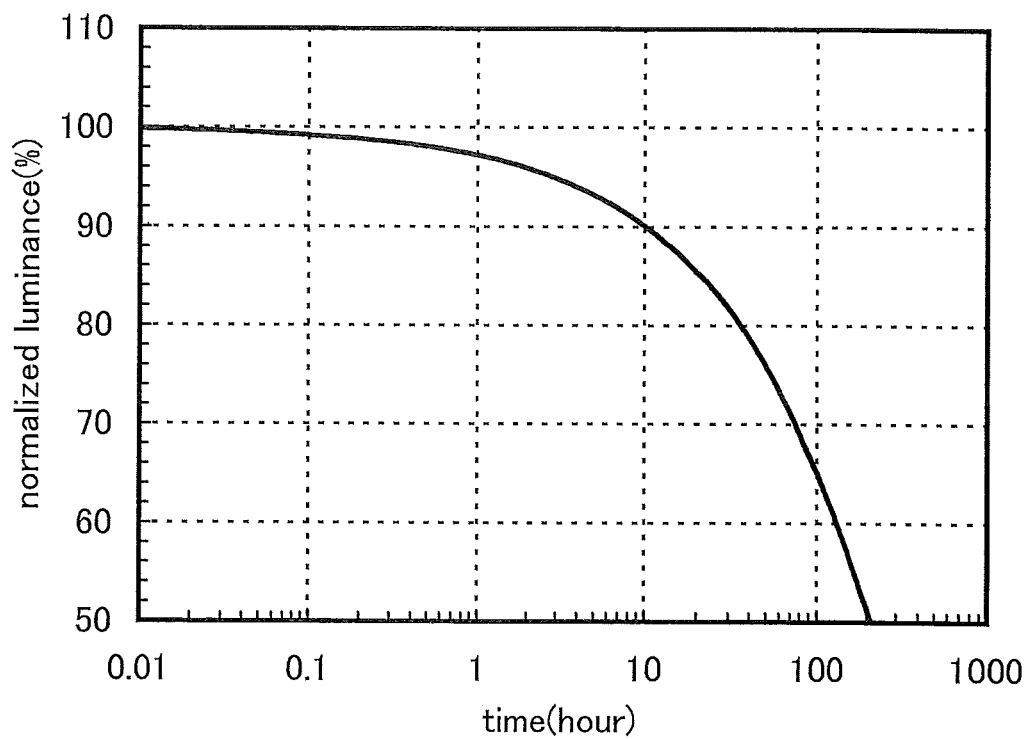
FIG. 79 shows normalized luminance versus time characteristics of the light-emitting element 9.

Next, the initial luminance is set at 5000 cd/m², the element was driven under a condition where the current density was constant, and changes in luminance with respect to the driving time were examined. FIG. 79 shows normalized luminance versus time characteristics. From FIG. 79, it is found that the light-emitting element 9 shows favorable characteristics and has high reliability.

Example 16

Synthesis Example 10

In this example is described a method of synthesizing 3,3'-di(dibenzothiophen-4-yl)-N,N'-(1,3-phenylene)bicarbazole (abbreviation: mDBTCz2P-II), which is one of the carbazole derivatives described in Embodiment 1. A structure of mDBTCz2P-II is illustrated in the following structural formula (12).

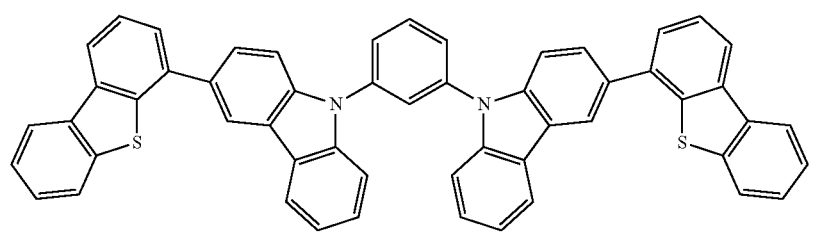

(12)

Step 1: Synthesis of 3-(Dibenzothiophen-4-yl)-9H-carbazol

This was synthesized as in Step 1 in Synthesis Example 1.

Step 2: Synthesis of 3,3'-Di(dibenzothiophen-4-yl)-N,N'-(1,3-phenylene)bicarbazole (abbreviation: mDBTCz2P-II)

In a 200-mL three-neck flask were put 1.2 g (5.0 mmol) of 1,3-dibromobenzene and 3.5 g (10 mmol) of 3-(dibenzothiophen-4-yl)-9H-carbazole (abbreviation: DBTCz), and the air in the flask was replaced with nitrogen. To this mixture were added 40 mL of toluene, 0.10 mL of tri(tert-butyl) phosphine (a 10 wt % hexane solution), and 0.98 g (10 mmol)) of sodium tert-butoxide. This mixture was degassed while being stirred under reduced pressure. After this mixture was stirred at 80° C. and dissolution of the materials was confirmed, 61 mg (0.11 mmol) of bis(dibenzylideneacetone) palladium(0) was added thereto. This mixture was refluxed at 110° C. for 55 hours. After the reflux, the mixture was cooled to room temperature, and the precipitated white solid was collected by suction filtration. The obtained solid was washed with water and toluene to give 1.2 g of a white solid which was the object of the synthesis in 70% yield. The synthesis scheme of Step 2 is illustrated in the following formula (f-10).

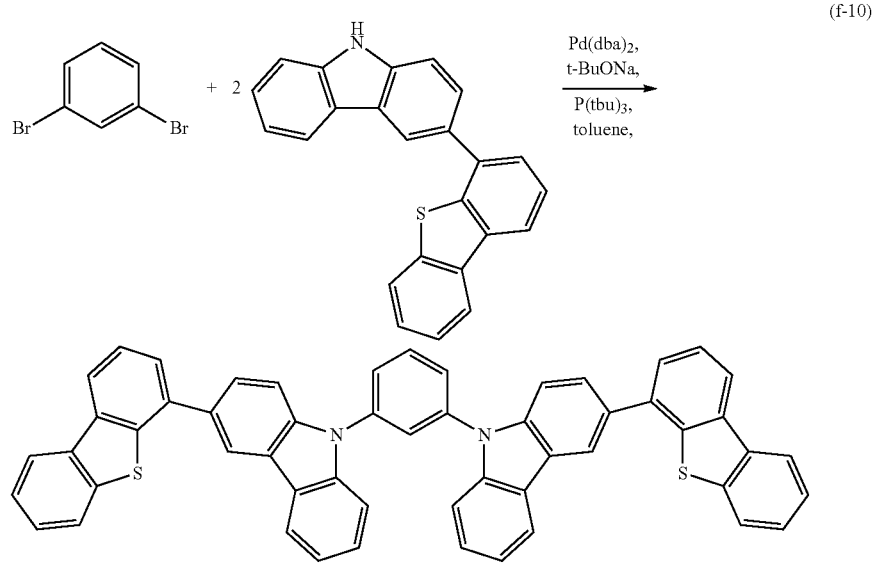

(f-10)

By a train sublimation method, 1.1 g of the obtained white solid was purified. The purification was conducted by heating of the white solid at 350° C. under a pressure of 2.8 Pa with a flow rate of argon gas of 10 mL/min. After the purification, 0.89 g of a colorless transparent solid was obtained in a yield of 83%.

Figure 80A:
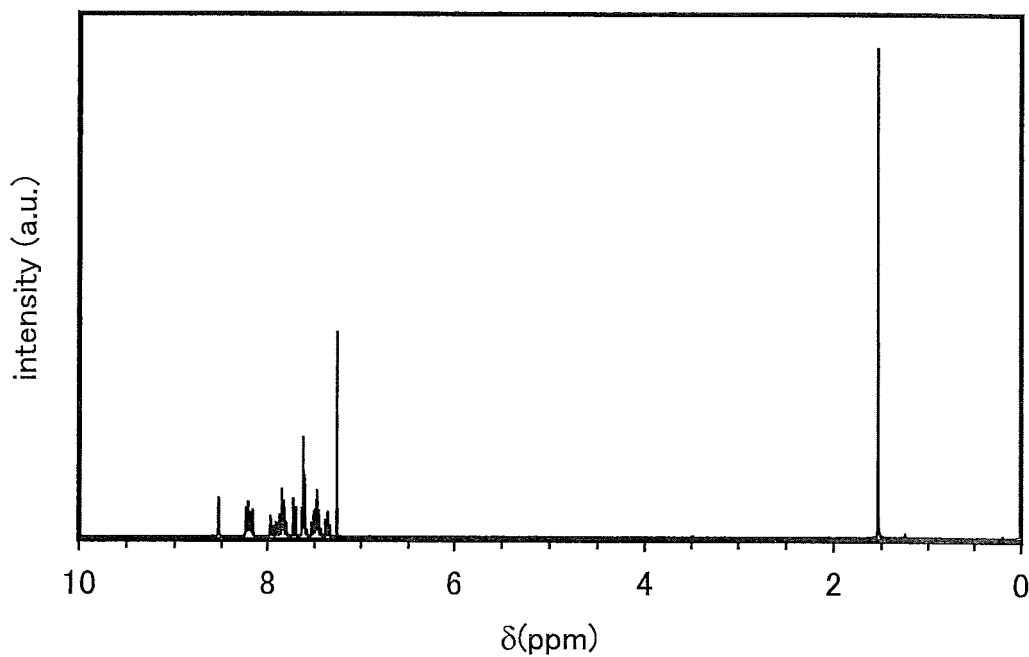
FIGS. 80A and 80B are NMR charts of mDBTCz2P-II.
Figure 80B:
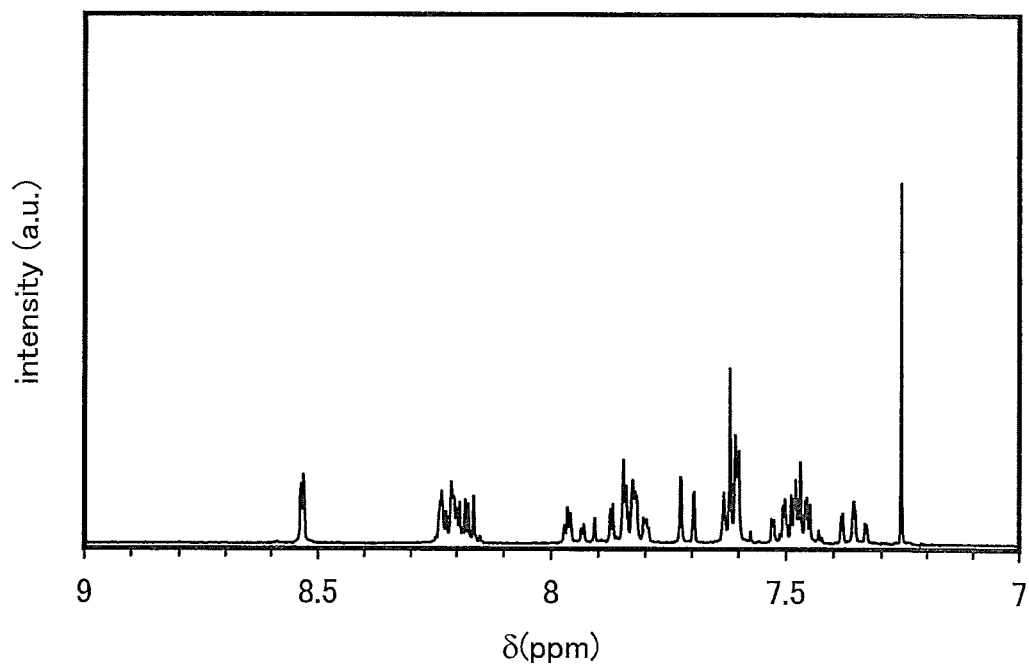

This compound was subjected to nuclear magnetic resonance (NMR) spectroscopy. In addition, $^1$H NMR charts are shown in FIGS. 80A and 80B. Note that FIG. 80B is a chart where the range of from 7 ppm to 9 ppm in FIG. 80A is enlarged. In addition, $^1$H NMR data of the obtained compound are shown below.

$^1$H NMR (CDCl$_3$, 300 MHz): δ (ppm)=7.36 (td, $J_1$=0.9 Hz, $J_2$=7.8 Hz, 2H), 7.43-7.53 (m, 6H), 7.58-7.63 (m, 6H), 7.71 (d, J=8.7 Hz, 2H), 7.80-7.97 (m, 8H), 8.15-8.24 (m, 6H), 8.53 (d, J=1.5 Hz, 2H)

It is thus confirmed that the solid obtained in this synthesis example was 3,3'-di(dibenzothiophen-4-yl)-N,N'-(1,3-phenylene)bicarbazole (abbreviation: mDBTCz2P-II).

Figure 81A:
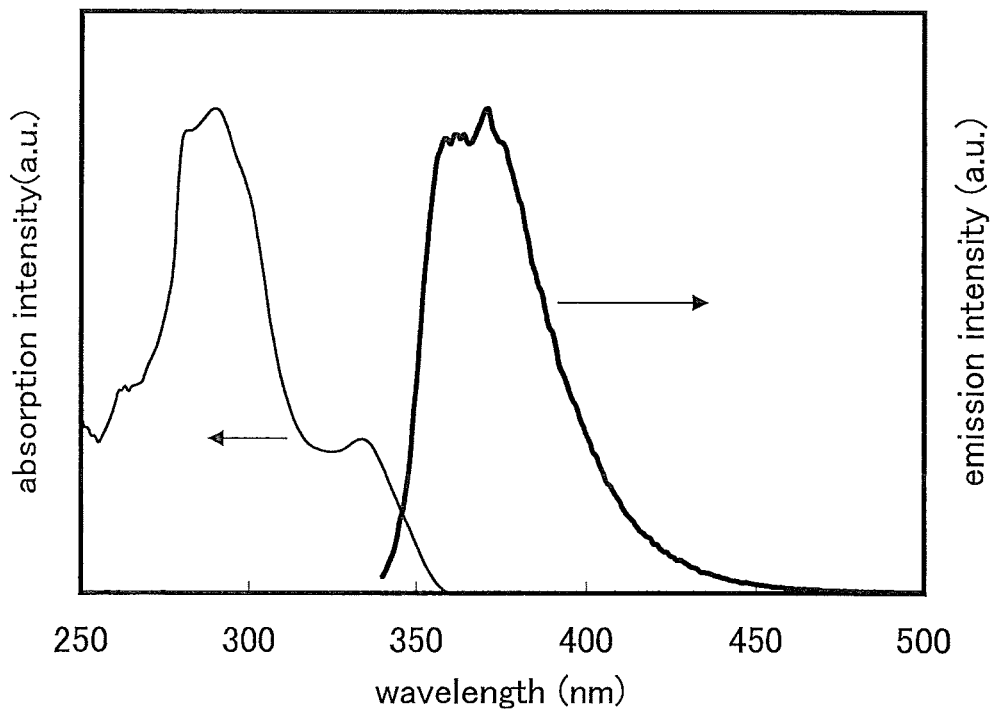
FIGS. 81A and 81B show an absorption and emission spectra of mDBTCz2P-II.
Figure 81B:
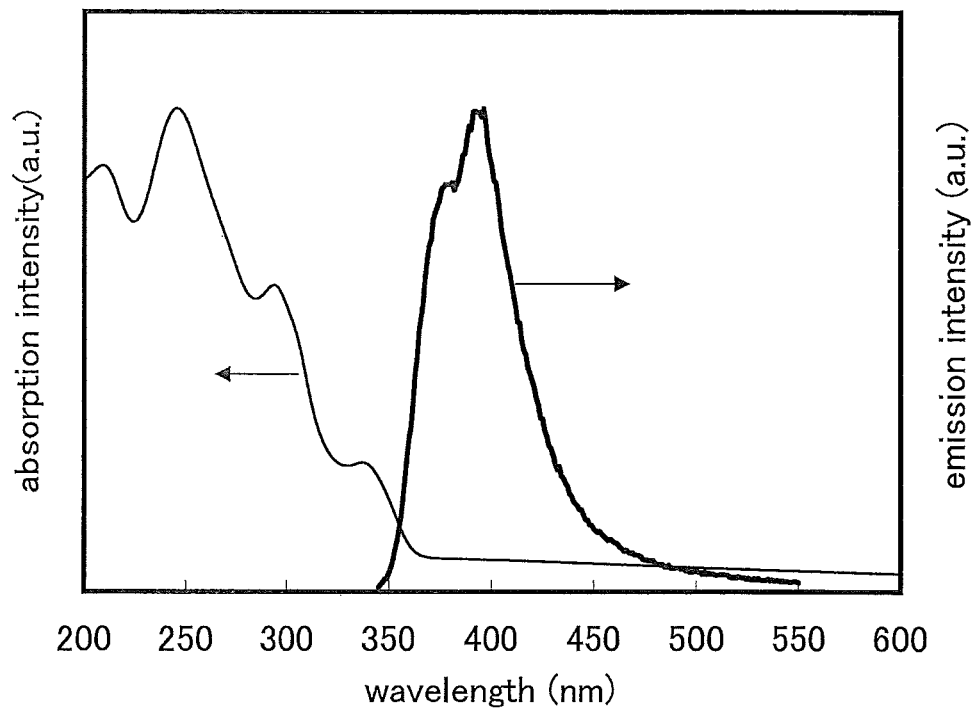

Further, an absorption and emission spectra of mDBTCz2P-II in a toluene solution of mDBTCz2P-II are shown in FIG. 81A, and an absorption and emission spectra of a thin film of mDBTCz2P-II are shown in FIG. 81B. An ultraviolet-visible spectrophotometer (V-550, manufactured by JASCO Corporation) was used for the measurements of the spectra. The spectra of the toluene solution were measured with a toluene solution of mDBTCz2P-II put in a quartz cell. The spectra of the thin film were measured with a sample prepared by evaporation of mDBTCz2P-II on a quartz substrate. Note that as the absorption spectrum of the toluene solution, the absorption spectrum obtained by subtraction of the absorption spectra of only the quartz cell and toluene from the measured spectra is shown in the drawing, and as the absorption spectrum of the thin film, the absorption spectrum obtained by subtraction of that of the quartz substrate from the measured spectra is shown in the drawing.

FIG. 81A shows that the absorption peak wavelengths of mDBTCz2P-II in the toluene solution of mDBTCz2P-II were around 332 nm, 288 nm and 281 nm, and the emission peak wavelength thereof was around 370 nm (at an excitation wavelength of 334 nm). Further, FIG. 81B shows that the absorption peak wavelengths of the thin film of mDBTCz2P-II were around 337 nm, 294 nm, 246 nm and 209 nm, and the emission peak wavelengths thereof were around 393 nm and 380 nm (at an excitation wavelength of 342 nm).

Further, the ionization potential of mDBTCz2P-II in a thin film state was measured by a photoelectron spectrometer (AC-2, manufactured by Riken Keiki, Co., Ltd.) in air. The obtained value of the ionization potential was converted to a negative value, so that the HOMO level of mDBTCz2P-II was −5.93 eV. From the data of the absorption spectra of the thin film in FIG. 81B, the absorption edge of mDBTCz2P-II, which was obtained from Tauc plot with an assumption of direct transition, was 3.45 eV. Therefore, the optical energy gap of mDBTCz2P-II in the solid state was estimated at 3.45 eV; from the values of the HOMO level obtained above and this energy gap, the LUMO level of mDBTCz2P-II was able to be estimated at −2.48 eV. It was thus found that mDBTCz2P-II had a wide energy gap of 3.45 eV in the solid state.

Example 17

In this example described is a light-emitting element in which 3,3'-di(dibenzothiophen-4-yl)-N,N'-(1,3-phenylene)bicarbazole (abbreviation: mDBTCz2P-II, a structural formula (12)), which is a carbazole derivative described in Embodiment 1, is used as a material for a hole-transport layer adjacent to a light-emitting layer using an emission center substance that emits blue fluorescence. Note that in this example, mDBTCz2P-II is also used for a composite material with molybdenum oxide in a hole-injection layer.

The molecular structures of organic compounds used in this example are represented by the structural formulae (iv), (viii), (ix), and (12) below. In the element structure in FIG. 1A, an electron-injection layer is provided between an electron-transport layer 114 and a second electrode 104.

[Fabrication of Light-Emitting Element 10]

First, a glass substrate 101 over which indium tin oxide containing silicon (ITSO) with a thickness of 110 nm was formed as a first electrode 102 was prepared.

The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

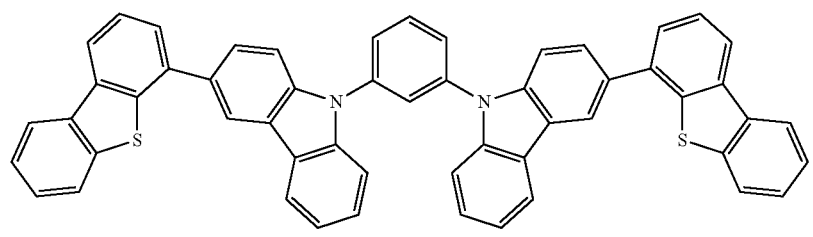

mDBTCz2P-II (12)

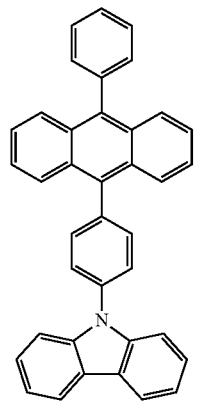

CzPA (viii)

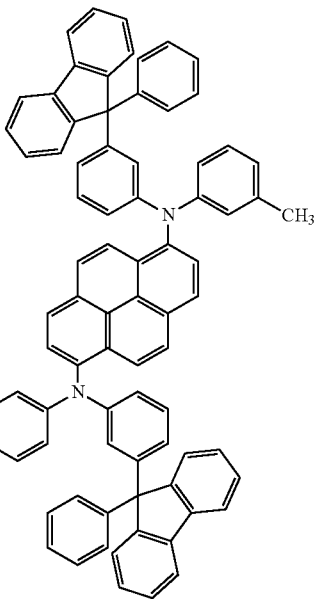

1,6mMemFLPAPrn (ix)

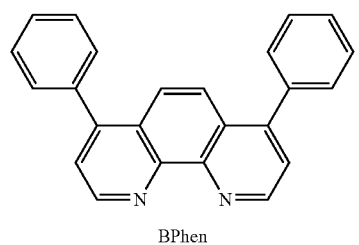

BPhen (iv)

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 3,3'-di(dibenzothiophen-4-yl)-N,N'-(1,3-phenylene)bicarbazole (abbreviation: mDBTCz2P-II), which is a carbazole derivative described in Embodiment 1 represented by the above structural formula (12), and molybdenum(VI) oxide such that the ratio of mDBTCz2P-II:molybdenum(VI) oxide was 2:1 (weight ratio). The thickness of was the layer was set to 50 nm. Note that the co-evaporation is an evaporation method in which a plurality of different substances is concurrently vaporized from the respective different evaporation sources.

Next, mDBTCz2P-II was evaporated to a thickness of 10 nm, so that the hole-transport layer 112 was formed.

Further, the light-emitting layer 113 was formed on the hole-transport layer 112 in such a way that 9-[4-(10-phenyl-9-anthryl)phenyl]-9H-carbazole (abbreviation: CzPA), which is the carbazole derivative represented by the above structural formula (viii), and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (ix) were evaporated to form a 30-nm-thick film so that the ratio of CzPA to 1,6mMemFLPAPrn was 1:0.04 (weight ratio).

Next, CzPA was evaporated to a thickness of 10 nm, and then bathophenanthroline (abbreviation: BPhen) represented by the above structural formula (iv) was evaporated to a thickness of 15 nm, so that the electron-transport layer 114 was formed.

Further, lithium fluoride was evaporated to a thickness of 10 nm on the electron-transport layer 114, so that the electron-injection layer was formed. Lastly, an aluminum film was formed to a thickness of 200 nm as the second electrode 104 functioning as a cathode, so that the light-emitting element 10 was completed. Note that in the above evaporation processes, evaporation was all performed by a resistance heating method.

[Operation Characteristics of Light-Emitting Element 10]

The light-emitting element 10 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 82:
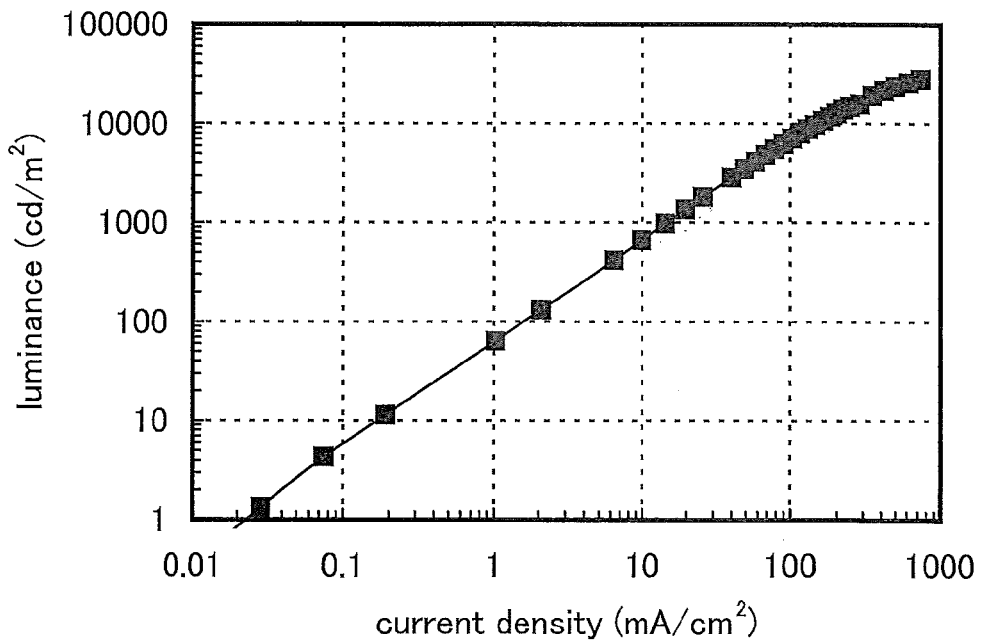
FIG. 82 shows luminance versus current density characteristics of light-emitting element 10.
Figure 83:
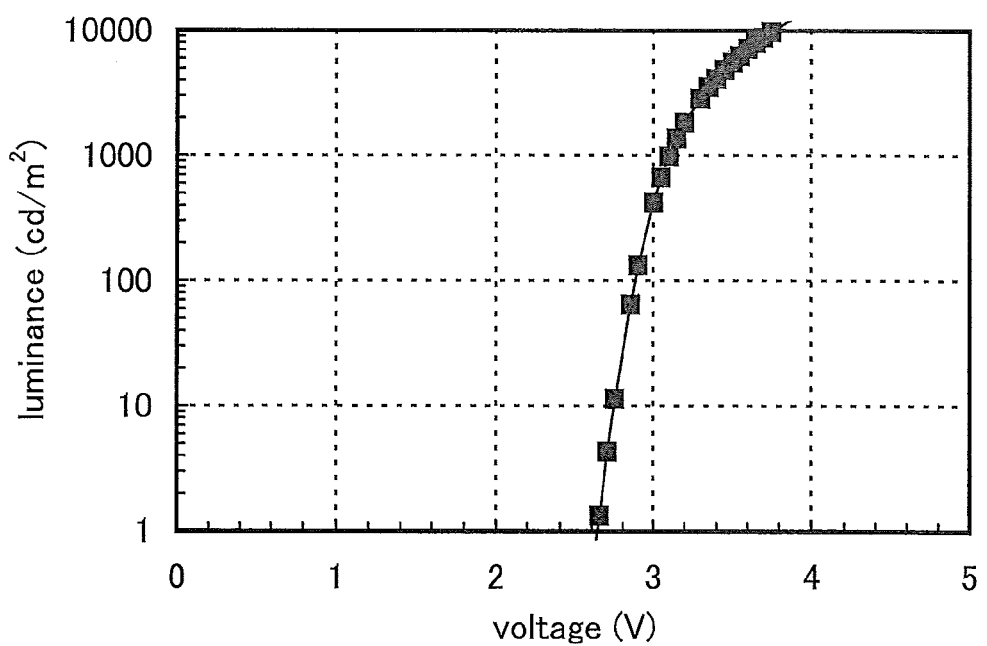
FIG. 83 shows luminance versus voltage characteristics of a light-emitting element 10.
Figure 84:
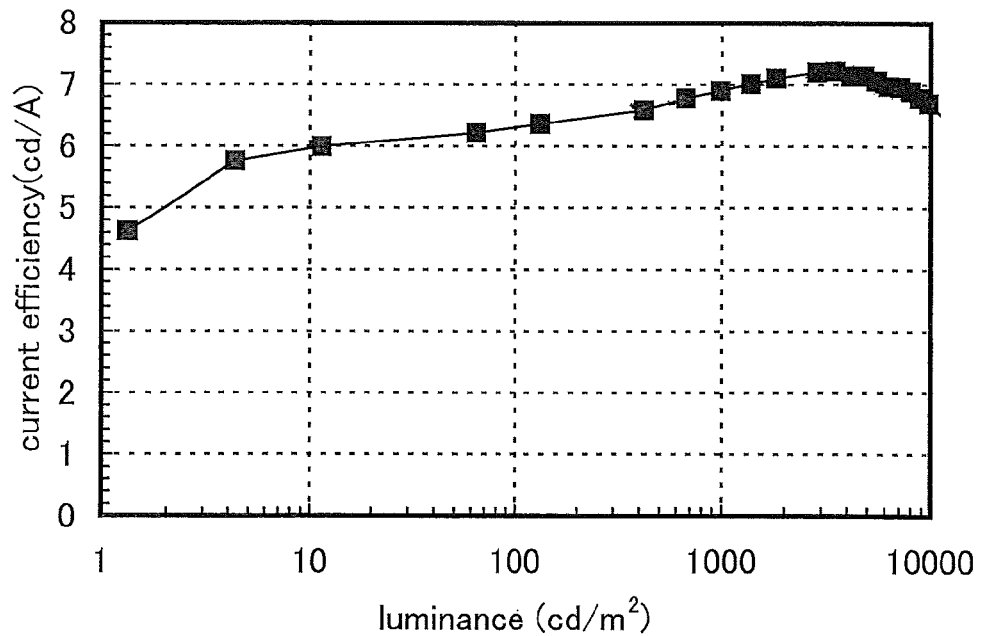
FIG. 84 shows current efficiency versus luminance characteristics of the light-emitting element 10.
Figure 85:
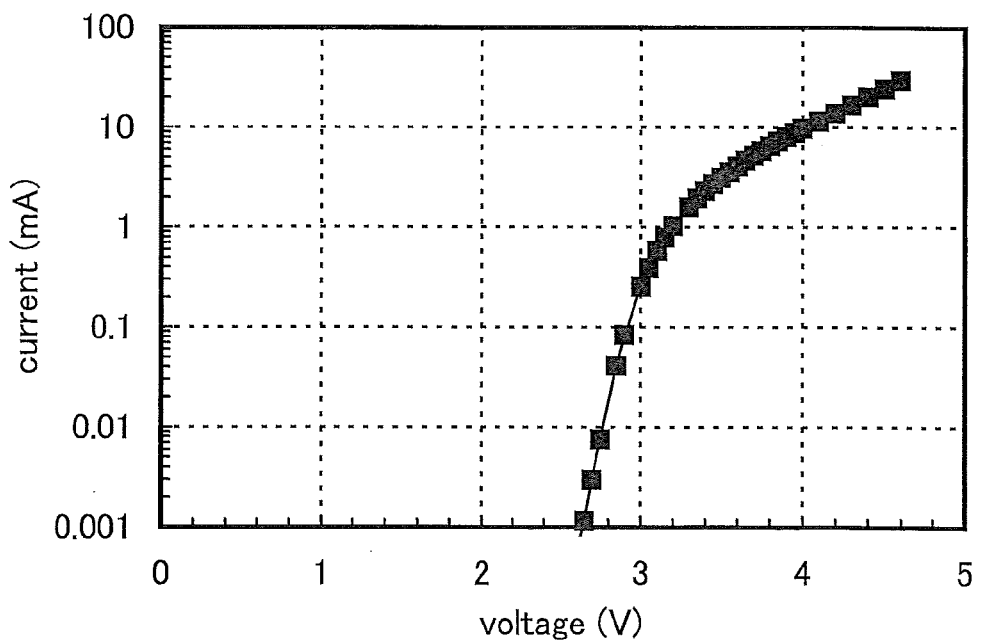
FIG. 85 shows current versus voltage characteristics of the light-emitting element 10.

FIG. 82 shows luminance versus current density characteristics of the light-emitting element 10, FIG. 83 shows luminance versus voltage characteristics thereof, FIG. 84 shows current efficiency versus luminance characteristics thereof, and FIG. 85 shows current versus voltage characteristics thereof. In FIG. 82, the vertical axis represents luminance ($cd/m^2$), and the horizontal axis represents current density ($mA/cm^2$). In FIG. 83, the vertical axis represents luminance ($cd/m^2$), and the horizontal axis represents voltage (V). In FIG. 84, the vertical axis represents current efficiency (cd/A), and the horizontal axis represents luminance ($cd/m^2$). In FIG. 85, the vertical axis represents current (mA), and the horizontal axis represents voltage (V).

FIG. 82 reveals that the light-emitting element, in which the carbazole derivative represented by the general formula (G1) is used as a hole-transport material adjacent to a light-emitting layer for emitting blue fluorescence and used for a hole-injection layer (as a composite material with molybdenum oxide), has favorable luminance versus current efficiency characteristics and high emission efficiency. Here, CzPA as the host material of the light-emitting layer in the light-emitting element 10 is a material having a relatively high electron-transport property. It is therefore understood that the light-emitting region in the light-emitting layer is localized on the hole-transport layer side. A reason why the light-emitting element having high emission efficiency can be obtained even in such a state is that any of the carbazole derivatives represented by the general formula (G1) has a wide energy gap. Since mDBTCz2P-II, which is any of the carbazole derivatives described in Embodiment 1, has a wide energy gap, even when it is used for the hole-transport layer adjacent to the emission center substance that emits blue fluorescence, a reduction in emission efficiency is suppressed without transfer of excitation energy to the hole-transport layer.

In addition, FIG. 83 reveals that the light-emitting element, in which the carbazole derivative represented by the general formula (G1) is used as a host material for a light-emitting layer for emitting blue fluorescence, has favorable luminance versus voltage characteristics and can be driven with a low voltage. This indicates that any of the carbazole derivatives represented by the general formula (G1) has an excellent carrier-transport property and the composite material including any of the carbazole derivatives represented by the general formula (G1) has an excellent carrier-injection property.

Figure 86:
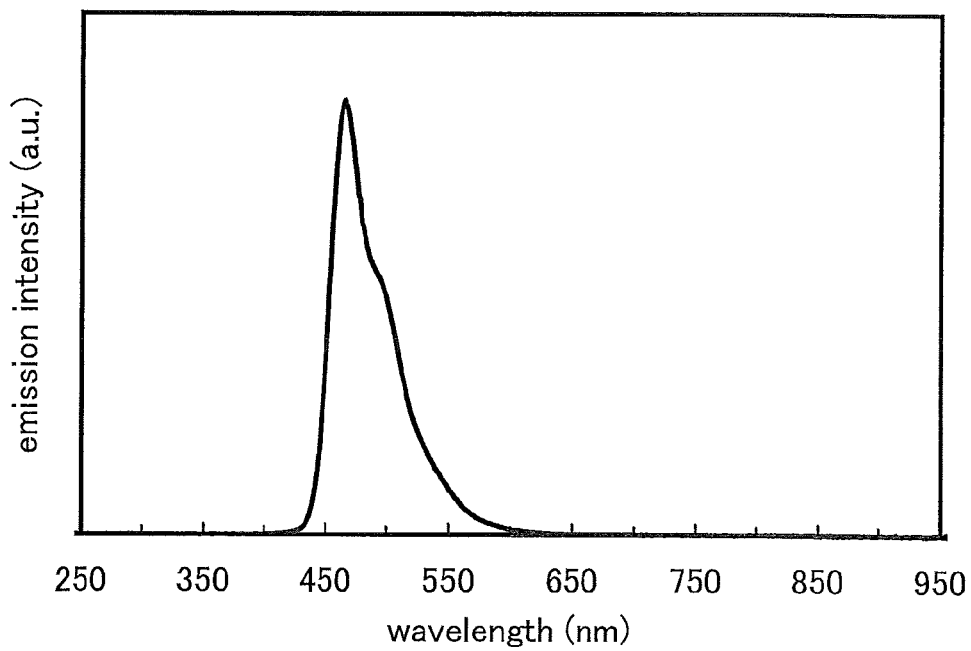
FIG. 86 shows an emission spectrum of the light-emitting element 10.

FIG. 86 shows an emission spectrum when a current of 1 mA was made to flow in the fabricated light-emitting element 10. In FIG. 86, the vertical axis represents emission intensity (arbitrary unit), and the horizontal axis represents wavelength (nm). The emission intensity is shown as a value relative to the greatest emission intensity assumed to be 1. FIG. 86 reveals that the light-emitting element 10 emits blue light due to 1,6mMemFLPAPrn, which is the emission center substance.

Figure 87:
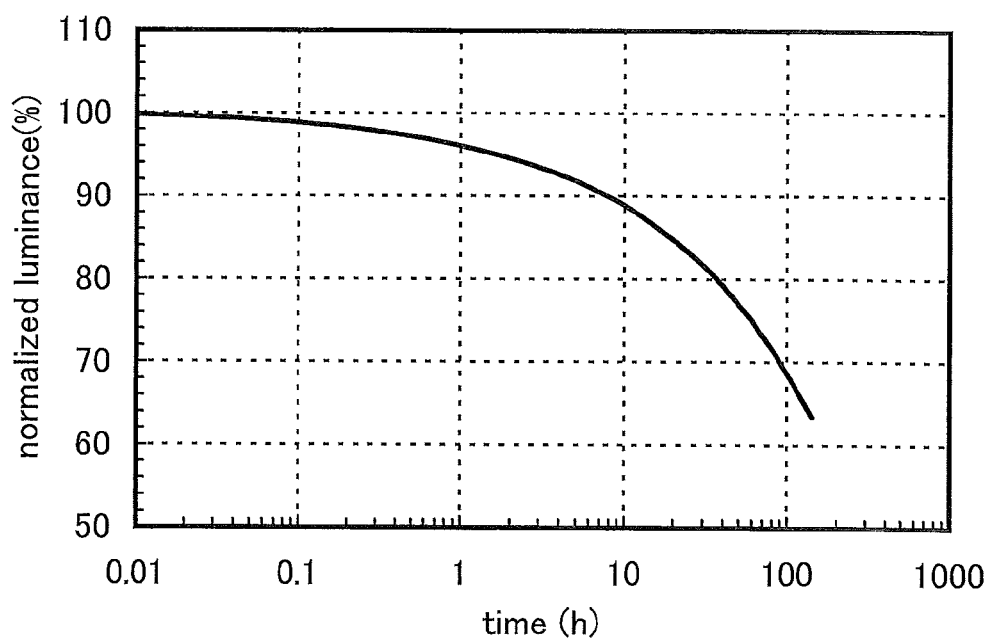
FIG. 87 shows normalized luminance versus time characteristics of the light-emitting element 10.

Next, the initial luminance is set at 1000 $cd/m^2$, the light-emitting element 10 was driven under a condition where the current density was constant, and changes in luminance with respect to the driving time were examined. FIG. 87 shows normalized luminance versus time characteristics. From FIG. 87, it is found that the light-emitting element 10 shows favorable characteristics and has high reliability.

Example 18

In this example described is a light-emitting element (light-emitting element 11) in which an emission center substance that emits blue phosphorescence is used for a light-emitting layer and 3,3'-di(dibenzothiophen-4-yl)-N,N'-(1,3-phenylene)bicarbazole (abbreviation: mDBTCz2P-II, a structural formula (12)) which is an carbazole derivative described Embodiment 1, is used as a host material for the light-emitting layer, and of a light-emitting element (light-emitting element 12) in which an emission center substance that emits blue phosphorescence is used for a light-emitting layer and mDBTCz2P-II is used as a material for a hole-transport layer adjacent to the light-emitting layer.

The molecular structures of organic compounds used in this example are represented by the structural formulae (iv), (x) to (xiii), and (12) below. In the element structure in FIG. 1A, an electron-injection layer is provided between an electron-transport layer 114 and a second electrode 104.

(x)

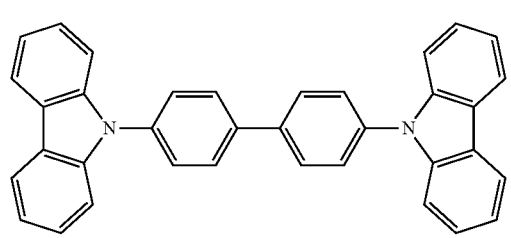

CBP (xi)

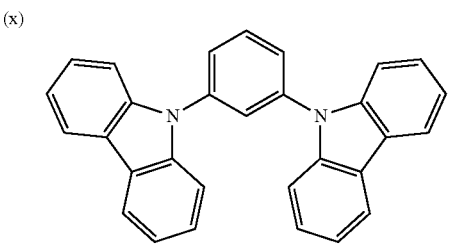

mDBTCz2P-II (12)

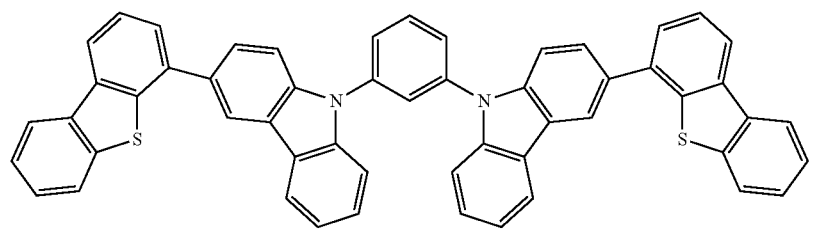

mDBTCz2P-II (xii)

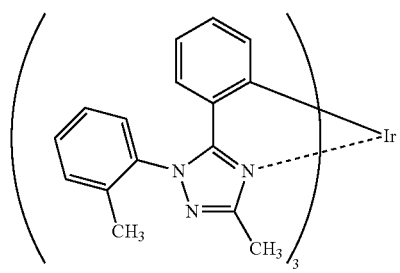

[Ir(Mptz1-mp)₃]

(xiii)

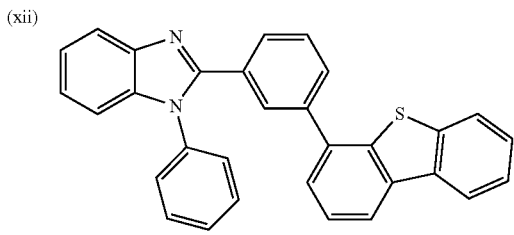

mDBTBIm-II (iv)

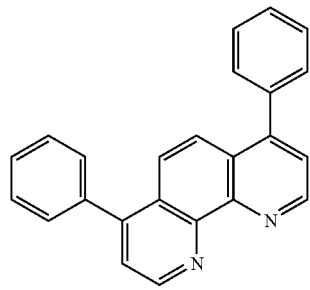

BPhen

[Fabrication of Light-Emitting Element 11 and Light-Emitting Element 12]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 4,4'-bis(N-carbazolyl)biphenyl (abbreviation: CBP) represented by the above structural formula (x) and molybdenum(VI) oxide such that the ratio of CBP:molybdenum(VI) oxide was 2:1 (weight ratio). The thickness of was the layer was set to 60 nm Note that the co-evaporation is an evaporation method in which a plurality of different substances is concurrently vaporized from the respective different evaporation sources.

Next, 1,3-bis(N-carbazolyl)benzene (abbreviation: mCP) represented by the above structural formula (xi) was evaporated to a thickness of 20 nm to form the hole-transport layer 112 of the light-emitting element 11, and 3,3'-di(dibenzothiophen-4-yl)-N,N'-(1,3-phenylene)bicarbazole (abbreviation: mDBTCz2P-II) represented by the above structural formula (12) described in Embodiment 1 was evaporated to a thickness of 20 nm to form the hole-transport layer 112 of the light-emitting element 12.

Further, for the light-emitting element 11, the light-emitting layer 113 was formed on the hole-transport layer 112 by forming a stacked layer in such a way that mDBTCz2P-II and tris[3-methyl-1-(2-methylphenyl)-5-phenyl-1H-1,2,4-triazolato]iridium(III) (abbreviation: [Ir(Mptz1-mp)$_3$]) represented by the above structural formula (xii) were evaporated to a thickness of 30 nm so that the ratio of mDBTCz2P-II to [Ir(Mptz1-mp)$_3$] was 1.0.08 (weight ratio), and thereon, 2-[3-(dibenzothiophen-4-yl)phenyl]-1-phenyl-1H-benzimidazole (abbreviation: mDBTBIm-II) represented by the above structural formula (xiii) and [Ir(Mptz1-mp)$_3$] were evaporated to a thickness of 10 nm so that the ratio of mDBTBIm-II to [Ir (Mptz1-mp)$_3$] was 1:0.08 (weight ratio).

For the light-emitting element 12, the light-emitting layer 113 was formed by forming a stacked layer in such a way that mCP and [Ir(Mptz1-mp)$_3$] were evaporated to a thickness of 30 so that the ratio of mCP to [Ir(Mptz1-mp)$_3$] was 1.0.08 (weight ratio), and thereon, mDBTBIm-II and [Ir(Mptz1-mp)$_3$] were then evaporated to a thickness of 10 so that the ratio of mDBTBIm-II to [Ir(Mptz1-mp)$_3$] was 1:0.08 (weight ratio).

Next, bathophenanthroline (abbreviation: BPhen) represented by the above structural formula (iv) was evaporated to a thickness of 15 nm, so that an electron-transport layer 114 was formed.

Further, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting elements 11 and 12 were completed. Note that in the above evaporation processes, evaporation was all performed by a resistance heating method.

[Operation Characteristics of Light-Emitting Elements 11 and 12]

The light-emitting elements 11 and 12 thus obtained were sealed in a glove box under a nitrogen atmosphere without being exposed to the air. Then, the operation characteristics of these light-emitting elements were measured. Note that the measurements were carried out at room temperature (in an atmosphere kept at 25° C.).

Figure 88:
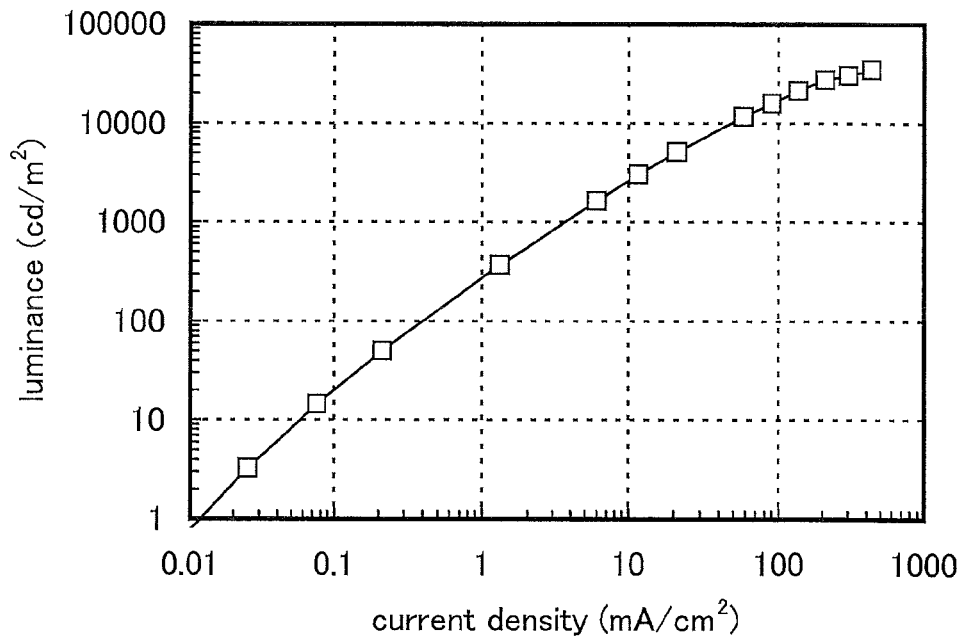
FIG. 88 shows luminance versus current density characteristics of light-emitting element 11.
Figure 89:
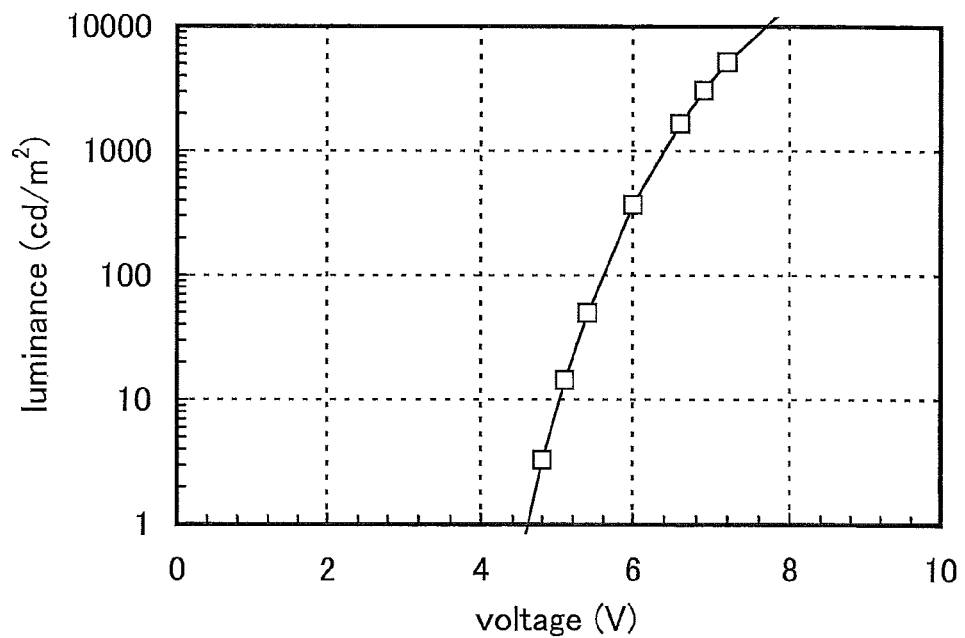
FIG. 89 shows luminance versus voltage characteristics of a light-emitting element 11.
Figure 90:
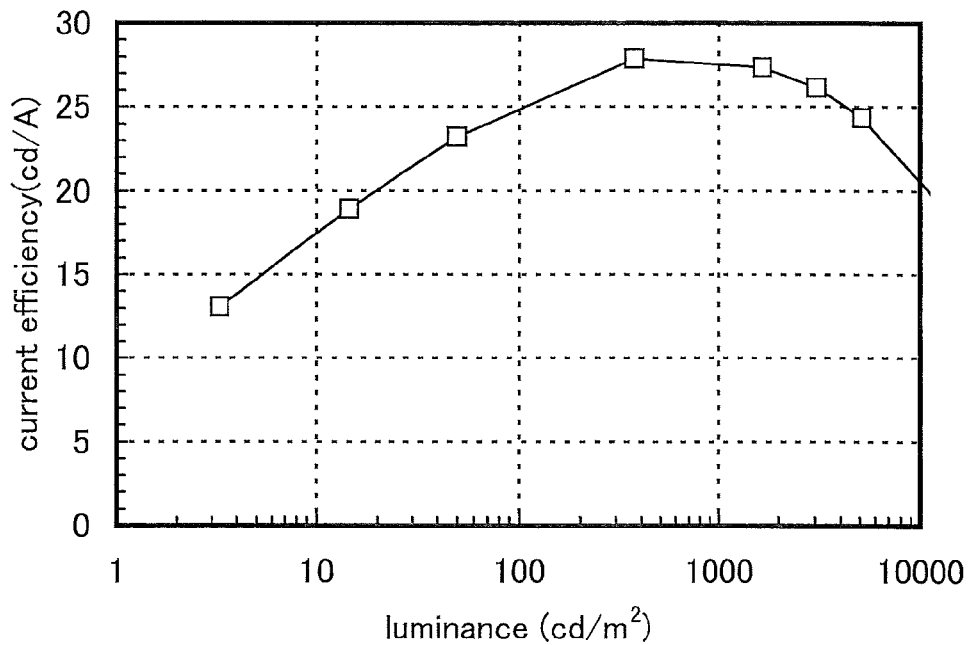
FIG. 90 shows current efficiency versus luminance characteristics of the light-emitting element 11.
Figure 91:
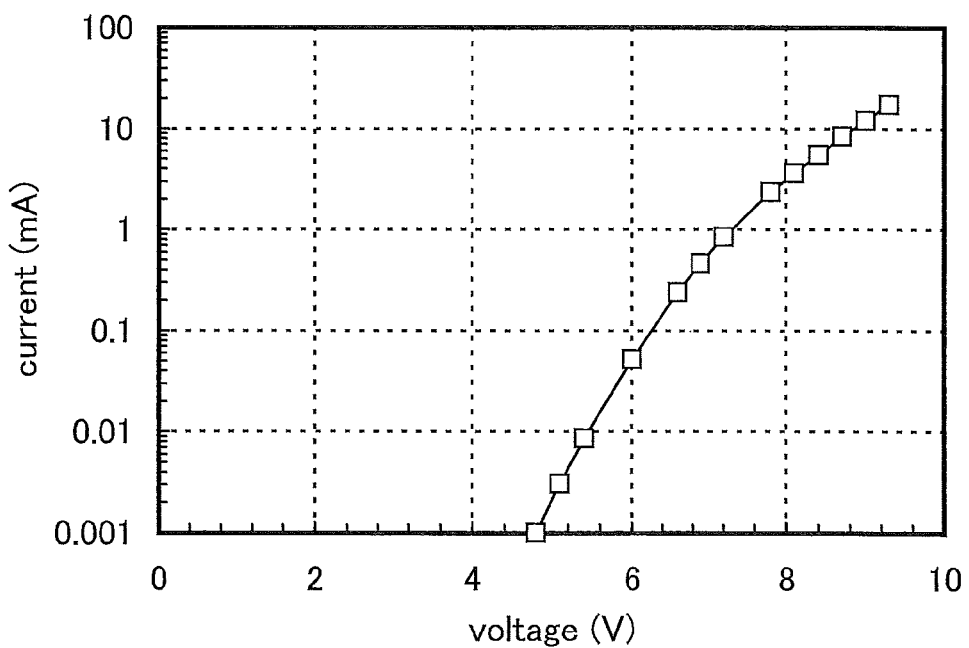
FIG. 91 shows current versus voltage characteristics of the light-emitting element 11.
Figure 92:
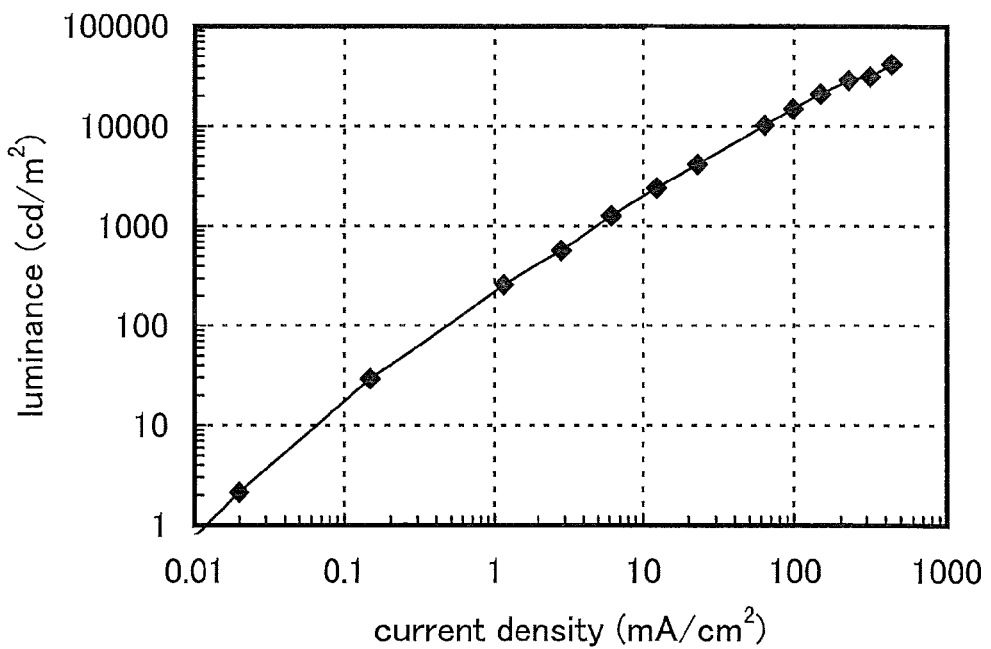
FIG. 92 shows luminance versus current density characteristics of a light-emitting element 12.
Figure 93:
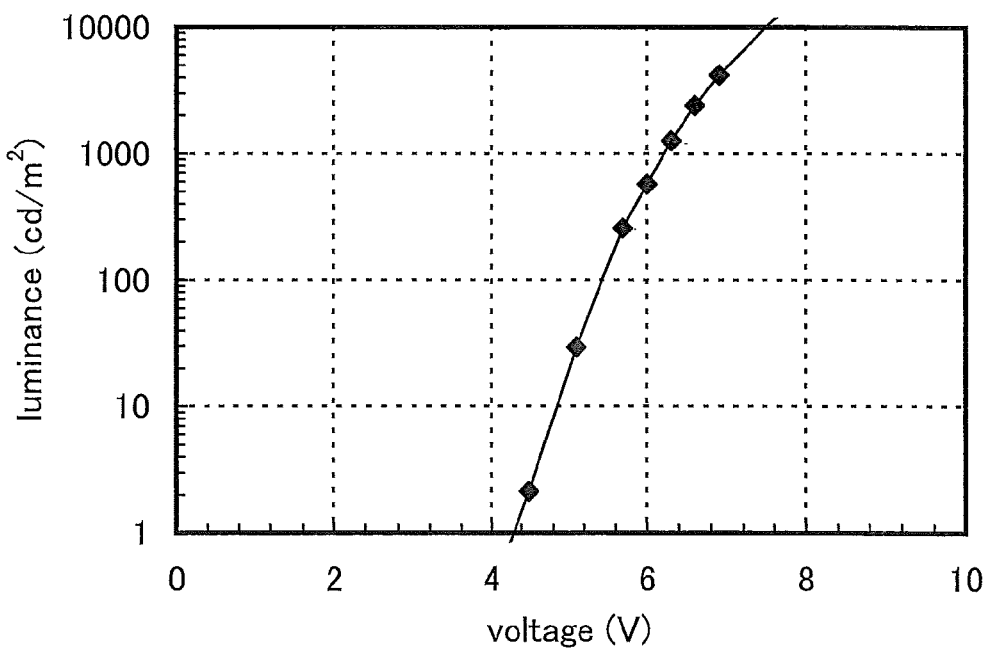
FIG. 93 shows luminance versus voltage characteristics of the light-emitting element 12.
Figure 94:
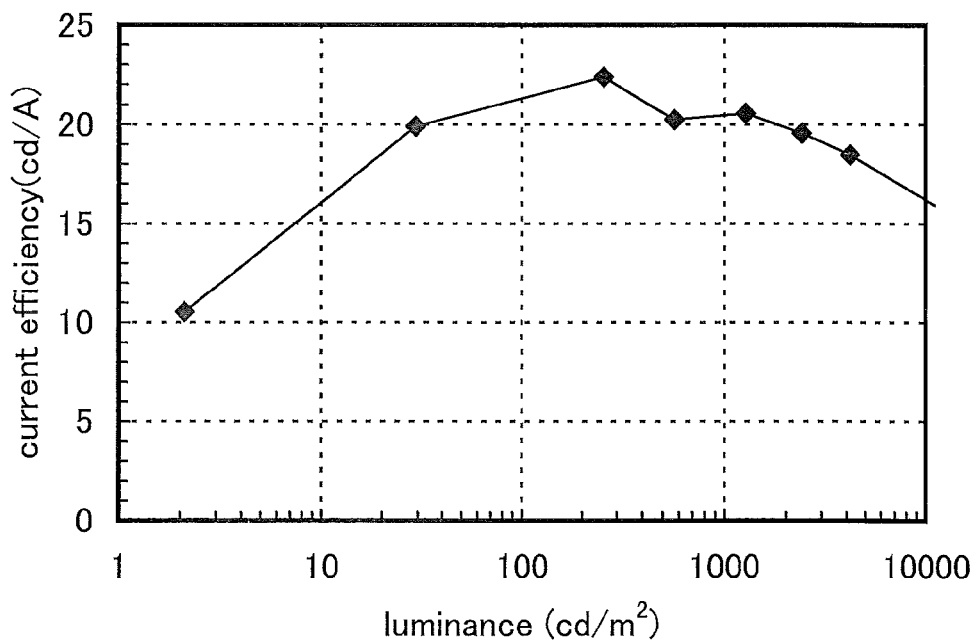
FIG. 94 shows current efficiency versus luminance characteristics of the light-emitting element 12.
Figure 95:
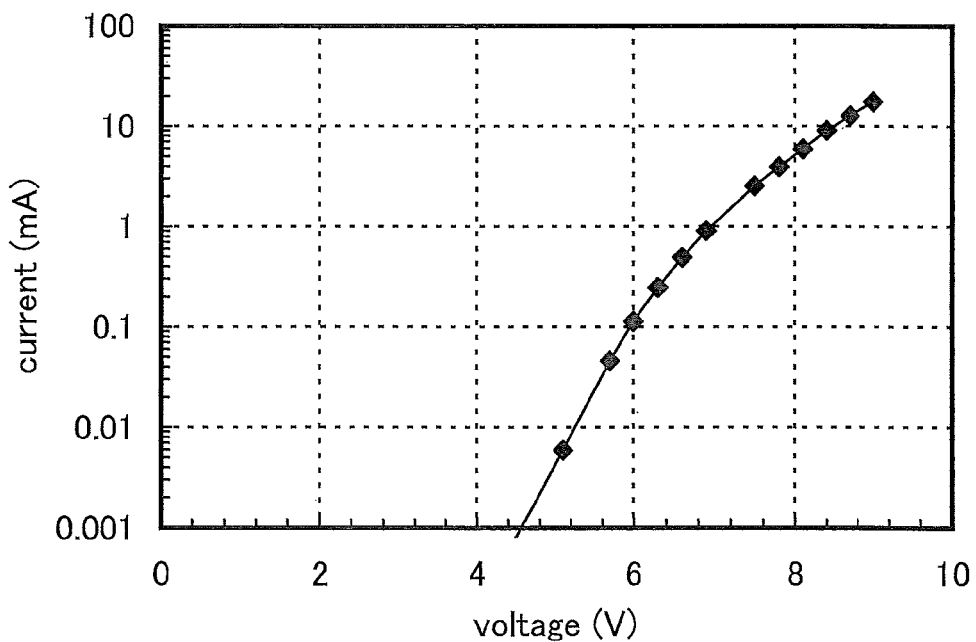
FIG. 95 shows current versus voltage characteristics of the light-emitting element 12.

FIG. 88 shows luminance versus current density characteristics of the light-emitting element 11, FIG. 89 shows luminance versus voltage characteristics thereof, FIG. 90 shows current efficiency versus luminance characteristics thereof, and FIG. 91 shows current versus voltage characteristics thereof. FIG. 92 shows luminance versus current density characteristics of the light-emitting element 12, FIG. 93 shows luminance versus voltage characteristics thereof, FIG. 94 shows current efficiency versus luminance characteristics thereof, and FIG. 95 shows current versus voltage characteristics thereof. In FIG. 88 and FIG. 92, the vertical axis represents luminance (cd/m$^2$), and the horizontal axis represents current density (mA/cm$^2$). In FIG. 89 and FIG. 93, the vertical axis represents luminance (cd/m$^2$), and the horizontal axis represents voltage (V). In FIG. 90 and FIG. 94, the vertical axis represents current efficiency (cd/A), and the horizontal axis represents luminance (cd/m$^2$). In FIG. 91 and FIG. 95, the vertical axis represents current (mA), and the horizontal axis represents voltage (V).

FIG. 90 reveals that the light-emitting element 11, in which the carbazole derivative represented by the general formula (G1) is used as a host material of a light-emitting layer for emitting blue phosphorescence, has favorable luminance versus current characteristics and high emission efficiency. This is because the carbazole derivative represented by the general formula (G1) has a wide energy gap, and thus even a light-emitting substance that emits blue phosphorescence gap can be efficiently excited. In addition, FIG. 89 reveals that the light-emitting element, in which the carbazole derivative represented by the general formula (G1) is used as a host material of a light-emitting for emitting blue phosphorescence, has favorable luminance versus voltage characteristics and can be driven with a low voltage. This indicates that any of the carbazole derivatives represented by the general formula (G1) has an excellent carrier-transport property.

FIG. 94 reveals that the light-emitting element 12, in which the carbazole derivative represented by the general formula (G1) is used as a hole-transport material adjacent to a light-emitting layer for emitting blue phosphorescence, has favorable luminance versus current efficiency characteristics and high emission efficiency. This is because since mDBTCz2P-II, which is any of the carbazole derivatives described in Embodiment 1, has a wide energy gap and a high triplet excitation energy accordingly, even when it is used for the hole-transport layer adjacent to the emission center substance that emits blue phosphorescence, a reduction in emission efficiency is suppressed without transfer of excitation energy to the hole-transport layer. In addition, FIG. 93 reveals that the light-emitting elements in each of which the carbazole derivative represented by the general formula (G1) is used as a host material of a light-emitting layer for emitting blue phosphorescence, has favorable luminance versus voltage characteristics and can be driven with a low voltage. This indicates that each carbazole derivative represented by the general formula (G1) has an excellent carrier-transport property.

Figure 96:
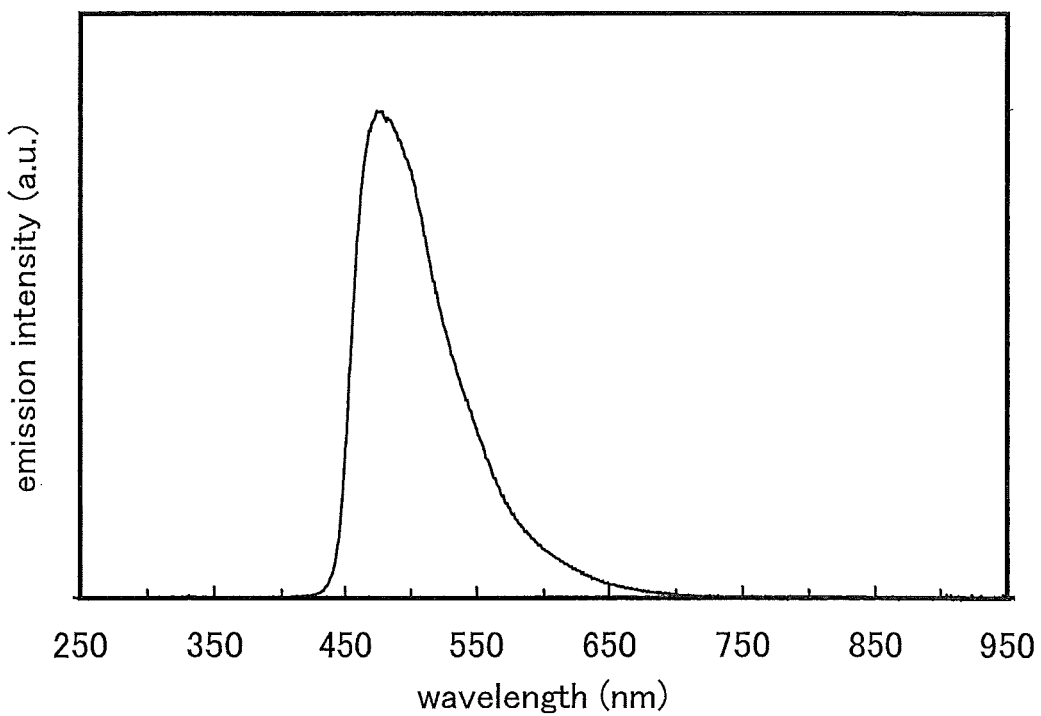
FIG. 96 shows an emission spectrum of the light-emitting element 11.
Figure 97:
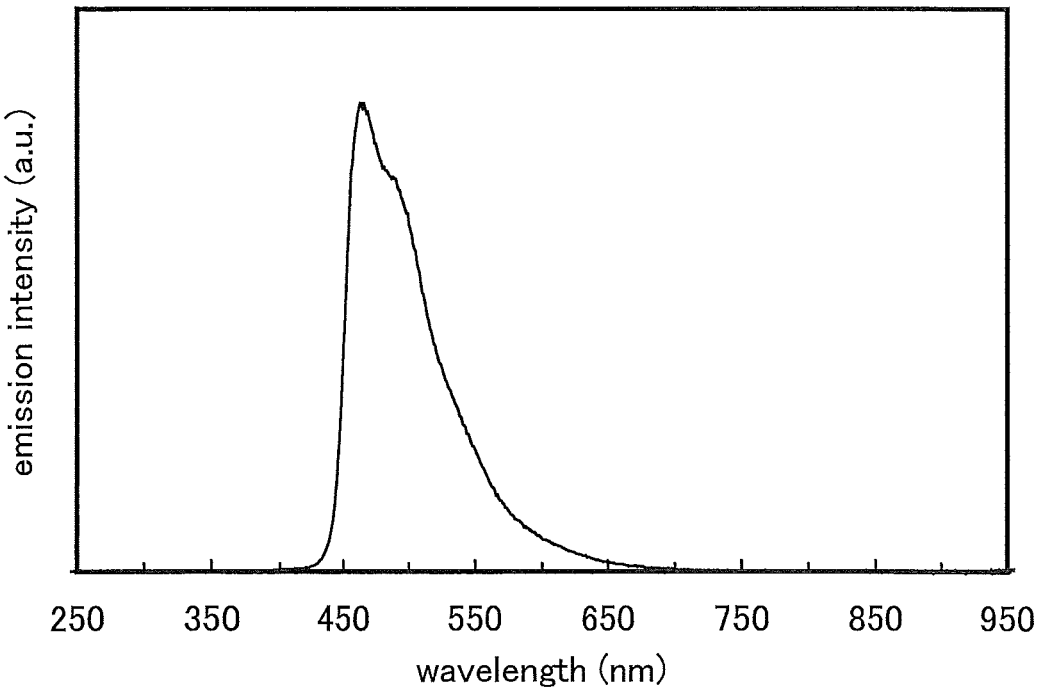
FIG. 97 shows an emission spectrum of the light-emitting element 12.

FIG. 96 shows an emission spectrum when a current of 0.1 mA was made to flow in the fabricated light-emitting element 11, and FIG. 97 shows an emission spectrum when a current of 0.1 mA was made to flow in the light-emitting element 12. In FIG. 96 and FIG. 97, the vertical axis represents absorption intensity (arbitrary unit), and the horizontal axis represents wavelength (nm). The emission intensity is shown as a value relative to the greatest emission intensity assumed to be 1. FIG. 96 and FIG. 97 reveal that the light-emitting elements 11 and 12 each blue green light due to [Ir(Mptz1-mp)$_3$], which is the emission center substance.

Figure 98:
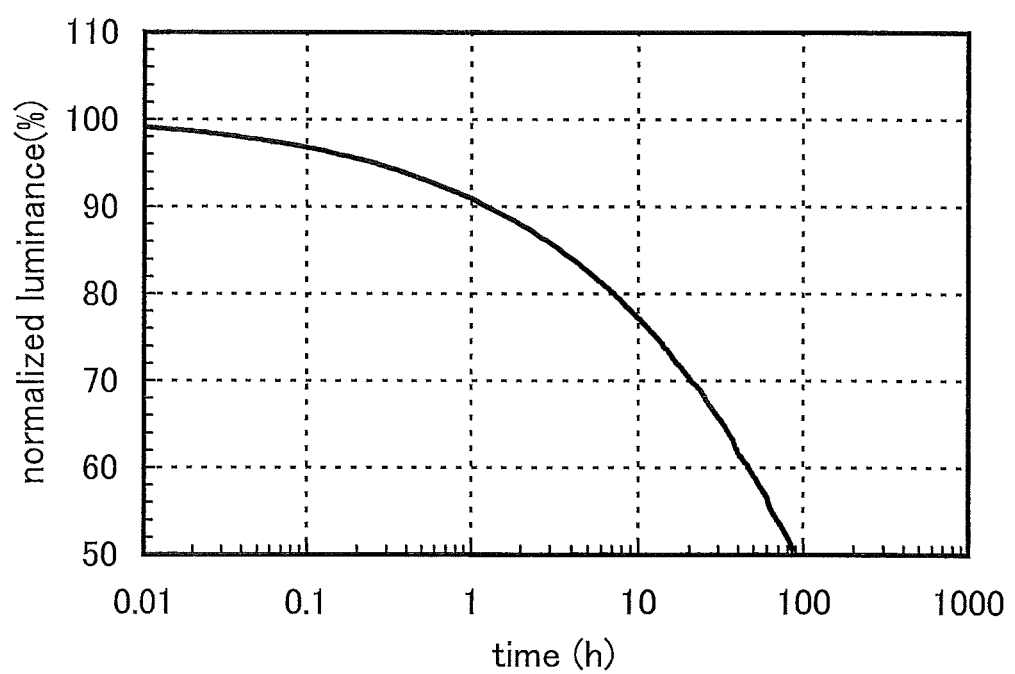
FIG. 98 shows normalized luminance versus time characteristics of the light-emitting element 11.
Figure 99:
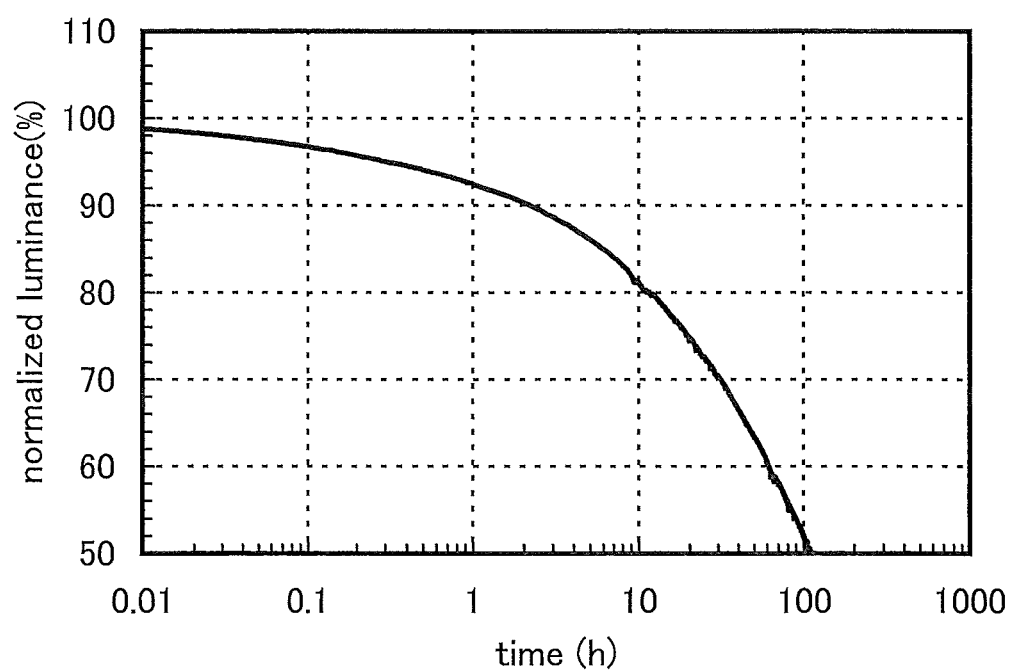
FIG. 99 shows normalized luminance versus time characteristics of the light-emitting element 12.

Next, the initial luminance is set at 1000 cd/m$^2$, these elements were driven under a condition where the current density was constant, and changes in luminance with respect to the driving time were examined. FIG. 98 shows normalized luminance versus time characteristics of the light-emitting element 11, and FIG. 99 shows those of the light-emitting element 12. From FIG. 98 and FIG. 99, it is found that each of the light-emitting elements 11 and 12 has high reliability with a small reduction in luminance with respect to driving time.

Thus, a light-emitting element, in which an emission center substance emits blue phosphorescence and a carbazole derivative described in Embodiment 1 is used as a host material or as a hole-transport material, can have high emission efficiency by efficient excitation for blue phosphorescence which is the light emission from the high triplet excitation energy or by prevention of a loss due to energy transfer. This means that any of the carbazole derivatives described in Embodiment 1 has very high triplet excitation energy.

Example 19

Synthesis Example 11

In this example is described a method of synthesizing 3-(dibenzothiophen-4-yl)-9-[3-(10-phenyl-9-anthryl)phenyl]-9H-carbazole (abbreviation: mDBTCzPA-II), which is one of the carbazole derivatives described in Embodiment 1. A structure of mDBTCzPA-II is illustrated in the following structural formula (13).

(13)

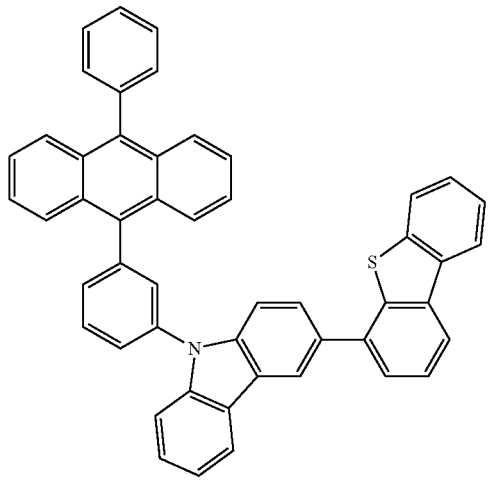

Step 1: Synthesis of 3-(Dibenzothiophen-4-yl)-9H-carbazole (abbreviation: DBTCz-II)

This was synthesized as in Step 1 in Example 1.

Step 2: Synthesis of 3-(Dibenzothiophen-4-yl)-9-[3-(10-phenyl-9-anthryl)phenyl]-9H-carbazole (abbreviation: mDBTCzPA-II)

In a 50-mL three-neck flask were put 1.2 g (3.0 mmol) of 9-(3-bromophenyl)-10-phenylanthracene, 1.1 g (3.0 mmol) of 3-(dibenzothiophen-4-yl)-9H-carbazole, and 0.87 g (9.1 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 87 mg (0.15 mmol) of bis(dibenzylideneacetone)palladium(0) was added to this mixture. This mixture was stirred at 110° C. for 5 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The filtrate was concentrated to give a yellow solid. The obtained solid was recrystallized from toluene. The obtained crystal was purified by high performance liquid column chromatography (abbreviation: HPLC) (chloroform as the developing solvent). The obtained fraction was concentrated to give 1.5 g of a pale yellow solid in 72% yield. The synthesis scheme of Step 2 is illustrated in (b-11).

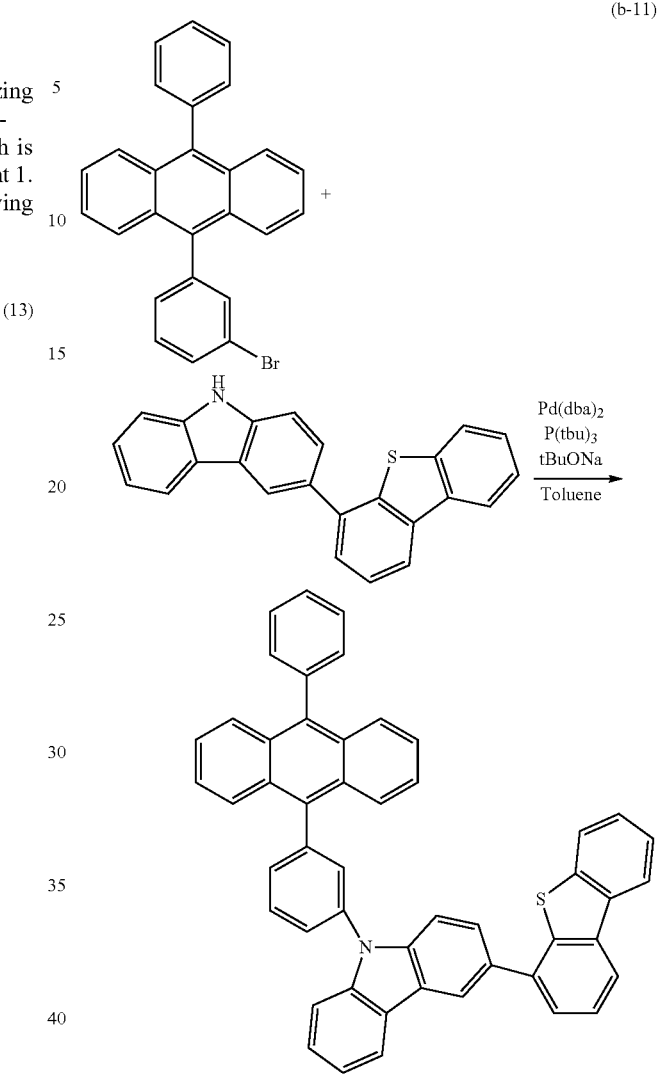

(b-11)

By a train sublimation method, the obtained pale yellow solid was purified. The purification was conducted by heating of 1.0 g of the pale yellow solid at 300° C. under a pressure of 2.6 Pa with a flow rate of argon gas of 5 mL/min. After the purification, 0.79 g of a white solid was obtained in a yield of 79%.

The pale yellow solid after the above purification was subjected to nuclear magnetic resonance (NMR) spectroscopy. The measurement data are shown below.

$^1$H NMR (CDCl$_3$, 300 MHz): δ=7.30-7.52 (m, 10H), 7.55-7.68 (m, 7H), 7.71-7.77 (m, 3H), 7.81-7.92 (m, 7H), 8.14-8.23 (m, 3H), 8.51 (d, J$_1$=0.90 Hz, 1H)

Figure 100A:
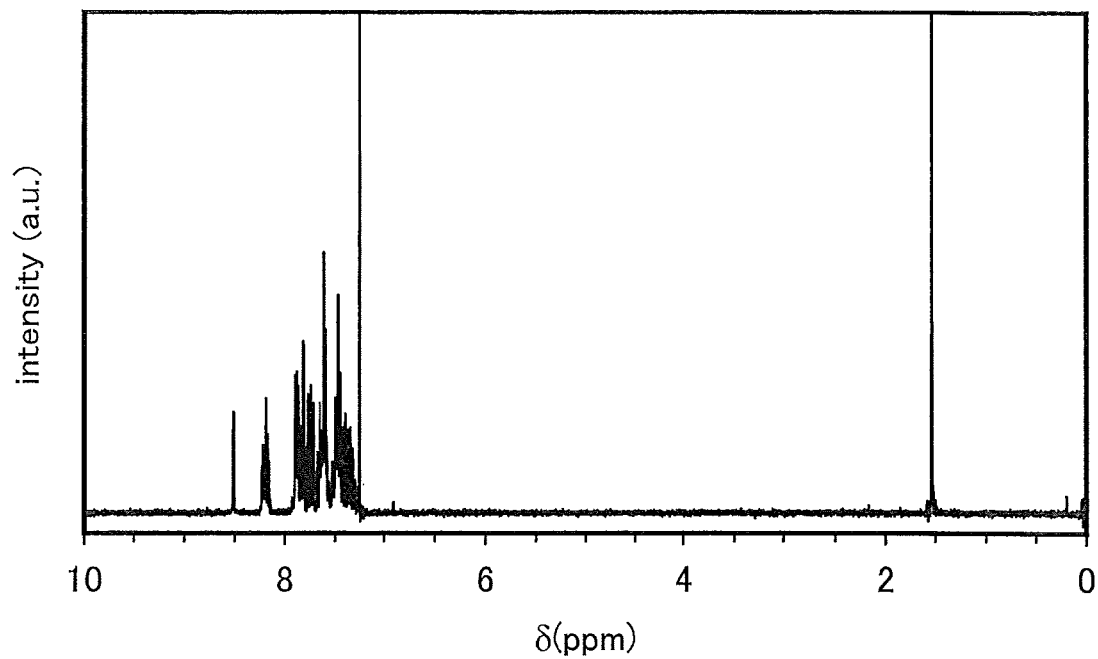
FIGS. 100A and 100B are NMR charts of mDBTCzPA-II.
Figure 100B:
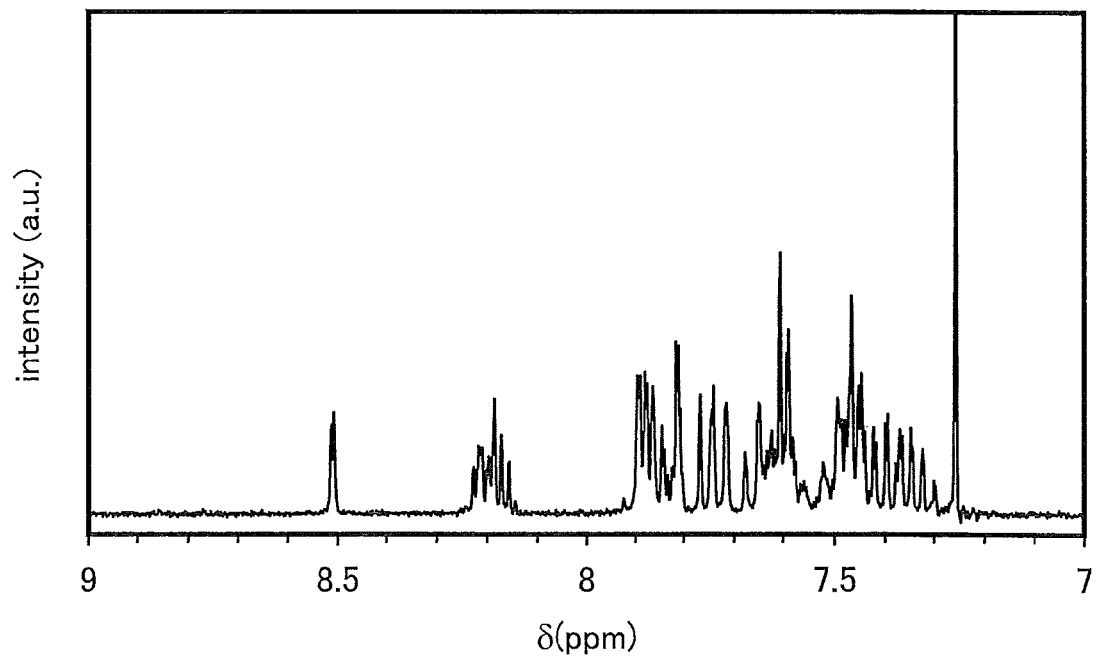

In addition, $^1$H NMR charts are shown in FIGS. 100A and 100B. Note that FIG. 100B is a chart where the range of from 7 ppm to 9 ppm in FIG. 100A is enlarged. The measurement results showed that mDBTCzPA-II, which is the carbazole derivative represented by the above structural formula, was obtained.

Figure 101A:
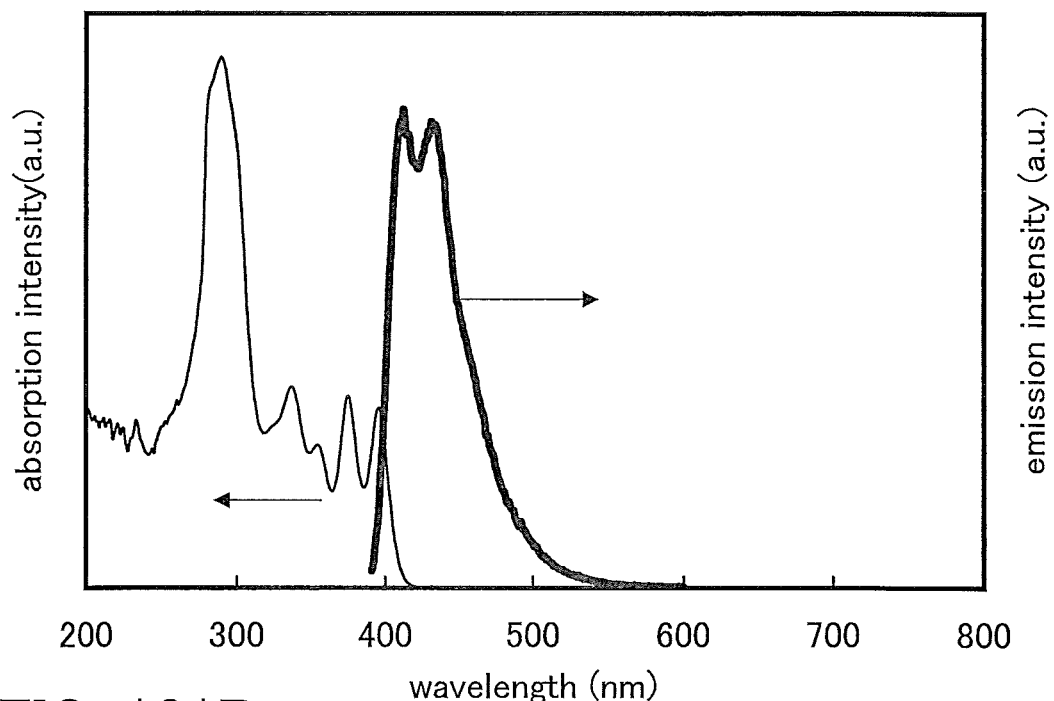
FIGS. 101A and 101B show an absorption and emission spectra of mDBTCzPA-II.
Figure 101B:
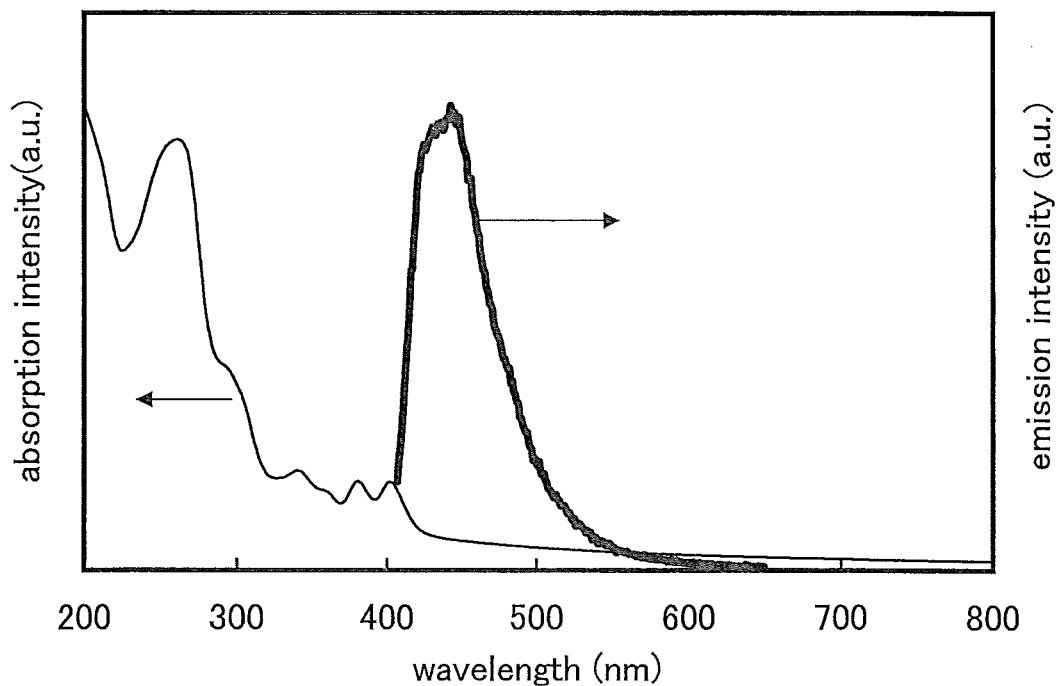

Further, an absorption and emission spectra of mDBTCzPA-II in a toluene solution of mDBTCzPA-II are shown in FIG. 101A, and an absorption and emission spectra of a thin film of mDBTCzPA-II are shown in FIG. 101B. An ultraviolet-visible spectrophotometer (V-550, manufactured by JASCO Corporation) was used for the measurements of the absorption spectra. In the case of the toluene solution, the measurements were made with the toluene solution of mDBTCzPA-II put in a quartz cell, and the absorption spectrum obtained by subtraction of the absorption spectra of the quartz cell and toluene from the measured spectra is shown in the drawing. In addition, as for the absorption spectrum of the thin film, a sample was prepared by evaporation of mDBTCzPA-II on a quartz substrate, and the absorption spectrum obtained by subtraction of that of quartz from the spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum was measured with the toluene solution of mDBTCzPA-II put in a quartz cell, and the emission spectrum of the thin film was measured with a sample prepared by evaporation of mDBTCzPA-II on a quartz substrate. Thus, it was found that the absorption peak wavelengths of mDBTCzPA-II in the toluene solution of mDBTCzPA-II were around 396 nm, 375 nm, 354 nm, 336 nm and 290 nm and the emission peak wavelengths thereof were around 412 nm and 433 nm (at an excitation wavelength of 376 nm), and that the absorption peak wavelengths of the thin film of mDBTCzPA-II were around 402 nm, 381 nm, 359 nm, 340 nm, 291 nm, 261 nm and 207 nm and the greatest emission wavelength thereof was around 443 nm (at an excitation wavelength of 402 nm).

Further, the ionization potential of mDBTCzPA-II in a thin film state was measured by a photoelectron spectrometer (AC-2, manufactured by Riken Keiki, Co., Ltd.) in air. The obtained value of the ionization potential was converted to a negative value, so that the HOMO level of mDBTCzPA-II was −5.77 eV. From the data of the absorption spectra of the thin film in FIG. 101B, the absorption edge of mDBTCzPA-II, which was obtained from Tauc plot with an assumption of direct transition, was 2.95 eV. Therefore, the optical energy gap of mDBTCzPA-II in the solid state was estimated at 2.95 eV; from the values of the HOMO level obtained above and this energy gap, the LUMO level of mDBTCzPA-II was able to be estimated at −2.82 eV. It was thus found that mDBTCzPA-II had a wide energy gap of 2.95 eV in the solid state.

Further, the oxidation reaction characteristics of mDBTCzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.04 V to 1.15 V and then changed from 1.15 V to −0.04 V was one cycle, and 100 cycles were performed.

The measurement results revealed that mDBTCzPA-II showed properties effective against repetition of redox reactions between an oxidized state and a neutral state without a large variation in oxidation peak even after the 100 cycles in the measurements.

Further, the HOMO level of mDBTCzPA-II was determined also by calculation from the CV measurement results.

First, the potential energy of the reference electrode with respect to the vacuum level used was found to be −4.94 eV, as determined in Example 6. The oxidation peak potential $E_{pa}$ of mDBTCzPA-II was 0.95 V. In addition, the reduction peak potential $E_{pc}$, thereof was 0.83 V. Therefore, a half-wave potential (an intermediate potential between $E_{pa}$ and $E_{pc}$) can be calculated at 0.89 V. This means that mDBTCzPA-II is oxidized by an electric energy of 0.89 [V versus Ag/Ag$^+$], and this energy corresponds to the HOMO level. Here, since the potential energy of the reference electrode, which was used in this example, with respect to the vacuum level is −4.94 [eV] as described above, the HOMO level of mDBTCzPA-II was calculated as follows: −4.94−0.89=−5.83 [eV].

Example 20

In this example described is a light-emitting element in which 3-(dibenzothiophen-4-yl)-9-[3-(10-phenyl-9-anthryl)phenyl]-9H-carbazole (abbreviation: mDBTCzPA-II, a structural formula (13)), which is one of the carbazole derivatives represented by the general formula (G1), is used as a host material such that an emission center substance that emits blue fluorescence is dispersed therein.

The molecular structures of organic compounds used in this example are represented by the structural formulae (13), (iv), and (iv) below.

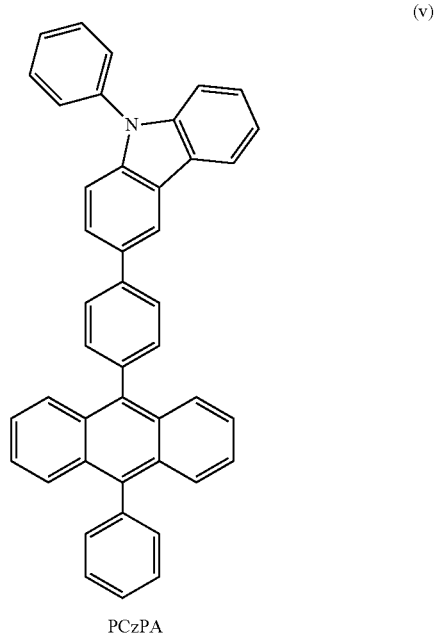

(v)

PCzPA

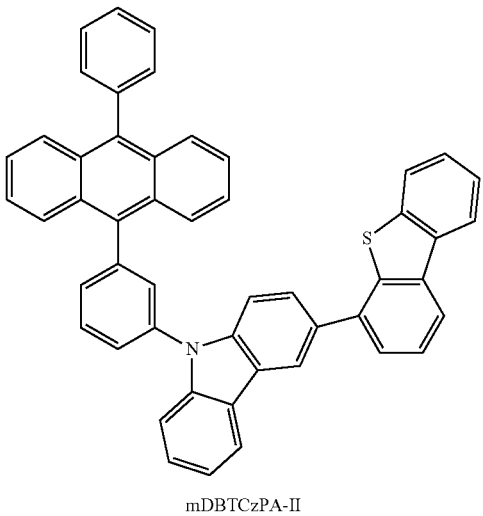

mDBTCzPA-II

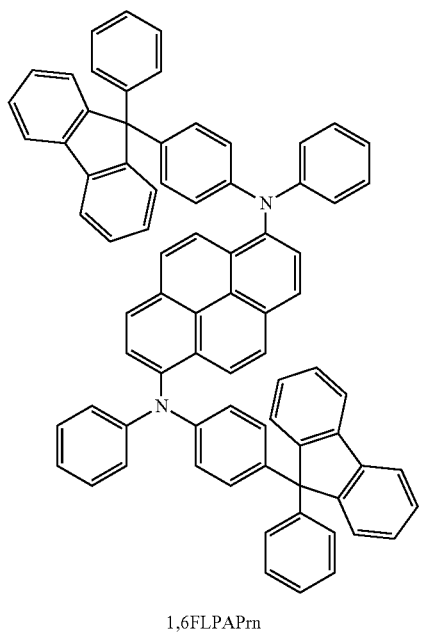

1,6FLPAPrn

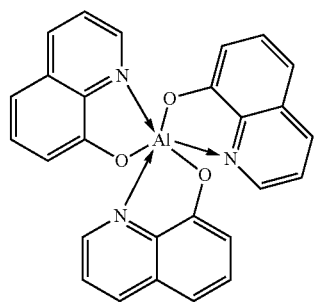

Alq₃

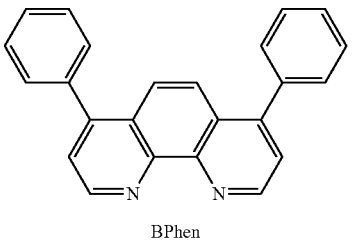

BPhen

In the element structure in FIG. 1A, an electron-injection layer is provided between an electron-transport layer 114 and a second electrode 104.

[Fabrication of Light-Emitting Element 13]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 9-[4-(9-phenylcarbazol-3-yl)]phenyl-10-phenylanthracene (abbreviation: PCzPA) represented by the above structural formula (v) and molybdenum(VI) oxide such that the ratio of PCzPA:molybdenum(VI) oxide was 2:1 (weight ratio). The thickness of was the layer was set to 50 nm. Note that the co-evaporation is an evaporation method in which a plurality of different substances is concurrently vaporized from the respective different evaporation sources.

Next, PCzPA was evaporated to a thickness of 10 nm, so that the hole-transport layer 112 was formed.

Further, the light-emitting layer 113 was formed on the hole-transport layer 112 in such a way that 3-(dibenzothiophen-4-yl)-9-[3-(10-phenyl-9-anthryl)phenyl]-9H-carbazole (abbreviation: mDBTCzPA-II) represented by the above structural formula (13) and N,N'-bis[4-(9-phenyl-9H-fluoren-9-yl)phenyl]-N,N'-diphenyl-pyrene-1,6-diamine (abbreviation: 1,6FLPAPrn) represented by the structural formula (vi) were evaporated to form a 30-nm-thick film so that the ratio of mDBTCzPA-II to 1,6FLPAPrn was 1:0.03 (weight ratio).

Next, on the light-emitting layer 113, tris(8-quinolinolato)aluminum(III) (abbreviation: Alq) represented by the above structural formula (vii) was evaporated to a thickness of 10 nm, and then bathophenanthroline (abbreviation: BPhen) represented by the above structural formula (iv) was evaporated to a thickness of 15 nm, so that the electron-transport layer 114 was formed. Then, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 13 was completed. Note that in the above evaporation processes, evaporation was all performed by a resistance heating method.

[Operation Characteristics of Light-Emitting Element 13]

The light-emitting element 13 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 102:
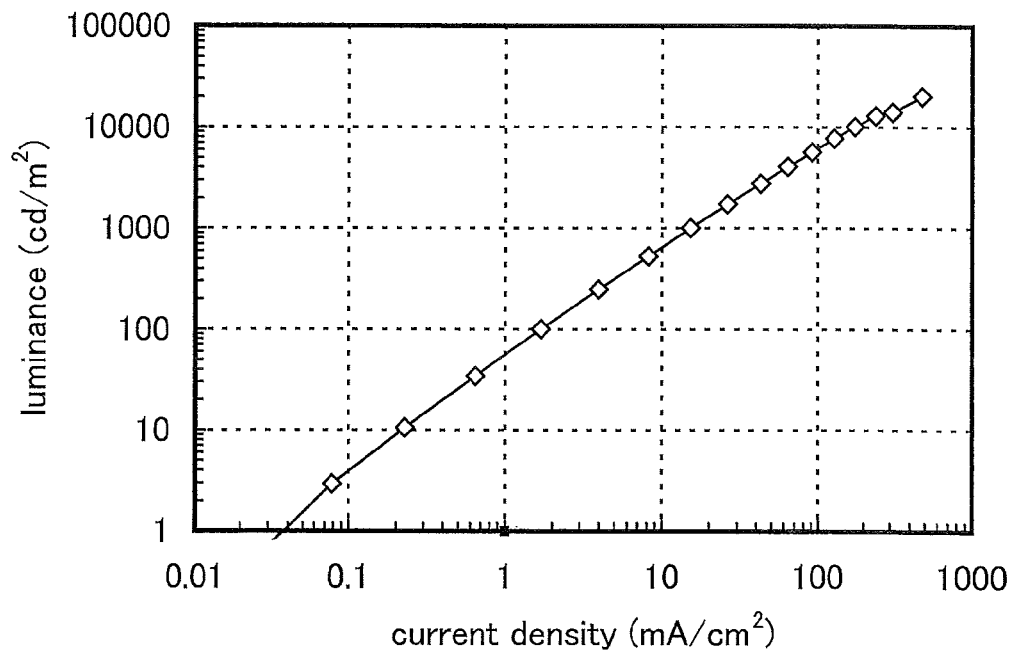
FIG. 102 shows luminance versus current density characteristics of a light-emitting element 13.
Figure 103:
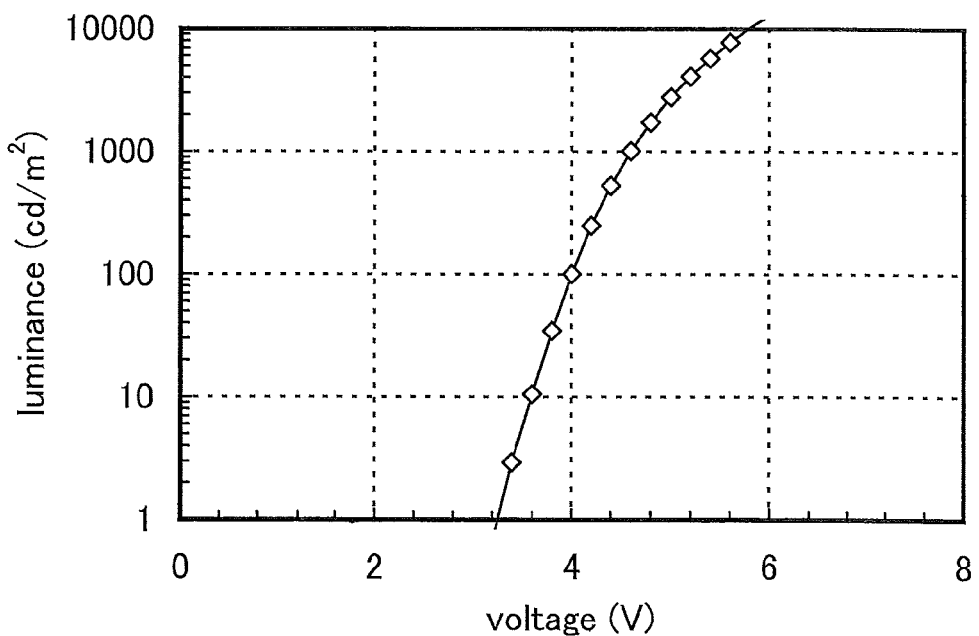
FIG. 103 shows luminance versus voltage characteristics of the light-emitting element 13.
Figure 104:
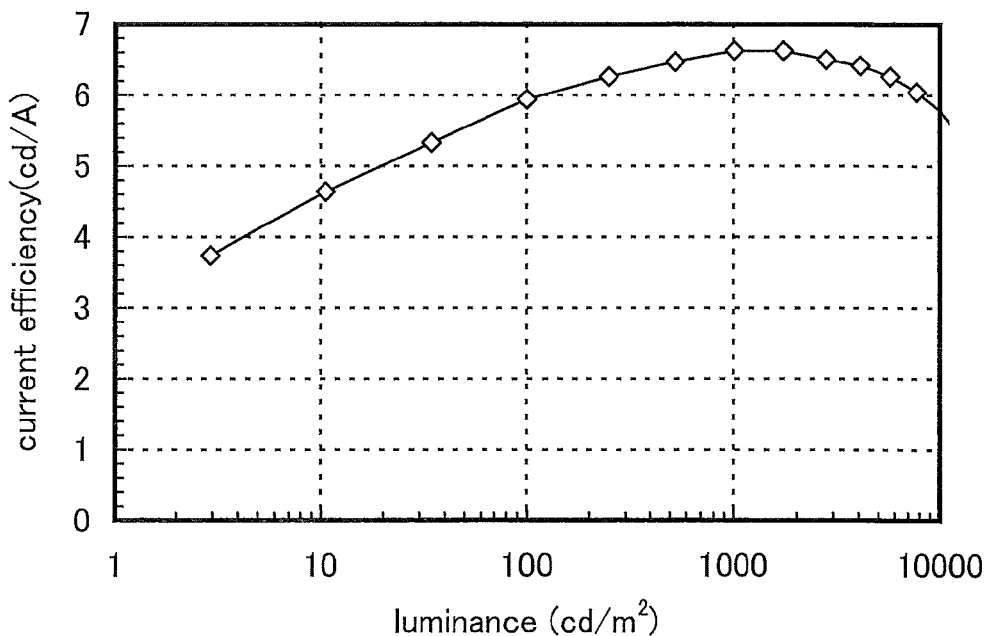
FIG. 104 shows current efficiency versus luminance characteristics of the light-emitting element 13.
Figure 105:
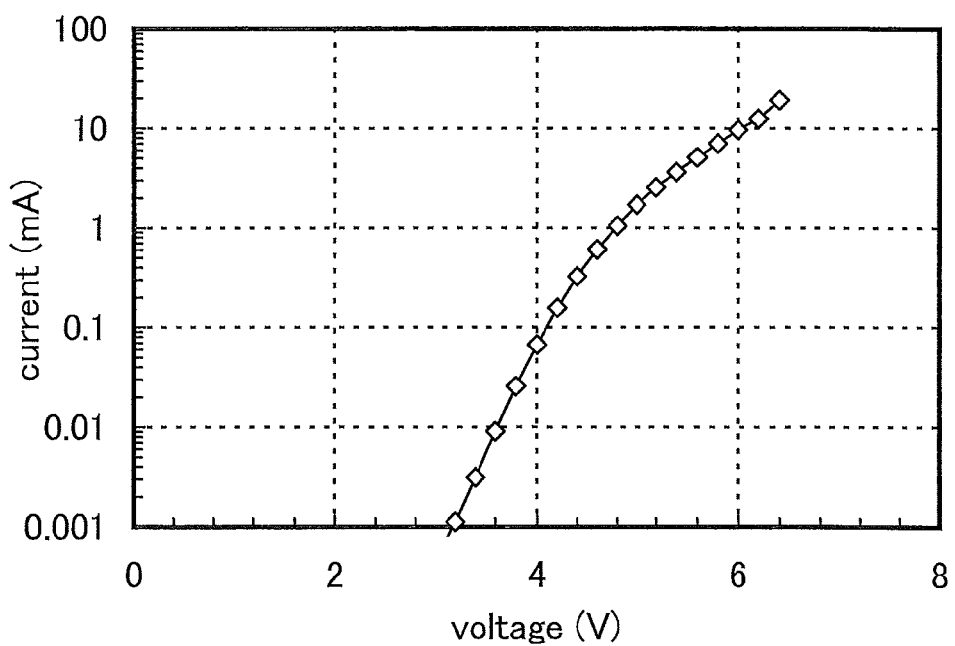
FIG. 105 shows current versus voltage characteristics of the light-emitting element 13.

FIG. 102 shows luminance current density characteristics of the light-emitting element 13, FIG. 103 shows luminance versus voltage characteristics thereof, FIG. 104 shows current efficiency versus luminance characteristics thereof, and FIG. 105 shows current versus voltage characteristics thereof. In FIG. 102, the vertical axis represents luminance (cd/m$^2$), and the horizontal axis represents current density (mA/cm$^2$). In FIG. 103, the vertical axis represents luminance (cd/m$^2$), and the horizontal axis represents voltage (V). In FIG. 104, the vertical axis represents current efficiency (cd/A), and the horizontal axis represents luminance (cd/m$^2$). In FIG. 105, the vertical axis represents current (mA), and the horizontal axis represents voltage (V).

FIG. 104 reveals that the light-emitting elements in each of which the carbazole derivative represented by the general formula (G1) is used as a host material of a light-emitting layer for emitting blue fluorescence, has favorable current efficiency versus luminance characteristics and high emission efficiency. This is because each carbazole derivative represented by the general formula (G1) has a wide energy gap, and thus even a light-emitting substance that emits blue fluorescence and has a wide energy gap can be efficiently excited. In addition, FIG. 102 reveals that the light-emitting elements in each of which the carbazole derivative represented by the general formula (G1) is used as a host material of a light-emitting layer for emitting blue fluorescence, has favorable luminance versus voltage characteristics and can be driven with a low voltage. This indicates that each carbazole derivative represented by the general formula (G1) has an excellent carrier-transport property.

Figure 106:
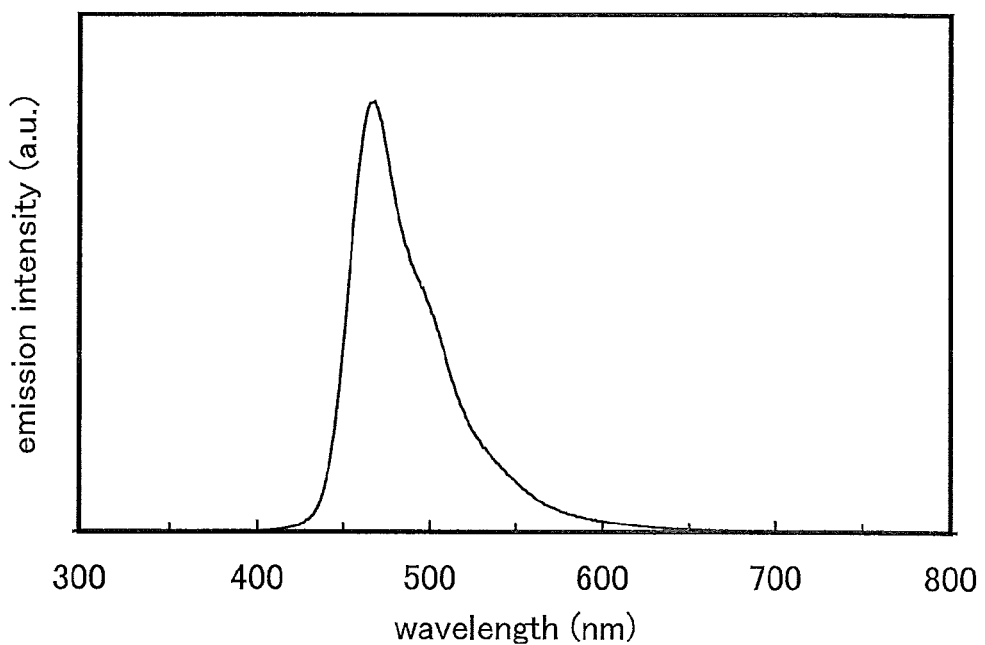
FIG. 106 shows an emission spectrum of the light-emitting element 13.

FIG. 106 shows an emission spectrum when a current of 1 mA was made to flow in the fabricated light-emitting element 13. The emission intensity is shown as a value relative to the greatest emission intensity assumed to be 1. FIG. 106 reveals that the light-emitting element 13 emits blue light due to 1,6FLPAPrn, which is the emission center substance.

Figure 107:
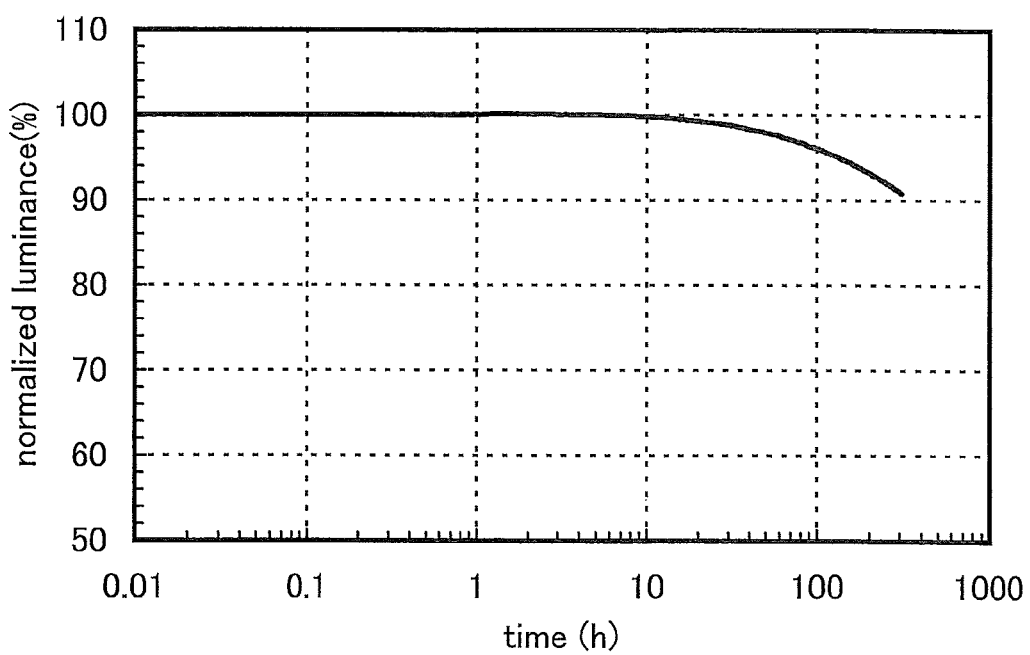
FIG. 107 shows normalized luminance versus time characteristics of the light-emitting element 13.

Next, the initial luminance is set at 5000 cd/m$^2$, the element was driven under a condition where the current density was constant, and changes in luminance with respect to the driving time were examined. FIG. 107 shows normalized luminance versus time characteristics. From FIG. 107, it is found that the light-emitting element 13 shows favorable characteristics and has high reliability.

Example 21

Synthesis Example 12

In this example is described a method of synthesizing 3-(dibenzofuran-4-yl)-9-[3-(10-phenyl-9-anthryl)phenyl]-9H-carbazole (abbreviation: mDBFCzPA-II), which is one of the carbazole derivatives described as the structural formula (14) in Embodiment 1. A structure of mDBFCzPA-II is illustrated in the following structural formula.

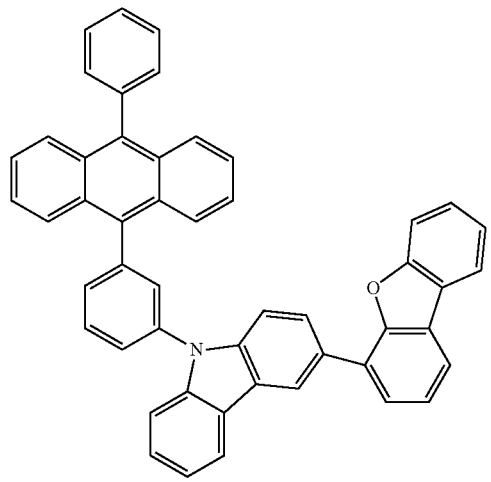

(14)

Step 1: Synthesis of 3-(Dibenzofuran-4-yl)-9H-carbazole (abbreviation: DBFCz-II)

This was synthesized as in Step 1 in Example 2.

Step 2: Synthesis of 3-(Dibenzofuran-4-yl)-9-[3-(10-phenyl-9-anthryl)phenyl]-9H-carbazole (abbreviation: mDBFCzPA-II)

In a 100-mL three-neck flask were put 1.2 g (3.0 mmol) of 9-(3-bromophenyl)-10-phenylanthracene, 1.0 g (3.0 mmol) of 3-(dibenzofuran-4-yl)-9H-carbazole, and 0.87 g (9.1 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 87 mg (0.15 mmol) of bis(dibenzylideneacetone)palladium(0) was added to this mixture. This mixture was stirred at 110° C. for 6 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The filtrate was concentrated to give a yellow solid. The obtained solid was recrystallized from toluene to give 1.8 g of a white solid which was the object of the synthesis in 88% yield. The synthesis scheme of Step 2 is illustrated in (b-12).

(b-12)

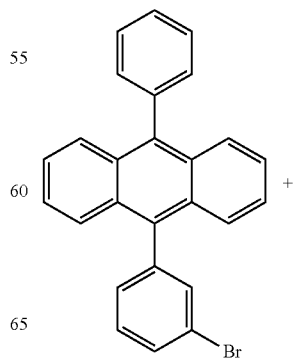

-continued

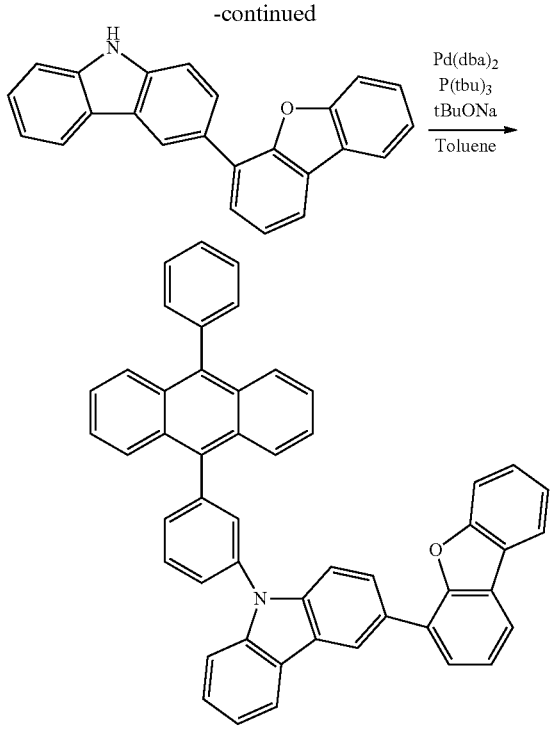

By a train sublimation method, the obtained white solid was purified. The purification was conducted by heating of 1.2 g of the white solid at 300° C. under a pressure of 2.6 Pa with a flow rate of argon gas of 5 mL/min. After the purification, 1.1 g of a white solid was obtained in a yield of 89%.

The white solid after the above purification was subjected to nuclear magnetic resonance (NMR) spectroscopy. The measurement data are shown below.

$^1$H NMR (CDCl$_3$, 300 MHz): δ=7.31-7.40 (m, 4H), 7.42-7.67 (m, 13H), 7.70-7.81 (m, 5H), 7.85-7.92 (m, 4H), 7.95 (dd, $J_1$=1.5 Hz, $J_2$=7.8 Hz, 1H), 7.99-8.03 (m, 2H), 8.24 (d, $J_1$=7.8 Hz, 1H), 8.65 (d, $J_1$=1.5 Hz, 1H)

Figure 108A:
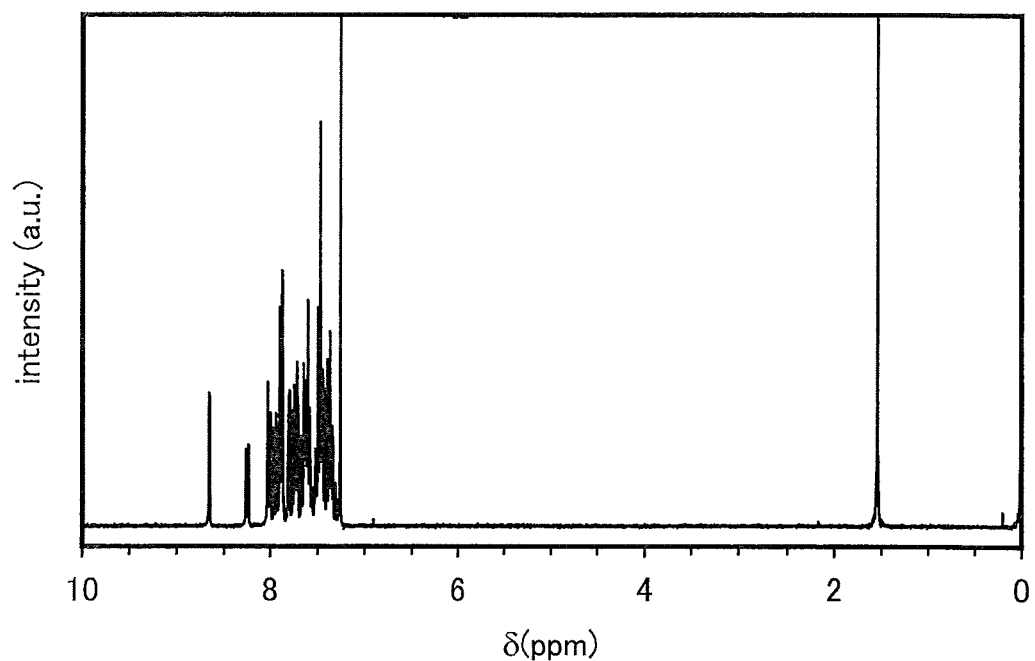
FIGS. 108A and 108B are NMR charts of mDBFCzPA-II.
Figure 108B:
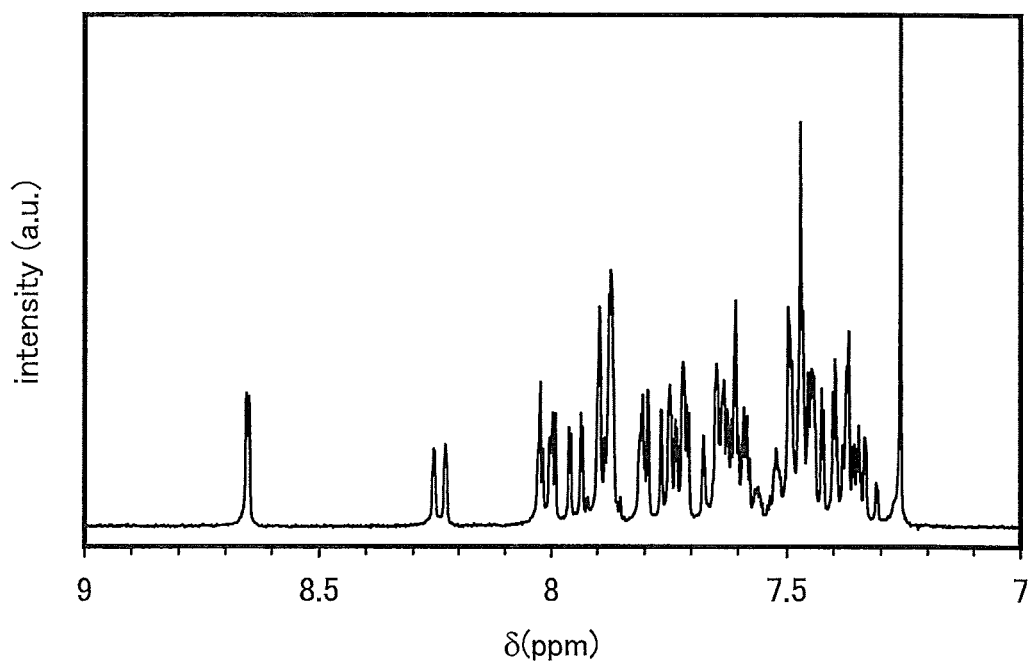

In addition, $^1$H NMR charts are shown in FIGS. 108A and 108B. Note that FIG. 108B is a chart where the range of from 7 ppm to 9 ppm in FIG. 108A is enlarged. The measurement results showed that mDBFCzPA-II, which is the carbazole derivative represented by the above structural formula, was obtained.

Figure 109A:
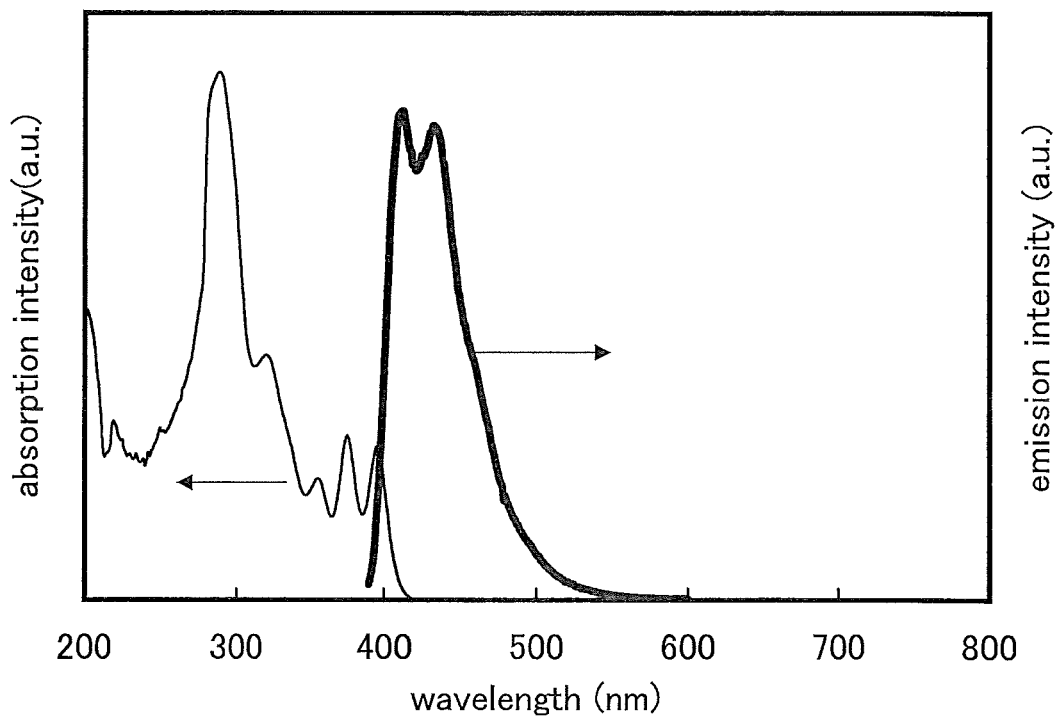
FIGS. 109A and 109B show an absorption and emission spectra of mDBFCzPA-II.
Figure 109B:
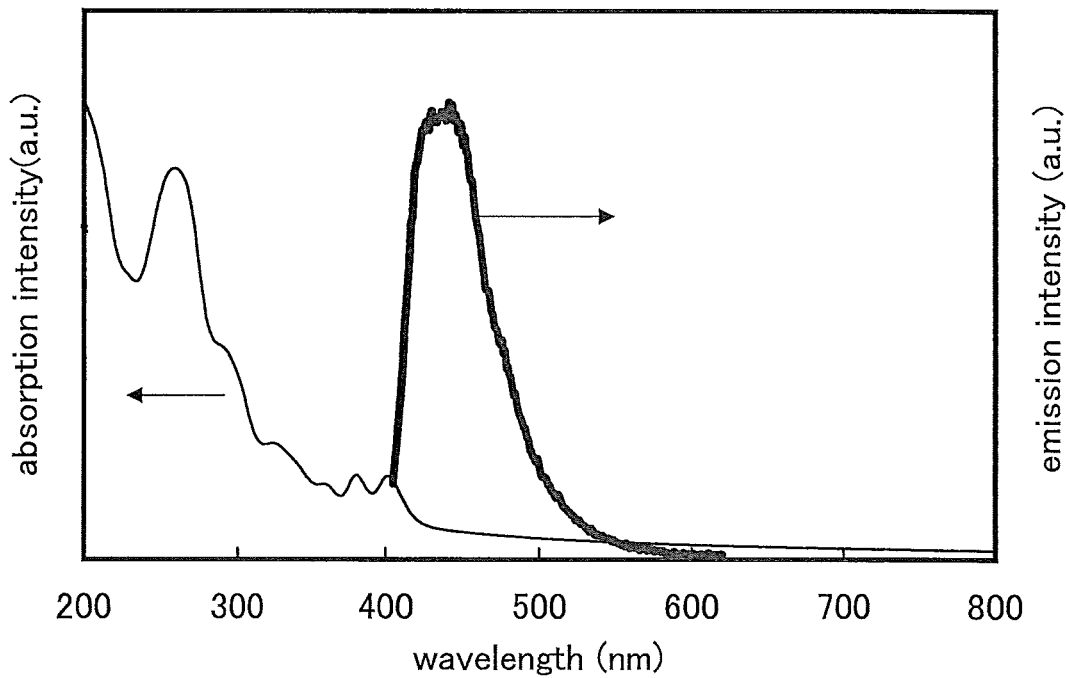

Further, an absorption and emission spectra of mDBFCzPA-II in a toluene solution of mDBFCzPA-II are shown in FIG. 109A, and an absorption and emission spectra of a thin film of mDBFCzPA-II are shown in FIG. 109B. An ultraviolet-visible spectrophotometer (V-550, manufactured by JASCO Corporation) was used for the measurements of the absorption spectra. In the case of the toluene solution, the measurements were made with the toluene solution of mDBFCzPA-II put in a quartz cell, and the absorption spectrum obtained by subtraction of the absorption spectra of the quartz cell and toluene from the measured spectra is shown in the drawing. In addition, as for the absorption spectrum of the thin film, a sample was prepared by evaporation of mDBFCzPA-II on a quartz substrate, and the absorption spectrum obtained by subtraction of that of quartz from the spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum was measured with the toluene solution of mDBFCzPA-II put in a quartz cell, and the emission spectrum of the thin film was measured with a sample prepared by evaporation of mDBFCzPA-II on a quartz substrate. Thus, it was found that the absorption peak wavelengths of mDBFCzPA-II in the toluene solution of mDBFCzPA-II were around 396 nm, 375 nm, 354 nm, 336 nm and 290 nm and the emission peak wavelengths thereof were around 412 nm and 433 nm (at an excitation wavelength of 375 nm), and that the absorption peak wavelengths of the thin film of mDBFCzPA-II were around 402 nm, 381 nm, 359 nm, 340 nm, 291 nm, 261 nm and 207 nm and the greatest emission wavelength thereof was around 443 nm (at an excitation wavelength of 402 nm).

Further, the ionization potential of mDBFCzPA-II in a thin film state was measured by a photoelectron spectrometer (AC-2, manufactured by Riken Keiki, Co., Ltd.) in air. The obtained value of the ionization potential was converted to a negative value, so that the HOMO level of mDBFCzPA-II was −5.77 eV. From the data of the absorption spectra of the thin film in FIG. 109B, the absorption edge of mDBFCzPA-II, which was obtained from Tauc plot with an assumption of direct transition, was 2.95 eV. Therefore, the optical energy gap of mDBFCzPA-II in the solid state was estimated at 2.95 eV; from the values of the HOMO level obtained above and this energy gap, the LUMO level of mDBFCzPA-II was able to be estimated at −2.82 eV. It was thus found that mDBFCzPA-II had a wide energy gap of 2.95 eV in the solid state.

Further, the oxidation reaction characteristics of mDBFCzPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.04 V to 1.15 V and then changed from 1.15 V to −0.04 V was one cycle, and 100 cycles were performed.

The measurement results revealed that mDBFCzPA-II showed properties effective against repetition of redox reactions between an oxidized state and a neutral state without a large variation in oxidation peak even after the 100 cycles in the measurements.

Further, the HOMO level of mDBFCzPA-II was determined also by calculation from the CV measurement results.

First, the potential energy of the reference electrode with respect to the vacuum level used was found to be −4.94 eV, as determined in Example 6. The oxidation peak potential $E_{pa}$ of mDBFCzPA-II was 0.95 V. In addition, the reduction peak potential $E_{pc}$ thereof was 0.83 V. Therefore, a half-wave potential (an intermediate potential between $E_{pa}$ and $E_{pc}$) can be calculated at 0.89 V. This means that mDBFCzPA-II is oxidized by an electric energy of 0.89 [V versus Ag/Ag$^+$], and this energy corresponds to the HOMO level. Here, since the potential energy of the reference electrode, which was used in this example, with respect to the vacuum level is −4.94 [eV] as described above, the HOMO level of mDBFCzPA-II was calculated as follows: −4.94−0.89=−5.83 [eV].

Example 22

In this example described is a light-emitting element in which 3-(dibenzofuran-4-yl)-9-[3-(10-phenyl-9-anthryl)phenyl]-9H-carbazole (abbreviation: mDBFCzPA-II, a structural formula (14)), which is one of the carbazole derivatives represented by the general formula (G1), is used as a host material such that an emission center substance that emits blue fluorescence is dispersed therein.

The molecular structures of organic compounds used in this example are represented by the structural formulae (14), (iv), and (iv) below.

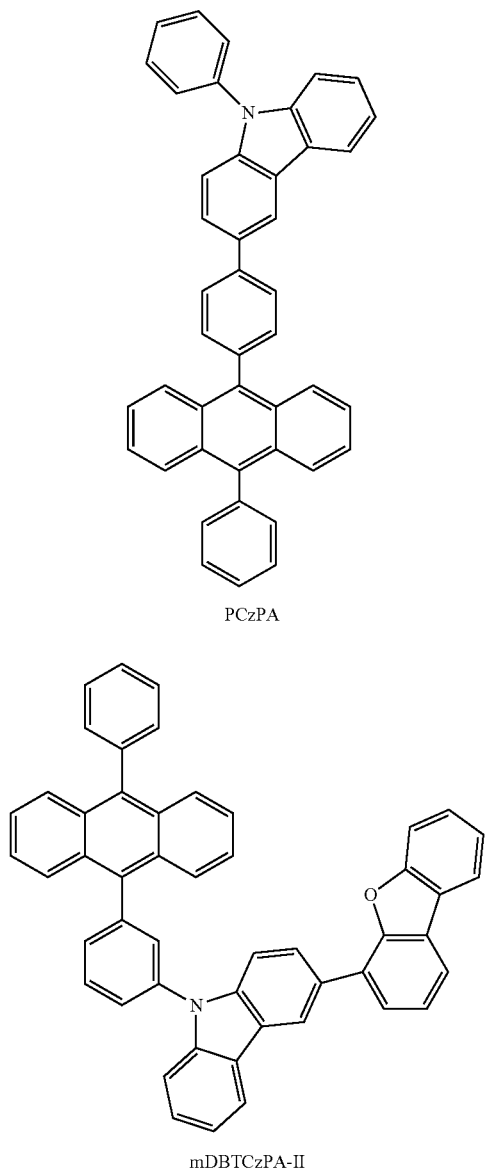

PCzPA (14)

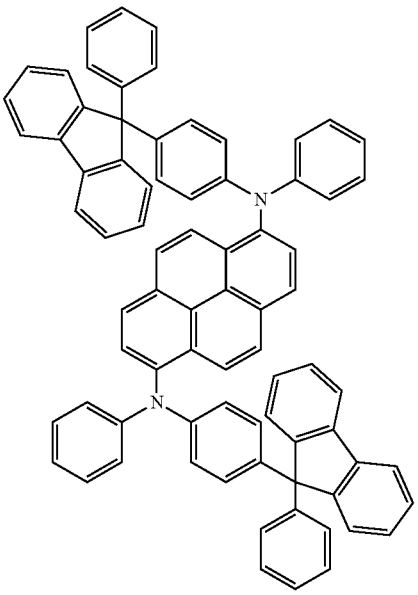

1,6FLPAPrn

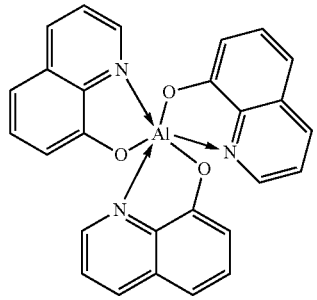

Alq$_3$

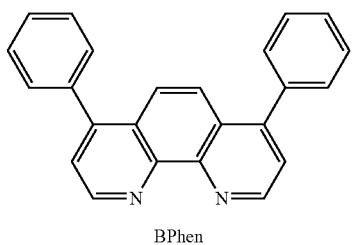

BPhen

In the element structure in FIG. 1A, an electron-injection layer is provided between an electron-transport layer 114 and a second electrode 104.

[Fabrication of Light-Emitting Element 14]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 9-[4-(9-phenylcarbazol-3-yl)]phenyl-10-phenylanthracene (abbreviation: PCzPA) represented by the above structural formula (v) and molybdenum(VI) oxide such that the ratio of PCzPA:molybdenum(VI) oxide was 2:1 (weight ratio). The thickness of was the layer was set to 50 nm Note that the co-evaporation is an evaporation method in which a plurality of different substances is concurrently vaporized from the respective different evaporation sources.

Next, PCzPA was evaporated to a thickness of 10 nm, so that the hole-transport layer 112 was formed.

Further, the light-emitting layer 113 was formed on the hole-transport layer 112 in such a way that 3-(dibenzofuran-4-yl)-9-[3-(10-phenyl-9-anthryl)phenyl]-9H-carbazole (abbreviation: mDBFCzPA-II) represented by the above structural formula (14) and N,N'-bis[4-(9-phenyl-9H-fluoren-9-yl)phenyl]-N,N'-diphenyl-pyrene-1,6-diamine (abbreviation: 1,6FLPAPrn) represented by the structural formula (vi) were evaporated to form a 30-nm-thick film so that the ratio of mDBFCzPA-II to 1,6FLPAPrn was 1:0.05 (weight ratio).

Next, on the light-emitting layer 113, tris(8-quinolinolato) aluminum(III) (abbreviation: Alq) represented by the above structural formula (vii) was evaporated to a thickness of 10 nm, and then bathophenanthroline (abbreviation: BPhen) represented by the above structural formula (iv) was evaporated to a thickness of 15 nm, so that the electron-transport layer 114 was formed. Then, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 14 was completed. Note that in the above evaporation processes, evaporation was all performed by a resistance heating method.

[Operation Characteristics of Light-Emitting Element 14]

The light-emitting element 14 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 110:
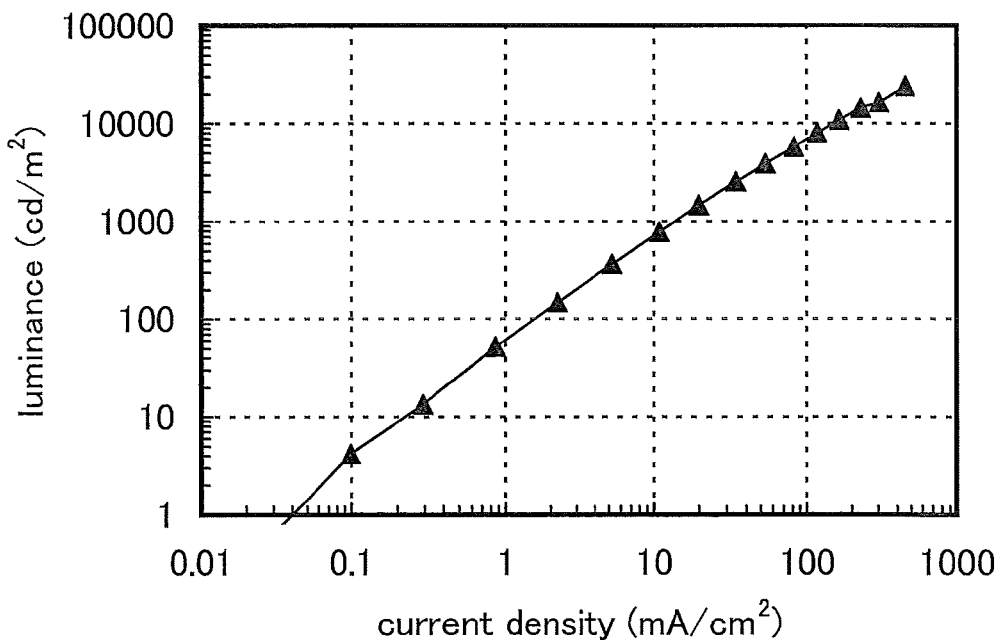
FIG. 110 shows luminance versus current density characteristics of a light-emitting element 14.
Figure 111:
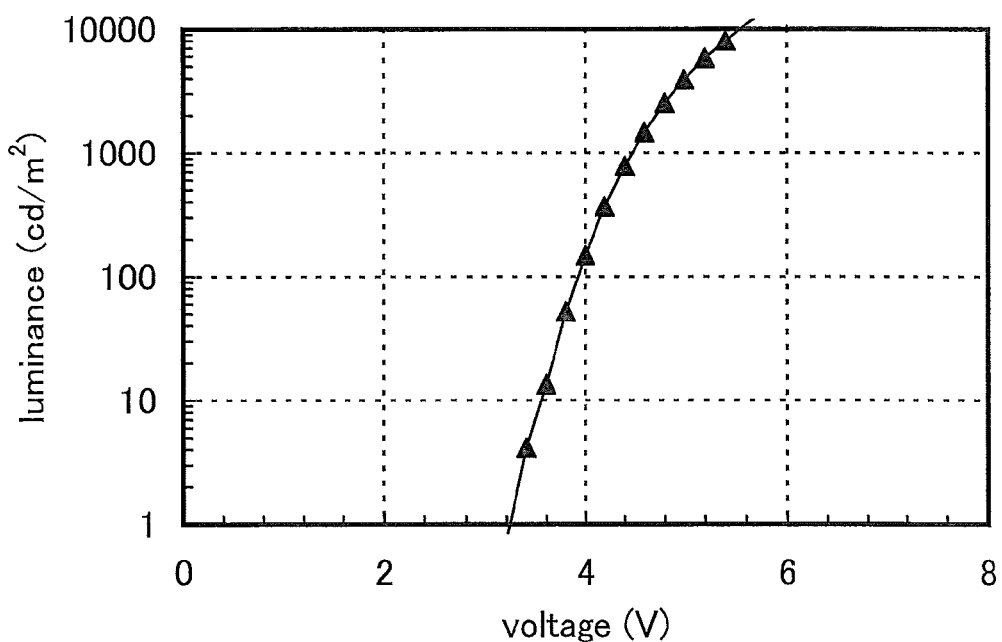
FIG. 111 shows luminance versus voltage characteristics of the light-emitting element 14.
Figure 112:
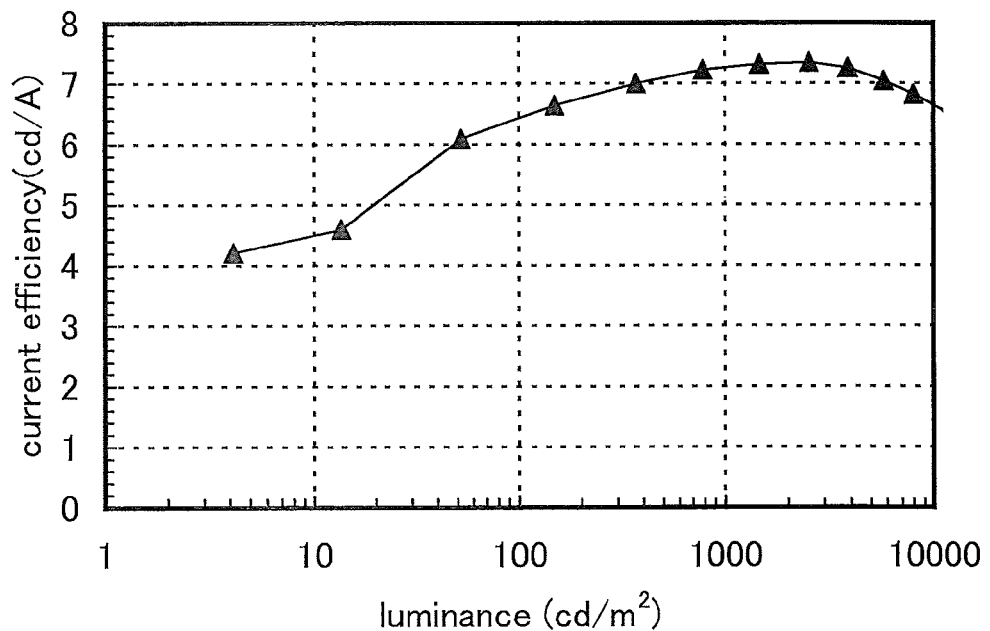
FIG. 112 shows current efficiency versus luminance characteristics of the light-emitting element 14.
Figure 113:
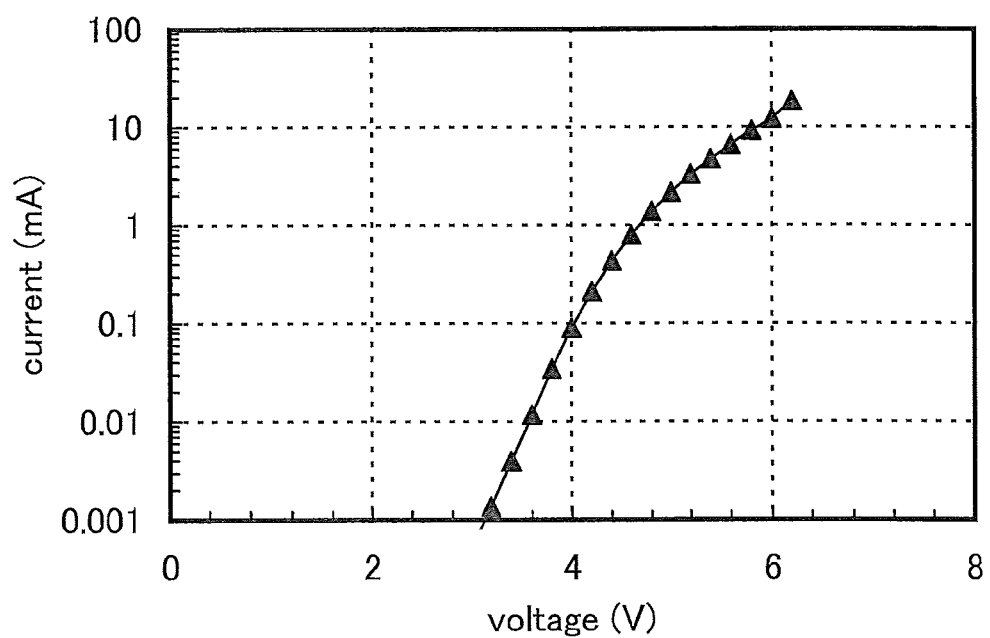
FIG. 113 shows current versus voltage characteristics of the light-emitting element 14.

FIG. 110 shows luminance current density characteristics of the light-emitting element 14, FIG. 111 shows luminance versus voltage characteristics thereof, FIG. 112 shows current efficiency versus luminance characteristics thereof, and FIG. 113 shows current versus voltage characteristics thereof. In FIG. 110, the vertical axis represents luminance (cd/m²), and the horizontal axis represents current density (mA/cm²). In FIG. 111, the vertical axis represents luminance (cd/m²), and the horizontal axis represents voltage (V). In FIG. 112, the vertical axis represents current efficiency (cd/A), and the horizontal axis represents luminance (cd/m²). In FIG. 113, the vertical axis represents current (mA), and the horizontal axis represents voltage (V).

FIG. 112 reveals that the light-emitting elements in each of which the carbazole derivative represented by the general formula (G1) is used as a host material of a light-emitting layer for emitting blue fluorescence, has favorable luminance versus emission efficiency characteristics and high emission efficiency. This is because each carbazole derivative represented by the general formula (G1) has a wide energy gap, and thus even a light-emitting substance that emits blue fluorescence and has a wide energy gap can be efficiently excited. In addition, FIG. 110 reveals that the light-emitting elements in each of which the carbazole derivative represented by the general formula (G1) is used as a host material of a light-emitting layer for emitting blue fluorescence, has favorable luminance versus voltage characteristics and can be driven with a low voltage. This indicates that each carbazole derivative represented by the general formula (G1) has an excellent carrier-transport property.

Figure 114:
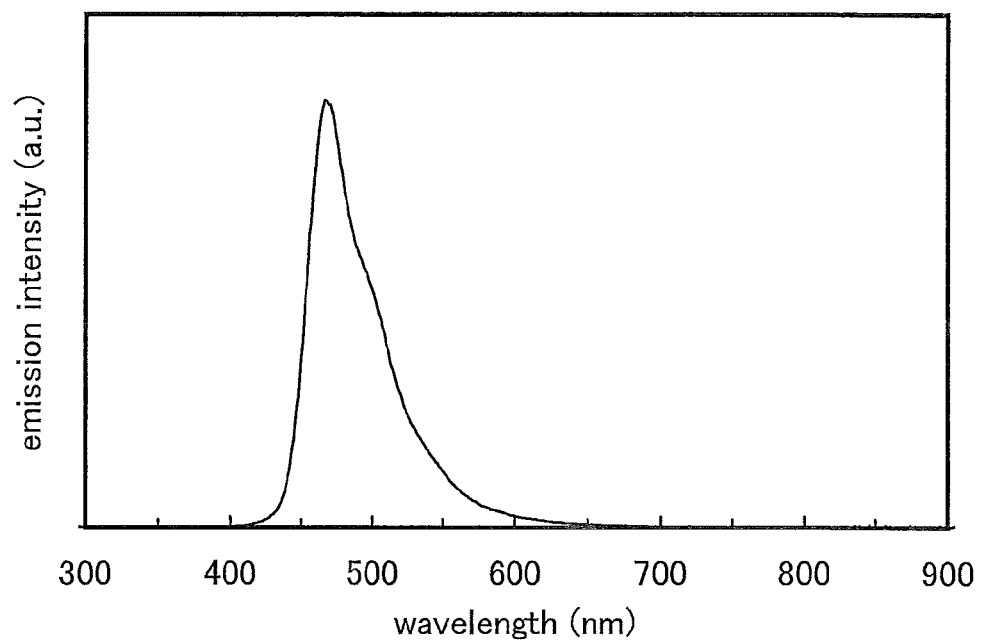
FIG. 114 shows an emission spectrum of the light-emitting element 14.

FIG. 114 shows an emission spectrum when a current of 1 mA was made to flow in the fabricated light-emitting element 14. The emission intensity is shown as a value relative to the greatest emission intensity assumed to be 1. FIG. 114 reveals that the light-emitting element 14 emits blue light due to 1,6FLPAPrn, which is the emission center substance.

Figure 115:
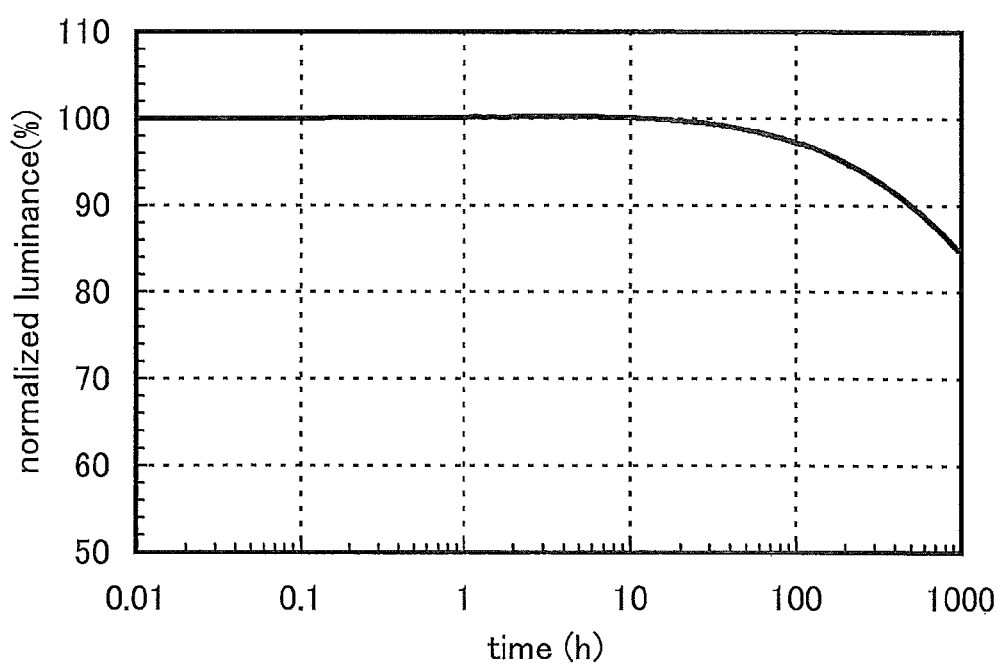
FIG. 115 shows normalized luminance versus time characteristics of the light-emitting element 14.

Next, the initial luminance is set at 5000 cd/m², the element was driven under a condition where the current density was constant, and changes in luminance with respect to the driving time were examined. FIG. 115 shows normalized luminance versus time characteristics. From FIG. 115, it is found that the light-emitting element 14 shows favorable characteristics and has high reliability.

Example 23

Synthesis Example 13

In this example is described a method of synthesizing 3-(6-phenyldibenzothiophen-4-yl)-9-[4-(10-phenyl-9-anthryl)phenyl]-9H-carbazole (abbreviation: DBTCzPA-IV), which is one of the carbazole derivatives described as the structural formula (15) in Embodiment 1. A structure of DBTCzPA-IV is illustrated in the following structural formula.

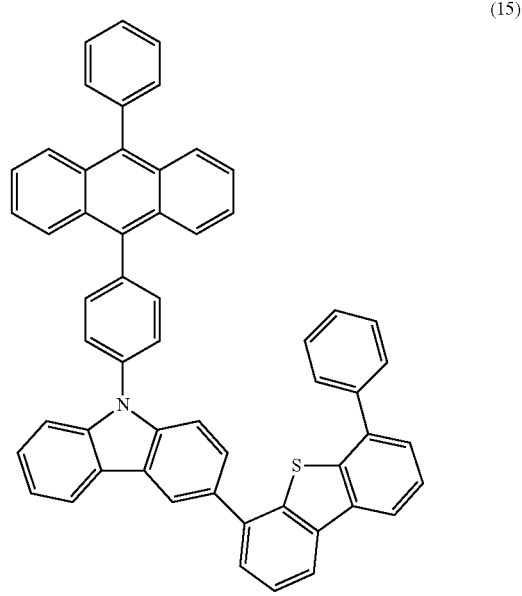 [SMILES: c1ccc(-c2c3ccccc3c(-c3ccc(-n4c5ccccc5c5cc(-c6cccc7c6sc6c(-c8ccccc8)cccc67)ccc54)cc3)c3ccccc23)cc1]

(15)

Step 1: Synthesis of 3-(6-Phenyldibenzothiophen-4-yl)-9H-carbazole (abbreviation: DBTCz-IV)

In a 50-mL three-neck flask were put 1.0 g (4.1 mmol) of 3-bromocarbazole, 1.2 g (4.1 mmol) of 6-phenyl-4-dibenzothienylboronic acid, and 62 mg (0.20 mmol) of tris(2-methylphenyl)phosphine. To this mixture were added 15 mL of toluene, 5 mL of ethanol, and 5 mL of a 2.0M aqueous sodium carbonate solution. This mixture was degassed by being stirred while the pressure was reduced. To this mixture was added 9 mg (0.041 mmol) of palladium(II) acetate, and the mixture was stirred at 80° C. for 3 hours under a nitrogen stream. After the stirring, the aqueous layer of this mixture was subjected to, extraction with toluene, and the solution of the extract and the organic layer were combined and washed with saturated brine. The organic layer was dried over magnesium sulfate. This mixture was separated by gravity filtration, and the filtrate was concentrated to give a solid. This solid was purified by silica gel column chromatography (a developing solvent in which the toluene/hexane ratio was 1:2 and then a developing solvent in which the toluene/hexane ratio was 3:2). Addition of ethyl acetate/hexane to the obtained solid was followed by irradiation with ultrasonic waves, and the solid was collected by suction filtration, so that 1.0 g of a white solid which was the object of the synthesis in 59% yield. The synthesis scheme of Step 1 is illustrated in (a-13).

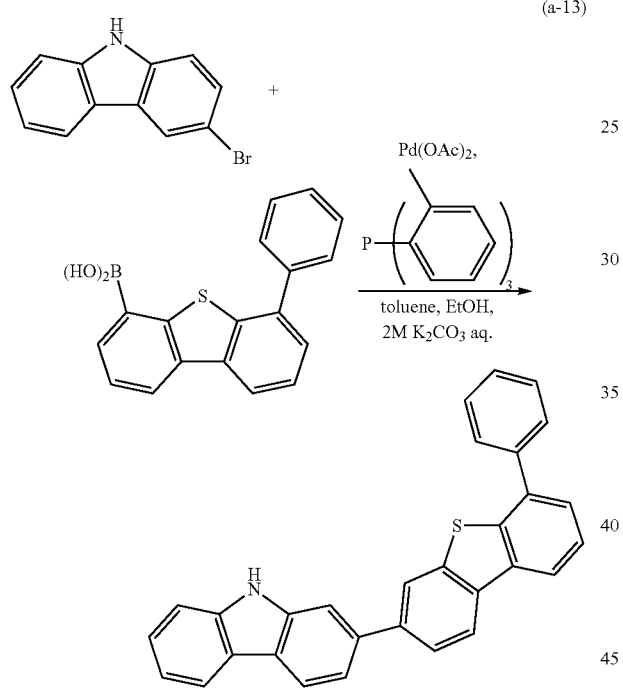

(a-13)

The obtained white solid was subjected to nuclear magnetic resonance (NMR) spectroscopy. The measurement data are shown below.

$^1$H NMR (CDCl$_3$, 300 M Hz): δ=7.34-7.55 (m, 7H), 7.56 (d, J$_1$=4.2 Hz, 1H), 7.58-7.64 (m, 3H), 7.68-7.72 (m, 2H), 7.78 (dd, J$_1$=1.8 Hz, J$_2$=8.4 Hz, 1H), 8.10 (dd, J$_1$=0.90 Hz, J$_2$=1.8 Hz, 1H), 8.15 (s, 1H), 8.19-8.23 (m, 2H), 8.36 (d, J$_1$=1.5 Hz, 1H)

Step 2: Synthesis of 3-(6-Phenyldibenzothiophen-4-yl)-9-[4-(10-phenyl-9-anthryl)phenyl]-9H-carbazole (abbreviation: DBTCzPA-IV)

In a 50-mL three-neck flask were put 1.3 g (3.3 mmol) of 9-(4-bromophenyl)-10-phenylanthracene, 1.0 g (2.4 mmol) of 3-(6-phenyldibenzothiophen-4-yl)-9H-carbazole, and 0.95 g (9.9 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 11 mg (0.18 mmol) of bis(dibenzylideneacetone)palladium (0) was added to this mixture. This mixture was stirred at 110° C. for 6 hours under a nitrogen stream. After the stirring, the aqueous layer of this mixture was subjected to extraction with toluene, and the solution of the extract and the organic layer were combined and washed with saturated brine. The organic layer was dried over magnesium sulfate. This mixture was gravity-filtered, and the filtrate was concentrated to give a solid. The obtained solid was purified by silica gel column chromatography (a developing solvent in which the toluene/hexane ratio was 1:9 and then a developing solvent in which the toluene/hexane ratio was 3:7). The obtained solid was recrystallized from toluene/hexane to give 1.4 g of a pale yellow solid which was the object of the synthesis in a yield of 80%. The synthesis scheme of Step 2 is illustrated in (b-13).

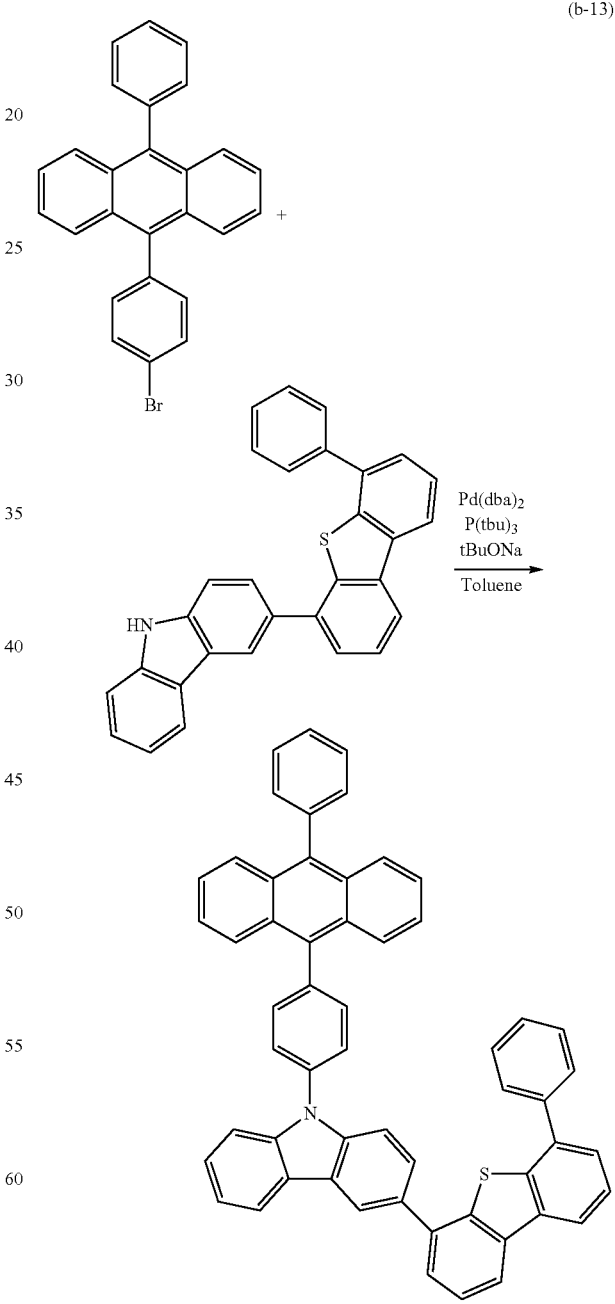

(b-13)

By a train sublimation method, 1.4 g of the obtained pale yellow solid was purified. The purification was conducted by heating of the pale yellow solid at 360° C. under a pressure of 2.9 Pa with a flow rate of argon gas of 5 mL/min. After the purification, 1.2 g of a pale yellow solid was obtained in a yield of 86%.

The pale yellow solid after the above purification was subjected to nuclear magnetic resonance (NMR) spectroscopy. The measurement data are shown below.

$^1$H NMR (CDCl$_3$, 300 MHz): δ=7.34-7.49 (m, 9H), 7.51-7.54 (m, 3H), 7.57 (t, J$_1$=1.5 Hz, 1H), 7.59-7.66 (m, 5H), 7.67-7.80 (m, 8H), 7.84-7.90 (m, 5H), 8.22-8.25 (m, 3H), 8.49 (d, J$_1$=1.5 Hz, 1H).

Figure 116A:
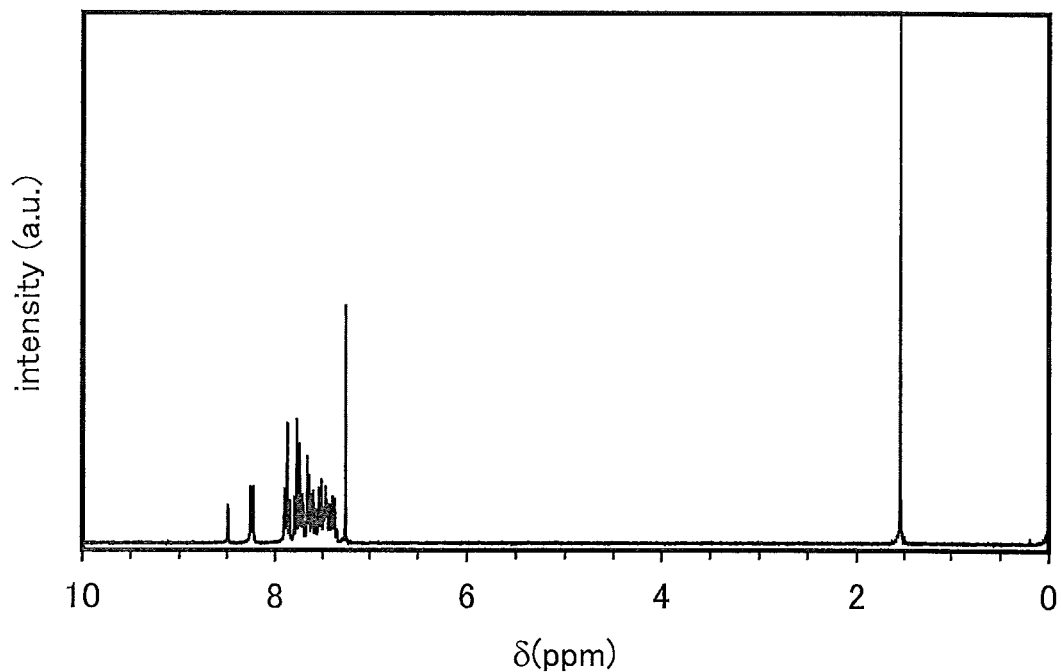
FIGS. 116A and 116B are NMR charts of DBTCzPA-IV.
Figure 116B:
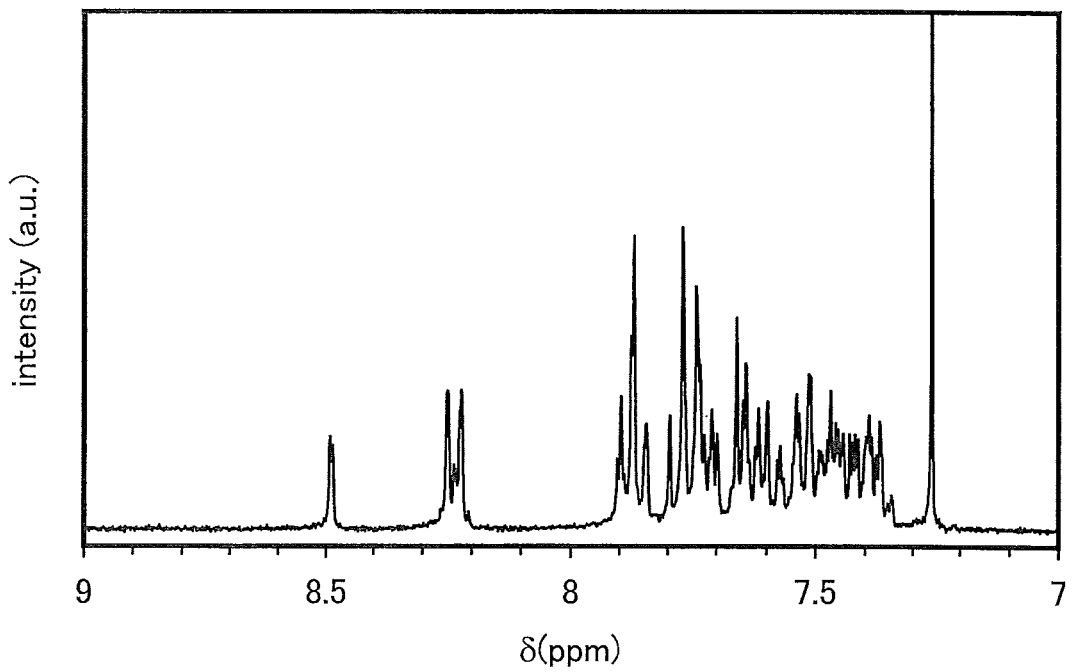

In addition, $^1$H NMR charts are shown in FIGS. 116A and 116B. Note that FIG. 116B is a chart where the range of from 7 ppm to 9 ppm in FIG. 116A is enlarged. The measurement results showed that DBTCzPA-IV, which is the carbazole derivative represented by the above structural formula, was obtained.

Figure 117A:
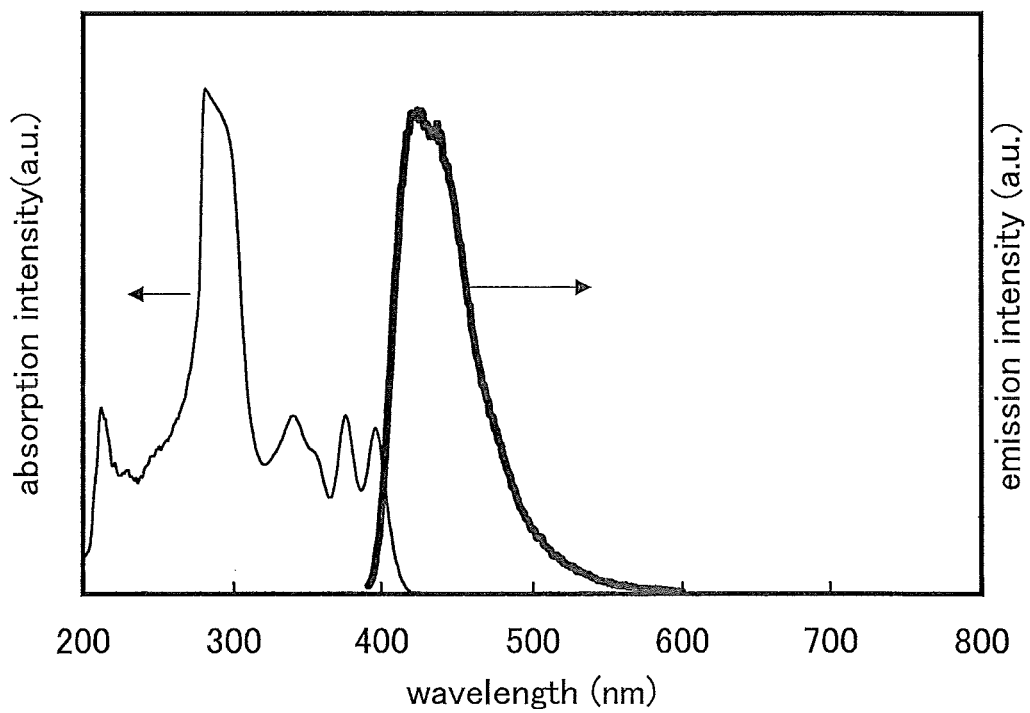
FIGS. 117A and 117B show an absorption and emission spectra of DBTCzPA-IV.
Figure 117B:
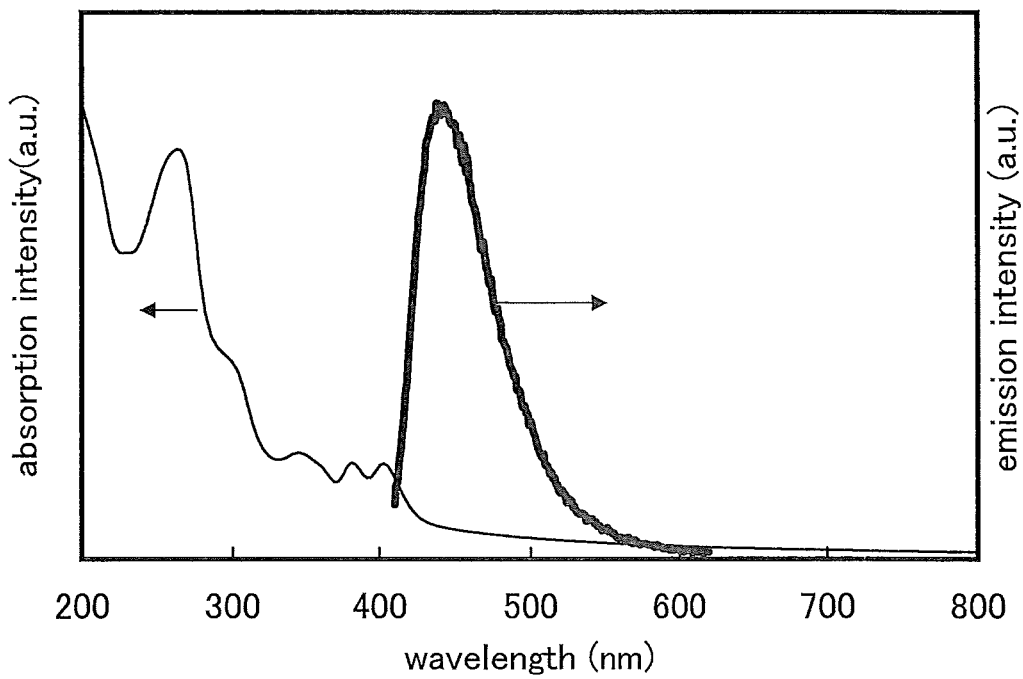

Further, an absorption and emission spectra of DBTCzPA-IV in a toluene solution of DBTCzPA-IV are shown in FIG. 117A, and an absorption and emission spectra of a thin film of DBTCzPA-IV are shown in FIG. 117B. An ultraviolet-visible spectrophotometer (V-550, manufactured by JASCO Corporation) was used for the measurements of the absorption spectra. In the case of the toluene solution, the measurements were made with the toluene solution of DBTCzPA-IV put in a quartz cell, and the absorption spectrum obtained by subtraction of the absorption spectra of the quartz cell and toluene from the measured spectra is shown in the drawing. In addition, as for the absorption spectrum of the thin film, a sample was prepared by evaporation of DBTCzPA-IV on a quartz substrate, and the absorption spectrum obtained by subtraction of that of quartz from the spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum was measured with the toluene solution of DBTCzPA-IV put in a quartz cell, and the emission spectrum of the thin film was measured with a sample prepared by evaporation of DBTCzPA-IV on a quartz substrate. Thus, it was found that the absorption peak wavelengths of DBTCzPA-IV in the toluene solution of DBTCzPA-IV were around 396 nm, 376 nm, 340 nm, and 281 nm and the emission peak wavelengths thereof were around 423 nm and 437 nm (at an excitation wavelength of 376 nm), and that the absorption peak wavelengths of the thin film of DBTCzPA-IV were around 403 nm, 382 nm, 356 nm, 345 nm, 296 nm, and 264 nm and the greatest emission wavelength thereof was around 443 nm (at an excitation wavelength of 403 nm).

Further, the ionization potential of DBTCzPA-IV in a thin film state was measured by a photoelectron spectrometer (AC-2, manufactured by Riken Keiki, Co., Ltd.) in air. The obtained value of the ionization potential was converted to a negative value, so that the HOMO level of DBTCzPA-IV was −5.80 eV. From the data of the absorption spectra of the thin film in FIG. 117B, the absorption edge of DBTCzPA-IV, which was obtained from Tauc plot with an assumption of direct transition, was 2.93 eV. Therefore, the optical energy gap of DBTCzPA-IV in the solid state was estimated at 2.93 eV; from the values of the HOMO level obtained above and this energy gap, the LUMO level of DBTCzPA-IV was able to be estimated at −2.87 eV. It was thus found that DBTCzPA-IV had a wide energy gap of 2.93 eV in the solid state.

Further, the oxidation reaction characteristics of DBTCzPA-IV were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.02 V to 0.93 V and then changed from 0.93 V to −0.02 V was one cycle, and 100 cycles were performed.

The measurement results revealed that DBTCzPA-IV showed properties effective against repetition of redox reactions between an oxidized state and a neutral state without a large variation in oxidation peak even after the 100 cycles in the measurements.

Further, the HOMO level of DBTCzPA-IV was determined also by calculation from the CV measurement results.

First, the potential energy of the reference electrode with respect to the vacuum level used was found to be −4.94 eV, as determined in Example 6. The oxidation peak potential $E_{pa}$ of DBTCzPA-IV was 0.89 V. In addition, the reduction peak potential $E_{pc}$ thereof was 0.79 V. Therefore, a half-wave potential (an intermediate potential between $E_{pa}$ and $E_{pc}$) can be calculated at 0.84 V. This means that DBTCzPA-IV is oxidized by an electric energy of 0.84 [V versus Ag/Ag$^+$], and this energy corresponds to the HOMO level. Here, since the potential energy of the reference electrode, which was used in this example, with respect to the vacuum level is −4.94 [eV] as described above, the HOMO level of DBTCzPA-IV was calculated as follows: −4.94−0.84=−5.78.

Example 24

In this example described is a light-emitting element in which 3-(6-phenyldibenzothiophen-4-yl)-9-[4-(10-phenyl-9-anthryl)phenyl]-9H-carbazole (abbreviation: DBTCzPA-IV, a structural formula (15)), which is one of the carbazole derivatives represented by the general formula (G1), is used as a host material such that an emission center substance that emits blue fluorescence is dispersed therein.

The molecular structures of organic compounds used in this example are represented by the structural formulae (15), (iv), and (iv) below.

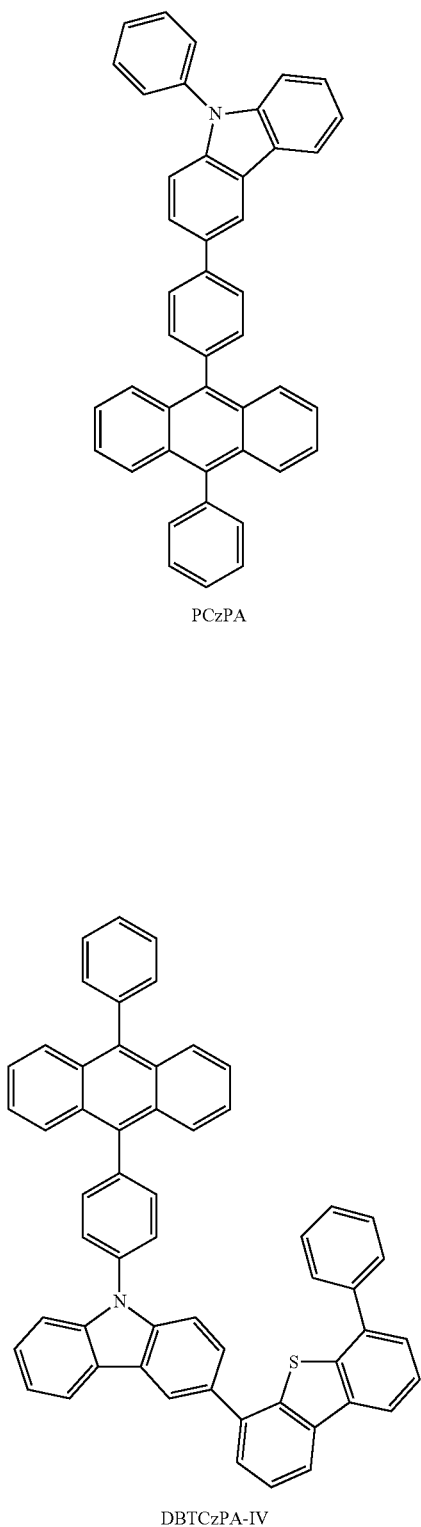

PCzPA (15)

DBTCzPA-IV

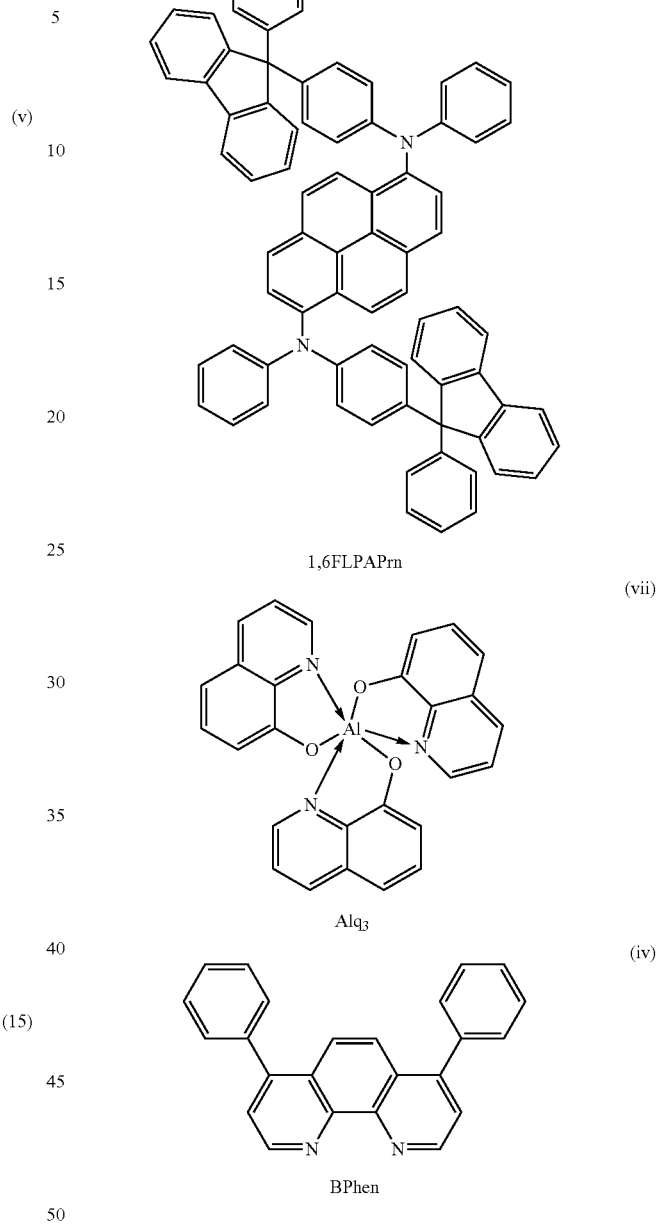

1,6FLPAPrn

Alq₃

BPhen

In the element structure in FIG. 1A, an electron-injection layer is provided between an electron-transport layer 114 and a second electrode 104.

[Fabrication of Light-Emitting Element 15]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 9-[4-(9-phenylcarbazol-3-yl)]phenyl-10-phenylanthracene (abbreviation: PCzPA) represented by the above structural formula (v) and molybdenum(VI) oxide such that the ratio of PCzPA:molybdenum(VI) oxide was 2:1 (weight ratio). The thickness of was the layer was set to 50 nm. Note that the co-evaporation is an evaporation method in which a plurality of different substances is concurrently vaporized from the respective different evaporation sources.

Next, PCzPA was evaporated to a thickness of 10 nm, so that the hole-transport layer 112 was formed.

Further, the light-emitting layer 113 was formed red on the hole-transport layer 112 in such a way that 3-(6-phenyldibenzothiophen-4-yl)-9-[4-(10-phenyl-9-anthryl)phenyl]-9H-carbazole (abbreviation: DBTCzPA-IV) represented by the above structural formula (15) and N,N'-bis[4-(9-phenyl-9H-fluoren-9-yl)phenyl]-N,N'-diphenyl-pyrene-1,6-diamine (abbreviation: 1,6FLPAPrn) represented by the structural formula (vi) were evaporated to form a 30-nm-thick film so that the ratio of DBTCzPA-IV to 1,6FLPAPrn was 1:0.03 (weight ratio).

Next, on the light-emitting layer 113, tris(8-quinolinolato) aluminum(III) (abbreviation: Alq) represented by the above structural formula (vii) was evaporated to a thickness of 10 nm, and then bathophenanthroline (abbreviation: BPhen) represented by the above structural formula (iv) was evaporated to a thickness of 15 nm, so that the electron-transport layer 114 was formed. Then, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 15 was completed. Note that in the above evaporation processes, evaporation was all performed by a resistance heating method.

[Operation Characteristics of Light-Emitting Element 15]

The light-emitting element 15 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 118:
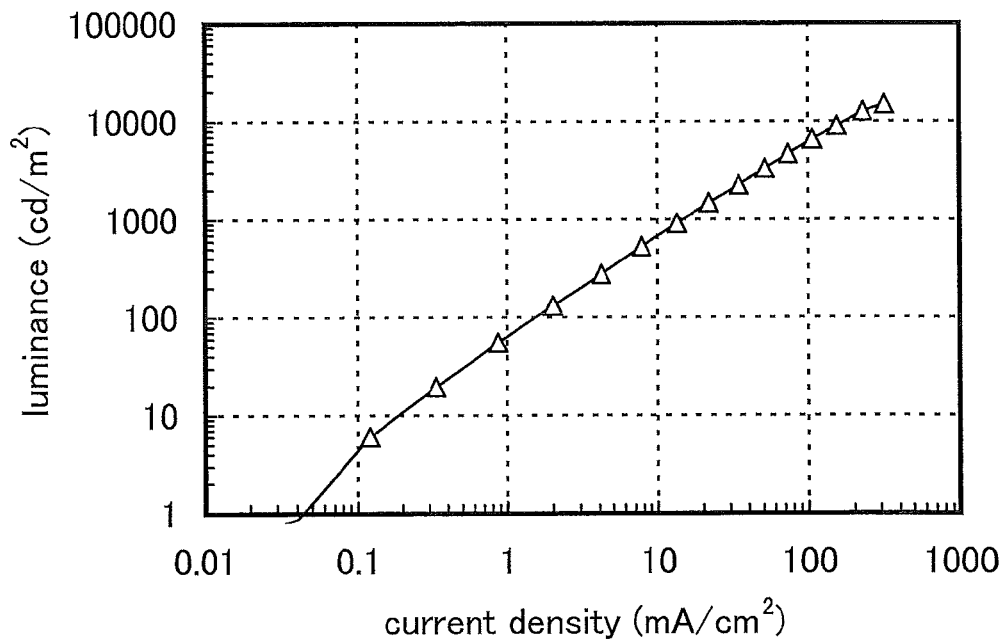
FIG. 118 shows luminance versus current density characteristics of a light-emitting element 15.
Figure 119:
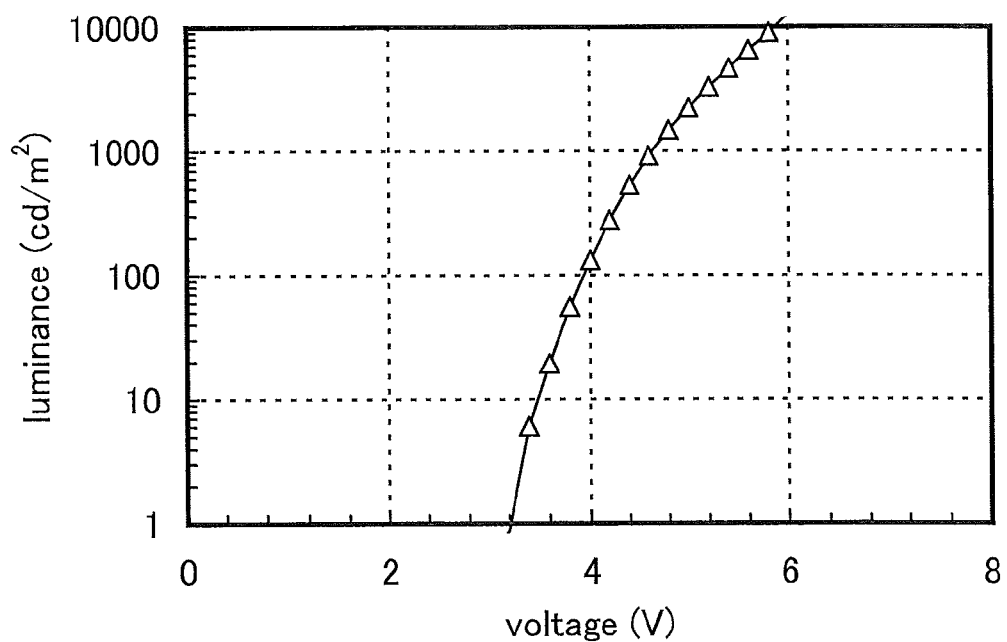
FIG. 119 shows luminance versus voltage characteristics of the light-emitting element 15.
Figure 120:
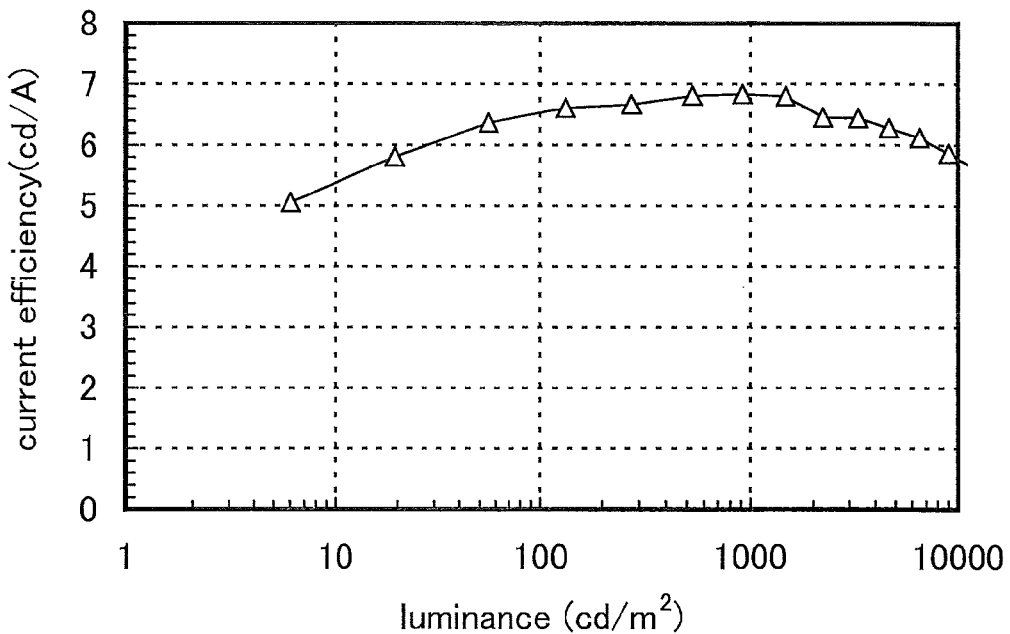
FIG. 120 shows current efficiency versus luminance characteristics of the light-emitting element 15.
Figure 121:
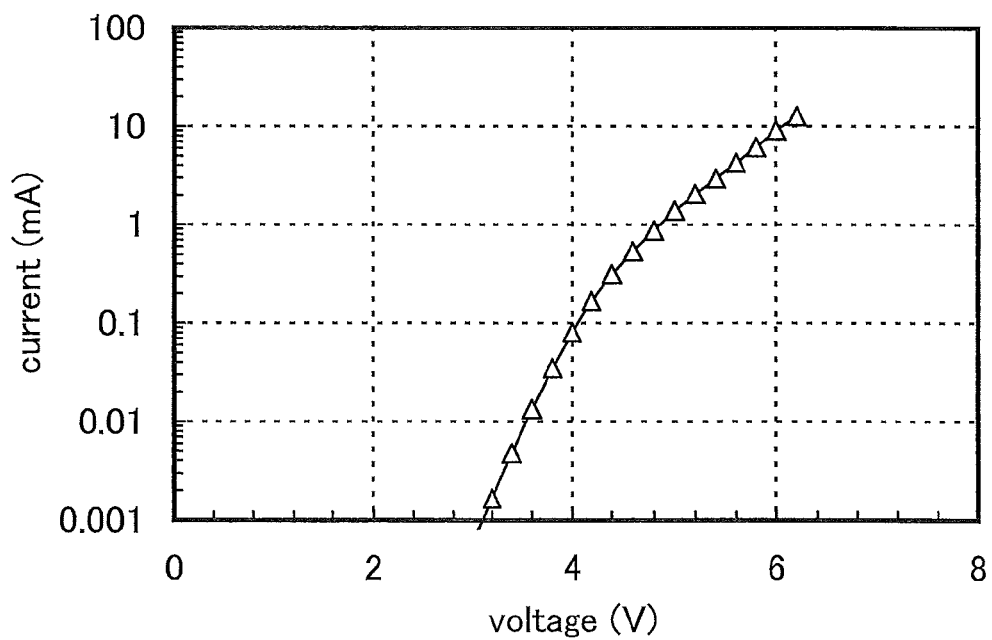
FIG. 121 shows current versus voltage characteristics of the light-emitting element 15.

FIG. 118 shows luminance current density characteristics of the light-emitting element 15, FIG. 119 shows luminance versus voltage characteristics thereof, FIG. 120 shows current efficiency versus luminance characteristics thereof, and FIG. 121 shows current versus voltage characteristics thereof. In FIG. 118, the vertical axis represents luminance (cd/m$^2$), and the horizontal axis represents current density (mA/cm$^2$). In FIG. 119, the vertical axis represents luminance (cd/m$^2$), and the horizontal axis represents voltage (V). In FIG. 120, the vertical axis represents current efficiency (cd/A), and the horizontal axis represents luminance (cd/m$^2$). In FIG. 121, the vertical axis represents current (mA), and the horizontal axis represents voltage (V).

FIG. 120 reveals that the light-emitting elements in each of which the carbazole derivative represented by the general formula (G1) is used as a host material of a light-emitting layer for emitting blue fluorescence, has favorable current efficiency versus luminance characteristics and high emission efficiency. This is because each carbazole derivative represented by the general formula (G1) has a wide energy gap, and thus even a light-emitting substance that emits blue fluorescence and has a wide energy gap can be efficiently excited. In addition, FIG. 119 reveals that the light-emitting elements in each of which the carbazole derivative represented by the general formula (G1) is used as a host material of a light-emitting layer for emitting blue fluorescence, has favorable luminance versus voltage characteristics and can be driven with a low voltage. This indicates that each carbazole derivative represented by the general formula (G1) has an excellent carrier-transport property.

Figure 122:
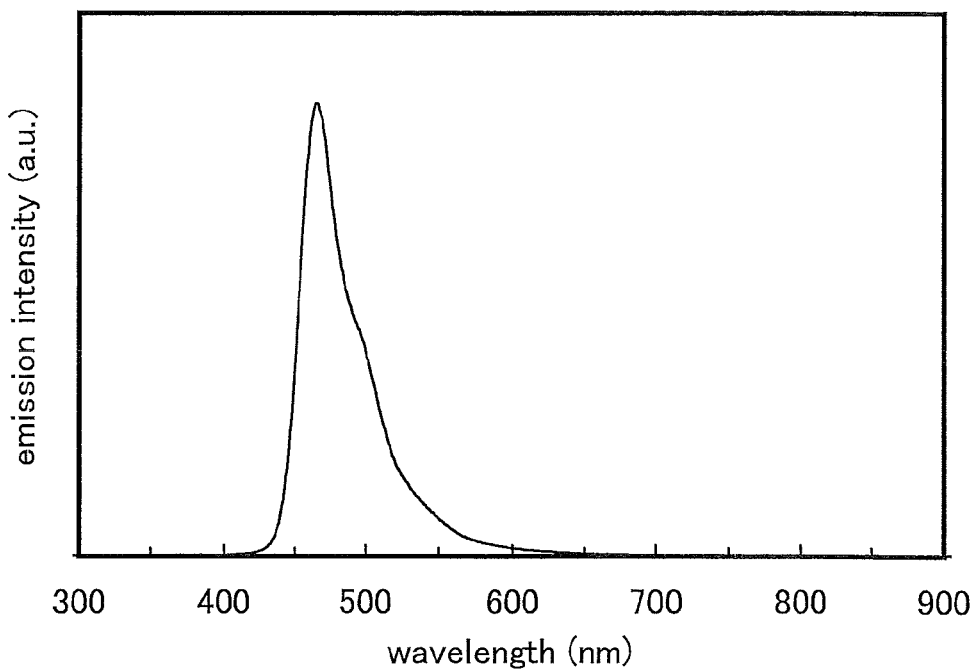
FIG. 122 shows an emission spectrum of the light-emitting element 15.

FIG. 122 shows an emission spectrum when a current of 1 mA was made to flow in the fabricated light-emitting element 15. The emission intensity is shown as a value relative to the greatest emission intensity assumed to be 1. FIG. 122 reveals that the light-emitting element 15 emits blue light due to 1,6FLPAPrn, which is the emission center substance.

Figure 123:
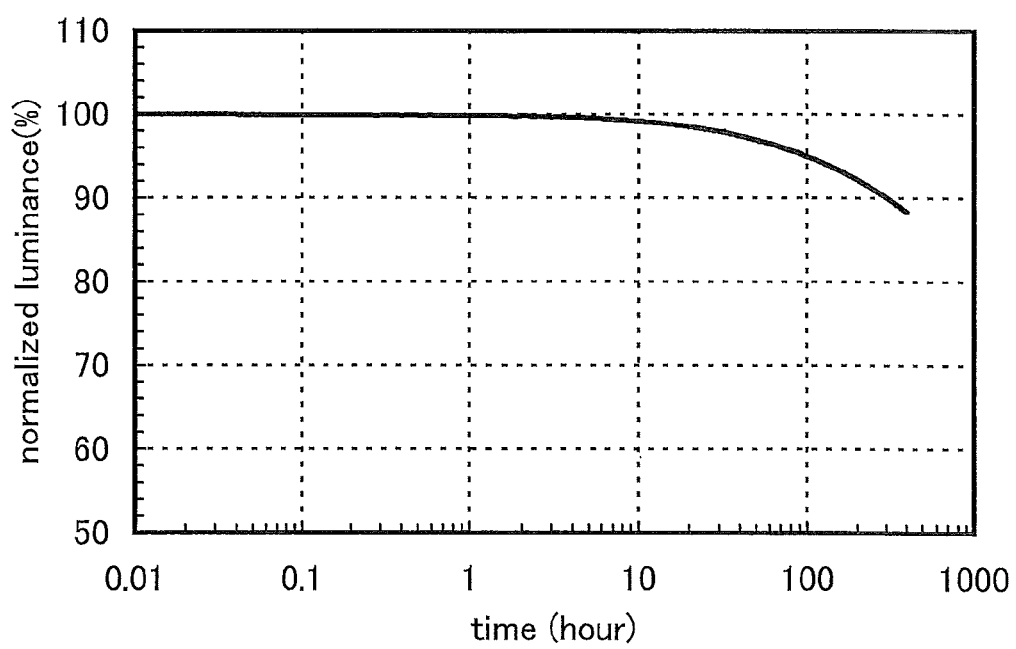
FIG. 123 shows normalized luminance versus time characteristics of the light-emitting element 15.

Next, the initial luminance is set at 5000 cd/m$^2$, the element was driven under a condition where the current density was constant, and changes in luminance with respect to the driving time were examined. FIG. 123 shows normalized luminance versus time characteristics. From FIG. 123, it is found that the light-emitting element 15 shows favorable characteristics and has high reliability.

Example 25

Synthesis Example 14

In this example is described a method of synthesizing 3-(dibenzothiophen-4-yl)-9-[4-(9,10-diphenyl-2-anthryl)phenyl]-9H-carbazole (abbreviation: 2DBTCzPPA-II), which is one of the carbazole derivatives described as the structural formula (16) in Embodiment 1. A structure of 2DBTCzPPA-II is illustrated in the following structural formula.

(16)

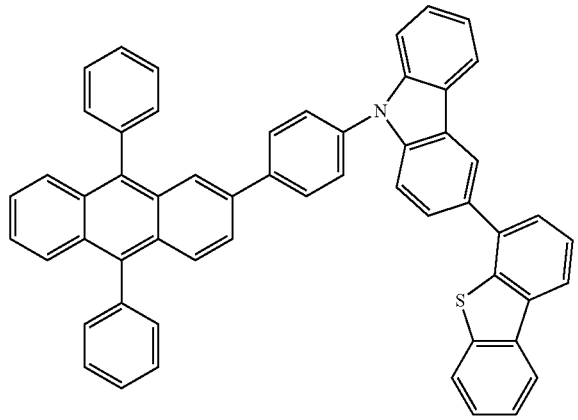

Step 1: Synthesis of
3-(Dibenzothiophen-4-yl)-9H-carbazole
(abbreviation: DBTCz-II)

This was synthesized as in Step 1 in Synthesis Example 1.

Step 2: Synthesis of 3-(Dibenzothiophen-4-yl)-9-[4-(9,10-diphenyl-2-anthryl)phenyl]-9H-carbazole (abbreviation: 2DBTCzPPA-II)

In a 50-mL three-neck flask were put 1.3 g (2.7 mmol) of 2-(4-bromophenyl)-9,10-diphenylanthracene, 0.93 g (2.7 mmol) of 3-(dibenzothiophen-4-yl)-9H-carbazole, and 0.76 g (8.0 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 76 mg (0.13 mmol) of bis(dibenzylideneacetone)palladium(0) was added to this mixture. This mixture was stirred at 110° C. for 4 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135), and the filtrate was concentrated to give a solid. The obtained solid was purified by silica gel column chromatography (a developing solvent in which the hexane/toluene ratio was 5:1). A suspension was formed by addition of toluene/hexane to the obtained solid, and the suspension was irradiated with ultrasonic wave. Then, a solid was collected by suction filtration, so that 1.2 g of a yellow solid which was the object of the synthesis was obtained in a yield of 61%. The synthesis scheme of Step 2 is illustrated in (b-14).

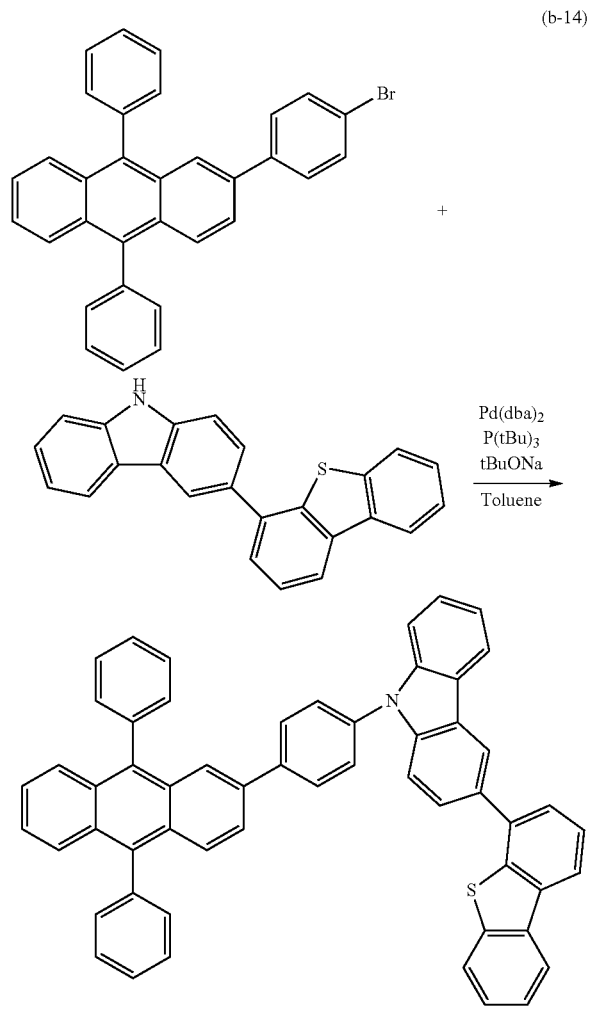

(b-14)

By a train sublimation method, the obtained yellow solid was purified. The purification was conducted by heating of 1.2 g of the yellow solid at 335° C. under a pressure of 2.6 Pa with a flow rate of argon gas of 5 mL/min. After the purification, 1.01 g of a yellow solid was obtained in a yield of 83%.

The yellow solid after the above purification was subjected to nuclear magnetic resonance (NMR) spectroscopy. The measurement data are shown below.

$^1$H NMR (CDCl$_3$, 300 MHz): δ=7.29-7.39 (m, 3H), 7.41-7.51 (m, 4H), 7.52-7.75 (m, 18H), 7.78-7.88 (m, 5H), 8.03 (d, J$_1$=1.5 Hz, 1H), 8.15-8.23 (m, 3H), 8.51 (d, J$_1$=0.90 Hz, 1H).

Figure 124A:
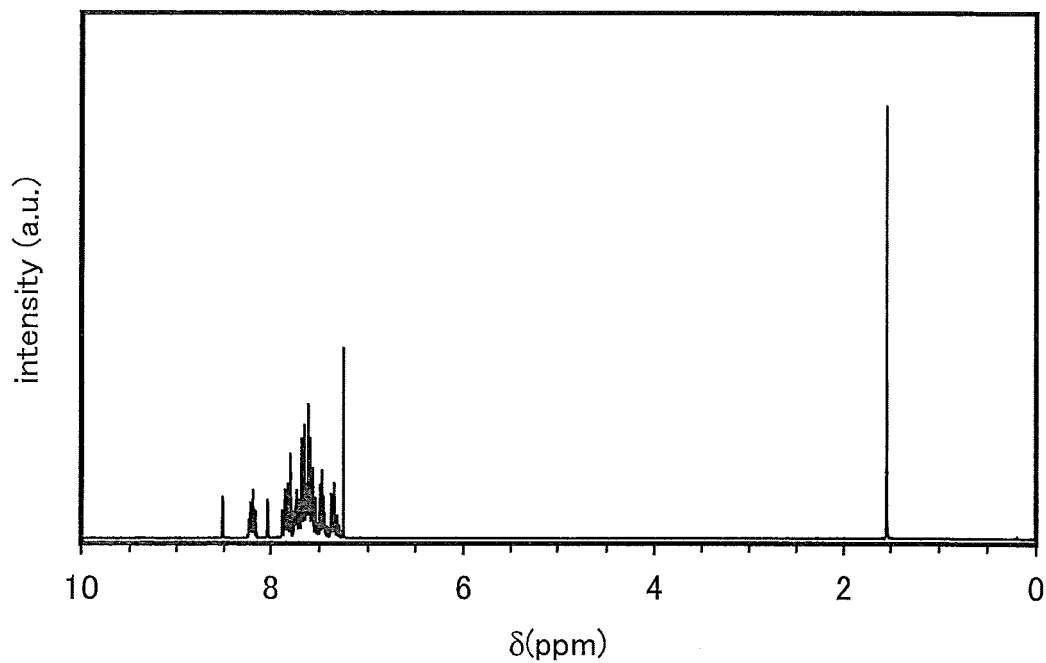
FIGS. 124A and 124B are NMR charts of 2DBTCzPPA-II.
Figure 124B:
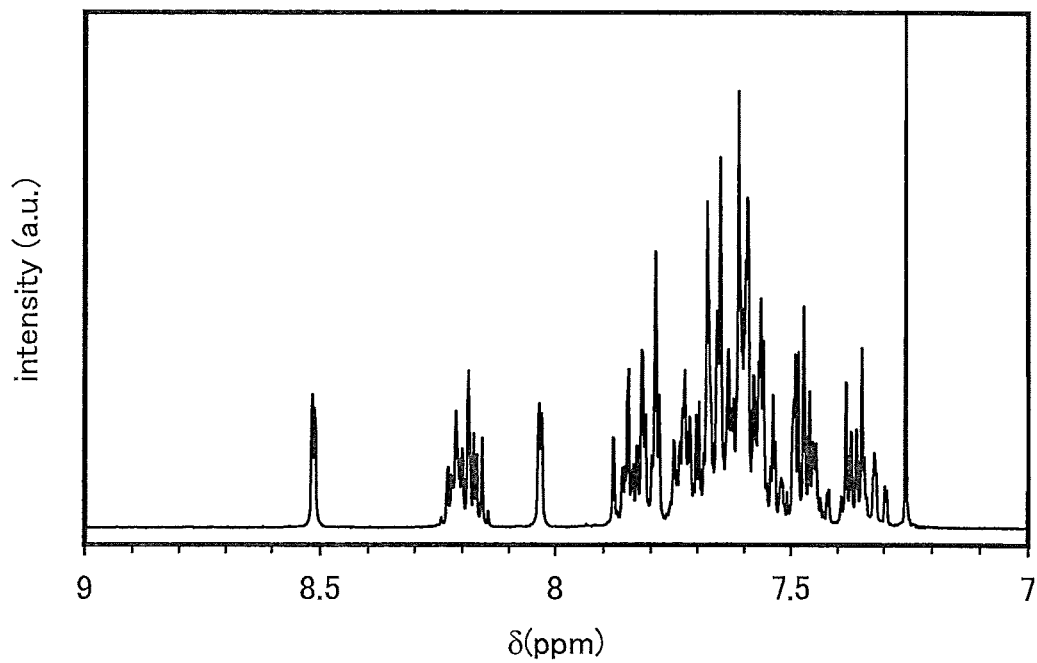

In addition, $^1$H NMR charts are shown in FIGS. 124A and 124B. Note that FIG. 124B is a chart where the range of from 7 ppm to 9 ppm in FIG. 124A is enlarged. The measurement results showed that 2DBTCzPPA-II, which is the carbazole derivative represented by the above structural formula, was obtained.

Figure 125A:
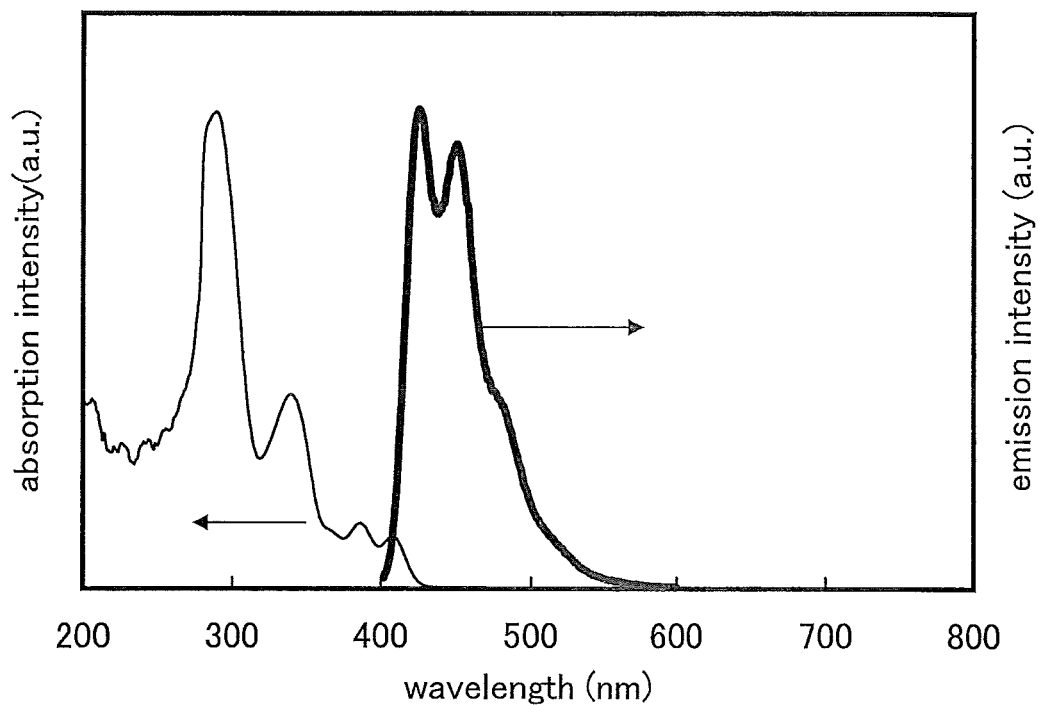
FIGS. 125A and 125B show an absorption and emission spectra of 2DBTCzPPA-II.
Figure 125B:
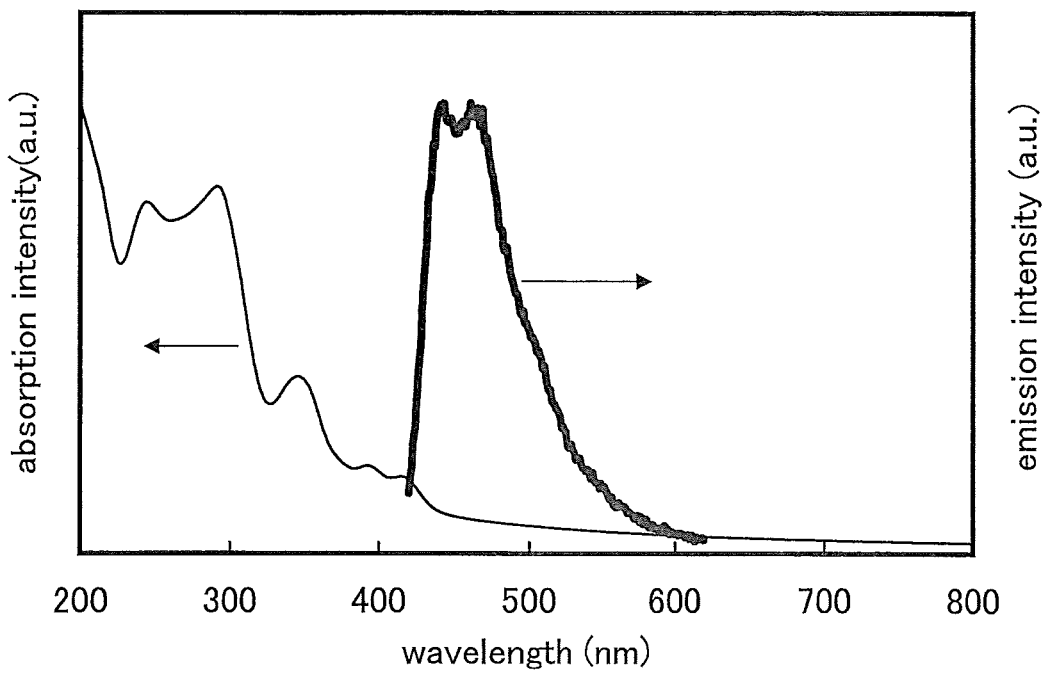

Further, an absorption and emission spectra of 2DBTCz-PPA-II in a toluene solution of 2DBTCzPPA-II are shown in FIG. 125A, and an absorption and emission spectra of a thin, film of 2DBTCzPPA-II are shown in FIG. 125B. An ultraviolet-visible spectrophotometer (V-550, manufactured by JASCO Corporation) was used for the measurements of the absorption spectra. In the case of the toluene solution, the measurements were made with the toluene solution of 2DBTCzPPA-II put in a quartz cell, and the absorption spectrum obtained by subtraction of the absorption spectra of the quartz cell and toluene from the measured spectra is shown in the drawing. In addition, as for the absorption spectrum of the thin film, a sample was prepared by evaporation of 2DBTC-zPPA-II on a quartz substrate, and the absorption spectrum obtained by subtraction of that of quartz from the spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum was measured with the toluene solution of 2DBTCzPPA-II put in a quartz cell, and the emission spectrum of the thin film was measured with a sample prepared by evaporation of 2DBTCzPPA-II on a quartz substrate. Thus, it was found that the absorption peak wavelengths of 2DBTC-zPPA-II in the toluene solution of 2DBTCzPPA-II were around 404 nm, 382 nm, 336 nm, and 285 nm and the emission peak wavelengths thereof were around 483 nm, 452 nm, and 427 nm (at an excitation wavelength of 387 nm), and that the absorption peak wavelengths of the thin film of 2DBTC-zPPA-II were around 415 nm, 393 nm, 346 nm, 291 nm, and 244 nm and the emission peak wavelengths thereof were around 461 nm and 442 nm (at an excitation wavelength of 415 nm).

Further, the ionization potential of 2DBTCzPPA-II in a thin film state was measured by a photoelectron spectrometer (AC-2, manufactured by Riken Keiki, Co., Ltd.) in air. The obtained value of the ionization potential was converted to a negative value, so that the HOMO level of 2DBTCzPPA-II was −5.70 eV. From the data of the absorption spectra of the thin film in FIG. 125B, the absorption edge of 2DBTCzPPA-II, which was obtained from Tauc plot with an assumption of direct transition, was 2.81 eV. Therefore, the optical energy gap of 2DBTCzPPA-II in the solid state was estimated at 2.81 eV; from the values of the HOMO level obtained above and this energy gap, the LUMO level of 2DBTCzPPA-II was able to be estimated at −2.89 eV. It was thus found that 2DBTC-zPPA-II had a wide energy gap of 2.81 eV in the solid state.

Further, the oxidation reaction characteristics of 2DBTCzPPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.31 V to 0.92 V and then changed from 0.92 V to 0.31 V was one cycle, and 100 cycles were performed.

The measurement results revealed that 2DBTCzPPA-II showed properties effective against repetition of redox reactions between an oxidized state and a neutral state without a large variation in oxidation peak even after the 100 cycles in the measurements.

Further, the HOMO level of 2DBTCzPPA-II was determined also by calculation from the CV measurement results.

First, the potential energy of the reference electrode with respect to the vacuum level used was found to be −4.94 eV, as determined in Example 6. The oxidation peak potential E$_{pa}$ of 2DBTCzPPA-II was 0.88 V. In addition, the reduction peak potential E$_{pc}$ thereof was 0.80 V. Therefore, a half-wave potential (an intermediate potential between E$_{pa}$ and E$_{pc}$) can be calculated at 0.84 V. This means that 2DBTCzPPA-II is oxidized by an electric energy of 0.84 [V versus Ag/Ag$^+$], and this energy corresponds to the HOMO level. Here, since the potential energy of the reference electrode, which was used in this example, with respect to the vacuum level is −4.94 [eV] as described above, the HOMO level of 2DBTCzPPA-II was calculated as follows: −4.94−0.84=−5.78 [eV].

Example 26

In this example described is a light-emitting element in which 3-(dibenzothiophen-4-yl)-9-[4-(9,10-diphenyl-2-anthryl)phenyl]-9H-carbazole (abbreviation: 2DBTCzPPA-II, a structural formula (16)), which is one of the carbazole derivatives represented by the general formula (G1), is used as a host material such that an emission center substance that emits blue fluorescence is dispersed therein.

The molecular structures of organic compounds used in this example are represented by the structural formulae (16), (iv), and (iv) below.

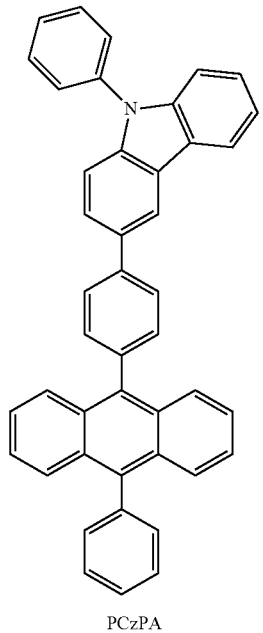

PCzPA (v)

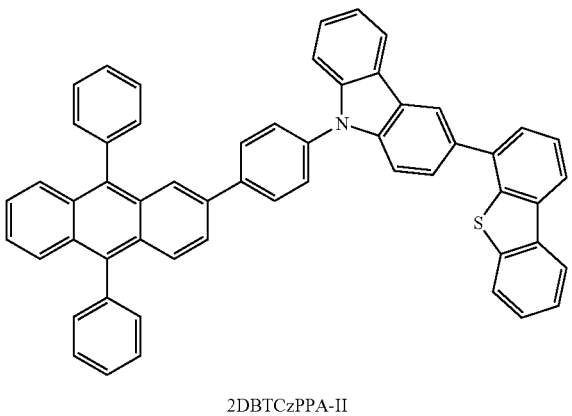

2DBTCzPPA-II (16)

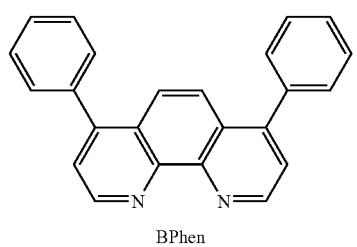

BPhen (iv)

-continued (vi)

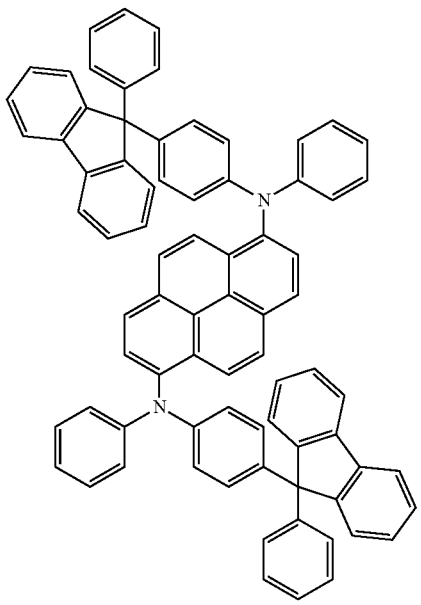

1,6FLPAPrn (vii)

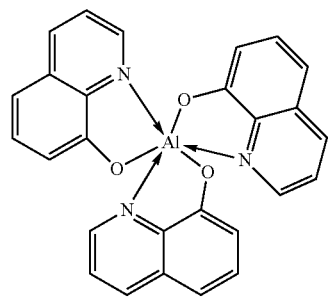

Alq₃

In the element structure in FIG. 1A, an electron-injection layer is provided between an electron-transport layer 114 and a second electrode 104.

[Fabrication of Light-Emitting Element 16]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 9-[4-(9-phenylcarbazol-3-yl)]phenyl-10-phenylanthracene (abbreviation: PCzPA) represented by the above structural formula (v) and molybdenum(VI) oxide such that the ratio of PCzPA:molybdenum(VI) oxide was 2:1 (weight ratio). The thickness of was the layer was set to 50 nm. Note that the co-evaporation is an evaporation method in which a plurality of different substances is concurrently vaporized from the respective different evaporation sources.

Next, PCzPA was evaporated to a thickness of 10 nm, so that the hole-transport layer 112 was formed.

Further, the light-emitting layer 113 was formed on the hole-transport layer 112 in such a way that 3-(dibenzothiophen-4-yl)-9-[4-(9,10-diphenyl-2-anthryl)phenyl]-9H-carbazole (abbreviation: 2DBTCzPPA-II) represented by the above structural formula (16) and N,N'-bis[4-(9-phenyl-9H-fluoren-9-yl)phenyl]-N,N'-diphenyl-pyrene-1,6-diamine (abbreviation: 1,6FLPAPrn) represented by the structural formula (vi) were evaporated to form a 30-nm-thick film so that the ratio of 2DBTCzPPA-II to 1,6FLPAPrn was 1:0.05 (weight ratio).

Next, on the light-emitting layer 113, tris(8-quinolinolato)aluminum(III) (abbreviation: Alq) represented by the above structural formula (vii) was evaporated to a thickness of 10 nm, and then bathophenanthroline (abbreviation: BPhen) represented by the above structural formula (iv) was evaporated to a thickness of 15 nm, so that the electron-transport layer 114 was formed. Then, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 16 was completed. Note that in the above evaporation processes, evaporation was all performed by a resistance heating method.

[Operation Characteristics of Light-Emitting Element 16]

The light-emitting element 16 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 126:
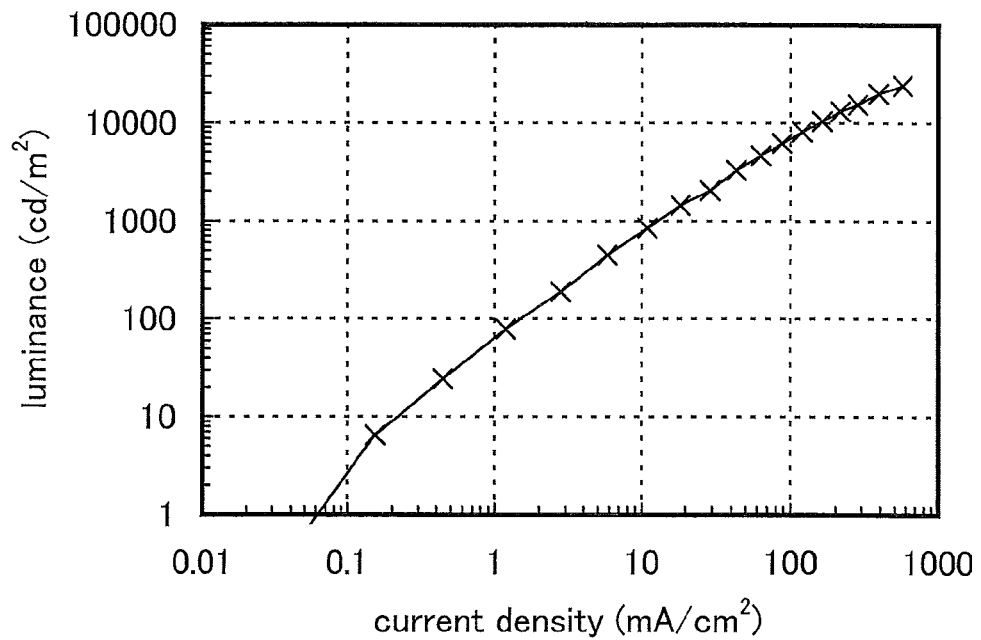
FIG. 126 shows luminance versus current density characteristics of a light-emitting element 16.
Figure 127:
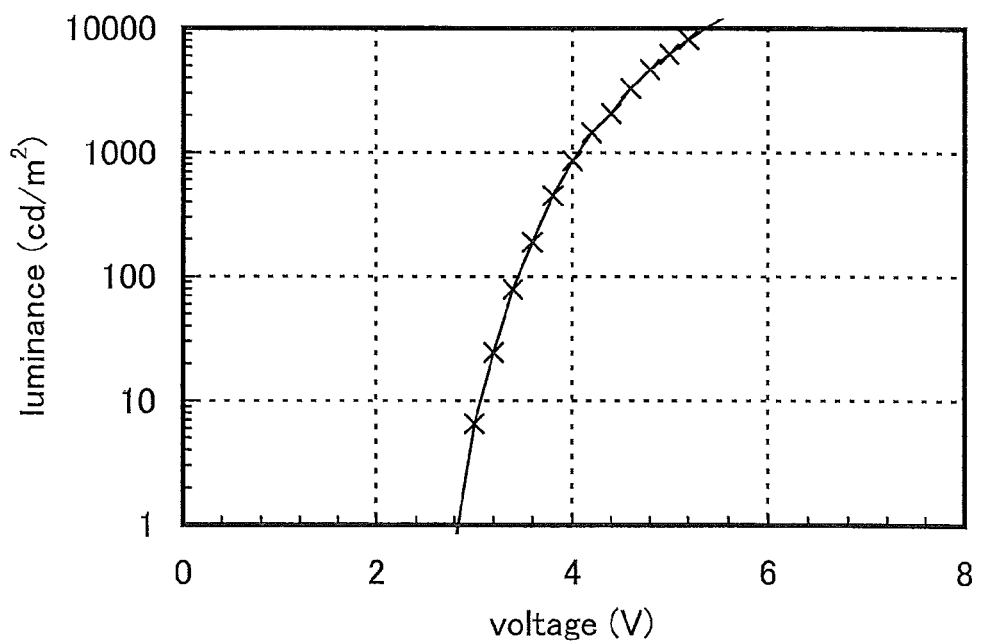
FIG. 127 shows luminance versus voltage characteristics of the light-emitting element 16.
Figure 128:
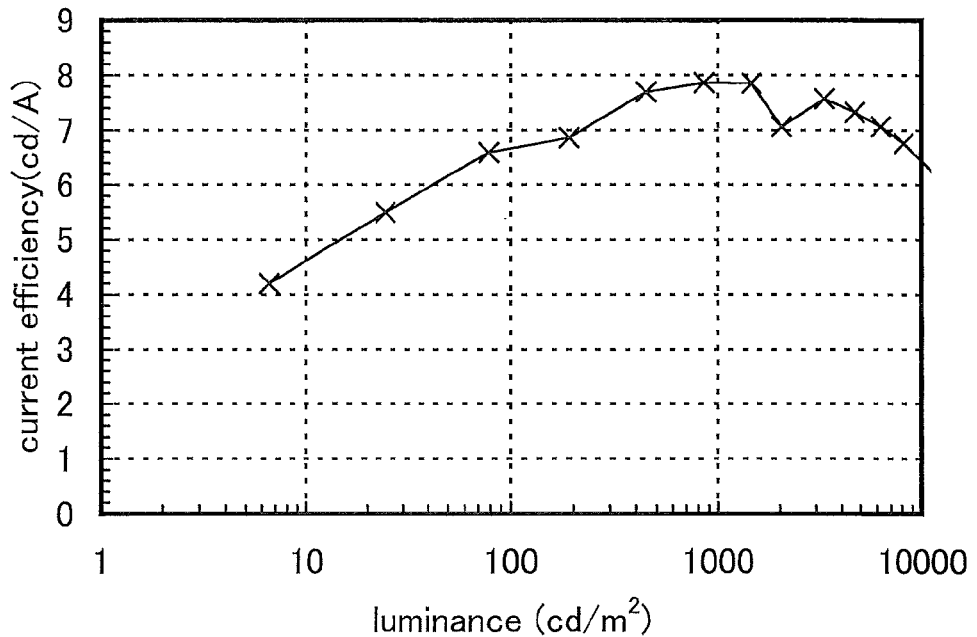
FIG. 128 shows current efficiency versus luminance characteristics of the light-emitting element 16.
Figure 129:
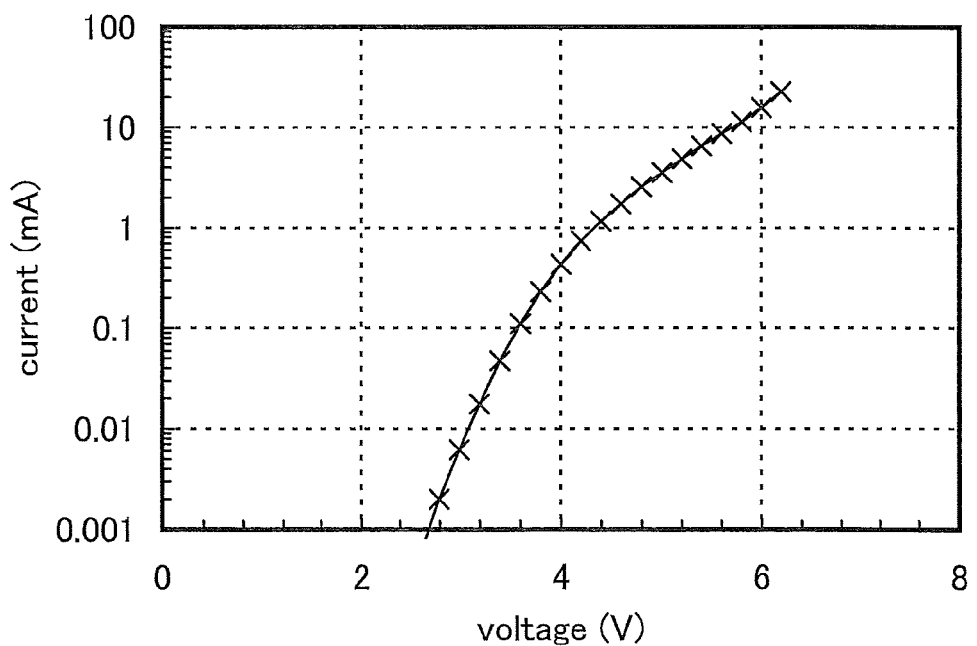
FIG. 129 shows current versus voltage characteristics of the light-emitting element 16.

FIG. 126 shows luminance current density characteristics of the light-emitting element 16, FIG. 127 shows luminance versus voltage characteristics thereof, FIG. 128 shows current efficiency versus luminance characteristics thereof, and FIG. 129 shows current versus voltage characteristics thereof. In FIG. 126, the vertical axis represents luminance (cd/m²), and the horizontal axis represents current density (mA/cm²). In FIG. 127, the vertical axis represents luminance (cd/m²), and the horizontal axis represents voltage (V). In FIG. 128, the vertical axis represents current efficiency (cd/A), and the horizontal axis represents luminance (cd/m²). In FIG. 129, the vertical axis represents current (mA), and the horizontal axis represents voltage (V).

FIG. 128 reveals that the light-emitting elements in each of which the carbazole derivative represented by the general formula (G1) is used as a host material of a light-emitting layer for emitting blue fluorescence, has favorable current efficiency versus luminance characteristics and high emission efficiency. This is because each carbazole derivative represented by the general formula (G1) has a wide energy gap, and thus even a light-emitting substance that emits blue fluorescence and has a wide energy gap can be efficiently excited. In addition, FIG. 127 reveals that the light-emitting elements in each of which the carbazole derivative represented by the general formula (G1) is used as a host material of a light-emitting layer for emitting blue fluorescence, has favorable luminance versus voltage characteristics and can be driven with a low voltage. This indicates that each carbazole derivative represented by the general formula (G1) has an excellent carrier-transport property.

Figure 130:
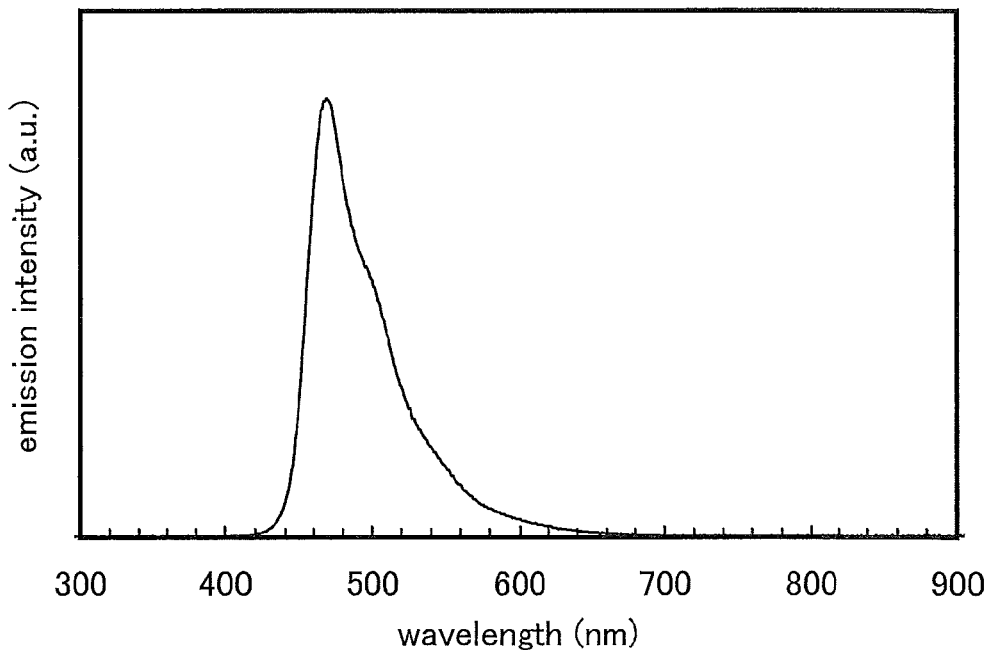
FIG. 130 shows an emission spectrum of the light-emitting element 16.

FIG. 130 shows an emission spectrum when a current of 1 mA was made to flow in the fabricated light-emitting element 16. The emission intensity is shown as a value relative to the greatest emission intensity assumed to be 1. FIG. 130 reveals that the light-emitting element 16 emits blue light due to 1,6FLPAPrn, which is the emission center substance.

Figure 131:
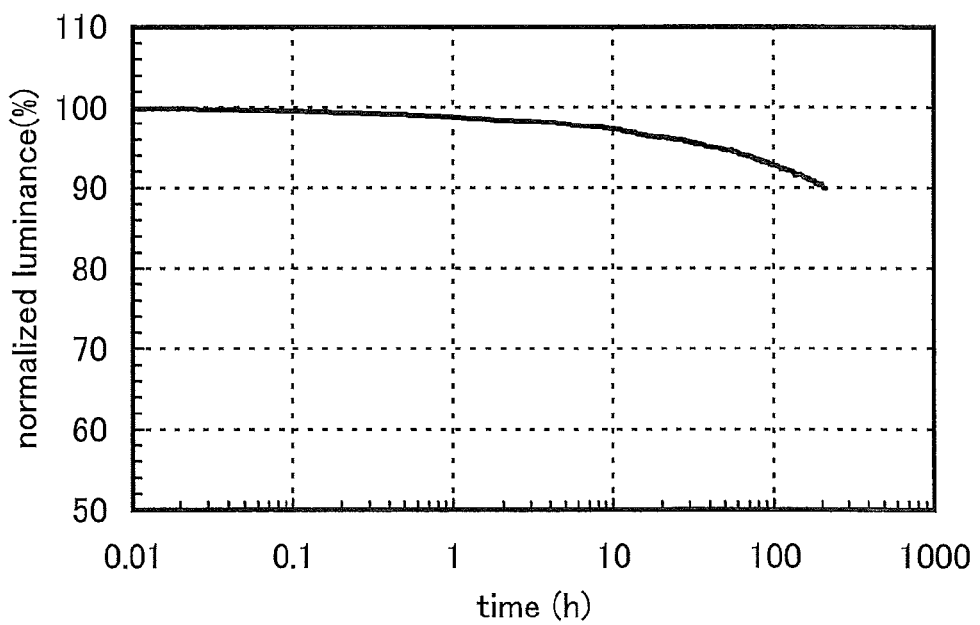
FIG. 131 shows normalized luminance versus time characteristics of the light-emitting element 16.

Next, the initial luminance is set at 1000 cd/m$^2$, the element was driven under a condition where the current density was constant, and changes in luminance with respect to the driving time were examined. FIG. 131 shows normalized luminance versus time characteristics. From FIG. 131, it is found that the light-emitting element 16 shows favorable characteristics and has high reliability.

Example 27

Synthesis Example 15

In this example is described a method of synthesizing 3-(dibenzofuran-4-yl)-9-[4-(9,10-diphenyl-2-anthryl)phenyl]-9H-carbazole (abbreviation: 2DBFCzPPA-II), which is one of the carbazole derivatives described as the structural formula (17) in Embodiment 1. A structure of 2DBFCzPPA-II is illustrated in the following structural formula.

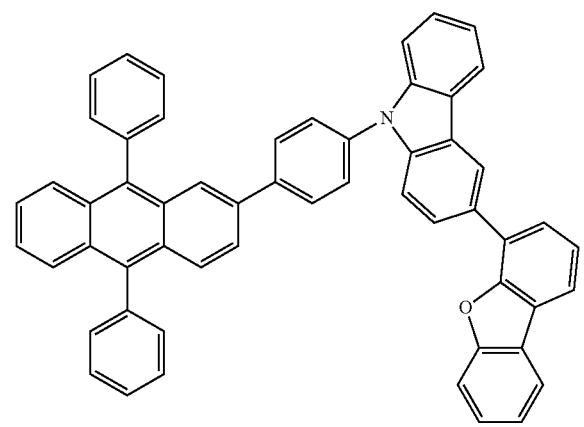

(17)

Step 1: Synthesis of
3-(Dibenzofuran-4-yl)-9H-carbazole
(abbreviation: DBFCz-II)

This was synthesized as in Step 1 in Synthesis Example 2.

Step 2: Synthesis of 3-(Dibenzofuran-4-yl)-9-[4-(9, 10-diphenyl-2-anthryl)phenyl]-9H-carbazole (abbreviation: 2DBFCzPPA-II)

In a 50-mL three-neck flask were put 1.3 g (2.7 mmol) of 2-(4-bromophenyl)-9,10-diphenylanthracene, 0.88 g (2.7 mmol) of 3-(dibenzofuran-4-yl)-9H-carbazole, and 0.76 g (8.0 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 76 mg (0.13 mmol) of bis(dibenzylideneacetone)palladium(0) was added to this mixture. This mixture was stirred at 110° C. for 4 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135), and the filtrate was concentrated to give a solid. This solid was purified by silica gel column chromatography (a developing solvent in which the hexane/toluene ratio was 5:1). This solid was purified by high performance liquid column chromatography (abbreviation: HPLC) (chloroform as the developing solvent). The obtained fraction was concentrated to give 1.4 g of a yellow solid which was the object of the synthesis in 71% yield. The synthesis scheme of Step 2 is illustrated in (b-15).

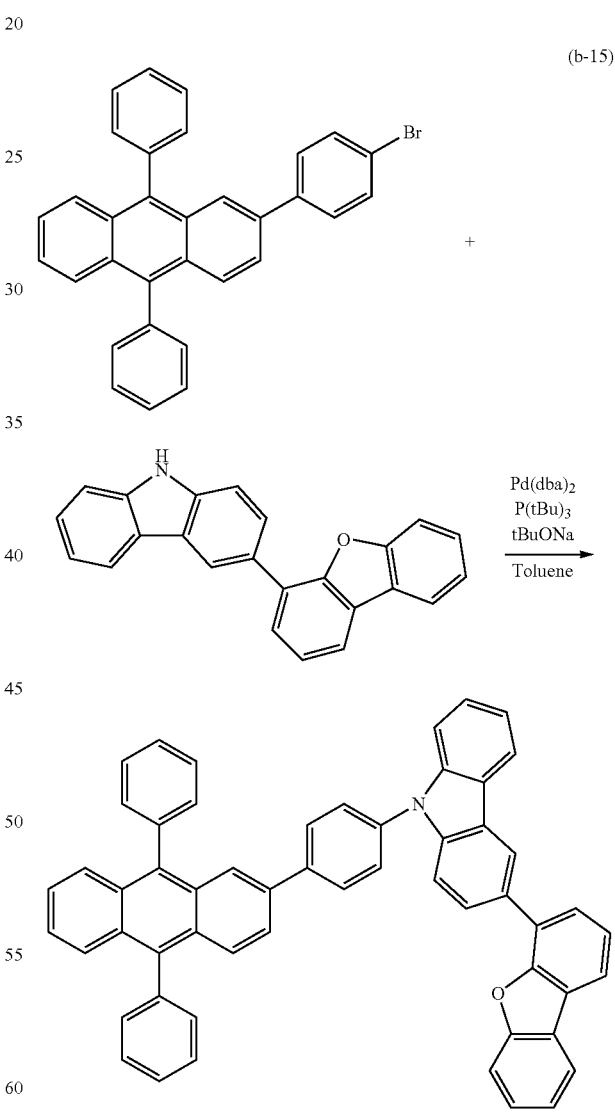

(b-15)

By a train sublimation method, the obtained yellow solid was purified. The purification was conducted by heating of 0.90 g of the yellow solid at 360° C. under a pressure of 2.6 Pa with a flow rate of argon gas of 5 mL/min. After the purification, 0.73 g of a yellow solid was obtained in a yield of 81%.

The yellow solid after the above purification was subjected to nuclear magnetic resonance (NMR) spectroscopy. The measurement data are shown below.

$^1$H NMR (CDCl$_3$, 300 MHz): δ=7.30-7.42 (m, 4H), 7.45-7.52 (m, 4H), 7.53-7.75 (m, 18H), 7.78-7.88 (m, 3H), 7.93-8.03 (m, 4H), 8.24 (d, J$_1$=7.5 Hz, 1H), 8.66 (d, J$_1$=1.5 Hz, 1H).

Figure 132A:
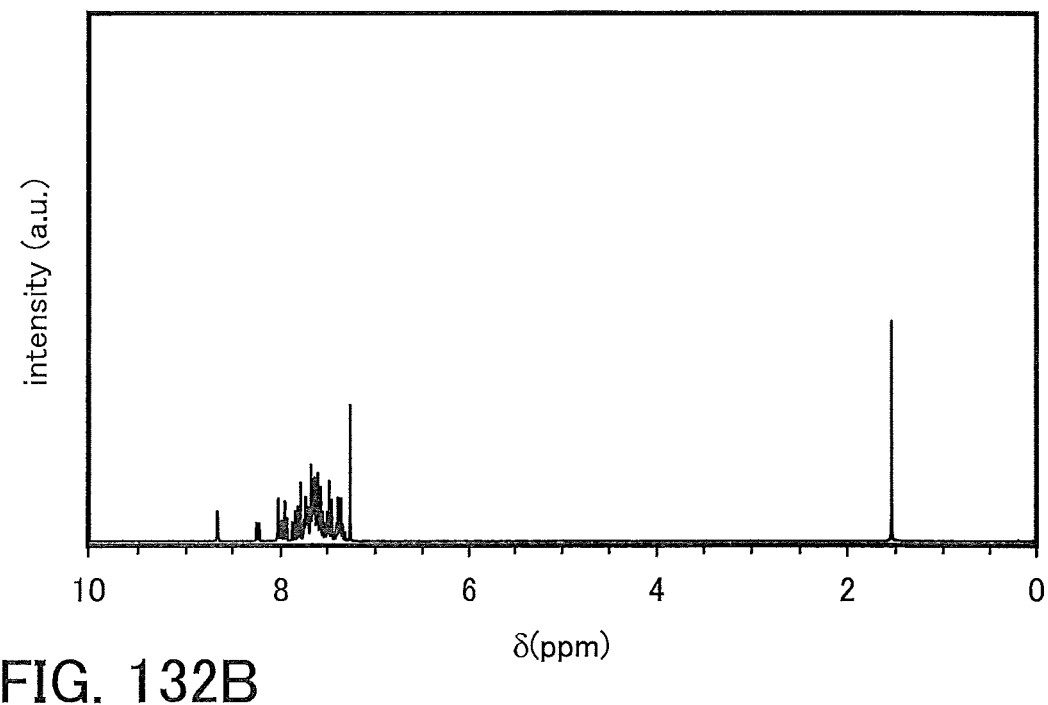
FIGS. 132A and 132B are NMR charts of 2DBFCzPPA-II.
Figure 132B:
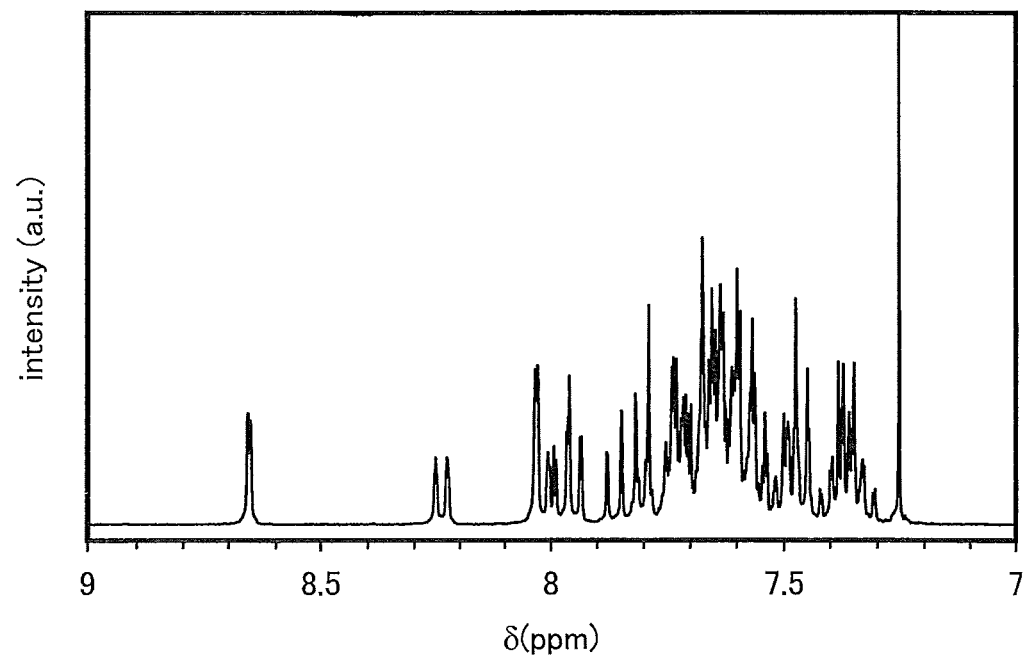

In addition, $^1$H NMR charts are shown in FIGS. 132A and 132B. Note that FIG. 132B is a chart where the range of from 7 ppm to 9 ppm in FIG. 132A is enlarged. The measurement results showed that 2DBFCzPPA-II, which is the carbazole derivative represented by the above structural formula, was obtained.

Figure 133A:
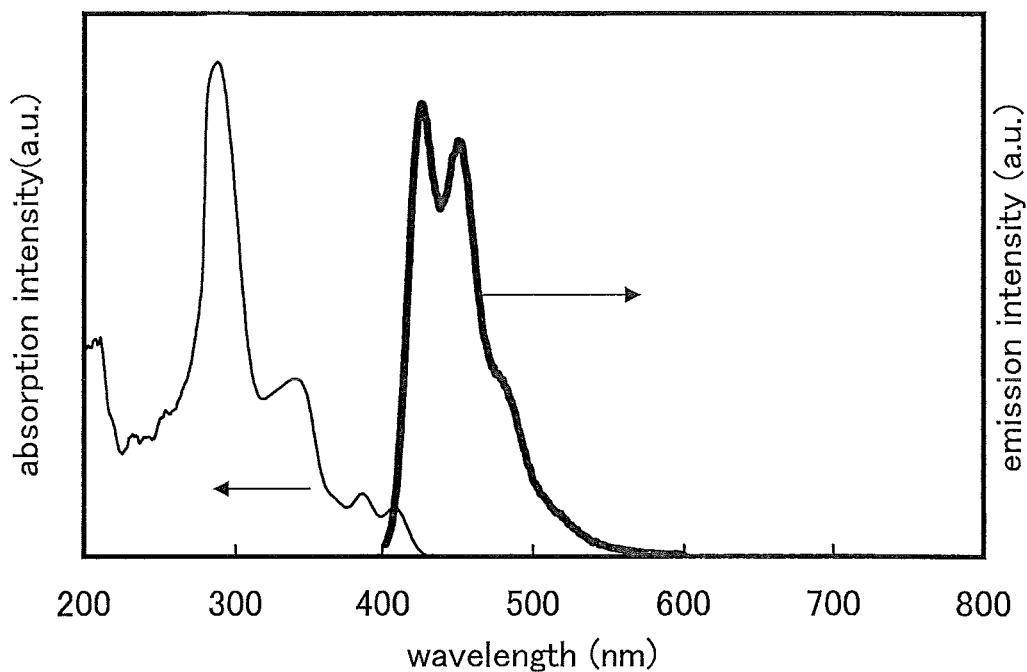
FIGS. 133A and 133B show an absorption and emission spectra of 2DBFCzPPA-II.
Figure 133B:
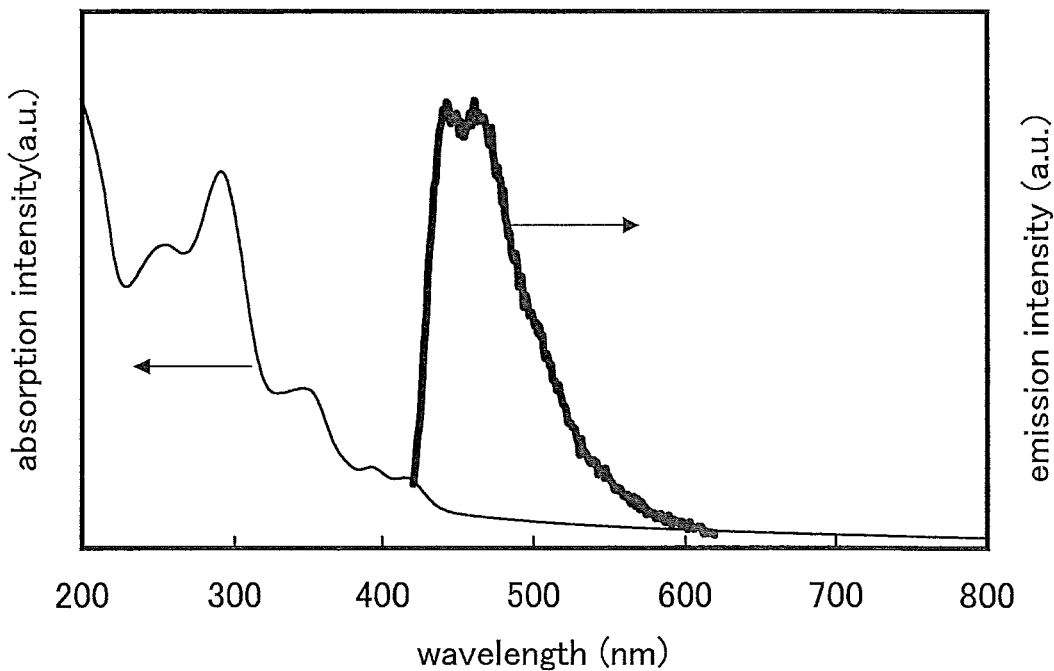

Further, an absorption and emission spectra of 2DBFCzPPA-II in a toluene solution of 2DBFCzPPA-II are shown in FIG. 133A, and an absorption and emission spectra of a thin film of 2DBFCzPPA-II are shown in FIG. 133B. An ultraviolet-visible spectrophotometer (V-550, manufactured by JASCO Corporation) was used for the measurements of the absorption spectra. In the case of the toluene solution, the measurements were made with the toluene solution of 2DBFCzPPA-II put in a quartz cell, and the absorption spectrum obtained by subtraction of the absorption spectra of the quartz cell and toluene from the measured spectra is shown in the drawing. In addition, as for the absorption spectrum of the thin film, a sample was prepared by evaporation of 2DBFCzPPA-II on a quartz substrate, and the absorption spectrum obtained by subtraction of that of quartz from the spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum was measured with the toluene solution of 2DBFCzPPA-II put in a quartz cell, and the emission spectrum of the thin film was measured with a sample prepared by evaporation of 2DBFCzPPA-II on a quartz substrate. Thus, it was found that the absorption peak wavelengths of 2DBFCzPPA-II in the toluene solution of 2DBFCzPPA-II were around 403 nm, 381 nm, 336 nm and 284 nm and the emission peak wavelengths thereof were around 453 nm and 427 nm (at an excitation wavelength of 387 nm), and that the absorption peak wavelengths of the thin film of 2DBFCzPPA-II were around 415 nm, 392 nm, 347 nm, 291 nm and 254 nm and the greatest emission wavelengths thereof were around 461 nm and 443 nm (at an excitation wavelength of 415 nm).

Further, the ionization potential of 2DBFCzPPA-II in a thin film state was measured by a photoelectron spectrometer (AC-2, manufactured by Riken Keiki, Co., Ltd.) in air. The obtained value of the ionization potential was converted to a negative value, so that the HOMO level of 2DBFCzPPA-II was −5.68 eV. From the data of the absorption spectra of the thin film in FIG. 133B, the absorption edge of 2DBFCzPPA-II, which was obtained from Tauc plot with an assumption of direct transition, was 2.81 eV. Therefore, the optical energy gap of 2DBFCzPPA-II in the solid state was estimated at 2.81 eV; from the values of the HOMO level obtained above and this energy gap, the LUMO level of 2DBFCzPPA-II was able to be estimated at −2.87 eV. It was thus found that 2DBFCzPPA-II had a wide energy gap of 2.81 eV in the solid state.

Further, the oxidation reaction characteristics of 2DBFCzPPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.27 V to 0.90 V and then changed from 0.90 V to 0.26 V was one cycle, and 100 cycles were performed.

The measurement results revealed that 2DBFCzPPA-II showed properties effective against repetition of redox reactions between an oxidized state and a neutral state without a large variation in oxidation peak even after the 100 cycles in the measurements.

Further, the HOMO level of 2DBFCzPPA-II was determined also by calculation from the CV measurement results.

First, the potential energy of the reference electrode with respect to the vacuum level used was found to be −4.94 eV, as determined in Example 6. The oxidation peak potential E$_{pa}$ of 2DBFCzPPA-II was 0.89 V. In addition, the reduction peak potential E$_{pc}$ thereof was 0.75 V. Therefore, a half-wave potential (an intermediate potential between E$_{pa}$ and E$_{pc}$) can be calculated at 0.82 V. This means that 2DBFCzPPA-II is oxidized by an electric energy of 0.82 [V versus Ag/Ag$^+$], and this energy corresponds to the HOMO level. Here, since the potential energy of the reference electrode, which was used in this example, with respect to the vacuum level is −4.94 [eV] as described above, the HOMO level of 2DBFCzPPA-II was calculated as follows: −4.94−0.82=−5.76 [eV].

Example 28

In this example described is a light-emitting element in which 3-(dibenzofuran-4-yl)-9-[4-(9,10-diphenyl-2-anthryl)phenyl]-9H-carbazole (abbreviation: 2DBFCzPPA-II, a structural formula (17)), which is one of the carbazole derivatives represented by the general formula (G1), is used as a host material such that an emission center substance that emits blue fluorescence is dispersed therein.

The molecular structures of organic compounds used in this example are represented by the structural formulae (17), (iv), and (iv) below.

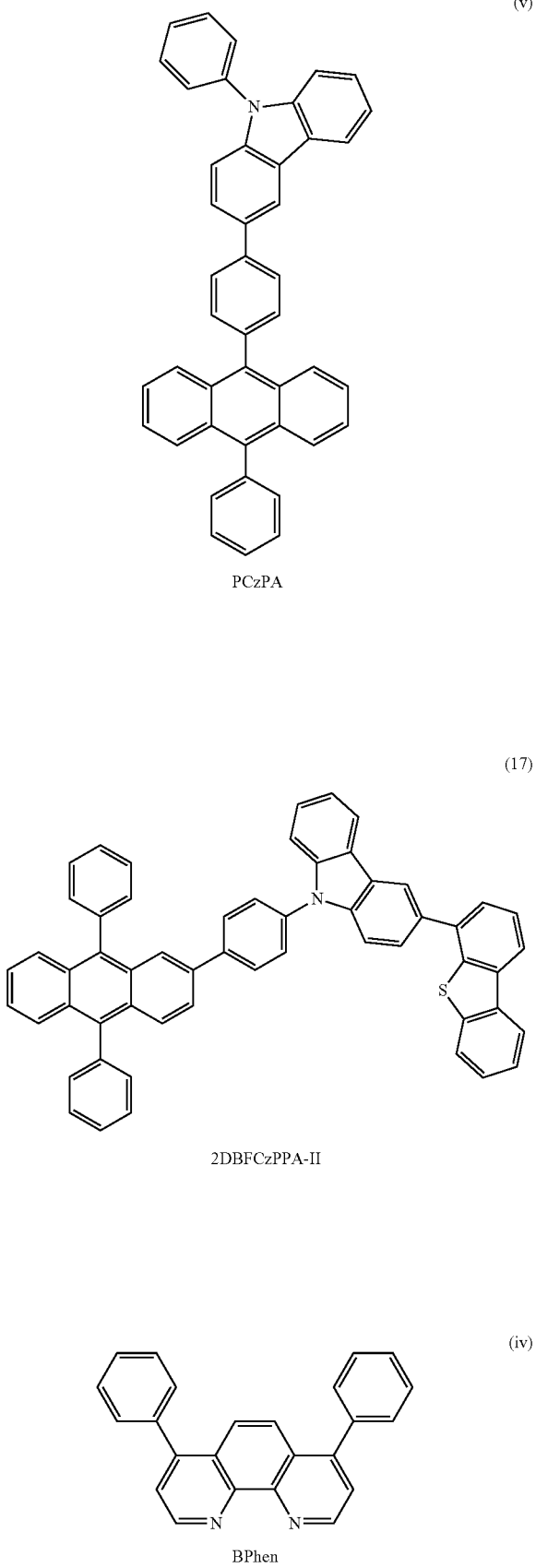

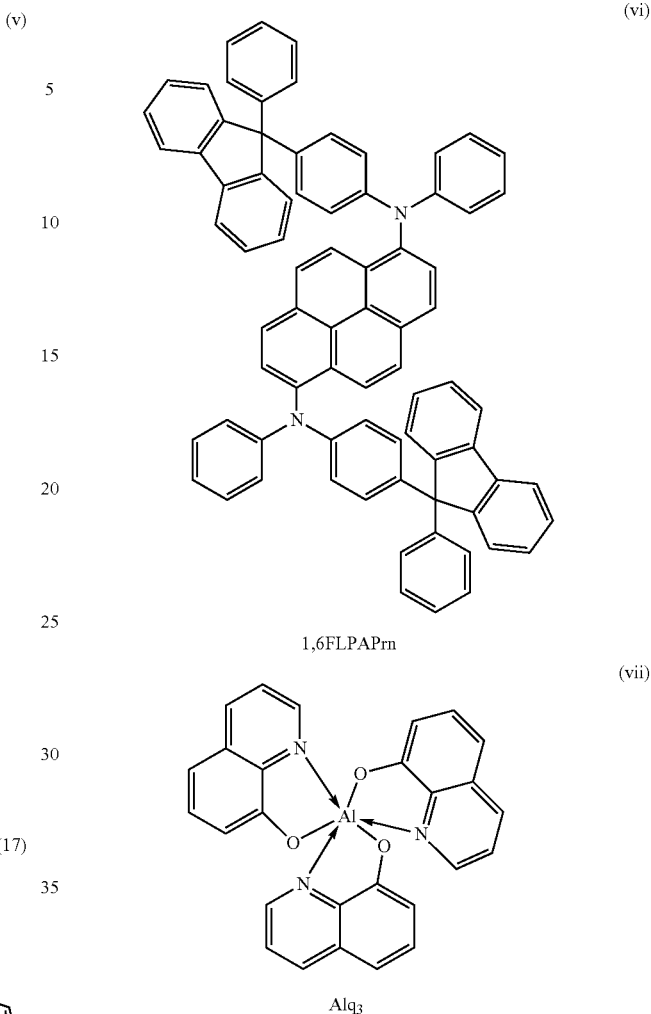

In the element structure in FIG. 1A, an electron-injection layer is provided between an electron-transport layer 114 and a second electrode 104.

[Fabrication of Light-Emitting Element 17]

First, a glass substrate 101 over which indium tin oxide containing silicon (ITSO) with a thickness of 110 nm was fainted as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 9-[4-(9-phenylcarbazol-3-yl)]phenyl- 10-phenylanthracene (abbreviation: PCzPA) represented by the above structural formula (v) and molybdenum(VI) oxide such that the ratio of PCzPA:molybdenum(VI) oxide was 2:1 (weight ratio). The thickness of was the layer was set to 50 nm Note that the co-evaporation is an evaporation method in which a plurality of different substances is concurrently vaporized from the respective different evaporation sources.

Next, PCzPA was evaporated to a thickness of 10 nm, so that the hole-transport layer 112 was formed.

Further, the light-emitting layer 113 was formed on the hole-transport layer 112 in such a way that 3-(dibenzofuran-4-yl)-9-[4-(9,10-diphenyl-2-anthryl)phenyl]-9H-carbazole (abbreviation: 2DBFCzPPA-II) represented by the above structural formula (17) and N,N'-bis[4-(9-phenyl-9H-fluoren-9-yl)phenyl]-N,N'-diphenyl-pyrene-1,6-diamine (abbreviation: 1,6FLPAPrn) represented by the structural formula (vi) were evaporated to form a 30-nm-thick film so that the ratio of 2DBFCzPPA-II to 1,6FLPAPrn was 1:0.05 (weight ratio).

Next, on the light-emitting layer 113, tris(8-quinolinolato) aluminum(III) (abbreviation: Alq) represented by the above structural formula (vii) was evaporated to a thickness of 10 nm, and then bathophenanthroline (abbreviation: BPhen) represented by the above structural formula (iv) was evaporated to a thickness of 15 nm, so that the electron-transport layer 114 was formed. Then, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 17 was completed. Note that in the above evaporation processes, evaporation was all performed by a resistance heating method.

[Operation Characteristics of Light-Emitting Element 17]

The light-emitting element 17 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 134:
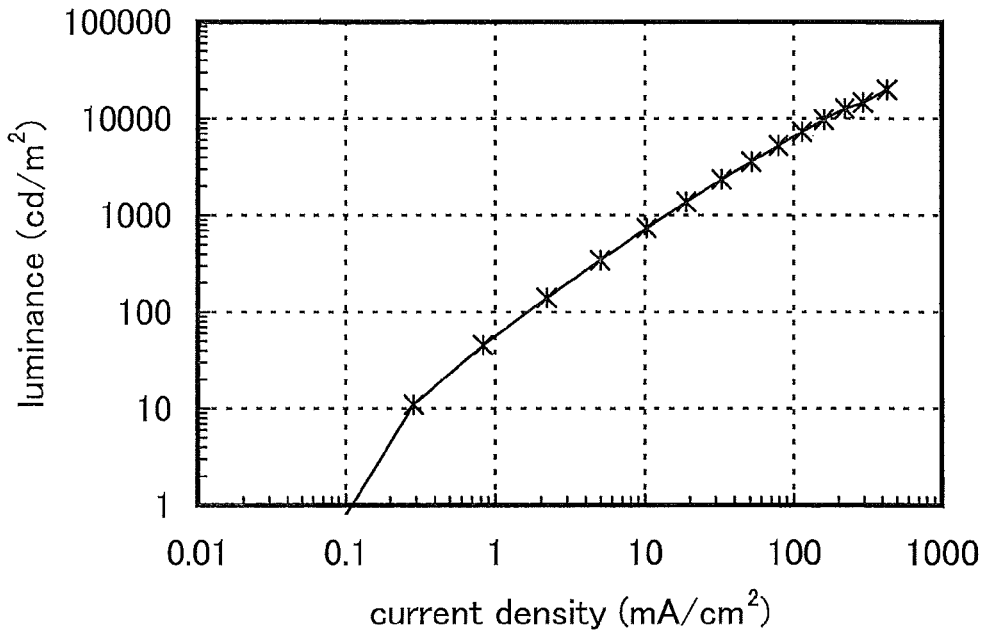
FIG. 134 shows luminance versus current density characteristics of a light-emitting element 17.
Figure 135:
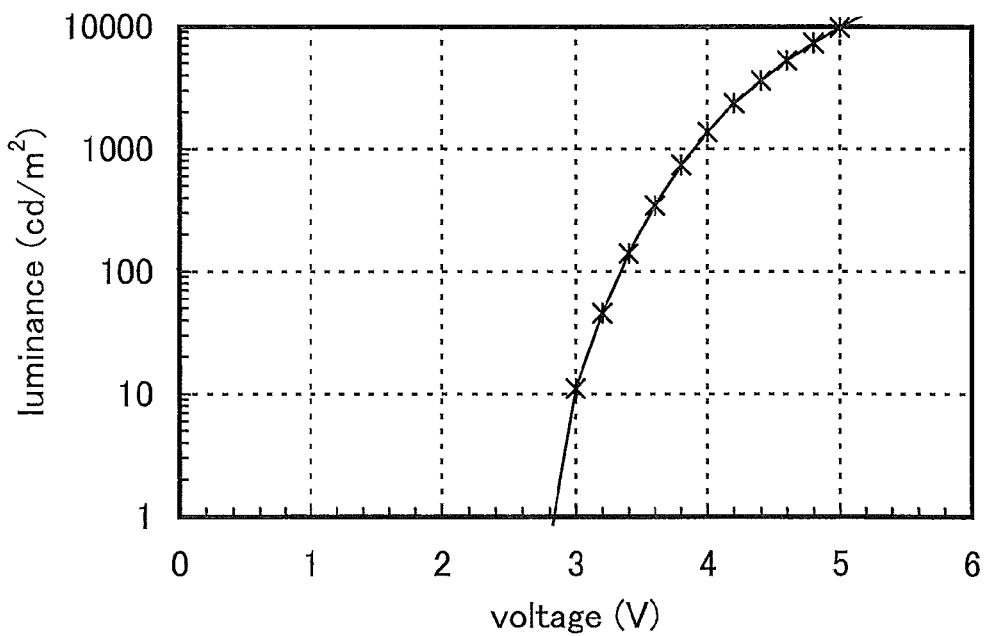
FIG. 135 shows luminance versus voltage characteristics of the light-emitting element 17.
Figure 136:
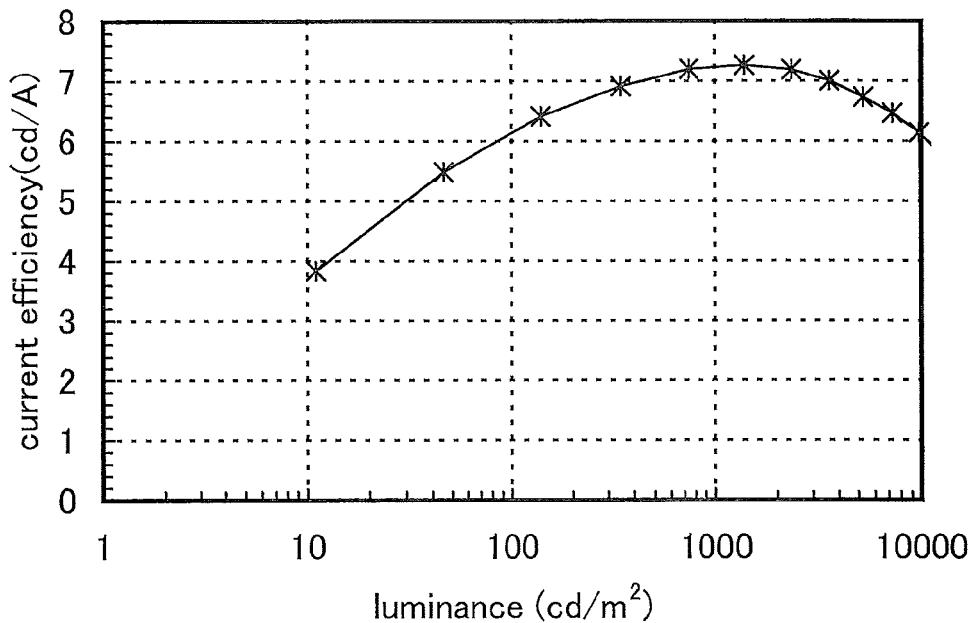
FIG. 136 shows current efficiency versus luminance characteristics of the light-emitting element 17.
Figure 137:
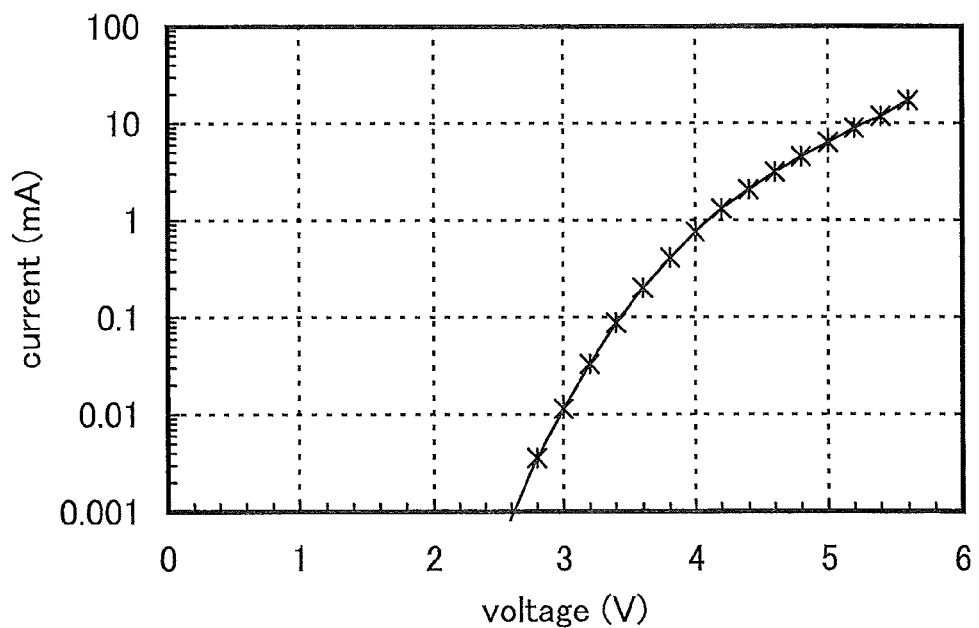
FIG. 137 shows current versus voltage characteristics of the light-emitting element 17.

FIG. 134 shows luminance current density characteristics of the light-emitting element 17, FIG. 135 shows luminance versus voltage characteristics thereof, FIG. 136 shows current efficiency versus luminance characteristics thereof, and FIG. 137 shows current versus voltage characteristics thereof. In FIG. 134, the vertical axis represents luminance (cd/m$^2$), and the horizontal axis represents current density (mA/cm$^2$). In FIG. 135, the vertical axis represents luminance (cd/m$^2$), and the horizontal axis represents voltage (V). In FIG. 136, the vertical axis represents current efficiency (cd/A), and the horizontal axis represents luminance (cd/m$^2$). In FIG. 137, the vertical axis represents current (mA), and the horizontal axis represents voltage (V).

FIG. 136 reveals that the light-emitting elements in each of which the carbazole derivative represented by the general formula (G1) is used as a host material of a light-emitting layer for emitting blue fluorescence, has favorable current efficiency versus luminance characteristics and high emission efficiency. This is because each carbazole derivative represented by the general formula (G1) has a wide energy gap, and thus even a light-emitting substance that emits blue fluorescence and has a wide energy gap can be efficiently excited. In addition, FIG. 135 reveals that the light-emitting elements in each of which the carbazole derivative represented by the general formula (G1) is used as a host material of a light-emitting layer for emitting blue fluorescence, has favorable luminance versus voltage characteristics and can be driven with a low voltage. This indicates that each carbazole derivative represented by the general formula (G1) has an excellent carrier-transport property.

Figure 138:
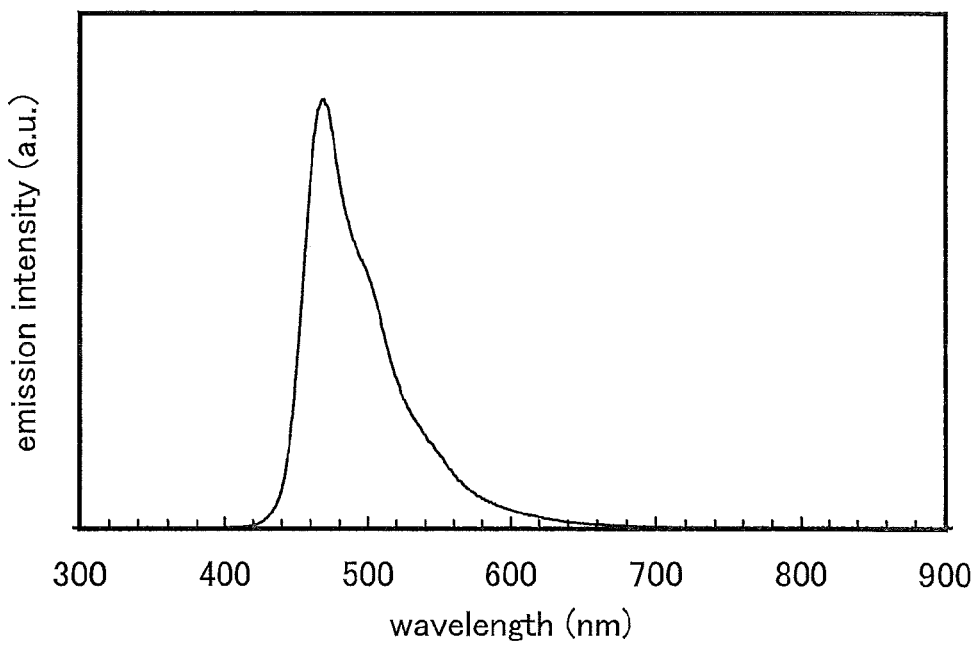
FIG. 138 shows an emission spectrum of the light-emitting element 17.

FIG. 138 shows an emission spectrum when a current of 1 mA was made to flow in the fabricated light-emitting element 17. The emission intensity is shown as a value relative to the greatest emission intensity assumed to be 1. FIG. 138 reveals that the light-emitting element 17 emits blue light due to 1,6FLPAPrn, which is the emission center substance.

Figure 139:
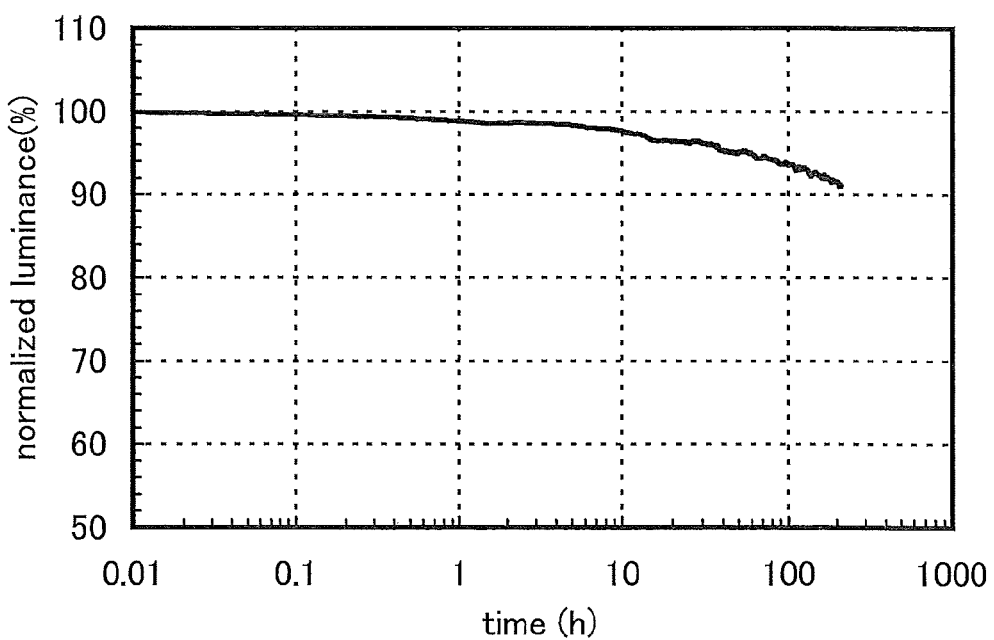
FIG. 139 shows normalized luminance versus time characteristics of the light-emitting element 17.

Next, the initial luminance is set at 1000 cd/m$^2$, the element was driven under a condition where the current density was constant, and changes in luminance with respect to the driving time were examined. FIG. 139 shows normalized luminance versus time characteristics. From FIG. 139, it is found that the light-emitting element 17 shows favorable characteristics and has high reliability.

Example 29

Synthesis Example 16

In this example is described a method of synthesizing 3-(dibenzothiophen-4-yl)-9-[3-(9,10-diphenyl-2-anthryl) phenyl]-9H-carbazole (abbreviation: 2mDBTCzPPA-II), which is one of the carbazole derivatives described as the structural formula (18) in Embodiment 1. A structure of 2mDBTCzPPA-II is illustrated in the following structural formula.

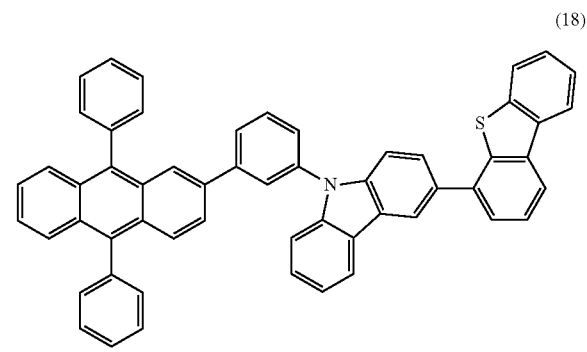

(18)

Step 1: Synthesis of
3-(Dibenzothiophen-4-yl)-9H-carbazole
(abbreviation: DBTCz-II)

This was synthesized as in Step 1 in Synthesis Example 1.

Step 2: Synthesis of 3-(Dibenzothiophen-4-yl)-9-[3-(9,10-diphenyl-2-anthryl)phenyl]-9H-carbazole (abbreviation: 2mDBTCzPPA-II)

In a 100-mL three-neck flask were put 1.0 g (2.1 mmol) of 2-(3-bromophenyl)-9,10-diphenylanthracene, 0.72 g (2.1 mmol) of 3-(dibenzothiophen-4-yl)-9H-carbazole, and 0.59 g (6.2 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 59 mg (0.10 mmol) of bis(dibenzylideneacetone)palladium(0) was added to this mixture. This mixture was stirred at 110° C. for 5 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The filtrate was concentrated to give a yellow solid. This solid was purified by silica gel column chromatography (a developing solvent in which the hexane/toluene ratio was 5:1). The obtained solid was recrystallized from toluene/hexane to give 1.1 g of a yellow solid in 70% yield. The synthesis scheme of Step 2 is illustrated in (b-16).

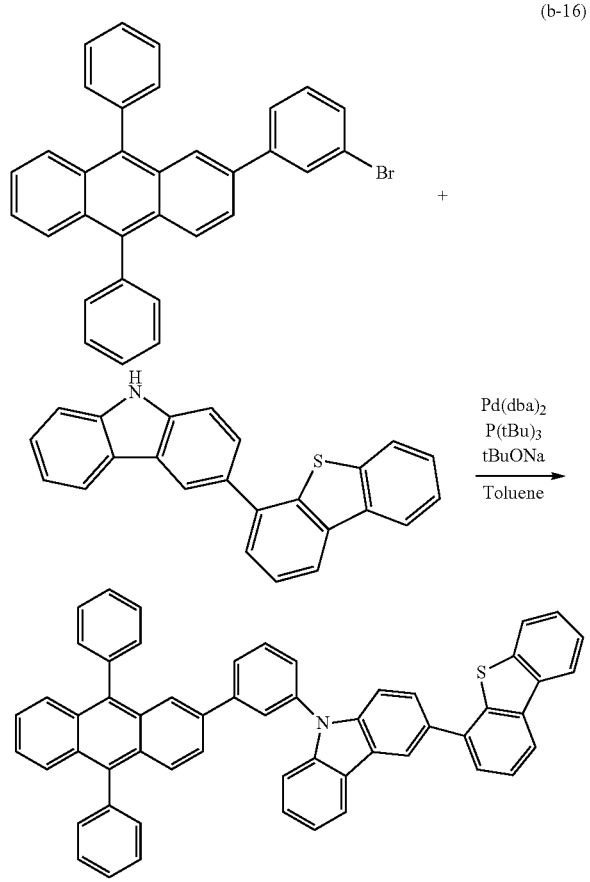

By a train sublimation method, the obtained yellow solid was purified. The purification was conducted by heating of 1.1 g of the yellow solid at 330° C. under a pressure of 2.9 Pa with a flow rate of argon gas of 5 mL/min. After the purification, 0.89 g of a yellow solid was obtained in a yield of 84%.

The yellow solid after the above purification was subjected to nuclear magnetic resonance (NMR) spectroscopy. The measurement data are shown below.

$^1$H NMR (CDCl$_3$, 300 MHz): δ=7.30-7.38 (m, 3H), 7.40-7.76 (m, 23H), 7.77-7.87 (m, 4H), 8.01 (d, J$_1$=0.90 Hz, 1H), 8.16-8.24 (m, 3H), 8.52 (d, J$_1$=1.2 Hz, 1H)

Figure 140A:
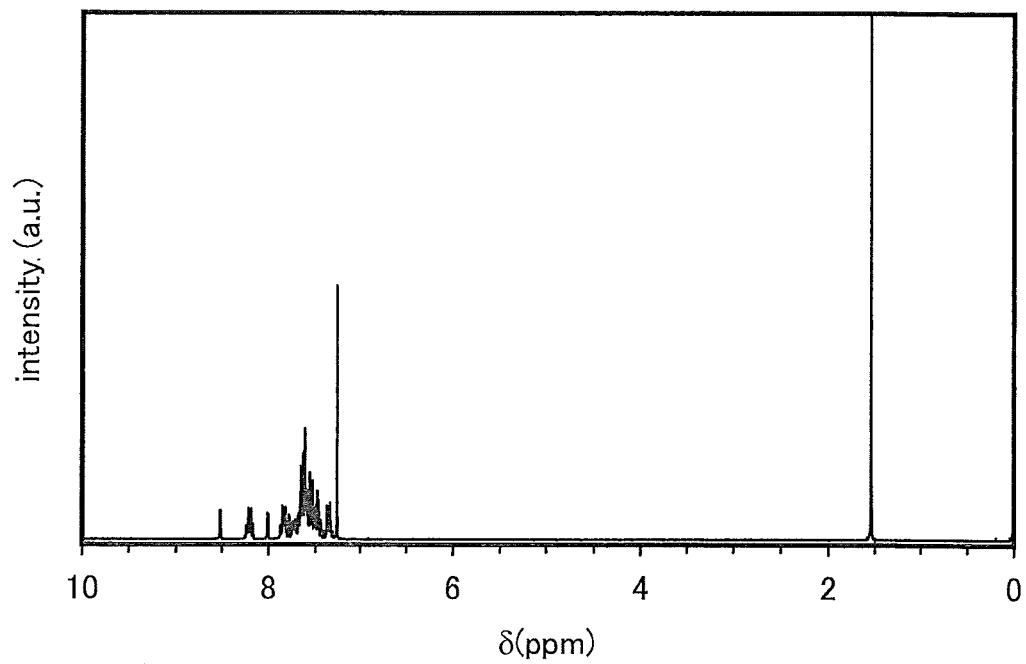
FIGS. 140A and 140B are NMR charts of 2mDBTCzPPA-II.
Figure 140B:
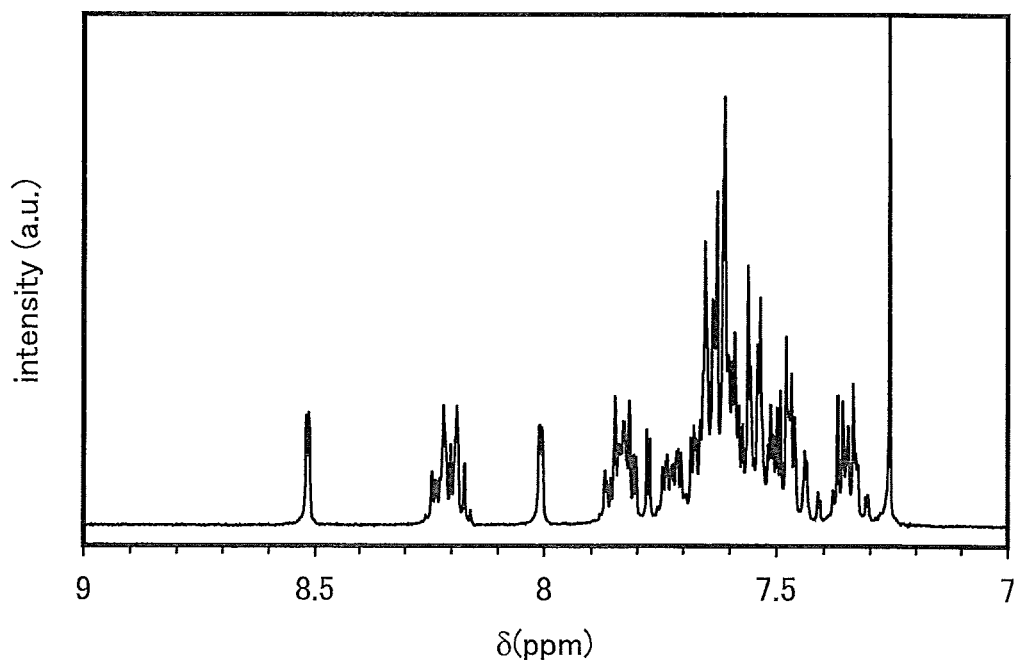

In addition, $^1$H NMR charts are shown in FIGS. 140A and 140B. Note that FIG. 140B is a chart where the range of from 7 ppm to 9 ppm in FIG. 140A is enlarged. The measurement results showed that 2mDBTCzPPA-II, which is the carbazole derivative represented by the above structural formula, was obtained.

Figure 141A:
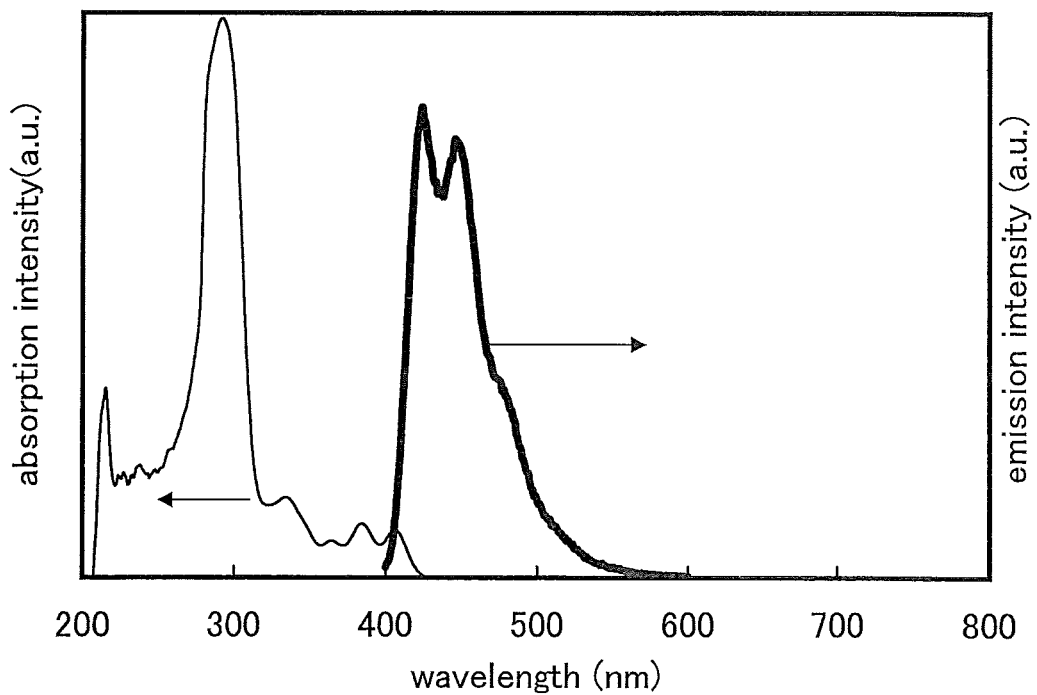
FIGS. 141A and 141B show an absorption and emission spectra of 2mDBTCzPPA-II.
Figure 141B:
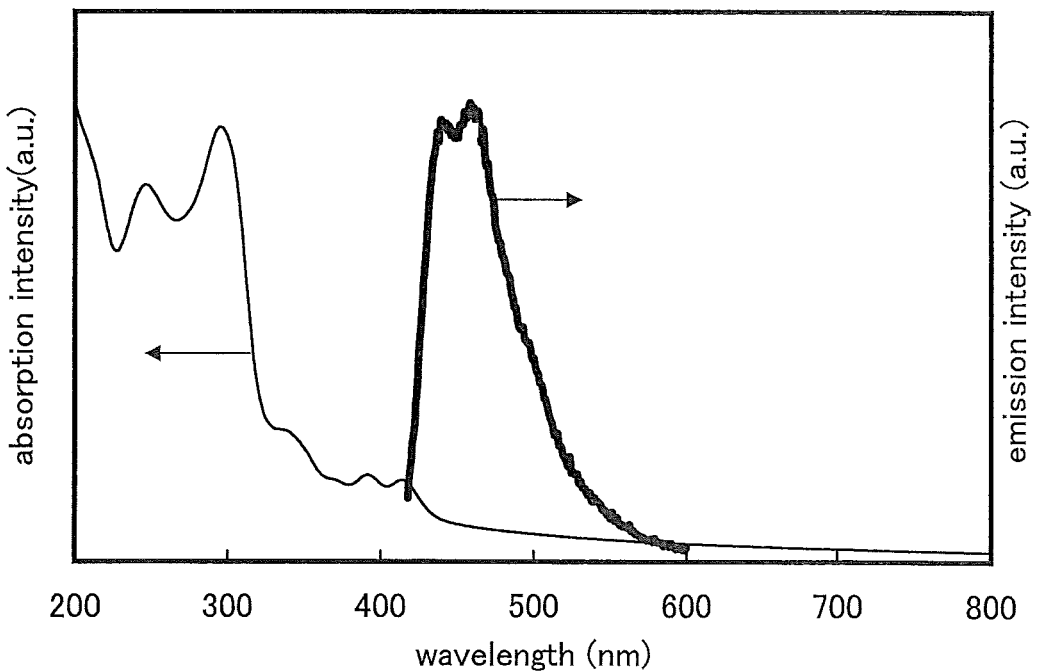

Further, an absorption and emission spectra of 2mDBTCzPPA-II in a toluene solution of 2mDBTCzPPA-II are shown in FIG. 141A, and an absorption and emission spectra of a thin film of 2mDBTCzPPA-II are shown in FIG. 141B. An ultraviolet-visible spectrophotometer (V-550, manufactured by JASCO Corporation) was used for the measurements of the absorption spectra. In the case of the toluene solution, the measurements were made with the toluene solution of 2mDBTCzPPA-II put in a quartz cell, and the absorption spectrum obtained by subtraction of the absorption spectra of the quartz cell and toluene from the measured spectra is shown in the drawing. In addition, as for the absorption spectrum of the thin film, a sample was prepared by evaporation of 2mDBTCzPPA-II on a quartz substrate, and the absorption spectrum obtained by subtraction of that of quartz from the spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum was measured with the toluene solution of 2mDBTCzPPA-II put in a quartz cell, and the emission spectrum of the thin film was measured with a sample prepared by evaporation of 2mDBTCzPPA-II on a quartz substrate. Thus, it was found that the absorption peak wavelengths of 2mDBTCzPPA-II in the toluene solution of 2mDBTCzPPA-II were around 406 nm, 385 nm, 365 nm, 335 nm and 292 nm and the emission peak wavelengths thereof were around 424 nm and 437 nm (at an excitation wavelength of 385 nm), and that the absorption peak wavelengths of the thin film of 2mDBTCzPPA-II were around 414 nm, 392 nm, 370 nm, 339 nm, 295 nm, 245 nm and 208 nm and the emission peak wavelengths thereof were around 492 nm, 459 nm and 440 nm (at an excitation wavelength of 403 nm).

Further, the ionization potential of 2mDBTCzPPA-II in a thin film state was measured by a photoelectron spectrometer (AC-2, manufactured by Riken Keiki, Co., Ltd.) in air. The obtained value of the ionization potential was converted to a negative value, so that the HOMO level of 2mDBTCzPPA-II was −5.74 eV. From the data of the absorption spectra of the thin film in FIG. 141B, the absorption edge of 2mDBTCzPPA-II, which was obtained from Tauc plot with an assumption of direct transition, was 2.84 eV. Therefore, the optical energy gap of 2mDBTCzPPA-II in the solid state was estimated at 2.84 eV; from the values of the HOMO level obtained above and this energy gap, the LUMO level of 2mDBTCzPPA-II was able to be estimated at −2.90 eV. It was thus found that 2mDBTCzPPA-II had a wide energy gap of 2.84 eV in the solid state.

Further, the oxidation reaction characteristics of 2mDBTCzPPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from 0.06 V to 1.05 V and then changed from 1.05 V to 0.06 V was one cycle, and 100 cycles were performed.

The measurement results revealed that 2mDBTCzPPA-II showed properties effective against repetition of redox reactions between an oxidized state and a neutral state without a large variation in oxidation peak even after the 100 cycles in the measurements.

Further, the HOMO level of 2mDBTCzPPA-II was determined also by calculation from the CV measurement results.

First, the potential energy of the reference electrode with respect to the vacuum level used was found to be −4.94 eV, as determined in Example 6. The oxidation peak potential $E_{pa}$ of 2mDBTCzPPA-II was 0.91 V. In addition, the reduction peak potential $E_{pc}$ thereof was 0.82 V. Therefore, a half-wave potential (an intermediate potential between $E_{pa}$ and $E_{pc}$) can be calculated at 0.87 V. This means that 2mDBTCzPPA-II is oxidized by an electric energy of 0.87 [V versus Ag/Ag$^+$], and this energy corresponds to the HOMO level. Here, since the potential energy of the reference electrode, which was used in this example, with respect to the vacuum level is −4.94 [eV] as described above, the HOMO level of 2mDBTCzPPA-II was calculated as follows: −4.94−0.87=−5.81 [eV].

Example 30

In this example described is a light-emitting element in which 3-(dibenzothiophen-4-yl)-9-[3-(9,10-diphenyl-2-anthryl)phenyl]-9H-carbazole (abbreviation: 2mDBTCzPPA-II, a structural formula (18)), which is one of the carbazole derivatives represented by the general formula (G1), is used as a host material such that an emission center substance that emits blue fluorescence is dispersed therein.

The molecular structures of organic compounds used in this example are represented by the structural formulae (18), (iv), and (iv) below.

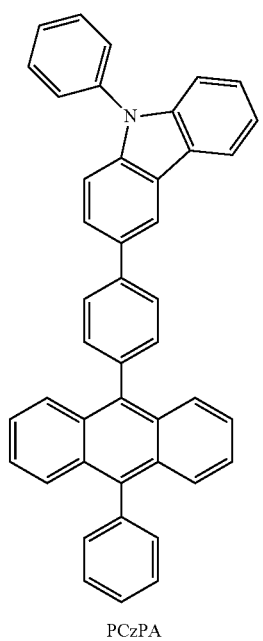

PCzPA (v)

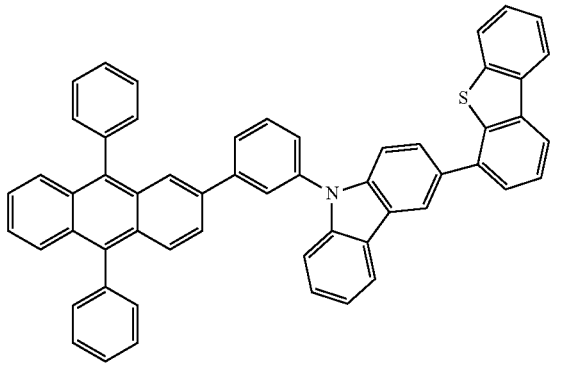

2mDBTCzPPA-II (18)

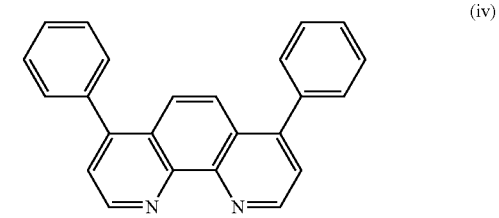

BPhen (iv)

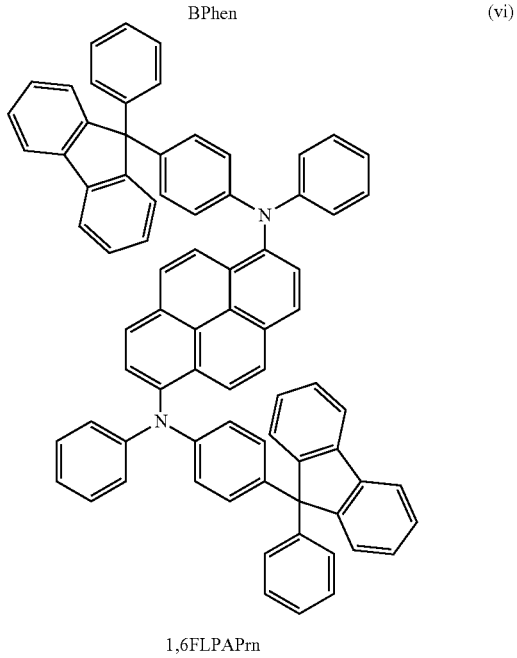

1,6FLPAPrn (vi)

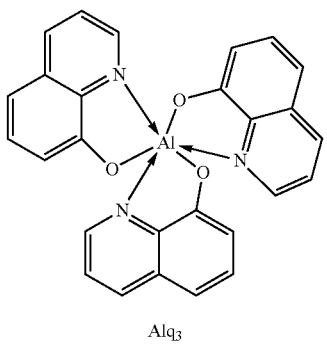

Alq$_3$ (vii)

In the element structure in FIG. 1A, an electron-injection layer is provided between an electron-transport layer 114 and a second electrode 104.

[Fabrication of Light-Emitting Element 18]

First, a glass substrate 101 over which indium tin oxide containing silicon (ITSO) with a thickness of 110 nm was fainted as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 9-[4-(9-phenylcarbazol-3-yl)]phenyl-10-phenylanthracene (abbreviation: PCzPA) represented by the above structural formula (v) and molybdenum(VI) oxide such that the ratio of PCzPA:molybdenum(VI) oxide was 2:1 (weight ratio). The thickness of was the layer was set to 50 nm Note that the co-evaporation is an evaporation method in which a plurality of different substances is concurrently vaporized from the respective different evaporation sources.

Next, PCzPA was evaporated to a thickness of 10 nm, so that the hole-transport layer 112 was formed.

Further, the light-emitting layer 113 was formed on the hole-transport layer 112 in such a way that 3-(dibenzothiophen-4-yl)-9-[3-(9,10-diphenyl-2-anthryl)phenyl]-9H-carbazole (abbreviation: 2mDBTCzPPA-II) represented by the above structural formula (18) and N,N'-bis[4-(9-phenyl-9H-fluoren-9-yl)phenyl]-N,N'-diphenyl-pyrene-1,6-diamine (abbreviation: 1,6FLPAPrn) represented by the structural formula (vi) were evaporated to form a 30-nm-thick film so that the ratio of 2mDBTCzPPA-II to 1,6FLPAPrn was 1:0.03 (weight ratio).

Next, on the light-emitting layer 113, tris(8-quinolinolato) aluminum(III) (abbreviation: Alq) represented by the above structural formula (vii) was evaporated to a thickness of 10 nm, and then bathophenanthroline (abbreviation: BPhen) represented by the above structural formula (iv) was evaporated to a thickness of 15 nm, so that the electron-transport layer 114 was formed. Then, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 18 was completed. Note that in the above evaporation processes, evaporation was all performed by a resistance heating method.

[Operation Characteristics of Light-Emitting Element 18]

The light-emitting element 18 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 142:
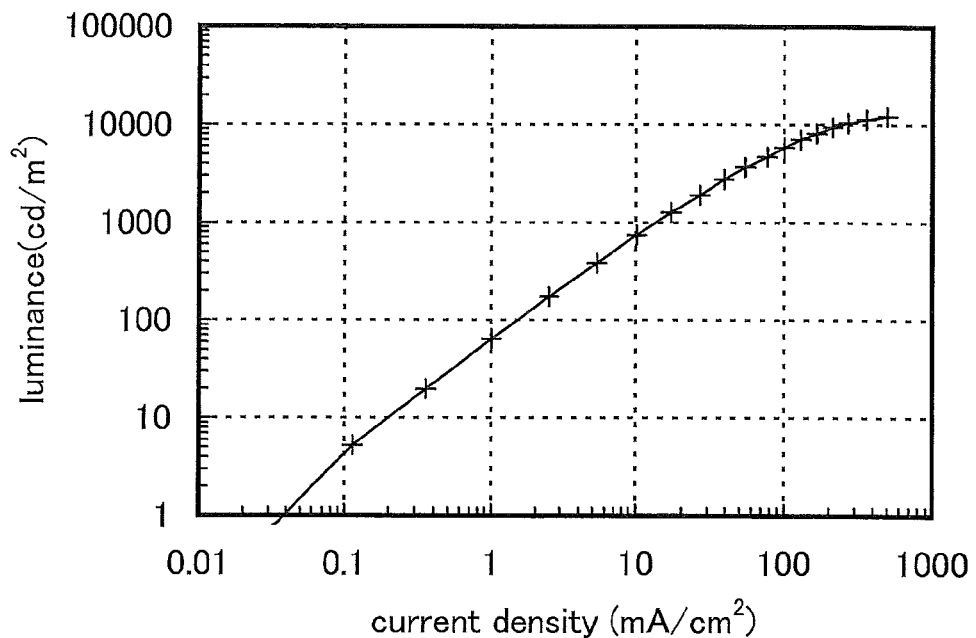
FIG. 142 shows luminance versus current density characteristics of a light-emitting element 18.
Figure 143:
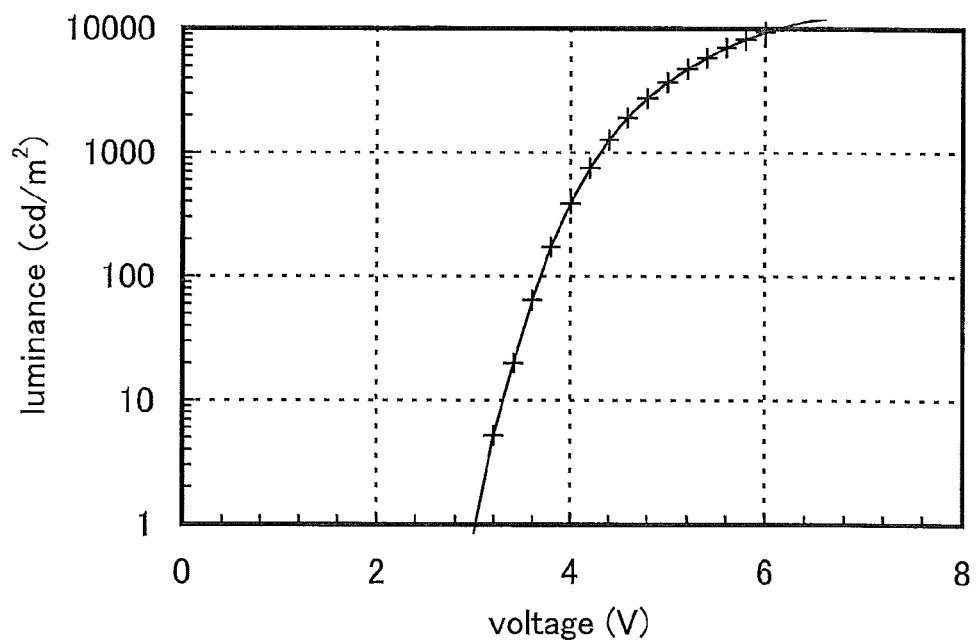
FIG. 143 shows luminance versus voltage characteristics of the light-emitting element 18.
Figure 144:
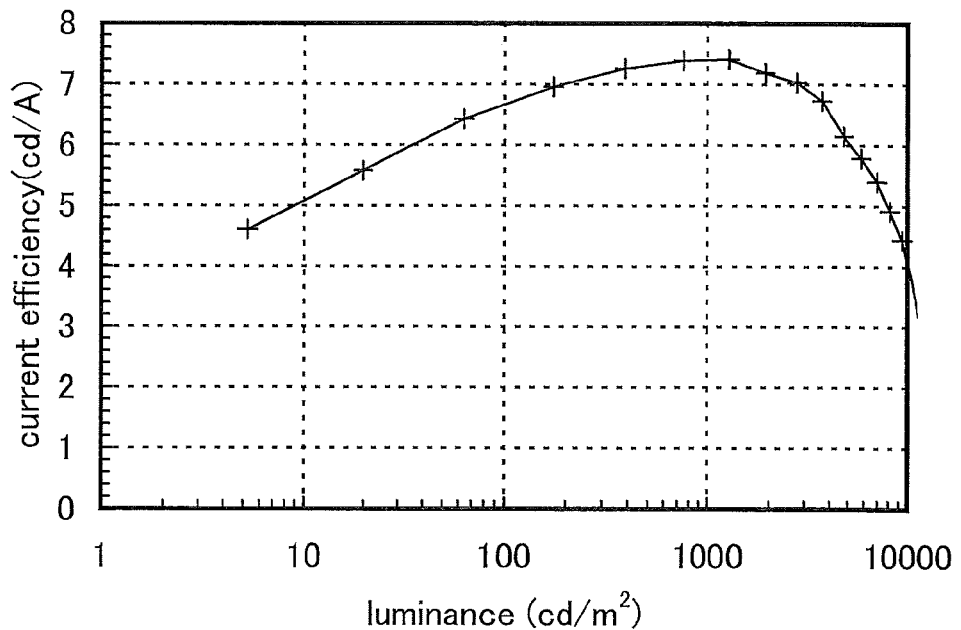
FIG. 144 shows current efficiency versus luminance characteristics of the light-emitting element 18.
Figure 145:
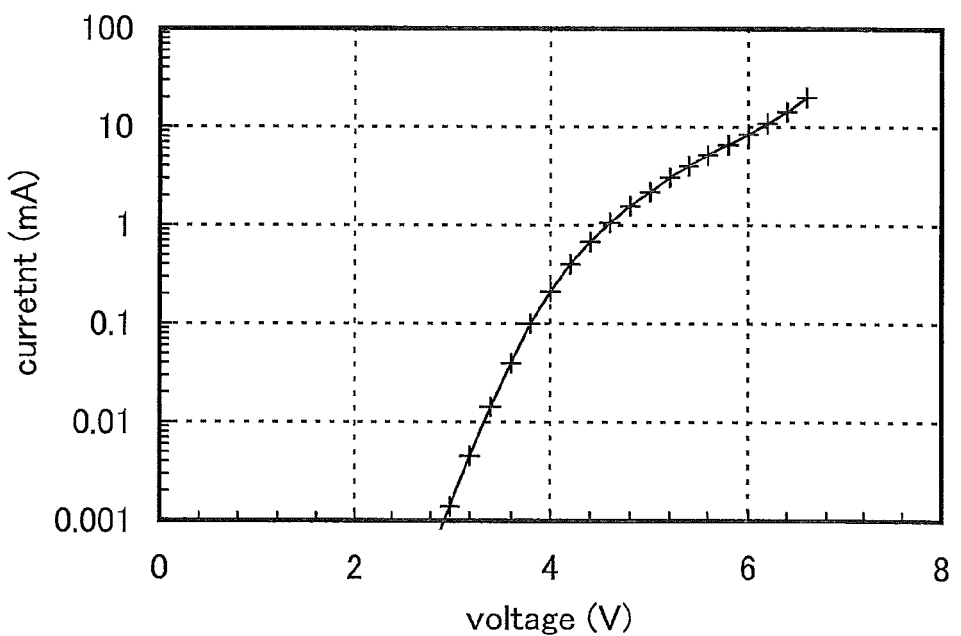
FIG. 145 shows current versus voltage characteristics of the light-emitting element 18.

FIG. 142 shows luminance current density characteristics of the light-emitting element 18, FIG. 143 shows luminance versus voltage characteristics thereof, FIG. 144 shows current efficiency versus luminance characteristics thereof, and FIG. 145 shows current versus voltage characteristics thereof. In FIG. 142, the vertical axis represents luminance ($cd/m^2$), and the horizontal axis represents current density ($mA/cm^2$). In FIG. 143, the vertical axis represents luminance ($cd/m^2$), and the horizontal axis represents voltage (V). In FIG. 144, the vertical axis represents current efficiency (cd/A), and the horizontal axis represents luminance ($cd/m^2$). In FIG. 145, the vertical axis represents current (mA), and the horizontal axis represents voltage (V).

FIG. 144 reveals that the light-emitting elements in each of which the carbazole derivative represented by the general formula (G1) is used as a host material of a light-emitting layer for emitting blue fluorescence, has favorable current efficiency versus luminance characteristics and high emission efficiency. This is because each carbazole derivative represented by the general formula (G1) has a wide energy gap, and thus even a light-emitting substance that emits blue fluorescence and has a wide energy gap can be efficiently excited. In addition, FIG. 143 reveals that the light-emitting elements in each of which the carbazole derivative represented by the general formula (G1) is used as a host material of a light-emitting layer for emitting blue fluorescence, has favorable luminance versus voltage characteristics and can be driven with a low voltage. This indicates that each carbazole derivative represented by the general formula (G1) has an excellent carrier-transport property.

Figure 146:
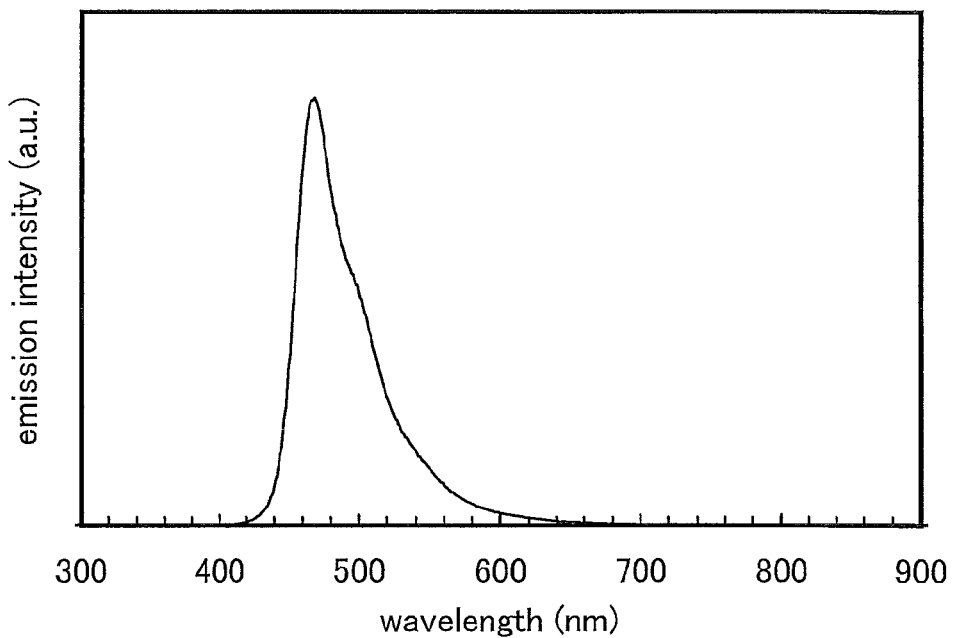
FIG. 146 shows an emission spectrum of the light-emitting element 18.

FIG. 146 shows an emission spectrum when a current of 1 mA was made to flow in the fabricated light-emitting element 18. The emission intensity is shown as a value relative to the greatest emission intensity assumed to be 1. FIG. 146 reveals that the light-emitting element 18 emits blue light due to 1,6FLPAPrn, which is the emission center substance.

Figure 147:
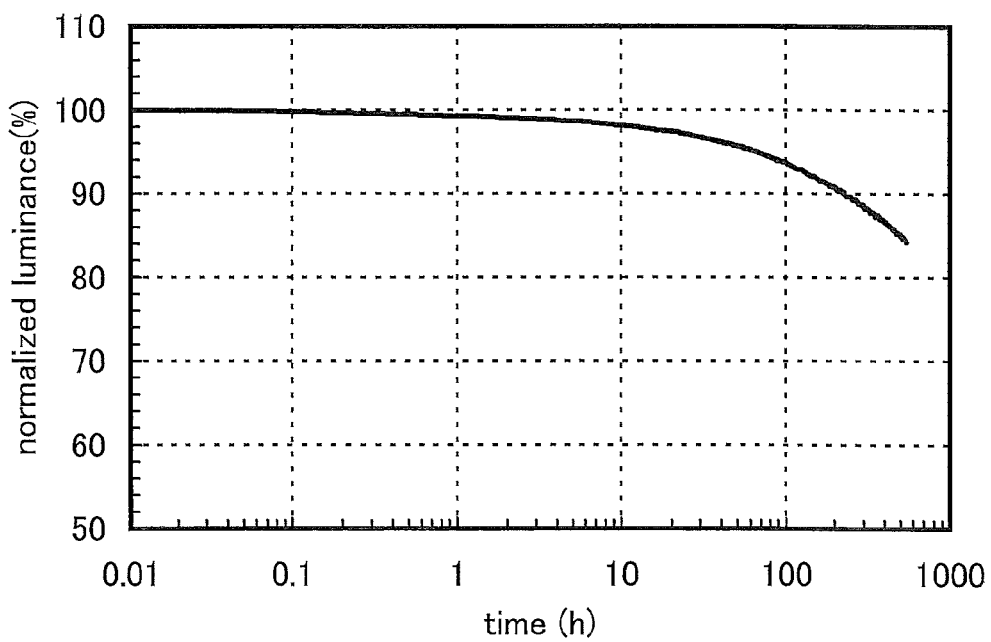
FIG. 147 shows normalized luminance versus time characteristics of the light-emitting element 18.

Next, the initial luminance is set at 1000 $cd/m^2$, the element was driven under a condition where the current density was constant, and changes in luminance with respect to the driving time were examined. FIG. 147 shows normalized luminance versus time characteristics. From FIG. 147, it is found that the light-emitting element 18 shows favorable characteristics and has high reliability.

Example 31

Synthesis Example 17

In this example is described a method of synthesizing 3-(dibenzofuran-4-yl)-9-[3-(9,10-diphenyl-2-anthryl)phenyl]-9H-carbazole (abbreviation: 2mDBFCzPPA-II), which is one of the carbazole derivatives described as the structural formula (19) in Embodiment 1. A structure of 2mDBFCzPPA-II is illustrated in the following structural formula.

(19)

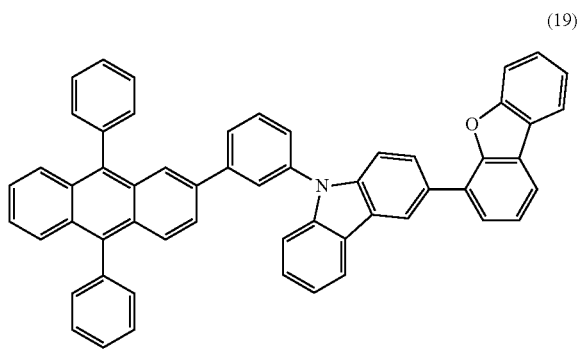 [SMILES: c1ccc(-c2c3ccccc3c(-c3ccccc3)c3cc(-c4cccc(-n5c6ccccc6c6cc(-c7cccc8c7oc7ccccc78)ccc65)c4)ccc23)cc1]

Step 1: Synthesis of
3-(Dibenzofuran-4-yl)-9H-carbazole (abbreviation: DBFCz-II)

This was synthesized as in Step 1 in Synthesis Example 2.

Step 2: Synthesis of 3-(Dibenzofuran-4-yl)-9-[3-(9,10-diphenyl-2-anthryl)phenyl]-9H-carbazole (abbreviation: 2mDBFCzPPA-II)

In a 100-mL three-neck flask were put 1.0 g (2.1 mmol) of 2-(3-bromophenyl)-9,10-diphenylanthracene, 0.69 g (2.1 mmol) of 3-(dibenzofuran-4-yl)-9H-carbazole, and 0.59 g (6.2 mmol) of sodium tert-butoxide. After the air in the flask was replaced with nitrogen, to this mixture were added 20 mL of toluene and 0.2 mL of tri(tert-butyl)phosphine (a 10 wt % hexane solution). This mixture was degassed by being stirred while the pressure was reduced. After the degassing, 59 mg (0.10 mmol) of bis(dibenzylideneacetone)palladium(0) was added to this mixture. This mixture was stirred at 110° C. for 5 hours under a nitrogen stream. After the stirring, the obtained mixture was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The filtrate was concentrated to give a yellow solid. The obtained solid was recrystallized from toluene, and the obtained crystal was purified by high performance liquid column chromatography (abbreviation: HPLC) (chloroform as the developing solvent). The obtained fraction was concentrated to give 0.91 g of a pale yellow solid in 60% yield. The synthesis scheme of Step 2 is illustrated in (b-17).

(b-17)

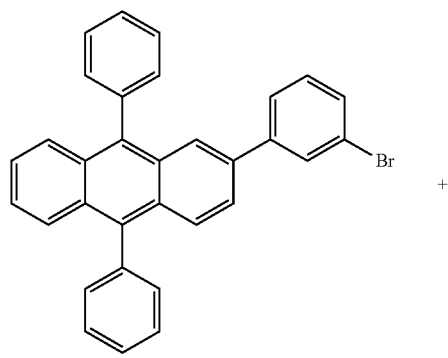

+

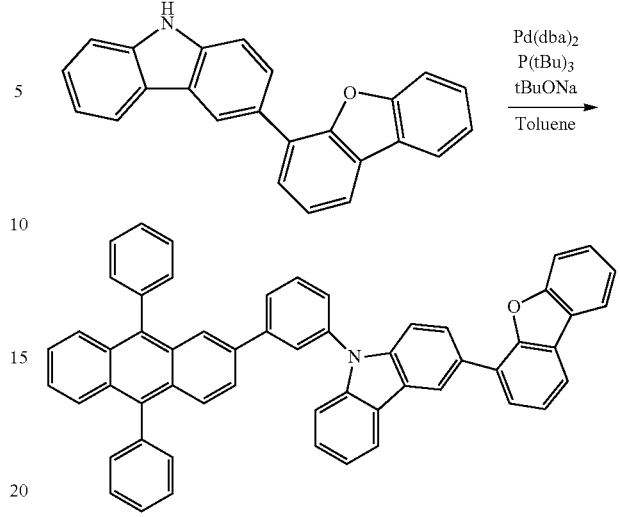

By a train sublimation method, the obtained pale yellow solid was purified. The purification was conducted by heating of 0.90 g of the pale yellow solid at 335° C. under a pressure of 2.7 Pa with a flow rate of argon gas of 5 mL/min. After the purification, 0.78 g of a pale yellow solid was obtained in a yield of 87%.

The yellow solid after the above purification was subjected to nuclear magnetic resonance (NMR) spectroscopy. The measurement data are shown below.

$^1$H NMR (CDCl$_3$, 300 MHz): δ=7.30-7.41 (m, 4H), 7.44-7.76 (m, 23H), 7.81-7.85 (m, 2H), 7.95-8.05 (m, 4H), 8.25 (d, $J_1$=7.5 Hz, 1H), 8.66 (d, $J_1$=1.5 Hz, 1H)

Figure 148A:
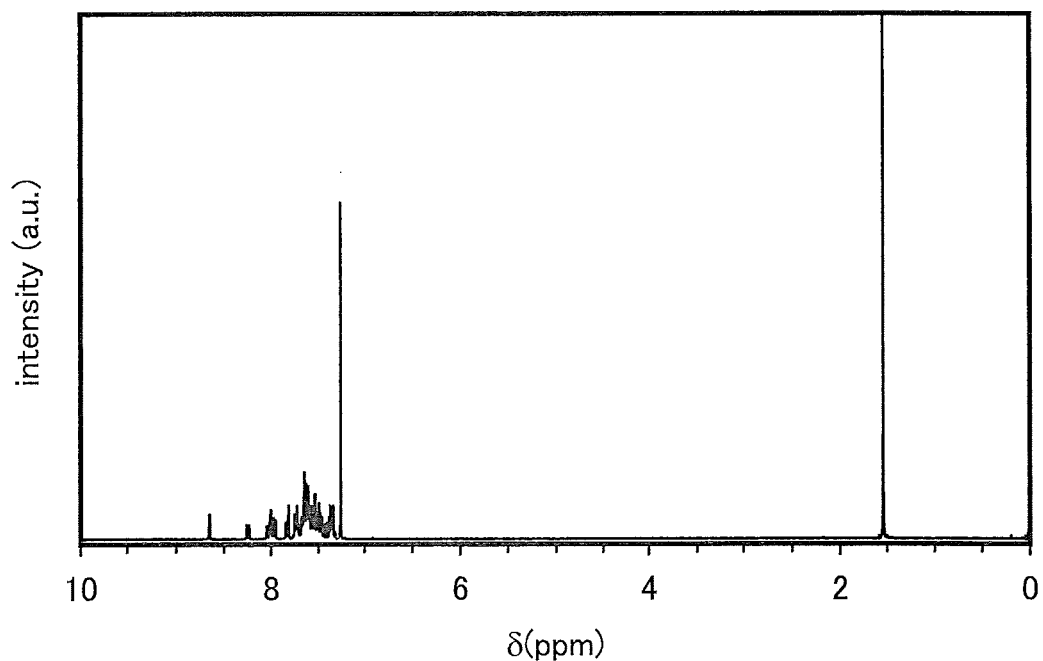
FIGS. 148A and 148B are NMR charts of 2mDBFCzPPA-II.
Figure 148B:
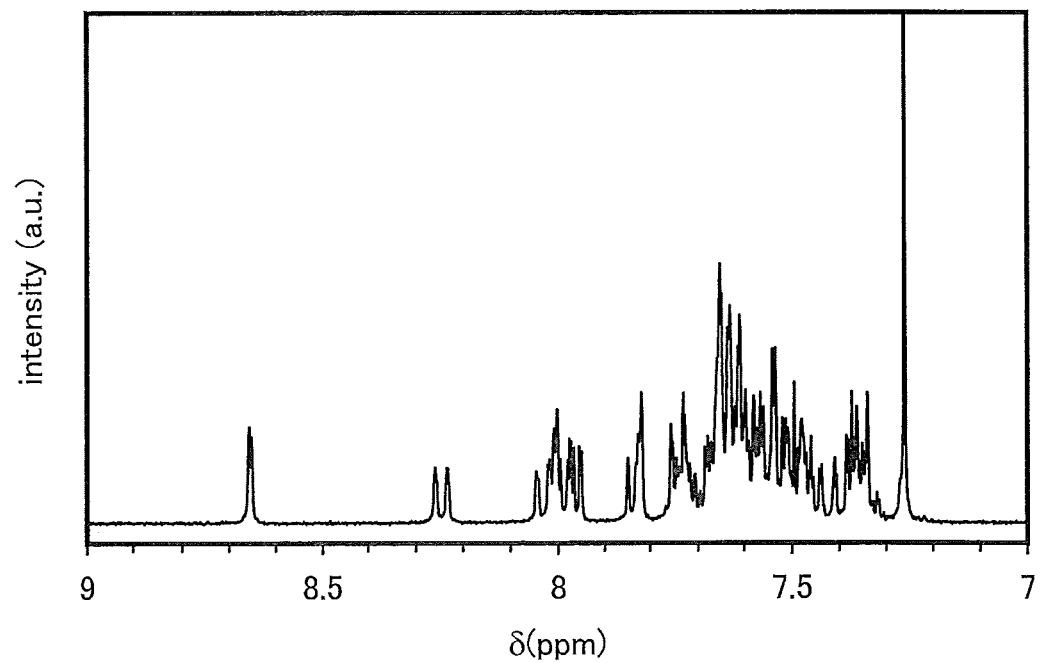

In addition, $^1$H NMR charts are shown in FIGS. 148A and 148B. Note that FIG. 148B is a chart where the range of from 7 ppm to 9 ppm in FIG. 148A is enlarged. The measurement results showed that 2mDBFCzPPA-II, which is the carbazole derivative represented by the above structural formula, was obtained.

Figure 149A:
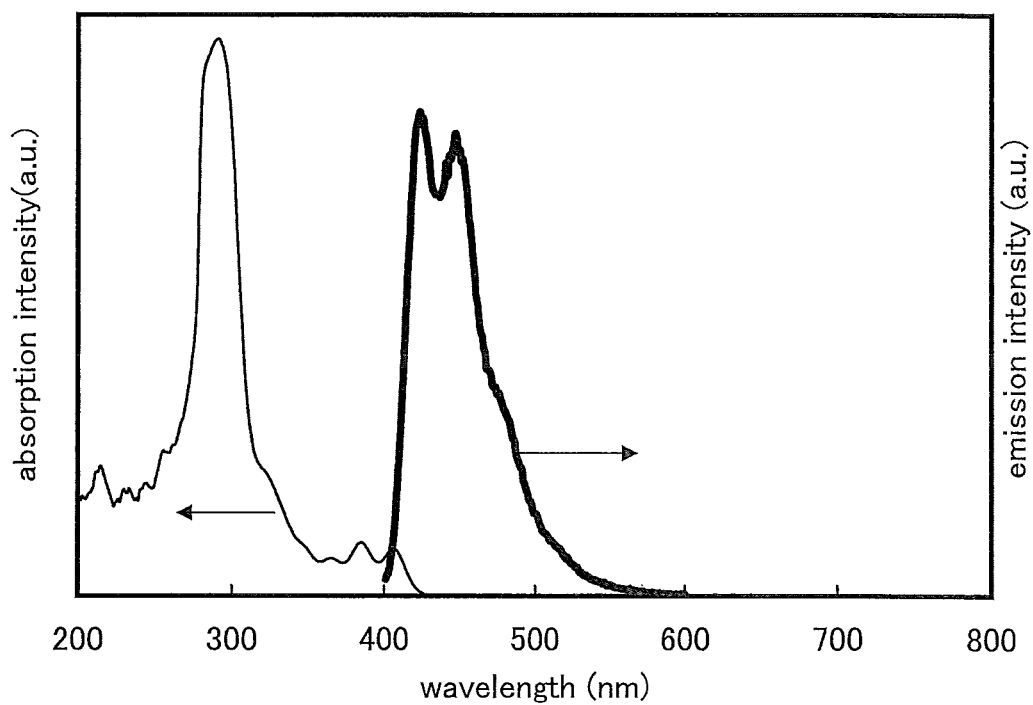
FIGS. 149A and 149B show an absorption and emission spectra of 2mDBFCzPPA-II.
Figure 149B:
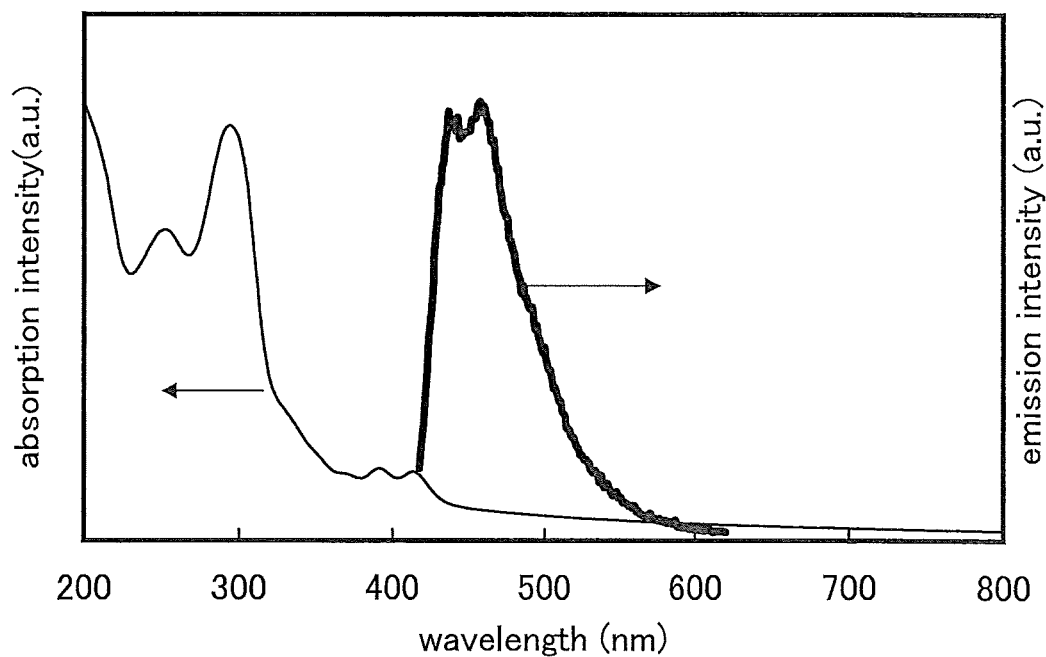

Further, an absorption and emission spectra of 2mDBFCzPPA-II in a toluene solution of 2mDBFCzPPA-II are shown in FIG. 149A, and an absorption and emission spectra of a thin film of 2mDBFCzPPA-II are shown in FIG. 149B. An ultraviolet-visible spectrophotometer (V-550, manufactured by JASCO Corporation) was used for the measurements of the absorption spectra. In the case of the toluene solution, the measurements were made with the toluene solution of 2mDBFCzPPA-II put in a quartz cell, and the absorption spectrum obtained by subtraction of the absorption spectra of the quartz cell and toluene from the measured spectra is shown in the drawing. In addition, as for the absorption spectrum of the thin film, a sample was prepared by evaporation of 2mDBFCzPPA-II on a quartz substrate, and the absorption spectrum obtained by subtraction of that of quartz from the spectrum of this sample is shown in the drawing. As in the measurements of the absorption spectra, an ultraviolet-visible spectrophotometer (V-550, manufactured by JASCO Corporation) was used for the measurements of the emission spectra. The emission spectrum was measured with the toluene solution of 2mDBFCzPPA-II put in a quartz cell, and the emission spectrum of the thin film was measured with a sample prepared by evaporation of 2mDBFCzPPA-II on a quartz substrate. Thus, it was found that the absorption peak wavelengths of 2mDBFCzPPA-II in the toluene solution of 2mDBFCzPPA-II were around 406 nm, 385 nm, 365 nm and 291 nm and the emission peak wavelengths thereof were around 436 nm and 424 nm (at an excitation wavelength of 386 nm), and that the absorption peak wavelengths of the thin film of 2mDBFCzPPA-II were around 414 nm, 391 nm, 369 nm, 328 nm, 294 nm and 252 nm and the emission peak wavelengths thereof were around 488 nm, 457 nm and 438 nm (at an excitation wavelength of 413 nm).

Further, the ionization potential of 2mDBFCzPPA-II in a thin film state was measured by a photoelectron spectrometer (AC-2, manufactured by Riken Keiki, Co., Ltd.) in air. The obtained value of the ionization potential was converted to a negative value, so that the HOMO level of 2mDBFCzPPA-II was −5.75 eV. From the data of the absorption spectra of the thin film in FIG. 149B, the absorption edge of 2mDBFCz-PPA-II, which was obtained from Tauc plot with an assumption of direct transition, was 2.84 eV. Therefore, the optical energy gap of 2mDBFCzPPA-II in the solid state was estimated at 2.84 eV; from the values of the HOMO level obtained above and this energy gap, the LUMO level of 2mDBFCzPPA-II was able to be estimated at −2.91 eV. It was thus found that 2mDBFCzPPA-II had a wide energy gap of 2.84 eV in the solid state.

Further, the oxidation reaction characteristics of 2mDBFCzPPA-II were measured. The oxidation reaction characteristics were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20° C. to 25° C.). The scan rates for the CV measurements were uniformly set to 0.1 V/s.

In the measurements, scanning in which the potential of the working electrode with respect to the reference electrode was changed from −0.41 V to 1.05 V and then changed from 1.05 V to −1.41 V was one cycle, and 100 cycles were performed.

The measurement results revealed that 2mDBFCzPPA-II showed properties effective against repetition of redox reactions between an oxidized state and a neutral state without a large variation in oxidation peak even after the 100 cycles in the measurements.

Further, the HOMO level of 2mDBFCzPPA-II was determined also by calculation from the CV measurement results.

First, the potential energy of the reference electrode with respect to the vacuum level used was found to be −4.94 eV, as determined in Example 6. The oxidation peak potential $E_{pa}$ of 2mDBFCzPPA-II was 0.93 V. In addition, the reduction peak potential $E_{pc}$ thereof was 0.82 V. Therefore, a half-wave potential (an intermediate potential between $E_{pa}$ and $E_{pc}$) can be calculated at 0.88 V. This means that 2mDBFCzPPA-II is oxidized by an electric energy of 0.88 [V versus Ag/Ag$^+$], and this energy corresponds to the HOMO level. Here, since the potential energy of the reference electrode, which was used in this example, with respect to the vacuum level is −4.94 [eV] as described above, the HOMO level of 2mDBFCzPPA-II was calculated as follows: −4.94−0.88=−5.82 [eV].

Example 32

In this example described is a light-emitting element in which 3-(dibenzofuran-4-yl)-9-[3-(9,10-diphenyl-2-anthryl)phenyl]-9H-carbazole (abbreviation: 2mDBFCzPPA-II, a structural formula (19)), which is one of the carbazole derivatives represented by the general formula (G1), is used as a host material such that an emission center substance that emits blue fluorescence is dispersed therein.

The molecular structures of organic compounds used in this example are represented by the structural formulae (19), (iv), and (iv) below.

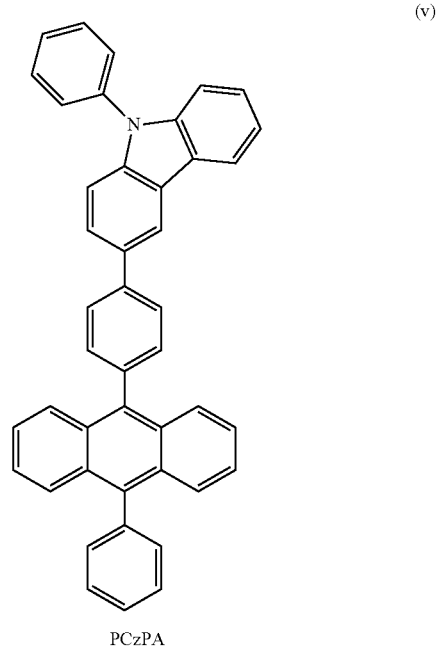

PCzPA

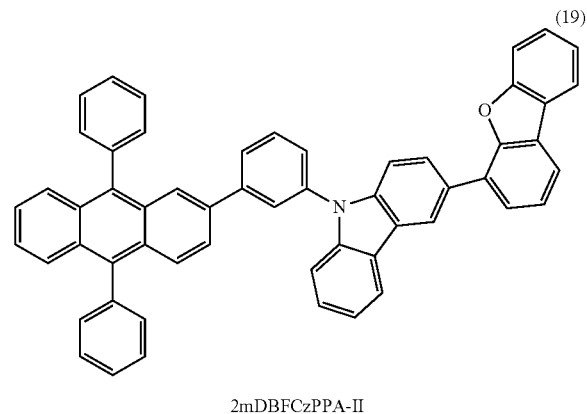

2mDBFCzPPA-II

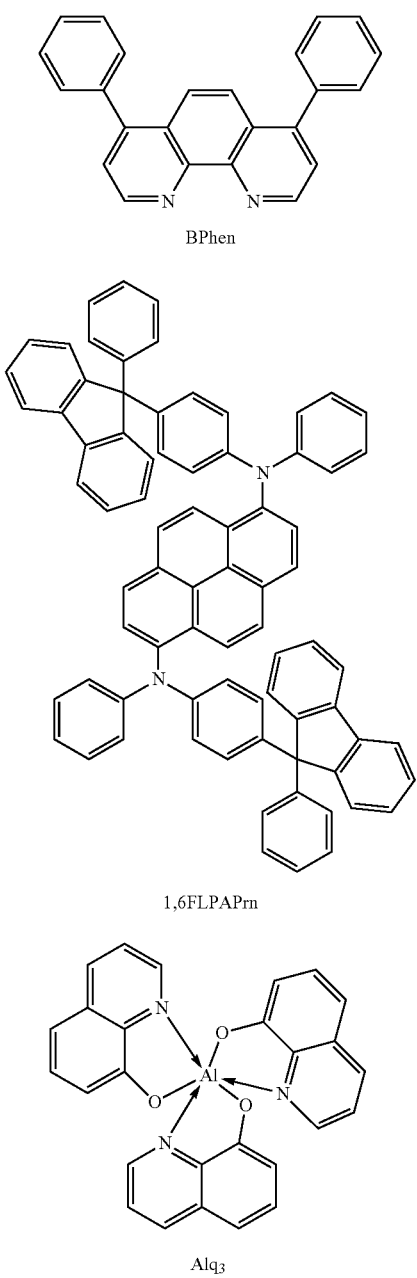

(iv) BPhen
(vi) 1,6FLPAPrn
(vii) Alq₃

In the element structure in FIG. 1A, an electron-injection layer is provided between an electron-transport layer 114 and a second electrode 104.

[Fabrication of Light-Emitting Element 19]

First, a glass substrate 101 over which indium tin oxide containing silicon (ITSO) with a thickness of 110 nm was formed as a first electrode 102 was prepared. The periphery of a surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 9-[4-(9-phenylcarbazol-3-yl)]phenyl-10-phenylanthracene (abbreviation: PCzPA) represented by the above structural formula (v) and molybdenum(VI) oxide such that the ratio of PCzPA:molybdenum(VI) oxide was 2:1 (weight ratio). The thickness of was the layer was set to 50 nm Note that the co-evaporation is an evaporation method in which a plurality of different substances is concurrently vaporized from the respective different evaporation sources.

Next, PCzPA was evaporated to a thickness of 10 nm, so that the hole-transport layer 112 was formed.

Further, the light-emitting layer 113 was formed on the hole-transport layer 112 in such a way that 3-(dibenzofuran-4-yl)-9-[3-(9,10-diphenyl-2-anthryl)phenyl]-9H-carbazole (abbreviation: 2mDBFCzPPA-II) represented by the above structural formula (19) and N,N'-bis[4-(9-phenyl-9H-fluoren-9-yl)phenyl]-N,N'-diphenyl-pyrene-1,6-diamine (abbreviation: 1,6FLPAPrn) represented by the structural formula (vi) were evaporated to form a 30-nm-thick film so that the ratio of 2mDBFCzPPA-II to 1,6FLPAPrn was 1:0.05 (weight ratio).

Next, on the light-emitting layer 113, tris(8-quinolinolato) aluminum(III) (abbreviation: Alq) represented by the above structural formula (vii) was evaporated to a thickness of 10 nm, and then bathophenanthroline (abbreviation: BPhen) represented by the above structural formula (iv) was evaporated to a thickness of 15 nm, so that the electron-transport layer 114 was formed. Then, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 19 was completed. Note that in the above evaporation processes, evaporation was all performed by a resistance heating method.

[Operation Characteristics of Light-Emitting Element 19]

The light-emitting element 19 thus obtained was sealed in a glove box under a nitrogen atmosphere without being exposed to the air. Then, the operation characteristics of the light-emitting element were measured. Note that the measurements were carried out at room temperature (in an atmosphere kept at 25° C.).

Figure 150:
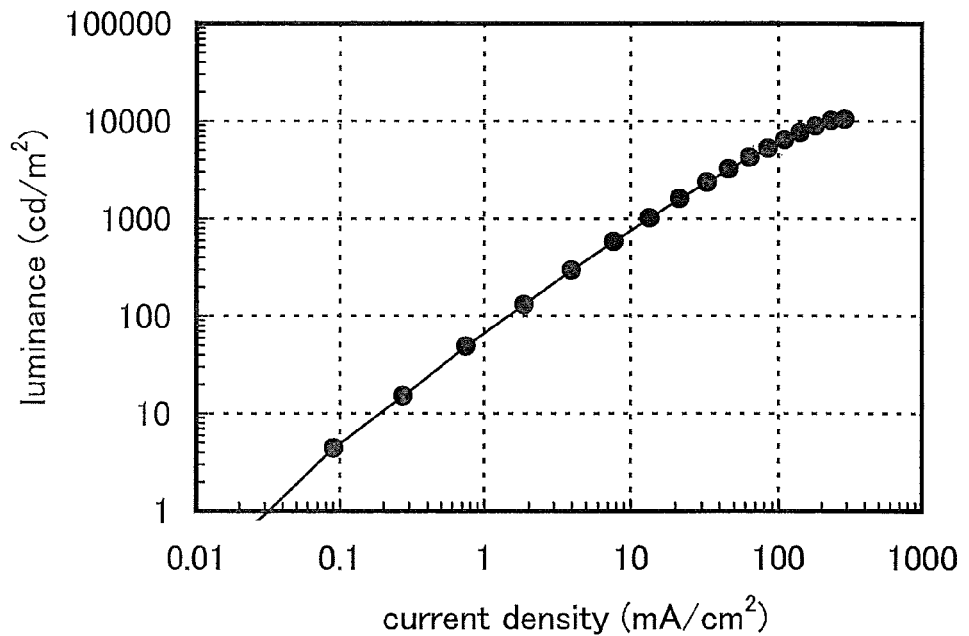
FIG. 150 shows luminance versus current density characteristics of a light-emitting element 19.
Figure 151:
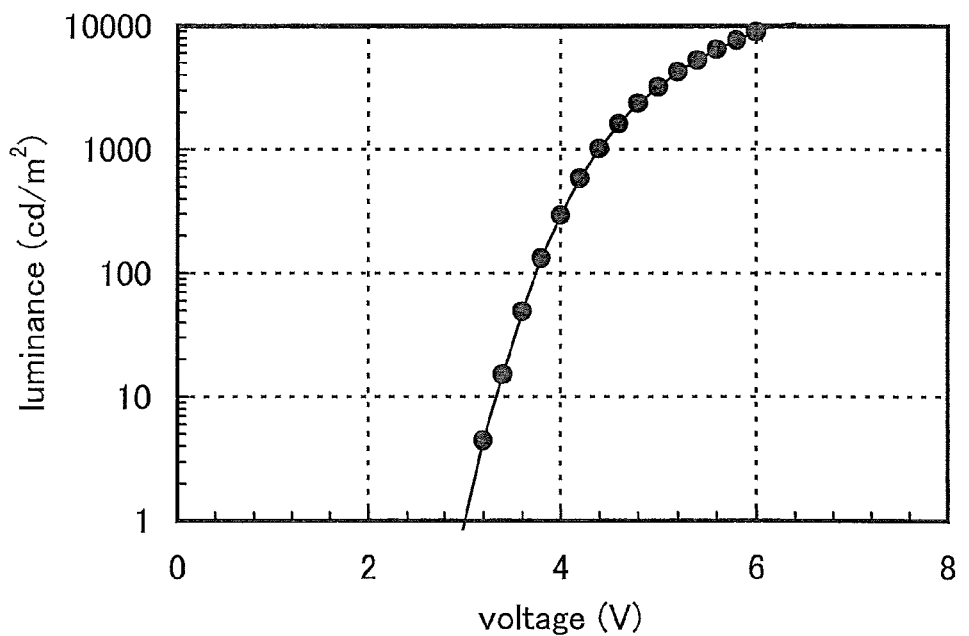
FIG. 151 shows luminance versus voltage characteristics of the light-emitting element 19.
Figure 152:
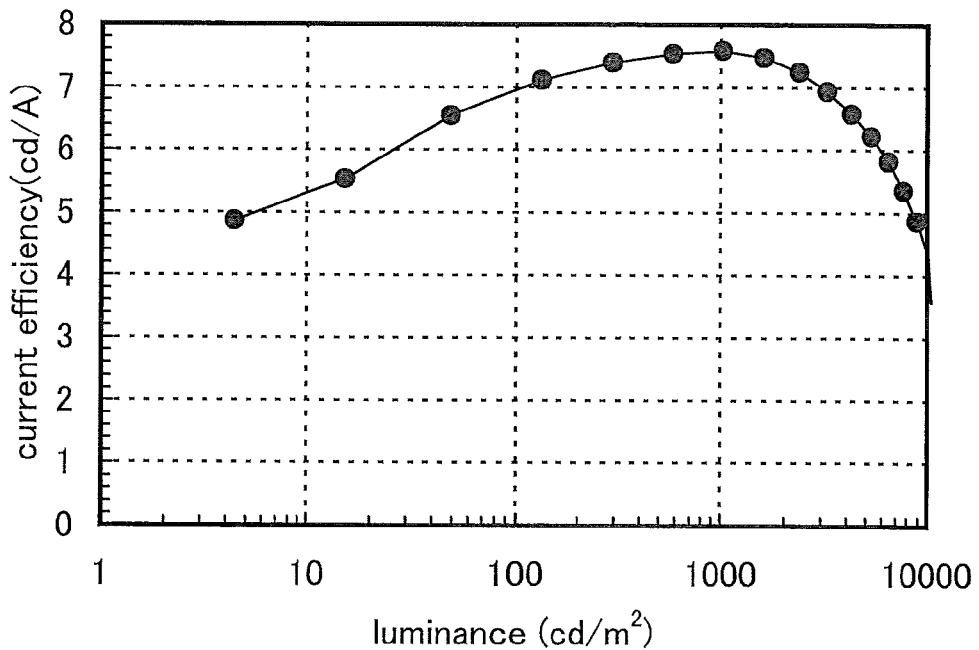
FIG. 152 shows current efficiency versus luminance characteristics of the light-emitting element 19.
Figure 153:
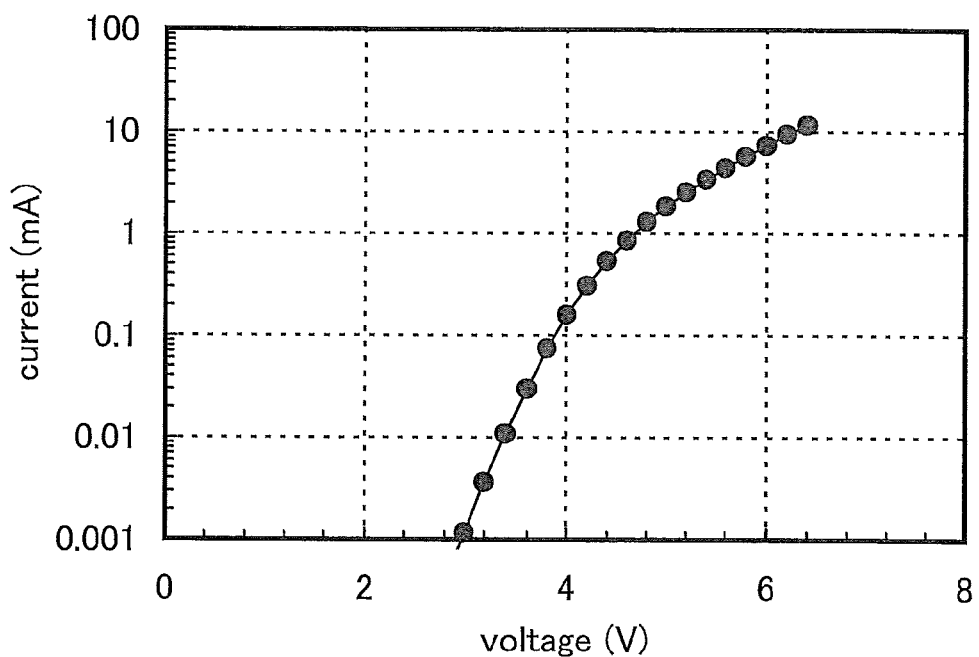
FIG. 153 shows current versus voltage characteristics of the light-emitting element 19.

FIG. 150 shows luminance current density characteristics of the light-emitting element 19, FIG. 151 shows luminance versus voltage characteristics thereof, FIG. 152 shows current efficiency versus luminance characteristics thereof, and FIG. 153 shows current versus voltage characteristics thereof. In FIG. 150, the vertical axis represents luminance (cd/m²), and the horizontal axis represents current density (mA/cm²). In FIG. 151, the vertical axis represents luminance (cd/m²), and the horizontal axis represents voltage (V). In FIG. 152, the vertical axis represents current efficiency (cd/A), and the horizontal axis represents luminance (cd/m²). In FIG. 153, the vertical axis represents current (mA), and the horizontal axis represents voltage (V).

FIG. 152 reveals that the light-emitting elements in each of which the carbazole derivative represented by the general formula (G1) is used as a host material of a light-emitting layer for emitting blue fluorescence, has favorable current efficiency versus luminance characteristics and high emission efficiency. This is because each carbazole derivative represented by the general formula (G1) has a wide energy gap, and thus even a light-emitting substance that emits blue fluorescence and has a wide energy gap can be efficiently excited. In addition, FIG. 151 reveals that the light-emitting elements in each of which the carbazole derivative represented by the general formula (G1) is used as a host material of a light-emitting layer for emitting blue fluorescence, has favorable luminance versus voltage characteristics and can be driven with a low voltage. This indicates that each carbazole derivative represented by the general formula (G1) has an excellent carrier-transport property.

Figure 154:
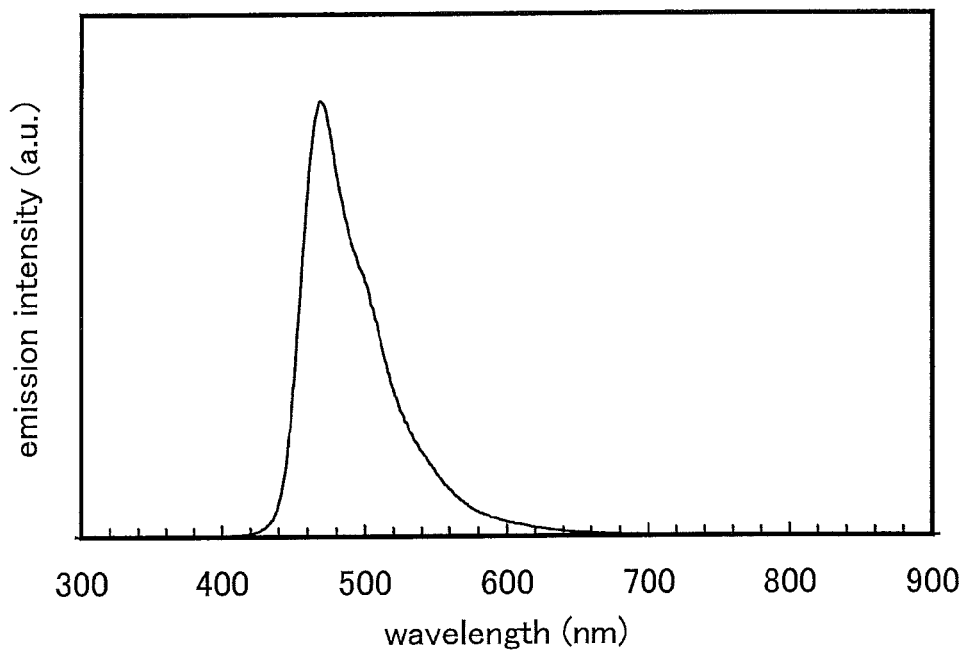

FIG. 154 shows an emission spectrum when a current of 1 mA was made to flow in the fabricated light-emitting element 19. The emission intensity is shown as a value relative to the greatest emission intensity assumed to be 1. FIG. 154 reveals that the light-emitting element 19 emits blue light due to 1,6FLPAPrn, which is the emission center substance.

Figure 155:
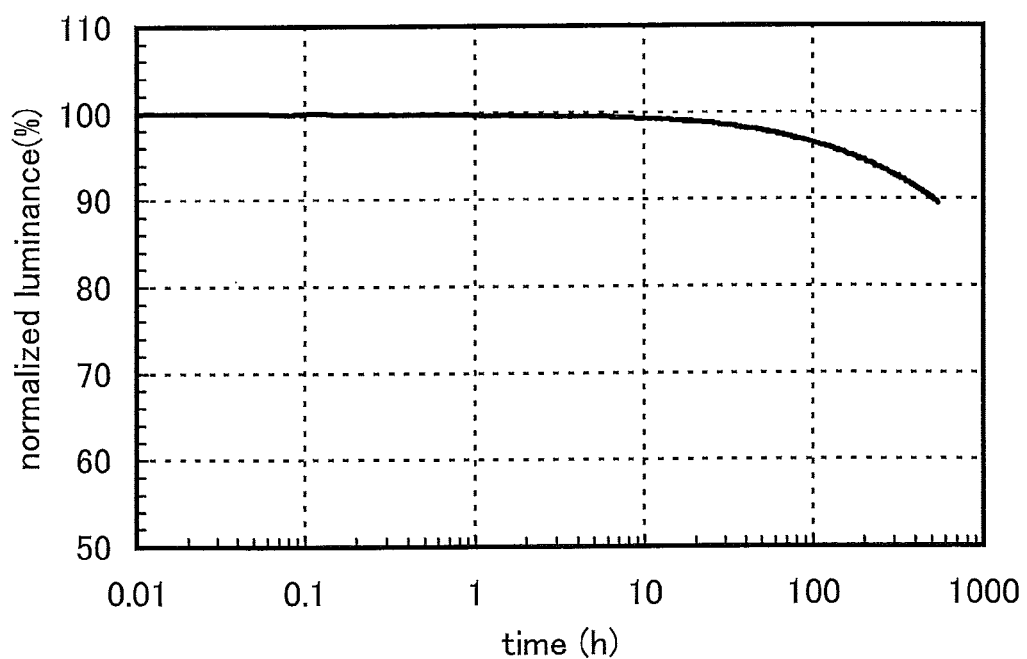

Next, the initial luminance is set at 1000 cd/m$^2$, the element was driven under a condition where the current density was constant, and changes in luminance with respect to the driving time were examined. FIG. 155 shows normalized luminance versus time characteristics. From FIG. 155, it is found that the light-emitting element 19 shows favorable characteristics and has high reliability Reference Example 1

A method of synthesizing 4-phenyl-4'-(9-phenylfluoren-9-yl)triphenylamine (abbreviation: BPAFLP) (structural formula (1)) used in the above Examples will be specifically described. A structure of BPAFLP is illustrated below.

(i)

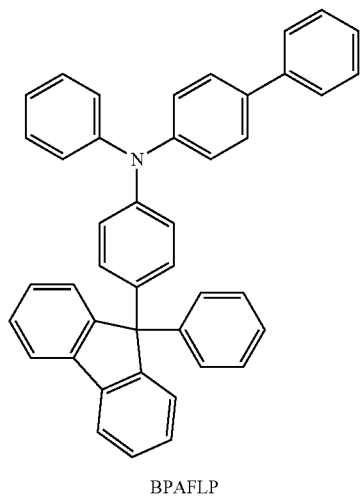

BPAFLP

Step 1: Method of Synthesizing
9-(4-Bromophenyl)-9-phenylfluorene

In a 100-mL three-neck flask, 1.2 g (50 mmol) of magnesium was heated and stirred for 30 minutes under reduced pressure to be activated. The activated magnesium was cooled to room temperature, and the flask was made to contain a nitrogen atmosphere. Then, several drops of dibromoethane were added, so that foam formation and heat generation were confirmed. After 12 g (50 mmol) of 2-bromobiphenyl dissolved in 10 mL of diethyl ether was slowly added dropwise to this mixture, the mixture was heated and stirred under reflux for 2.5 hours, so that a Grignard reagent was prepared.

Into a 500-mL three-neck flask were placed 10 g (40 mmol) of 4-bromobenzophenone and 100 mL of diethyl ether. After the Grignard reagent which was synthesized in advance was slowly added dropwise to this mixture, the mixture was heated and stirred under reflux for 9 hours.

After reaction, this mixture solution was filtered to give a residue. The obtained residue was dissolved in 150 mL of glacial acetic acid, and 1M hydrochloric acid was added to the mixture until it was made acid, which was then stirred for 2 hours. The organic layer of this mixture was washed with water, and magnesium sulfate was added thereto to adsorb moisture. This suspension was filtered, and the obtained filtrate was concentrated to give an oily substance.

Into a 500-mL recovery flask were placed this oily substance, 50 mL of glacial acetic acid, and 1.0 mL of hydrochloric acid. The mixture was stirred and heated at 130° C. for 1.5 hours under a nitrogen atmosphere to be reacted.

After the reaction, this reaction mixture solution was filtered to give a residue. The obtained residue was washed with water, an aqueous sodium hydroxide solution, water, and methanol in this order. Then, the mixture was dried, so that the substance which was the object of the synthesis was obtained as 11 g of a white powder in 69% yield. A reaction scheme of the above synthesis method is illustrated in the following (J-3).

(J-3)

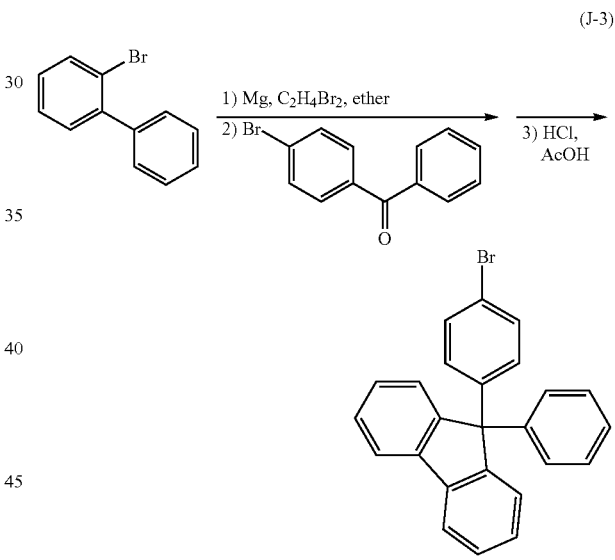

Step 2: Method of Synthesizing 4-Phenyl-4'-(9-phenylfluoren-9-yl)triphenylamine (abbreviation:
BPAFLP)

Into a 100-mL three-neck flask were placed 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the flask was replaced with nitrogen. Then, 20 mL of dehydrated xylene was added to this mixture. After the mixture was degassed by being stirred under reduced pressure, 0.2 mL (0.1 mmol) of tri(tert-butyl)phosphine (a 10 wt % hexane solution) was added to the mixture. This mixture was stirred and heated at 110° C. for 2 hours under a nitrogen atmosphere to be reacted.

After the reaction, 200 mL of toluene was added to this reaction mixture, and this suspension was filtered through Florisil (produced by Wako Pure Chemical Industries, Ltd., Catalog No. 540-00135) and Celite (produced by Wako Pure Chemical Industries, Ltd., Catalog No. 531-16855). The obtained filtrate was concentrated, and the resulting substance was purified by silica gel column chromatography (a developing solvent in which the toluene/hexane ratio was 1:4). The obtained fraction was concentrated, and acetone and methanol were added to the mixture. The mixture was irradiated with ultrasonic waves and then recrystallized, so that the substance which was the object of the synthesis was obtained as 4.1 g of a white powder in 92% yield. A reaction scheme of the above synthesis method is illustrated in the following (J-4).

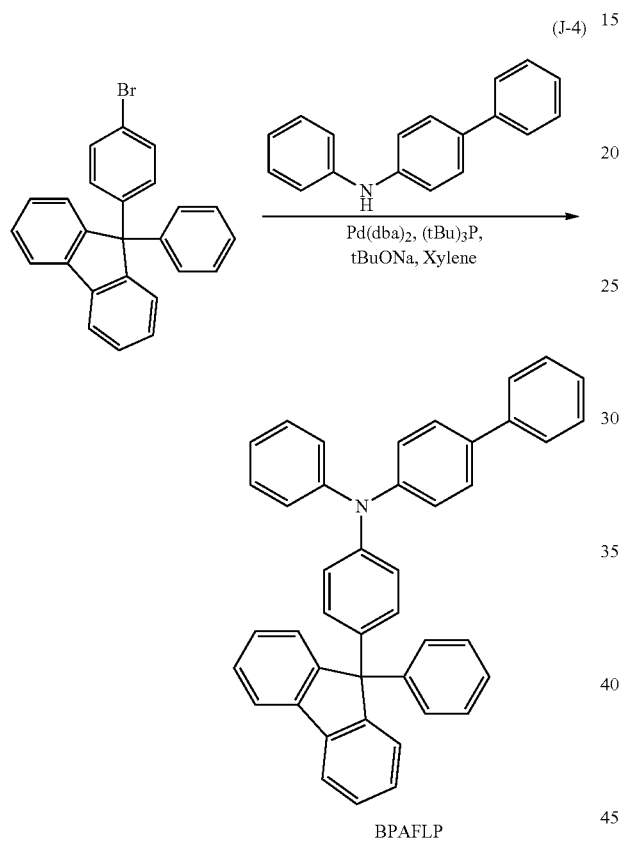

The Rf values of the substance that was the object of the synthesis, 9-(4-bromophenyl)-9-phenylfluorene, and 4-phenyl-diphenylamine were respectively 0.41, 0.51, and 0.27, which were found by silica gel thin layer chromatography (TLC) (a developing solvent in which the ethyl acetate/hexane ratio was 1:10).

The compound obtained in the above Step 2 was subjected to nuclear magnetic resonance (NMR) spectroscopy. The measurement data are shown below. The measurement results indicate that the obtained compound was BPAFLP, which is a fluorene derivative.

$^1$H NMR (CDCl$_3$, 300 MHz): δ (ppm)=6.63–7.02 (m, 3H), 7.06–7.11 (m, 6H), 7.19–7.45 (m, 18H), 7.53–7.55 (m, 2H), 7.75 (d, J=6.9, 2H).

Reference Example 2

A method of synthesizing N,N'-bis[4-(9-phenyl-9H-fluoren-9-yl)phenyl]-N,N'-diphenyl-pyrene-1,6-diamine (abbreviation: 1,6FLPAPrn) (structural formula (vi)) used in the above Examples will be specifically described. A structure of 1,6FLPAPrn is illustrated below.

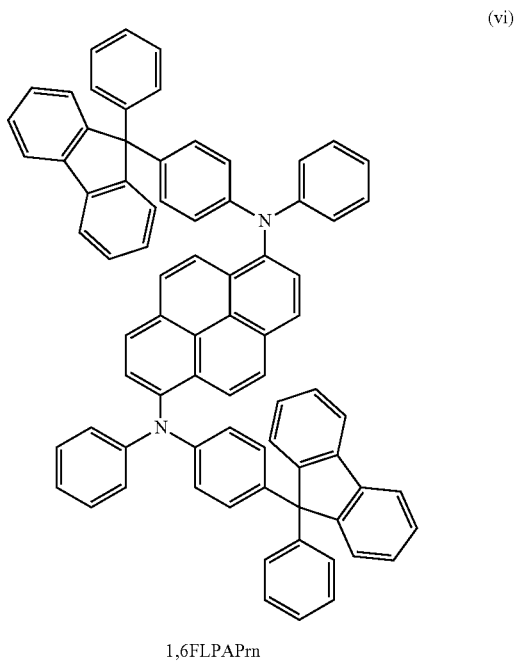 [SMILES: c1ccc(N(c2ccc(C3(c4ccccc4)c4ccccc4-c4ccccc43)cc2)c2ccc3ccc4c(N(c5ccccc5)c5ccc(C6(c7ccccc7)c7ccccc7-c7ccccc76)cc5)ccc5ccc2c3c54)cc1]

1,6FLPAPrn

Step 1: Method of Synthesizing 9-(4-Bromophenyl)-9-phenylfluorene

In a 100-mL three-neck flask, 1.2 g (50 mmol) of magnesium was heated and stirred for 30 minutes under reduced pressure to be activated. The activated magnesium was cooled to room temperature, and the flask was made to contain a nitrogen atmosphere. Then, several drops of dibromoethane were added, so that foam formation and heat generation were confirmed. After 12 g (50 mmol) of 2-bromobiphenyl dissolved in 10 mL of diethyl ether was slowly added dropwise to this mixture, the mixture was heated and stirred under reflux for 2.5 hours, so that a Grignard reagent was prepared.

Into a 500-mL three-neck flask were placed 10 g (40 mmol) of 4-bromobenzophenone and 100 mL of diethyl ether. After the Grignard reagent which was synthesized in advance was slowly added dropwise to this mixture, the mixture was heated and stirred under reflux for 9 hours.

After reaction, this mixture solution was filtered to give a residue. The obtained residue was dissolved in 150 mL of ethyl acetate, and 1M hydrochloric acid was added to the mixture, which was then stirred for 2 hours. The organic layer of this liquid was washed with water, and magnesium sulfate was added thereto to remove moisture. This suspension was filtered, and the obtained filtrate was concentrated to give an oily substance.

Into a 500-mL recovery flask were placed this oily substance, 50 mL of glacial acetic acid, and 1.0 mL of hydrochloric acid. The mixture was stirred and heated at 130° C. for 1.5 hours under a nitrogen atmosphere to be reacted.

After the reaction, this reaction mixture was filtered to give a residue. The obtained residue was washed with water, an aqueous sodium hydroxide solution, water, and methanol in this order. Then, the mixture was dried, so that the substance which was the object of the synthesis was obtained as 11 g of a white powder in 69% yield. The synthesis scheme of the above Step 1 is illustrated in (E1-1) below.

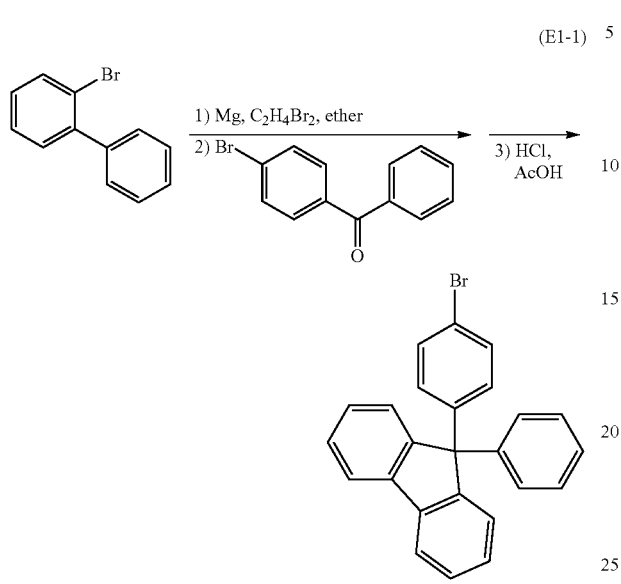

(E1-1)

Step 2: Method of Synthesizing 4-(9-Phenyl-9H-fluoren-9-yl)diphenylamine (abbreviation: FLPA)

In a 200 mL three-neck flask were put 5.8 g (14.6 mmol) of 9-(4-bromophenyl)-9-phenylfluorene, 1.7 mL (18.6 mmol) of aniline, and 4.2 g (44.0 mmol) of sodium tert-butoxide. The air in the flask was replaced with nitrogen. To this mixture were added 147.0 mL of toluene and 0.4 mL of a 10% hexane solution of tri(tert-butyl)phosphine. The temperature of this mixture was set to 60° C., and 66.1 mg (0.1 mmol) of bis(dibenzylideneacetone)palladium(0) was added to the mixture, followed by stirring for 3.5 hours. After the stirring, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina. The obtained filtrate was concentrated. The obtained filtrate was concentrated to give a solid, which was then purified by silica gel column chromatography (the developing solvent has a 2:1 ratio of hexane to toluene). The obtained fraction was concentrated to give 6.0 g of a white solid in 99% yield, which was the object of the synthesis. The synthesis scheme of Step 2 is shown in (E1-2) below.

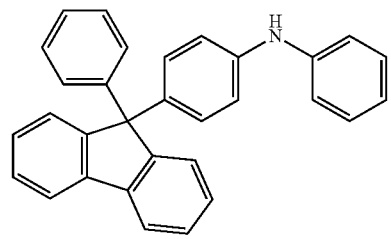

Step 3: Method of Synthesizing N,N'-Bis[4-(9-phenyl-9H-fluoren-9-yl)phenyl]-N,N'-diphenyl-pyrene-1,6-diamine (abbreviation: 1,6FLPAPrn)

In a 50 mL three-neck flask were put 0.4 g (1.2 mmol) of 1,6-dibromopyrene, 1.0 g (2.4 mmol) of 4-(9-phenyl-9H-fluoren-9-yl)diphenylamine (abbreviation: FLPA), which was obtained in Step 2 in Reference Example 2, and 0.3 g (3.6 mmol) of sodium tert-butoxide. The air in the flask was replaced with nitrogen. To this mixture were added 11.5 mL of toluene and 0.20 mL of a 10% hexane solution of tri(tert-butyl)phosphine. The temperature of this mixture was set to 70° C., and 31.1 mg (0.05 mmol) of bis(dibenzylideneacetone)palladium(0) was added to the mixture, followed by stirring for 4.0 hours. After the stirring, the mixture was suction-filtered through Florisil, Celite, and alumina. The obtained filtrate was concentrated. The obtained filtrate was concentrated to give a solid, which was then purified by silica gel column chromatography (the developing solvent was chloroform). The obtained fraction was concentrated to give a yellow solid. The obtained solid was washed with a mixed solvent of toluene and hexane, and then the mixture was suction-filtered to give a yellow solid. The obtained yellow solid was washed with a mixed solvent of chloroform and hexane, so that 0.8 g of a pale yellow powdered solid was obtained in 68% yield.

By a train sublimation method, 0.8 g of the obtained pale yellow solid was purified. Under a pressure of 2.7 Pa with a flow rate of argon at 5.0 mL/min, the sublimation purification was carried out at 360° C. After the purification, 0.4 g of the object of the synthesis was obtained in a yield of 56%. The synthesis scheme of the above Step 3 is shown in the following (E2-A).

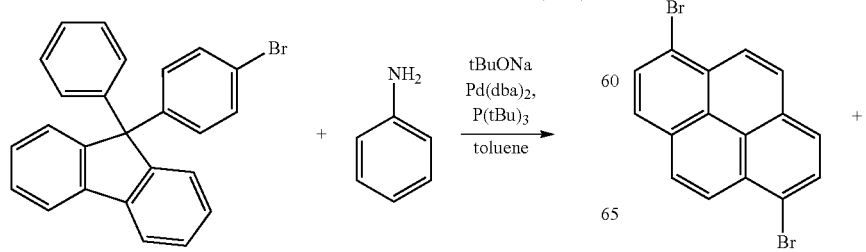

(E1-2)

(E2-A)

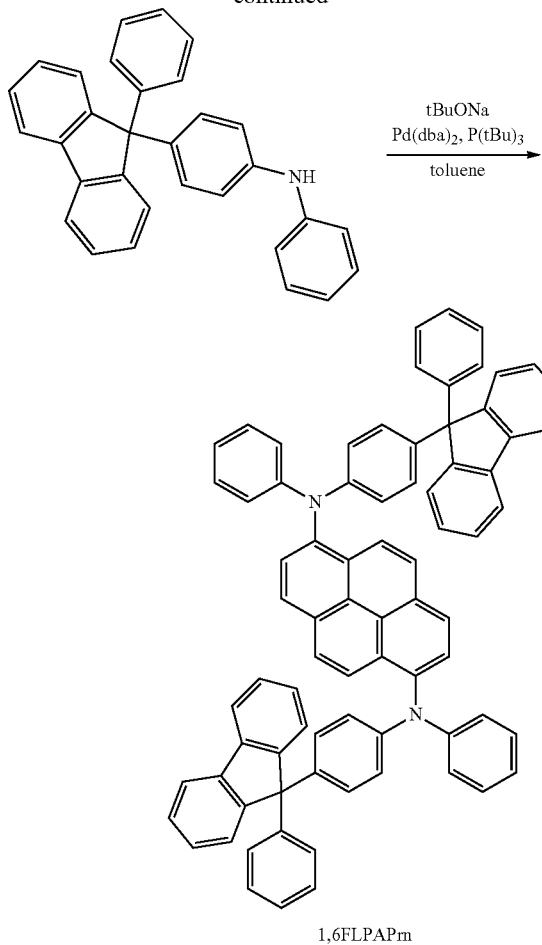

1,6FLPAPrn

A nuclear magnetic resonance (NMR) method and a mass spectrometry identified the obtained compound as N,N'-bis [4-(9-phenyl-9H-fluoren-9-yl)phenyl]-N,N'-diphenyl-pyrene-1,6-diamine (abbreviation: 1,6FLPAPrn). The $^1$H NMR data is given as follows.

$^1$H NMR data of the obtained compound are: $^1$H NMR (CDCl$_3$, 300 MHz): δ=6.88-6.91 (m, 6H), 7.00-7.03 (m, 8H), 7.13-7.40 (m, 26H), 7.73-7.80 (m, 6H), 7.87 (d, J=9.0 Hz, 2H), 8.06-8.09 (m, 4H).

Reference Example 3

In this reference example, a method of synthesizing N,N'-bis(3-methylphenyl)-N,N'-bis[3-(9-phenyl-9H-fluoren-9-yl) phenyl]-pyrene-1,6-diamine (abbreviation: 1,6mMemFLPA-Prn) used in the above Examples will be described.

Step 1: Method of Synthesizing 3-Methylphenyl-3-(9-phenyl-9H-fluoren-9-yl)phenylamine (abbreviation: mMemFLPA)

In a 200 mL three-neck flask were put 3.2 g (8.1 mmol) of 9-(3-bromophenyl)-9-phenylfluorene and 2.3 g (24.1 mmol) of sodium tert-butoxide. The air in the flask was replaced with nitrogen. To this mixture were added 40.0 mL of toluene, 0.9 mL (8.3 mmol) of m-toluidine, and 0.2 mL of a 10% hexane solution of tri(tert-butyl)phosphine. The temperature of this mixture was set to 60° C., and 44.5 mg (0.1 mmol) of bis (dibenzylideneacetone)palladium(0) was added to the mixture.

The temperature of the mixture was raised to 80° C., followed by stirring for 2.0 hours. After the stirring, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (the developing solvent has a 1:1 ratio of hexane to toluene). Recrystallization from a mixed solvent of toluene and hexane was performed. Accordingly, 2.8 g of a white solid was obtained in 82% yield, which was the object of the synthesis. The synthesis scheme of this Step 1 is illustrated below.

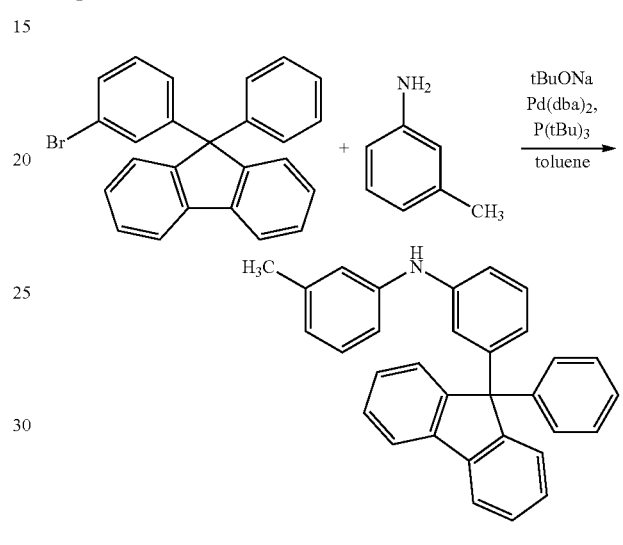

Step 2: Method of Synthesizing N,N'-Bis(3-methylphenyl)-N,N'-bis[3-(9-phenyl-9H-fluoren-9-yl) phenyl]-pyrene-1,6-diamine (abbreviation: 1,6mMemFLPAPrn)

In a 100 mL three-neck flask were put 0.6 g (1.7 mmol) of 1,6-dibromopyrene, 1.4 g (3.4 mmol) of 3-methylphenyl-3-(9-phenyl-9H-fluoren-9-yl)phenylamine, and 0.5 g (5.1 mmol) of sodium tert-butoxide. The air in the flask was replaced with nitrogen. To this mixture were added 21.0 mL of toluene and 0.2 mL of a 10% hexane solution of tri(tert-butyl)phosphine. The temperature of this mixture was set to 60° C., and 34.9 mg (0.1 mmol) of bis(dibenzylideneacetone) palladium(0) was added to the mixture. The temperature of this mixture was raised to 80° C., followed by stirring for 3.0 hours. After the stirring, 400 mL of toluene was added to the mixture, and the mixture was heated. While the mixture was kept hot, it was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (the developing solvent has a 3:2 ratio of hexane to toluene) to give a yellow solid. Recrystallization of the obtained yellow solid from a mixed solvent of toluene and hexane gave 1.2 g of a yellow solid in 67% yield, which was the object of the synthesis.

By a train sublimation method, 1.0 g of the obtained yellow solid was purified. In the purification, the yellow solid was heated at 317° C. under a pressure of 2.2 Pa with a flow rate of argon gas of 5.0 mL/min. After the purification, 1.0 g of a yellow solid was obtained in a yield of 93%, which was the object of the synthesis. The synthesis scheme of Step 2 is shown below.

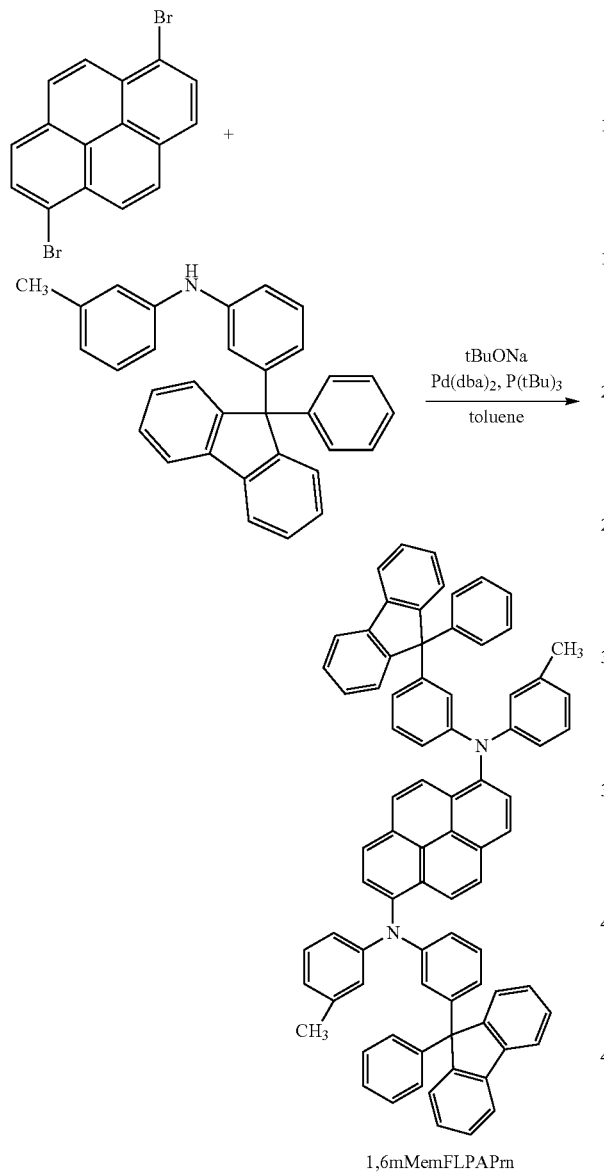

1,6mMemFLPAPrn

A nuclear magnetic resonance (NMR) method identified this compound as N,N'-bis(3-methylphenyl)-N,N'-bis[3-(9-phenyl-9H-fluoren-9-yl)phenyl]-pyrene-1,6-diamine (abbreviation: 1,6mMemFLPAPrn), which was the object of the synthesis.

$^1$H NMR data of the obtained compound are: $^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H).

Reference Example 4

A synthesis example of tris[3-methyl-1-(2-methylphenyl)-5-phenyl-1H-1,2,4-triazolato]iridium(III) (abbreviation: [Ir(Mptz1-mp)$_3$]), which was a material used in the Example, will be described.

Step 1: Synthesis of N-(1-Ethoxyethylidene)benzamide

First, 15.5 g of ethyl acetimidate hydrochloride, 150 mL of toluene, and 31.9 g of triethylamine (Et$_3$N) were put into a 500-mL three-neck flask and stirred at room temperature for 10 minutes. With a 50-mL dropping funnel, a mixed solution of 17.7 g of benzoyl chloride and 30 mL of toluene were added dropwise to this mixture, and the mixture was stirred at room temperature for 24 hours. After a predetermined time elapsed, the reaction mixture was suction-filtered, and the solid was washed with toluene. The obtained filtrate was concentrated to give N-(1-ethoxyethylidene)benzamide (a red oily substance, 82% yield). A scheme of the synthesis of Step 1 is shown below.

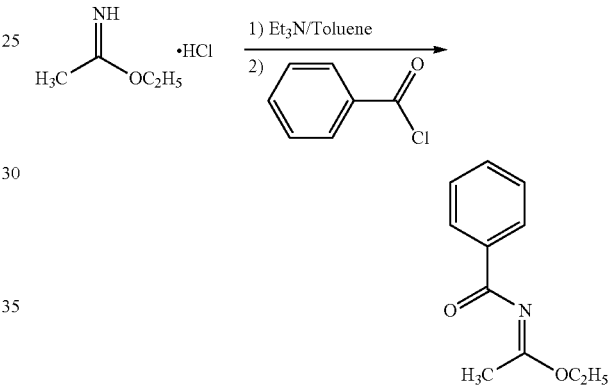

Step 2: Synthesis of 3-Methyl-1-(2-methylphenyl)-5-phenyl-1H-1,2,4-triazole (abbreviation: HMptz1-mp)

Next, into a 300-mL recovery flask were put 8.68 g of o-tolyl hydrazine hydrochloride, 100 mL of carbon tetrachloride, and 35 mL of triethylamine (Et$_3$N), and the mixture was stirred at room temperature for 1 hour. After a predetermined time elapsed, 8.72 g of N-(1-ethoxyethylidene)benzamide obtained in the above Step 1 was added to this mixture, and the mixture was stirred at room temperature for 24 hours. After a predetermined time elapsed, water was added to the reaction mixture, and the aqueous layer was subjected to extraction with chloroform. The organic layer of the resulting mixture was washed with saturated brine, and dried with anhydrous magnesium sulfate added thereto. The obtained mixture was gravity-filtered, and the filtrate was concentrated to give an oily substance. The obtained oily substance was purified by silica gel column chromatography. Dichloromethane was used as a developing solvent. The obtained fraction was concentrated to give 3-methyl-1-(2-methylphenyl)-5-phenyl-1H-1,2,4-triazole (abbreviation: HMptz1-mp) (an orange oily substance, 84% yield). A synthesis scheme of Step 2 is shown below.

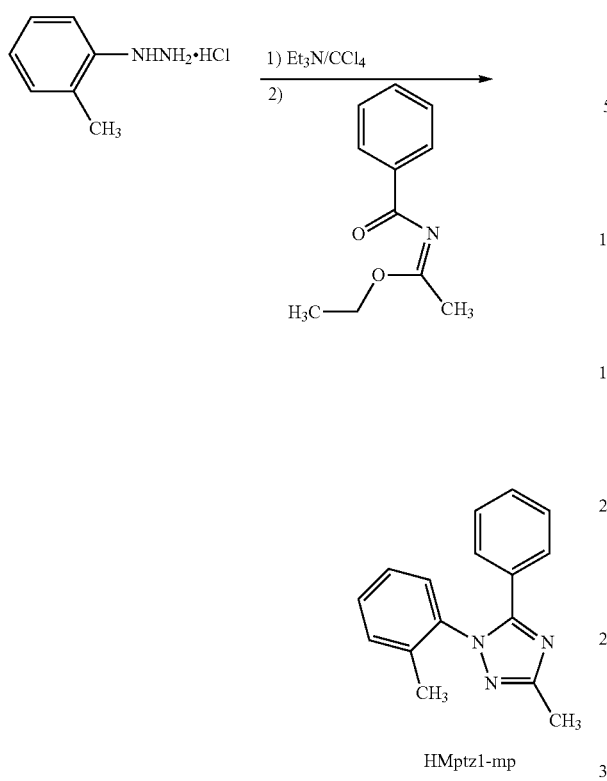

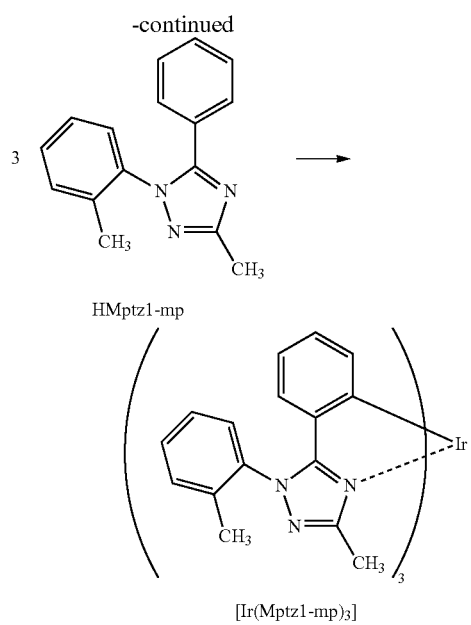

HMptz1-mp

Analysis results by nuclear magnetic resonance spectrometry ($^1$H-NMR) of the yellow powder obtained in the above Step 3 are shown below. Thus, [Ir(Mptz1-mp)$_3$] was found to be obtained.

$^1$H NMR data of the obtained substance are as follows: $^1$H NMR (CDCl$_3$): 1.94-2.21 (m, 18H), 6.47-6.76 (m, 12H), 7.29-7.52 (m, 12H).

Reference Example 5

A synthesis example of 2-[3-(dibenzothiophen-4-yl)phenyl]-1-phenyl-1H-benzimidazole (abbreviation: mDBTBIm-II), which was a material used in Example, will be described.

Step 3: Synthesis of

Tris[3-methyl-1-(2-methylphenyl)-5-phenyl-1H-1,2,4-triazolato]iridium(III) (abbreviation: [Ir(Mptz1-mp)$_3$])

Next, 2.71 g of the ligand HMptz1-mp obtained in the above Step 2 and 1.06 g of tris(acetylacetonato)iridium(III) were put into a reaction container provided with a three-way cock. The air in this flask was replaced with argon, and heated at 250° C. for 48 hours to be reacted. This reaction mixture was dissolved in dichloromethane and purified by silica gel column chromatography. As the developing solvent, dichloromethane was first used, and a mixed solvent of dichloromethane and ethyl acetate in a ratio of 10:1 (v/v) was then used. The obtained fraction was concentrated to give a solid. This solid was washed with ethyl acetate, and recrystallized from a mixed solvent of dichloromethane and ethyl acetate to give the organometallic complex Ir(Mptz1-mp)$_3$ (a yellow powder, 35% yield). A scheme of the synthesis of Step 3 is shown below.

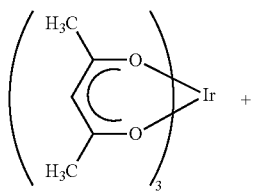

Synthesis of 2-[3-(Dibenzothiophen-4-yl)phenyl]-1-phenyl-1H-benzimidazole (abbreviation: mDBT-BIm-II)

Into a 50-mL three-neck flask were put 1.2 g (3.3 mmol) of 2-(3-bromophenyl)-1-phenyl-1H-benzimidazole, 0.8 g (3.3 mmol) of dibenzothiophen-4-boronic acid, and 50 mg (0.2 mmol) of tri(ortho-tolyl)phosphine. The air in the flask was replaced with nitrogen. To this mixture were added 3.3 mL of a 2.0 mmol/L aqueous solution of potassium carbonate, 12 mL of toluene, and 4 mL of ethanol. Under reduced pressure, this mixture was stirred to be degassed. Then, 7.4 mg (33 μmol) of palladium(II) acetate was added to this mixture, and the mixture was stirred at 80° C. for 6 hours under a nitrogen stream. After a predetermined time, the aqueous layer of the obtained mixture was subjected to extraction with toluene. The solution of the obtained extract combined with the organic layer was washed with saturated brine, and then the organic layer was dried over magnesium sulfate. This mixture was separated by gravity filtration, and the filtrate was concentrated to give an oily substance. This oily substance was purified by silica gel column chromatography. The silica gel column chromatography was carried out using toluene as a developing solvent. The obtained fraction was concentrated to give an oily substance. This oily substance was purified by high performance liquid chromatography. The high performance liquid chromatography was performed using chloroform as a developing solvent. The obtained fraction was concentrated to give an oily substance. This oily substance was recrystallized from a mixed solvent of toluene and hexane, so that the substance which was the object of the synthesis was obtained as 0.8 g of a pale yellow powder in 51% yield. The synthesis scheme is illustrated in the following formula.

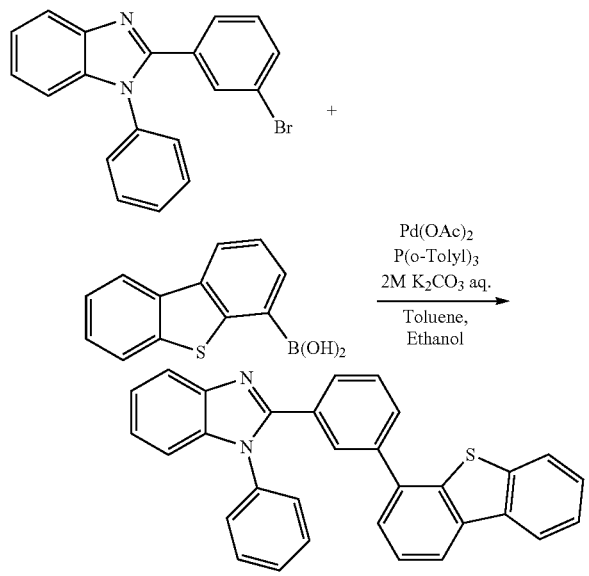

By a train sublimation method, 0.8 g of the obtained pale yellow powder was purified. In the purification, the pale yellow powder was heated at 215° C. under a pressure of 3.0 Pa with a flow rate of argon gas of 5 mL/min. After the purification, 0.6 g of a white powder of the substance which was the object of the synthesis was obtained in a yield of 82%.

This compound was identified as 2-[3-(dibenzothiophen-4-yl)phenyl]-1-phenyl-1H-benzimidazole (abbreviation: mDBTBIm-II), which was the object of the synthesis, by nuclear magnetic resonance (NMR) spectroscopy.

$^1$H NMR data of the obtained compound are as follows: $^1$H NMR (CDCl$_3$, 300 MHz): δ (ppm)=7.23-7.60 (m, 13H), 7.71-7.82 (m, 3H), 7.90-7.92 (m, 2H), 8.10-8.17 (m, 2H).

REFERENCE NUMERALS

101: substrate, 102: first electrode, 103: EL layer, 104: second electrode, 111: hole-injection layer, 112: hole-transport layer, 113: light-emitting layer, 114: electron-transport layer, 501: first electrode, 502: second electrode, 511: first light-emitting unit, 512: second light-emitting unit, 513: charge generation layer, 601: driver circuit portion: (source side driver circuit), 602: pixel portion, 603: driver circuit portion: (gate side driver circuit), 604: sealing substrate, 605: sealing material, 607: space, 608: wiring, 609: FPC (flexible printed circuit), 610: element substrate, 611: switching TFT, 612: current controlling TFT, 613: first electrode, 614: insulator, 616: layer containing organic compound, 617: second electrode, 618: light-emitting element, 623: n-channel TFT, 624: p-channel TFT, 901: housing, 902: liquid crystal layer, 903: backlight unit, 904: housing, 905: driver IC, 906: terminal, 951: substrate, 952: electrode, 953: insulating layer, 954: partition layer, 955: a layer containing an organic compound, 956: electrode, 2001: housing, 2002: light source, 3001: lighting device, 9101: housing, 9102: support, 9103: display portion, 9104: speaker portion, 9105: video input terminal, 9201: main body, 9202: housing, 9203: display portion, 9204: keyboard, 9205: external connection port, 9206: pointing device, 9401: main body, 9402: housing, 9403: display portion, 9404: audio input portion, 9405: audio output portion, 9406: operation key, 9407: external connection port, 9408: antenna, 9501: main body, 9502: display portion, 9503: housing, 9504: external connection port, 9505: remote control receiving portion, 9506: image receiving portion, 9507: battery, 9508: audio input portion, 9509: operation key, 9510: eye piece portion.

This application is based on Japanese Patent Application serial No. 2010-203396 filed with the Japan Patent Office on Sep. 10, 2010, the entire contents of which are hereby incorporated by reference.

What is claimed is:

1. An organic compound comprising: a carbazole group; and one of a dibenzothiophene group and a dibenzofuran group, wherein a 4-position of the dibenzothiophene group or a 4-position of the dibenzofuran group is bonded to a 2- or 3-position of the carbazole group, wherein a heteroaromatic group or an aryl group which comprises a π-electron deficient heteroaromatic ring is bonded to a 9-position of the carbazole group, and
   wherein the π-electron deficient heteroaromatic ring is selected from a benzimidazolyl group, a benzoxazolyl group, and an oxadiazolyl group.

2. The organic compound according to claim 1,
   wherein a 4-position of a dibenzothiophene group or a 4-position of a dibenzofuran group is further bonded to a 6- or 7-position of the carbazole group.

3. A light-emitting device comprising the organic compound according to claim 1.

4. An electronic device comprising the light-emitting device according to claim 3.

5. A lighting device comprising the light-emitting device according to claim 3.

6. An organic compound comprising: a carbazole group; and
   one of a dibenzothiophene group and a dibenzofuran group,
   wherein a 4-position of the dibenzothiophene group or a 4-position of the dibenzofuran group is bonded to 2- and 7-positions of the carbazole group or 3- and 6-positions of the carbazole group, wherein a heteroaromatic group or an aryl group which comprises a π-electron deficient heteroaromatic ring is bonded to a 9-position of the carbazole group, and wherein the π-electron deficient heteroaromatic ring is selected from a benzimidazolyl group, a benzoxazolyl group, and an oxadiazolyl group.

7. A light-emitting device comprising the organic compound according to claim 6.

8. An electronic device comprising the light-emitting device according to claim 7.

9. A lighting device comprising the light-emitting device according to claim 7.

10. An organic compound represented by a formula (G1):

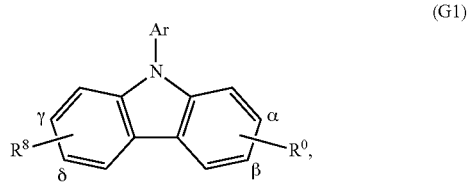

wherein:
Ar represents a heteroaromatic group or an aryl group which comprises a π-electron deficient heteroaromatic ring;
$R^0$ represents a substituent represented by a formula (g1) and is bonded to a carbon atom represented by either α or β:

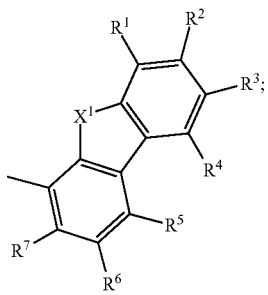

(g1)

$R^8$ represents any one of hydrogen, an alkyl group having 1 to 6 carbon atoms, an aryl group having 6 to 15 carbon atoms, and a substituent represented by a formula (g2) and is bonded to a carbon atom represented by either γ or δ:

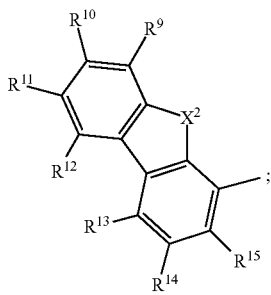

(g2)

$X^1$ and $X^2$ individually represent oxygen or sulfur; and
$R^1$ to $R^7$ and $R^9$ to $R^{15}$ individually represent any one of hydrogen, an alkyl group having 1 to 6 carbon atoms, and an aryl group having 6 to 15 carbon atoms, and
wherein the π-electron deficient heteroaromatic ring is selected from a benzimidazolyl group, a benzoxazolyl group, and an oxadiazolyl group.

11. The organic compound according to claim 10,
wherein $R^8$ is bonded to the carbon atom represented by γ when $R^8$ is the substituent represented by the formula (g2) and $R^0$ is bonded to the carbon atom represented by α, and
wherein $R^8$ is bonded to the carbon atom represented by δ when $R^8$ is the substituent represented by the formula (g2) and $R^0$ is bonded to the carbon atom represented by β.

12. The organic compound according to claim 10,
wherein $R^2$, $R^4$, $R^5$, $R^7$, $R^9$, $R^{10}$, $R^{12}$, $R^{13}$, and $R^{15}$ are each hydrogen.

13. The organic compound according to claim 10,
wherein $R^1$ to $R^7$ and $R^9$ to $R^{15}$ are each hydrogen.

14. The organic compound according to claim 10,
wherein the organic compound is represented by a formula (G2):

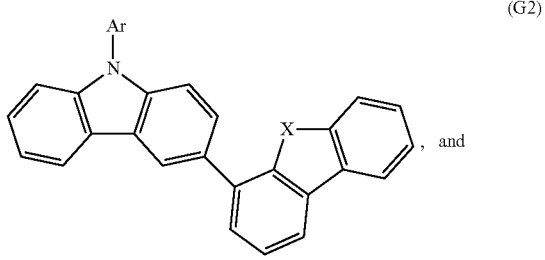

(G2)

, and wherein X represents oxygen or sulfur.

15. The organic compound according to claim 10,
wherein the organic compound is represented by any of formulae (G3) and (G4):

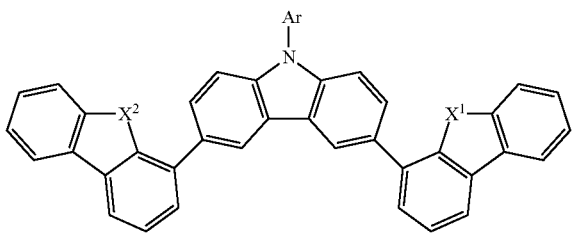

(G3)

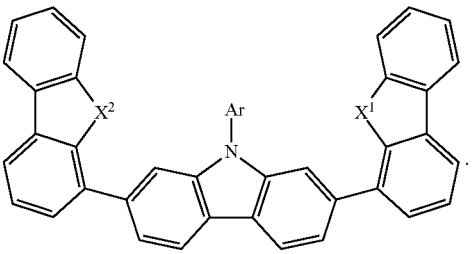

(G4)

16. The organic compound according to claim 15,
wherein $X^1$ and $X^2$ are each sulfur.

17. A light-emitting device comprising the organic compound according to claim 10.

18. An electronic device comprising the light-emitting device according to claim 10.

19. A lighting device comprising the light-emitting device according to claim 10.

* * * * *

UNITED STATES PATENT AND TRADEMARK OFFICE
CERTIFICATE OF CORRECTION

PATENT NO.        : 9,065,058 B2
APPLICATION NO.   : 14/208356
DATED             : June 23, 2015
INVENTOR(S)       : Satoshi Seo et al.

It is certified that error appears in the above-identified patent and that said Letters Patent is hereby corrected as shown below:

In the Specification:

Column 19, Line 16; Change "phenyl]-9," to --phenyl]-9,9'-bianthryl,--.

Column 20, Line 7; Change "[N,N',N"-" to --[N,N',N'- --.

Column 41, Line 26; Change "farmed" to --formed--.

Column 44, Line 17; Change "formula (1)" to --formula (i)--.

Column 44, Line 19; Change "get" to --set--.

Column 44, Line 57; Change "fruited." to --formed.--.

Column 47, Line 43; Change "formula (1)" to --formula (i)--.

Column 48, Line 59; Change "examined FIG. 17" to --examined. FIG. 17--.

Column 54, Line 16; Change "faulted" to --formed--.

Column 63, Line 37; Change "4-yl-9H" to --4-yl)-9H--.

Column 67, Line 46; Change "potential was" to --potential $E_{pc}$ was--.

Column 81, Line 18; Change "(5.0 mmol)" to --(5.0 mmol) of--.

Column 93, Line 2; Change "carbazol" to --carbazole--.

Column 97, Line 35; Change "10 nm" to --1 nm--.

Column 106, Line 15; Change "$E_{pc}$, thereof" to --$E_{pc}$ thereof--.

Column 111, Line 34; Change "of δ9%." to --of 89 %.--.

Column 117, Line 5; Change "to, extraction" to --to extraction--.

Column 123, Line 19; Change "formed red on" to --formed on--.

Column 126, Line 18; Change "thin," to --thin--.

Column 137, Line 4; Change "50 nm" to --50 nm.--.

Column 143, Line 7; Change "fainted" to --formed--.

Signed and Sealed this
First Day of March, 2016

Michelle K. Lee
*Director of the United States Patent and Trademark Office*

CERTIFICATE OF CORRECTION (continued)
U.S. Pat. No. 9,065,058 B2

In the Specification:

Column 143, Line 32; Change "50 nm" to --50 nm.--.

Column 150, Line 13; Change "50 nm" to --50 nm.--.

Column 151, Line 30 to 31; Change "formula (1))" to --formula (i))--.

In the Claims:

Column 164, Lines 59 to 67, Claim 10, formula (G1); Change

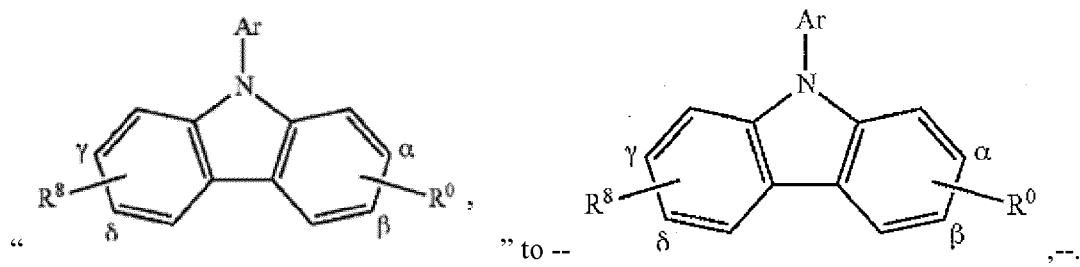

Column 165, Lines 10 to 20, formula (g1) Claim 10; Change

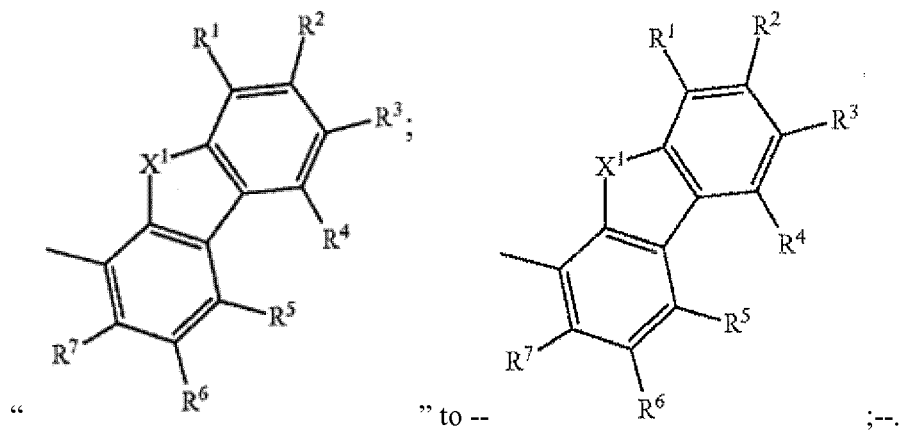

Column 165, Lines 30 to 40, formula (g2) Claim 10; Change

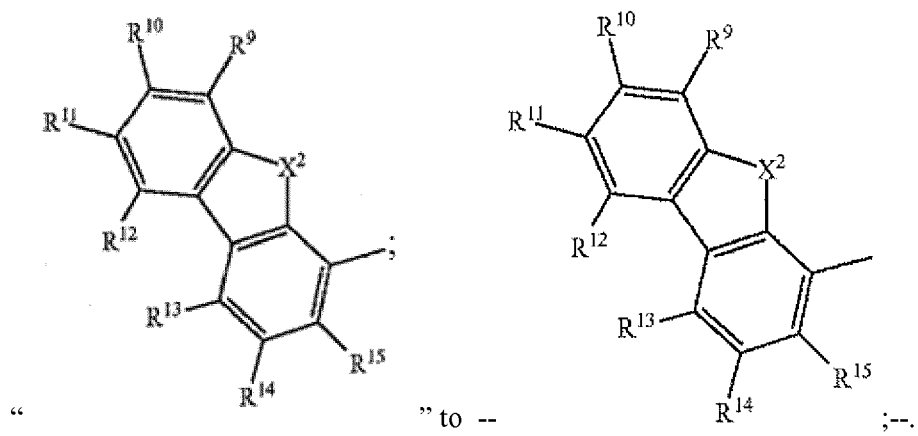

CERTIFICATE OF CORRECTION (continued)
U.S. Pat. No. 9,065,058 B2

In the Claims:

Column 166, Lines 10 to 20, Claim 14, formula (G2); Change

"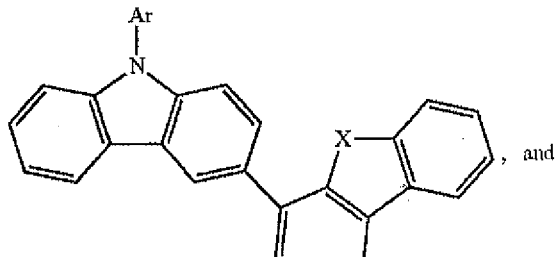, and" to

--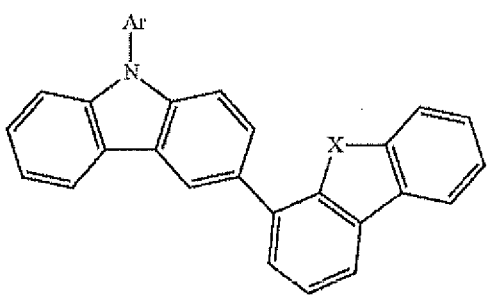, and --.

Column 166, Lines 38 to 49, Claim 15, formula (G4); Change

"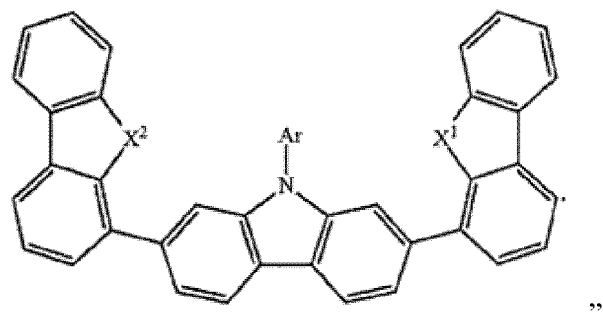"

to

--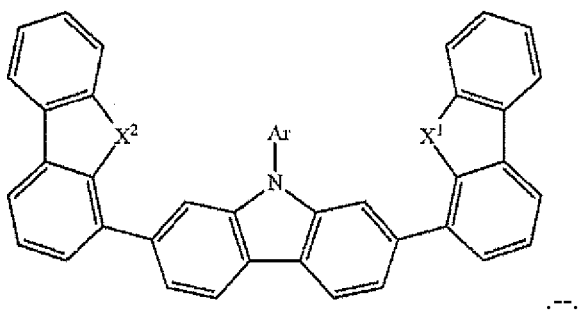.--.